(12) United States Patent
Taguchi et al.

(10) Patent No.: US 9,243,285 B2
(45) Date of Patent: Jan. 26, 2016

(54) HAIR SHAPE SUSCEPTIBILITY GENE

(75) Inventors: Hiroyuki Taguchi, Tochigi (JP); Hiroshi Yoshida, Tochigi (JP); Chie Fuse, Tochigi (JP); Tadao Arinami, Ibaraki (JP)

(73) Assignee: Kao Corporation, Tokyo (JP)

( * ) Notice: Subject to any disclaimer, the term of this patent is extended or adjusted under 35 U.S.C. 154(b) by 65 days.

(21) Appl. No.: 13/500,442

(22) PCT Filed: Oct. 5, 2010

(86) PCT No.: PCT/JP2010/067443
§ 371 (c)(1),
(2), (4) Date: Jun. 1, 2012

(87) PCT Pub. No.: WO2011/043332
PCT Pub. Date: Apr. 14, 2011

(65) Prior Publication Data
US 2012/0231094 A1 Sep. 13, 2012

(30) Foreign Application Priority Data

Oct. 5, 2009 (JP) ................. 2009-231997
Oct. 5, 2009 (JP) ................. 2009-232005
Oct. 5, 2009 (JP) ................. 2009-232028
Oct. 5, 2009 (JP) ................. 2009-232029

(51) Int. Cl.
*C12Q 1/68* (2006.01)
*G01N 33/68* (2006.01)

(52) U.S. Cl.
CPC ............ *C12Q 1/6827* (2013.01); *C12Q 1/6876* (2013.01); *C12Q 1/6883* (2013.01); *G01N 33/68* (2013.01); *C12Q 2600/124* (2013.01); *C12Q 2600/172* (2013.01)

(58) Field of Classification Search
None
See application file for complete search history.

(56) References Cited

U.S. PATENT DOCUMENTS

| | | | |
|---|---|---|---|
| 6,812,339 B1 | 11/2004 | Venter et al. | |
| 2002/0045188 A1* | 4/2002 | Kamb et al. | 435/7.1 |
| 2005/0208010 A1 | 9/2005 | De Lacharriere et al. | |
| 2005/0250180 A1 | 11/2005 | Jacobs et al. | |
| 2007/0065389 A1 | 3/2007 | De Lacharriere et al. | |
| 2011/0129844 A1* | 6/2011 | Ronai et al. | 435/6.14 |
| 2012/0276536 A1 | 11/2012 | Taguchi et al. | |
| 2012/0329726 A1 | 12/2012 | Taguchi et al. | |

FOREIGN PATENT DOCUMENTS

| | | |
|---|---|---|
| JP | 2002-238577 | 8/2002 |
| JP | 2005-532407 | 10/2005 |
| JP | 2006-042735 | 2/2006 |
| JP | 2006-254735 | 9/2006 |
| WO | WO 02/068649 A2 | 9/2002 |
| WO | WO 2007/086526 A1 | 8/2007 |
| WO | WO 2008/016356 A2 | 2/2008 |
| WO | WO 2008/021290 A2 | 2/2008 |
| WO | WO 2008/043644 A1 | 4/2008 |

OTHER PUBLICATIONS

Hirasawa et al., Methylation status of genes upregulated by demethylating agent 5-aza-2'-deoxycytidine in hepatocellular carcinoma; Oncology, vol. 71, pp. 77-85, 2006.*
Kaul et al., GenBank Accession No. AC096677.2, submitted Apr. 2, 2003; Accessed Sep. 3, 2014.*
GenBank Accession No. NM_004078.2 CSRP1 nucleotide sequence, accessed Sep. 3, 2014.*
GenPept Accession No. NP_004069.1 CSRP1 protein sequence, accessed Sep. 3, 2014.*
International Search Report (ISR) for PCT/JP2010/067443, I.A. fd: Oct. 5, 2010, mailed Dec. 7, 2010 from the Japanese Patent Office, Tokyo, Japan.
International Preliminary Report on Patentability (IPRP), Chapter I of the Patent Cooperation Treaty, including the Written Opinion for PCT/JP2010/067443, I.A. fd: Oct. 5, 2010, issued May 8, 2012, from the International Bureau of WIPO, Geneva, Switzerland.
*Homo sapiens* cysteine and glycine-rich protein 1, mRNA (cDNA clone MGC:40335 IMAGE:5244276, complete cds. Uploaded Jul. 15, 2006, NCBI Entrez Nucleotide, Accession No. BC032493 (GI:21595351) [Retrieved on Nov. 24, 2010, from the internet, www.ncbi.nlm.nih.gov/nuccore/21595351>.
*Homo sapiens* neuron navigator 1 (NAV1) mRNA, complete cds. Uploaded Jul. 1, 2002, NCBI Entrez Nucleotide, Accession No. AY043013 (GI:21654876) [Retrieved on Nov. 24, 2010, from the internet, www.ncbi.nlm.nih.gov/nuccore/21654876>.
*Homo sapiens* importin 9 (IPO9), mRNA, Uploaded Feb. 11, 2008, NCBI Entrez Nucleotide, Accession No. NM_018085 (GI:112734865) [Retrieved on Nov. 24, 2010, from the internet, www.ncbi.nlm.nih.gov/nuccore/112734865?sat=NCBI&satkey=20569420>.
*Homo sapiens* shisa homolog 4 (*Xenopus laevis*) (SHISA4), mRNA, Uploaded Sep. 3, 2009, NCBI Entrez Nucleotide, Accession No. NM_198149 (GI:39930574) [Retrieved on Nov. 24, 2010, from the internet, www.ncbi.nlm.nih.gov/nuccore/39930574?sat=NCBI&satkey=32433675>.

(Continued)

*Primary Examiner* — Jennifer Dunston
*Assistant Examiner* — Addison D Ault
(74) *Attorney, Agent, or Firm* — Sterne, Kessler, Goldstein & Fox P.L.L.C.

(57) ABSTRACT

A genetic polymorphism and a hair shape susceptibility gene that are related to hair shape, and a method for determining the genetic susceptibility to hair shape in individual test subjects are provided. Disclosed is a hair shape susceptibility gene, which overlaps with a haplotype block in the 1q32.1 to 1q32.2 region (D1S249 to D1S2891) of human chromosome 1 and comprises a portion or the entirety of the base sequence of the haplotype block, wherein the haplotype block is determined by a linkage disequilibrium analysis conducted on a single nucleotide polymorphism (SNP) marker whose allele frequency differs statistically significantly between a group having a curly hair trait and a group having a non-curly hair trait, and consists of a base sequence set forth in any one of SEQ ID NO:1 to NO:3.

19 Claims, 12 Drawing Sheets

(56) References Cited

OTHER PUBLICATIONS

*Homo sapiens* nuclear casein kinase and cyclin-dependent kinase substrate 1 (NUCKS1), mRNA, Uploaded Feb. 1, 2009, NCBI Entrez Nucleotide, Accession No. NM_022731 (GI:181336713) [Retrieved on Nov. 24, 2010, from the internet, www.ncbi.nlm.nih.gov/nuccore/181336713?sat=NCBI&satkey=27783208>.

Altshuler, D et al., "The common PPARγPro12Ala polymorphism is associated with decreased risk of type 2 diabetes," Nat Genet 26(1): 76-80 (Sep. 2000), Nature Pub. Co, New York, NY.

Cullen SI et al, "Acquired Progressive Kinking of the Hair," Arch Dermatol 125: 252-255 (Feb. 1989), American Medical Assn, Chicago, IL.

Du, X et al., "Velvet, a Dominant Egfr Mutation That Causes Wavy Hair and Defective Eyelid Development in Mice," Genetics 166: 331-340 (Jan. 2004), Genetics Society of America, Bethesda, MD.

Fujimoto, A, et al., "A scan for genetic determinants of human hair morphology: EDAR is associated with Asian hair thickness," Hum Mol Genet 17: 835-843 (Mar. 2008), IRL Press at Oxford University Press, Oxford, England.

Hanis, CL et al., "A genome-wide search for human non-insulin-dependent (type 2) diabetes genes reveals a major susceptibility locus on chromosome 2," Nat Genet 13(2): 161-166 (Jun. 1996), Nature Pub. Co, New York, NY.

Kjaer, KW et al., "Novel Connexin 43 (GJA1) mutation causes oculo-dento-digital dysplasia with curly hair," Am J Med Genet A, 127A(2): 152-157 (Jun. 2004), Wiley-Blackwell, Hoboken, N.J.

Mann, GB et al., "Mice with a null mutation of the TGFα gene have abnormal skin architecture, wavy hair, and curly whiskers and often develop corneal inflammation," Cell 73(2): 249-261 (Apr. 1993), MIT Press, Cambridge, MA.

Medland, SE et al., "Common variants in the trichohyalin gene are associated with straight hair in Europeans," Am J Hum Genet 85(5): 750-755 (Nov. 2009), American Society of Human Genetics, Baltimore, MD.

Møller, LB et al., "Identification and analysis of 21 novel disease-causing amino acid substitutions in the conserved part of ATP7A," Hum Mutat 26(2): 84-93 (Aug. 2005), Wiley-Liss, New York, NY.

Norgett, EE et al., "Recessive mutation in desmoplakin disrupts desmoplakin-intermediate filament interactions and causes dilated cardiomyopathy, woolly hair and keratoderma," Hum Mol Genet 9: 2761-2766 (Nov. 2000), IRL Press at Oxford University Press, Oxford, England.

Rostand, J et al., "An Atlas of Human Genetics," Hutchinson Scientific & Technical, London, England, pp. 26-29, 1964.

Sabeti, PC et al., "Genome-wide detection and characterization of positive selection in human populations," Nature 449(7164): 913-918 (Oct. 2007), plus supplementary online material, Nature Publishing Group, Basingstoke, England.

Sulem, P et al., "Genetic determinants of hair, eye and skin pigmentation in Europeans," Nat Genet 39(12): 1443-1452 (Dec. 2007), Nature Pub. Co., New York, NY.

Thibaut, S, et al., "Human hair shape is programmed from the bulb," Br J Dermatol 152(4): 632-638 (Apr. 2005), Blackwell Scientific Publications, Oxford, England.

Extended European search report including the supplementary European search report and the European search opinion, mailed May 17, 2013, for EP Application No. 10822000.5, the European Patent Office, Rijswijk, Netherlands.

Yusuke: "Submitted SNP (ss) Details: ss4940242," NCBI-dbSNP database, NCBI, Bethesda, MD, submitted Aug. 1, 2002, retrieved from the internet: www.ncbi.nlm.nih.gov/SNP/snp_ss.cgi?subsnp_id=4940242 retrieved on Apr. 16, 2013.

International Search Report (ISR) for PCT/JP2010/067441, I.A. fd: Oct. 5, 2010, mailed Nov. 30, 2010 from the Japanese Patent Office, Tokyo, Japan (counterpart to U.S. Appl. No. 13/500,439).

International Preliminary Report on Patentability (IPRP), Chapter I of the Patent Cooperation Treaty, including the Written Opinion for PCT/JP2010/067441, I.A. fd: Oct. 5, 2010, issued May 8, 2012, from the International Bureau of WIPO, Geneva, Switzerland Japan (corresponding to U.S. Appl. No. 13/500,439).

International Search Report (ISR) for PCT/JP2010/067444, I.A. fd: Oct. 5, 2010, mailed Dec. 7, 2010, from the Japanese Patent Office, Tokyo, Japan (counterpart to U.S. Appl. No. 13/500,462).

International Preliminary Report on Patentability (IPRP), Chapter I of the Patent Cooperation Treaty, including the Written Opinion for PCT/JP2010/067444, I.A. fd: Oct. 5, 2010, issued May 8, 2012, from the International Bureau of WIPO, Geneva, Switzerland (counterpart to U.S. Appl. No. 13/500,462).

Notification of First Office Action, for Chinese Patent Application No. CN 201080044858.8, mailed Dec. 24, 2012, from the Patent Office of the People's Republic of China, Beijing, China (counterpart to U.S. Appl. No. 13/500,439).

*Homo sapiens* annexin A9 (ANXA9), mRNA, Uploaded May 1, 2008, NCBI Entrez Nucleotide, Accession No. NM_003568 (GI:145864464), retrieved on Nov. 15, 2010, from the internet, www.ncbi.nlm.nih.gov/nuccore/145864464?sat=NCBI&satkey=22246716>.

*Homo sapiens* family with sequence similarity 63, member A (FAM63A), transcript variant 2, mRNA, Uploaded Aug. 5, 2009, NCBI Entrez Nucleotide, Accession No. NM_001040217 (GI:253795485), retrieved on Nov. 15, 2010, from the internet, www.ncbi.nlm.nih.gov/nuccore/NM_001040217.2>.

*Homo sapiens* late cornified envelope 5A (LCE5A), mRNA, Uploaded Sep. 20, 2009, NCBI Entrez Nucleotide, Accession No. NM_178438 (GI:110578661), retrieved on Nov. 15, 2010, from the internet, www.ncbi.nlm.nih.gov/nuccore/110578661?sat=NCBI&satkey=32699481>.

*Homo sapiens* cysteine-rich C-terminal 1 (CRCT1), mRNA, Uploaded Oct. 9, 2008, NCBI Entrez Nucleotide, Accession No. NM_019060 (GI:209180483), retrieved on Nov. 15, 2010, from the internet, www.ncbi.nlm.nih.gov/nuccore/209180483?sat=NCBI&satkey=25519550>.

*Homo sapiens* late cornified envelope 2B (LCE2B), mRNA, Uploaded Feb. 22, 2009, NCBI Entrez Nucleotide, Accession No. NM_014357 (GI:223633914), retrieved on Nov. 15, 2010, from the internet, www.ncbi.nlm.nih.gov/nuccore/223633914?sat=NCBI&satkey=28460288>.

*Homo sapiens* late cornified envelope 2A (LCE2A), mRNA, Uploaded Feb. 13, 2009, NCBI Entrez Nucleotide, Accession No. NM_178428 (GI:57242769), retrieved on Nov. 15, 2010, from the internet, www.ncbi.nlm.nih.gov/nuccore/57242769?sat=NCBI&satkey=283933204>.

*Homo sapiens* sperm mitochondria-associated cysteine-rich protein (SMCP), nuclear gene encoding mitochondrial protein, mRNA, Uploaded Feb. 11, 2008, NCBI Entrez Nucleotide, Accession No. NM_030663 (GI:25121988), retrieved on Nov. 15, 2010, from the internet, www.ncbi.nlm.nih.gov/nuccore/25121988?sat=NCBI&satkey=20570171>.

*Homo sapiens* involucrin (IVL), mRNA, Uploaded Sep. 20, 2009, NCBI Entrez Nucleotide, Accession No. NM_005547 (GI:44890058), retrieved on Nov. 15, 2010, from the internet, www.ncbi.nlm.nih.gov/nuccore/44890058?sat=NCBI&satkey=32698100>.

*Homo sapiens* organic anion transporter 3 (OAT3), mRNA, complete cds. Uploaded Mar. 9, 1999, NCBI Entrez Nucleotide, Accession No. AF097491 (GI:4378058), retrieved on Nov. 29, 2010, from the internet, www.ncbi.nlm.nih.gov/nuccore/4378058>.

*Homo sapiens* phosphofurin acidic cluster sorting protein 1 (PACS1), mRNA, complete cds. Uploaded Sep. 20, 2009, NCBI Entrez Nucleotide, Accession No. NM_018026 (GI:30089915), retrieved on Nov. 29, 2010, from the internet, www.ncbi.nlm.nih.gov/nuccore/30089915?sat=NCBI&satkey=32698503>.

*Homo sapiens* kinesin light chain 2 (KLC2), transcript variant 2, mRNA, Uploaded Sep. 3, 2009, NCBI Entrez Nucleotide, Accession No. NM_001134774 (GI:198041727), retrieved on Nov. 29, 2010, from the internet, www.ncbi.nlm.nih.gov/nuccore/198041727?sat=NCBI&satkey=32519240>.

*Homo sapiens* RAB1B, member RS oncogene family (RAB1B), mRNA, Uploaded Feb. 1, 2009, NCBI Entrez Nucleotide, Accession

(56) References Cited

OTHER PUBLICATIONS

No. NM_030981 (GI:116014337), retrieved on Nov. 29, 2010, from the internet, www.ncbi.nlm.nih.gov/nuccore/116014337?sat=NCBI&satkey=27780408>.

*Homo sapiens* cornichon homolog 2 (*Drosophila*) (CNIH2), mRNA, Uploaded Aug. 6, 2009, NCBI Entrez Nucleotide, Accession No. NM_182553 (GI:32698937), retrieved on Nov. 29, 2010, from the internet, www.ncbi.nlm.nih.gov/nuccore/32698937?sat=NCBI&satkey=31931907>.

*Homo sapiens* Yip1 interacting factor homolog A (*S. cerevisiae*) (YIF1A), mRNA, Uploaded Aug. 2, 2009, NCBI Entrez Nucleotide, Accession No. NM_020470 (GI:170932463), retrieved on Nov. 29, 2010, from the internet, www.ncbi.nlm.nih.gov/nuccore/170932463?sat=NCBI&satkey=31767219>.

*Homo sapiens* transmembrance protein 151A (TMEM151A), mRNA, Uploaded Aug. 6, 2009, NCBI Entrez Nucleotide, Accession No. NM_153266 (GI:221136815), retrieved on Nov. 29, 2010, from the internet, www.ncbi.nlm.nih.gov/nuccore/NM_153266.3.

*Homo sapiens* CD248 molecule, endosialin (CD248), mRNA, Uploaded Feb. 1, 2009, NCBI Entrez Nucleotide, Accession No. NM_020404 (GI:45387956), retrieved on Nov. 29, 2010, from the internet, www.ncbi.nlm.nih.gov/nuccore/45387956?sat=NCBI&satkey=27783461>.

*Homo sapiens* oral cancer overexpressed 1 (ORAOV1), mRNA, Uploaded Aug. 6, 2009, NCBI Entrez Nucleotide, Accession No. NM_153451 (GI:56676315), retrieved on Nov. 29, 2010, from the internet, www.ncbi.nlm.nih.gov/nuccore/56676315?sat=NCBI&satkey=31931818>.

*Homo sapiens* keratin associated protein 5-8 (KRTAP5-8), mRNA, Uploaded May 1, 2008, NCBI Entrez Nucleotide, Accession No. NM_021046 (GI:123173776), retrieved on Nov. 29, 2010, from the internet, www.ncbi.nlm.nih.gov/nuccore/123173776?sat=NCBI&satkey=22245774>.

*Homo sapiens* keratin associated protein 5-9 (KRTAP5-9), mRNA, Uploaded Feb. 26, 2008, NCBI Entrez Nucleotide, Accession No. NM_005553 (GI:123702037), retrieved on Nov. 29, 2010, from the internet, www.ncbi.nlm.nih.gov/nuccore/123702037?sat=NCBI&satkey=20831141>.

*Homo sapiens* keratin associated protein 5-10 (KRTAP5-10), mRNA, Uploaded May 1, 2008, NCBI Entrez Nucleotide, Accession No. NM_001012710 (GI:60593039), retrieved on Nov. 29, 2010, from the internet, www.ncbi.nlm.nih.gov/nuccore/60593039?sat=NCBI&satkey=22247595>.

Botchkarev, VA et al., "Edar signaling in the control of hair follicle development," J Investig Dermatol Symp Proc 10(3):247-251, (Dec. 2005), Nature Publishing Group, New York, New York.

Notification of First Office Action, for Chinese Patent Application No. CN 201080044857.3, mailed Dec. 24, 2012, from the Patent Office of the People's Republic of China, Beijing, China (counterpart to U.S. Appl. No. 13/500,462).

Notification of First Office Action, for Chinese Patent Application No. CN 201080044856.9, mailed Dec. 25, 2012, from the Patent Office of the People's Republic of China, Beijing, China (counterpart to U.S. Appl. No. 13/500,442).

Tand, D. et al., "Advances in Methods for SNP Detection," J. Shanghai Jiaotong University (Agricultural Science) 25(2):405-418 (Apr. 2007), China Academic Journal Electronic Publishing House, Beijing, China.

Wang, Q-s. et al., "Review of Association Analyses of Haplotype with Traits," J. Shanghai Jiaotong University (Agricultural Science) 26(3):255-257 (Jun. 2008), China Academic Journal Electronic Publishing House, Beijing, China.

Extended European search report for EP Appl. No. 10822002.1, including the supplementary European search report and the European search opinion, dated Feb. 12, 2013, European Patent Office, Munich, Germany.

Klacansky, I. et al., "Cell-type-specific patterns of gene expression, GenBank: locus FW48121.1" Feb. 21, 2008, XP055052019, Retrieved from the internet: www.ncbi.nlm.nih.gov/nuccore/fw548121, retrieved Feb. 1, 2013.

Kimura, K. et al., "Diversification of transcriptional modulation: Large-scale identification and characterization of putative alternative promoters of human gene," Genome Research, 16: 55-65, Jan. 2006, Cold Spring Harbor Laboratory Press, Woodbury, NY.

Mou, C, et al., "Enhanced ectodysplasin-A receptor (EDAR) signaling alters multiple fiber characteristics to produce the East Asian hair form," Hum Mutat, 29(12): 1405-1411 (Dec. 2008), Wiley-Liss, New York, NY.

Extended European search report including the supplementary European search report and the European search opinion, mailed Jun. 7, 2013, for EP Application No. 10822003.9, the European Patent Office, Munich, Germany.

Stoll, M et al., "Genetic variation in DLG5 is associated with inflammatory bowel disease," Nat Genet, May 2004; 36(5): 476-480, Nature Pub. Co, New York, NY.

Shimomura, Y et al., "Disruption of P2RY5, an orphan G protein-coupled receptor, underlies autosomal recessive woolly hair," Nat Genet, Mar. 2008; 40(3): 335-339, Nature Pub. Co, New York, NY.

Schlake, T, "Segmental Igfbp5 expression is specifically associated with the bent structure of zigzag hairs," Mech Dev, Sep. 2005; 122(9): 988-997, Elsevier, Limerick, Ireland.

Excerpted file history of U.S. Appl. No. 13/500,439: Final Office action mailed Nov. 24, 2014; Amendment and Reply filed Oct. 17, 2014; Office action mailed Apr. 22, 2014; reply to Restriction/election of species requirements filed Jan. 23, 2014 and Restriction/election of species requirements mailed Nov. 27, 2013.

Excerpted file history of U.S. Appl. No. 13/500,462: Final Office action mailed Sep. 10, 2014, Reply to first Office action filed Aug. 21, 2014; first Office action mailed Apr. 21, 2014; reply to restriction/election of species requirements filed Jan. 23, 2014; and restriction/election of species requirement mailed Nov. 27, 2013.

Hindorff, LA et al., "Genetic architecture of cancer and other complex diseases: lessons learned and future directions," Carcinogenesis, Jul. 2011; 32: 945-954, IRL Press, Oxford, England.

Liu, X et al., "Genetic variants at 5p12 and risk of breast cancer in Han Chinese," J Hum Genet, Oct. 2012; 57(10): 638-641, Nature Pub. Group, London, England.

*Homo sapiens* cysteine and glycine-rich protein 1 (CSRP1), transcript variant 1, mRNA, NCBI Accession NM_004078, version NM_004078.2 (GI:221316625), Jun. 24, 2009, last modification Feb. 26, 2014, printed from www.ncbi.nlm.nih.gov/nuccore/NM_004078.

Xie, Ji-sheng et al., "Difference in the polymorphism of exon 5 +3953C/T of interleukin-1 beta gene between Guangxi Zhuang population and Han population," Chinese J Clin. Rehabilitation 10:154-156 (Oct. 2006), Shenyang Shi, China.

Excerpted file history of U.S. Appl. No. 13/500,462: Amendment and reply filed Mar. 9, 2015.

Excerpted file history of U.S. Appl. No. 13/500,439: Amendment and Reply filed Mar. 20, 2015, filed with the United States Patent and Trademark Office, Alexandria, VA.

\* cited by examiner

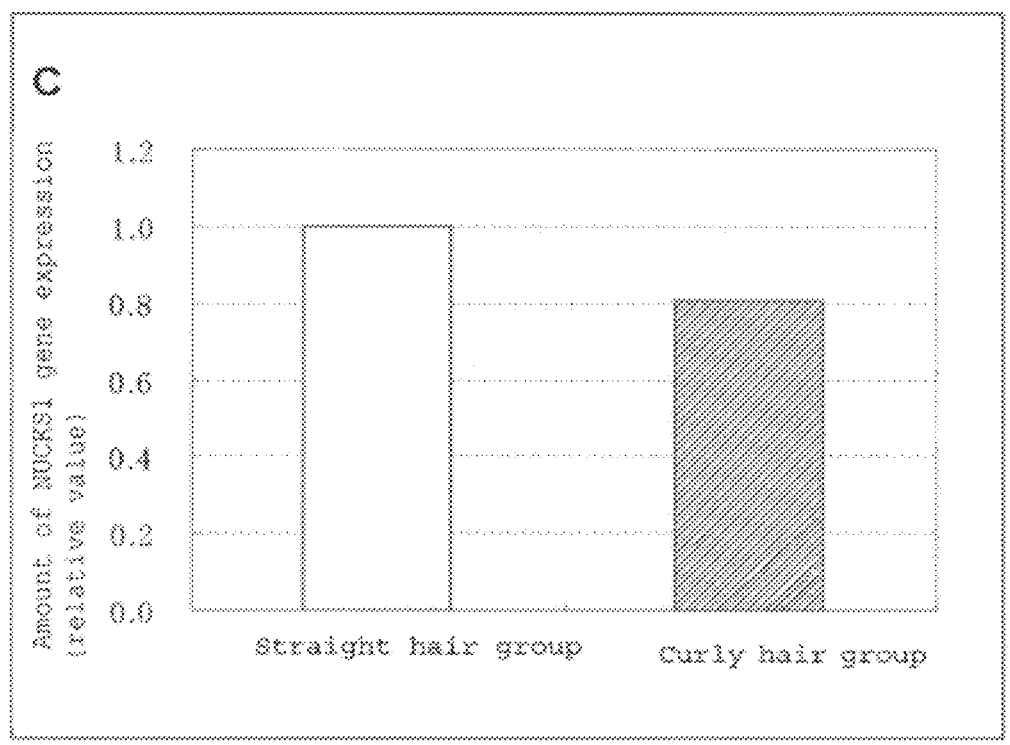

SEQUENCE LISTING

<160> NUMBER OF SEQ ID NOS: 50

<210> SEQ ID NO 1
<211> LENGTH: 3926
<212> TYPE: DNA
<213> ORGANISM: Homo sapiens

<400> SEQUENCE: 1

```
tgcctgcatg cctctctgcc tccaatagtg actccctaag ctgggactcc tcaggcttac      60
tctgagggac accaggaagc tcaacctctt tcccacagag gagaatctct gagatccaaa     120
aaacccagcc ttcccccctc ctcatcttgg tcttgcttcc ctctccctcc agcctgttgc     180
tgctgctcct ctgggtgcca agatgtgtcc tcaggtgtct tggtcagctg atgatggaca     240
```

```
cgcagcacag gaggctaaga acagagctct gtggggcgag gtgtggggag aggggcctgc      300
tctcacctag acccaaaaca ctgaggtctc ctactggtga tggtgtcaga tcccaggcct      360
ggggagccct ttagtggggt gggacctcag gcagacccccc aaaccaaagg gagccagatg     420
cccaagttca agtcattagt gatatgtggc agggctgaca gagaaataat cctggaggtc      480
tccaaagctg ctgggaatgg aatggcgatg aaaagcgcag gagtgggcag ggtgtggtgg      540
gtgatggtgg cctcactcag agtggaccaa ggccccagct ccttgcccaa aaccaaagcc      600
cttgggcccg aagtttttag cataacatcc tgcagagaga ggagagagat aagggcatgt      660
tcttcctcca cccccagcca caccaccac cctcctgctg aagatccccc actcctagtg       720
cccagccaga ctgctaggga aggaaggtcc actggtaccc cctcacctcc acagcacccc      780
aatctcaata gtaaaatagc gaagaggctc ttggttgtac cctgtaccca ttgcccctgc      840
caccaaaatt atagaagcat catctgctgt aagaacattg gactgggagt taggaagcca      900
gggtctagcc ctatgcctgc ctcaatttgc cagatgatgc tggccaagtt gctttccccc      960
tctggtcttg tttcctcatc tgtacaatga aggaatcata ctagatgttc agatcttgga     1020
tcccaaggcc aggaattagt ttacattcag caaaggcaaa actacttagc cccctaccc      1080 ccttgggcct cctgaccctc aattagaagt gaaaacaccc acctttgcag taaatctcgc     1140
catccttgtc tgccagggtg gttgactcaa ggcctttgcc acacttggca catcgaaagc     1200 aggcctatg ccaggactag gcagggaagg aaatagttaa tggctgccac cagtgatgag      1260
ggtaccctcc accccaggcc cactcccttt gacataacca tggtataagg gctcaagcca     1320
cttctgaagt ctactcagct ggtgctgctg ggaggacatg gcctatggtg caaggcagta     1380
gagggagaag gccagggacc acacgccacc tcgcaccatc ttccatgcta tgttgcaatg     1440
gcctgatgat tagggtcacc agctatacca caaaaggcag gtgaggggt gggtttaaca      1500 ccaaagtagc tgttaccccca ctggctgggc cagatgagcc ttctccagac ccatcttgcc    1560
agtagatcag tggtgtgagc cagggctttg cactcctcct ggtactgtca cttagtactt     1620
gaacagccct caccagaaag acctctctgc cctgtgttgc cttggggcct ctcatagaga     1680
cccaaagggt cttctgtggc ccctggagaa actactcctt aggactttcc ctgctgagtt     1740
taatgcattt catagactta ttctccttcc aaagtgatac tagacaacat tgactctggc     1800
ttcctctgtg ccaggccctg tgccaggcac tttacactgg tgaagtcagt tagtgttcac     1860
agctacccag tgagggacat actgccaccc tcccctccaa tagctgatag cctttgggca     1920
aaggaggcac ctaattctag aacttcagag gctgggctgg tccaggagaa tccaattaca     1980
aataccttct ctgtggccag gcatcatatg tttaaatatc tagtcctcac atgcattctg     2040
taacacaggg caaacagctg tcccagaaaa aaagtgaggc ccgagtttgt acacagtgat     2100
gggacgttgc acagacagac ttctccgcag ccagttccca tcaacagctg gcaggctaa      2160 gaggctgatg tgtagacagc tctgcttaac ccaggaaaag caagaggcag gcagcagtca     2220
gataagacaa aacaaggcct tttaagggca aagcactcc cagtgcccag gctggtggat      2280
gagaaaggaa attcatcccc tcagatttcc tggttgccta accttgcaca ttggcttctc     2340
ctccagagag ctgaaatggg gggacctggg tctaggtcag tgctggtgca acctcaatag     2400
tcacccagcc tttgctgcct cctctgtaaa gcaggggctg ctaccccaag ctctctaggc     2460
tggagaaaaa ctgaatcaca cctagaccaa cacctctcct catatttcct agccacctcc     2520
ctgccaaaat aagctgaatc cctttgctca ttcataagca cccaaaagta ctcccagctc     2580
aacatttctt gagcgaggca atagaaaggt ggggcttctc cctacctttt ccacttgaat     2640
```

```
gcaaaattct cttatcctac tccttagtac agccctaact ttaccttata gcctgcctaa    2700
gtaatggaaa tagtgattct tagctattct taataatttt ctattctcat aatgagatag    2760
aacaaaaaac ccaacttaat aataatatta atgtctcctg ttttcatatc ctttagtcaa    2820
tggcaaggat cttcattgtg acctcaaaat aatccctgaa ataaacaac  aataataata    2880 acaatagcaa aactgtactg aggacatacc aggcactaca ttgcacatta tacatgtact    2940
atctcattta atcattaaaa ctgccttgtt gttgggtgtg gtagctcaca cctgtaatcc    3000
cagcactttt ggaggccgag gtgggtggat cgtgaggtcc aggctggttc aagaccagcc    3060
tggccaacat ggtcaaaccc catcttcact aaaaatacaa aaattagctg ggtgtggtgg    3120
cgcgtgcctg tagtcccatc cacttgggag gctgaggcag gagaatcact tgaacccgga    3180
aggcagagtg ctaagatcgc gccactgtac tccagcctag gtgacaagtg tgaaattctg    3240
ccaaaagaaa acaaaaacaa aaacaaacaa acaaaaaaaa actgccttat tgtcagggg     3300 ccattacttg gtccactttg catttcctcc accatccagg cccactttag agctgaagaa    3360
ctgaggctta ggaaggctaa attttcccaa gttcgctcag ccaataaatg gcaaaactag    3420
gattcaaagc aggctgtcta gagtccaagc tcttaatcac cgtgctagga tcccctccca    3480
ttttgcagcc ttggaaatgg gtttgaagag gctaaatggc ccaaagtagc attaacagta    3540
gtaacagcag taagagcaag ggcttcggag tcagacaaac ctgggcttga gtctggctta    3600 gcccttcct agctagcgga tctgggcaaa ttatgtaatc ctcctgactc ccagtttctt     3660
catctgtaca acagggatac taatccccat ctctgtccaa ccatgactgt gagagtagag    3720
attctaacac tggcctaagt gttaattgtt taacatttct tgatcaattc ccctatccca    3780
ttcctcaagg tcaaaaagcc ttgaaagcca aaacctgaat ccagaagaga tgaagatggg    3840
ctccaggccc agacattcca taaccttgtt gtgtgatctt ggccaagtca cttttctatc    3900
tcaggcctca cgtgatgctc cagaat                                         3926

<210> SEQ ID NO 2
<211> LENGTH: 76945
<212> TYPE: DNA
<213> ORGANISM: Homo sapiens

<400> SEQUENCE: 2
aaagtaactt gttattgaga tagatatctc ctggtgatat agtaaatttc taaagatgct      60
gtcagactga tgccagaaat cattatttca tttataaatt atattatttt aaggaaatgt     120
tgcattatta ttagtagctt ttcaatttaa aagcattttc acacagatag tatttgtttt     180
caagaaagta aaaacaaaa  aaaaagccgg gtgcggtggc tcacgcctgt aatcccagca    240
ctttgggagg ccaaggcagg cggatcacaa ggtcaggaga tcgagaccgt cgtggctaac    300
acagtgaaac cccgtctcta ctaaaaatac aaaaaattag ctagatgtgg tggtgggcac    360
ctgtagtccc agctactcgg gaggctgagg cagaagaatg gcgtgaacct gggaggtgga    420
gcttgcagtg agccgagatc accgccactg cactccagcc tgggtgacag agggagactc    480
tgtctcaaaa aaaaaaaaaa aagttaaaa  aaaaaaaatt aagcattatg actaaagcgg    540
aaacatttcc tacttgaaaa atgaaattgt agggtcatga ggtttgtgca tgttaagttt    600
taatgaaacc taggcatcca tcagtagatg aatggataaa gaaatgtgg  tatatataca    660 cacaatggaa aattattcag ttgtaaaaaa ggaggaaatt caaagccagg catgatgatg    720
catgcctgta gtcccagcag ctactctgga agctgaggcg agaggatctc ttgagaccag    780
```

```
gagttaaagt ctagcctagg caacatagcg agaccttgtc acttaaaaaa aggtggggtg    840
gttgggggat ggggaagaaa ttctgtcatt tgcaacaaca tggataaacc tggaggacat    900
tatgttaagt gaaataagcc aggcacagaa agacaaatac tgcatgatct cacttataca    960
tagaatctaa tgaagtcaaa ctcagagcag cagaaagtag aatggtggtt accagaggct   1020
gggcaggggg gtaggtgagt aggagtggtt gaggagatgt tagtcaaagg atacaaaatt   1080
tcagttagga ggaataagtt caagagatat attgtaccat atggtgacta tagttaataa   1140
caatgtatca tatacttgaa actcactaag agaatagttt ttatttattt atttgtattt   1200
ttgagacgga gtttcactct tgttgcccag gctggagtgc aatggcggga tcttggctca   1260
ctgcaacctc cacctctcag gttcaagcga ttctcctgcc tcagcctccc aagtagctgg   1320
gattacaggc atgtgtcacc acgcccggct aattttgtat ttttagtaga cagggtttt    1380 ctccttgttg gtcaggctgg tctcgaactc ccagcctcag gcgatcttcc cacctcggcc   1440
tcccaaagtg ctgggattat aggtgtgagc catcgcacgc agctgagaat agattttaag   1500
tgttctcacc acacacacag aaatatgtga ggtaaagtca ggtgcagtgg ctcacacctg   1560
ttaatcccag cactttggga ggccaaggca ggtagatcat ctgaggtcag gagttcaaga   1620
ccaatctgac caacatgatg aaaccccatc tctactaaat acaaaaaatt agccgagcgt   1680
ggtggcacat gcctgtaatc ccagctagtt gggaggctga agtaggagaa taacttgaac   1740
ccagaaggca gagattgcag tgagccaaga ttgcaccatt gcactccagc ctgggcaaca   1800
agagcgaaac tccctctggg aaaaaatata tatgtaaggt aatacatacg ttaattagct   1860
tgatttagcc atcccacggc aaatacatat ttcataacat catgttatac atcataaatg   1920
catataattt tgttgatta aaaaatgaat aaaataaatt gaaaaaataa aaattaaata    1980 tttttttaaag ttttaataca atctgctaaa ttatcctcca aaattatttt acaattata    2040 ccaacttatt tccttgtttg gaaactcagg aaaactccac agaaatcaga gcctcgagga   2100
tttacatttg aggaagtgca cttttttttt tttttttttt ttgaggcaga gtcttgctct   2160
gtcatccagg ctgaagtgca gtggctcact gcaacctccg caggttcaag tgattctcct   2220
gcctcagcct cccaagtagg taggattata taggcacgca ccgccatgca tggctaattt   2280
tttttttctt ttttctttt agtagaaaca gggtttcacc acgttggcca ggctggtctt   2340
gaacttctga cctcaagtga tcttcctgtc ttggcctccc taaatgctgg gattacaggc   2400
atgagccact gcgcctggcc aggaagtgca tattttaag gagcctattt tttgtaggaa    2460
ctaccaaaag actgcatgaa caagcctcta atctgttaat tccccacagt aatcatattt   2520
caccttcttt ccaggtccat ggacagaaag ctgcttggga ggacccagtg gaatgggtcc   2580
gggacacact tccctggcca tcagcccaac aagaccaatc aaagctgtac cacctgcccc   2640
cacccaccgt gggccctcac agcattgcct cacctcccga ggataggaca gtcaaagaca   2700
gcaccccaag ttctctggac tcagatcctc tggtgagtag aagccattct agagtaaaaa   2760
taagactatt atagaactga attattgacc agcagggtgg ctcacacctg taatcccagc   2820
actttgagag gctgaggtgg gaggattgtt tgagttcaaa accagcctgg gcaacataat   2880
gagaccctgt ctgtatttca aaaagaaaa aataagtta aaaaaaaacc ctgaattctt     2940
cacacttttc atacatacac tgatgggggc ctggagagta aagagtgagc actagcaaag   3000
ccaggaccag gctaaggcca gtgaggagct ctaaatatca gaatctgggg ttataaagat   3060
catatgcctg agacctggct taagctaaat aatagtgcat cccagcaaga tgtattctag   3120
caaagaccca agtctcaggt agatctcatg atgtaggaat atcaaccaaa gaagtagagc   3180
```

```
agtagggcac actagcactc tctctacttc tgcttctcct ctgacgctat cctgaagact    3240
acttcagcta aatgagttca tggaactcct gtagaaagca ggctaagcca agtacaaact    3300
gggggaatat ctgcaatgcc tgtagccaga aaaagactgg tatctaaaat atctaaaatt    3360
tccaaacaga agaatggata aaagatataa acagctgggc acagtggctc acacctgtaa    3420
ttccagcagt ttgggaggct gagacaggag gaggatggct tgaggccagg agtgcaagac    3480
caacctgggc aacatactga gaccccatct ctagaaaaac aaaaaaatta gctgggtgtg    3540
atggcacatg cctacagtca caactactca ggaggctgag gtgggagatt gcttgagcct    3600
gggaagttga ggctacagtg agccgtgatt acaccactgc actccagccc aggtgacaaa    3660
gcaagacccc atctcttagg agaaagatat gaaggccagg cgtggtggct cacacctgta    3720
atccaagcac tttgagaggc caaggcgggc ggatcatgag gtcaagagat tgagaccatc    3780
ctggccaaca tggtgaaacc ccgtctctac taaaaataca aaaaattagc caggcgtggt    3840
ggcaggcacc tgtagtccca gctacttggg aggctgagga aggagaatca cttggacccg    3900
ggaggtggag cttgcagtga gccgagatca cgccactgca cactccagcc tggcgacaga    3960
gcgagactcc ctctcaaaaa aaaaaaaaaa agatatgagt agacatttgg ctagagcaaa    4020
tgcaaatggc caataaaaac ataaaaggat cctctgcctc tccaataatt gaggaaatgc    4080
aaattaaaac aagagatacc acttcacatt ggcaaaagta gtatgtatgg aagcatagac    4140
ttttatactc cgctggtggg agtggttgtt gataaaacca ttttggaaga taatttggca    4200
gattatatta aaacttaaca tgcgcaaatc ctgtgacctt acaattctat ctttcccata    4260
ggaaattctt ccaataatca taatacattt ttattaaaat tttgactttg ttaaaaacag    4320
atgctatctg tataaaaatg cttttaaatt ggaagcttat taataatcac gtagacagaa    4380
gagaattgtg gagagcagat tcaacagaaa atgcaccagg cttacttagc tgaaatggaa    4440
gtaccaatct tgacgtgtcc agagaaaaaa gtaagtaaag agaaggaagt gagtacatag    4500
aggtatttag acttgacatg aagcaacacg gttggtaagc tggagagaaa taggttcata    4560
ataatacagt gtctagctgc tggtttatac tctattggaa ggggaaattg ttattttata    4620
gcatttctca cattcctccc agtattcgtt ggtatgttca ggccttccct cctctcctgg    4680
agtgcaagca ccctgcaggc agaagtggtc tcattctttt ttggtattcc tccataaatg    4740
gtaccttgtc ccttgtatag caggcatact cccaagtaat tgttgtacat acacatgtgt    4800
cacagttatc attgaagaaa tcctcattgc cttttcacaa accactctaa actctgagct    4860
cttcatcact gagaaaccaa ggatcagacc catgatctag attttttttt tttttttttt    4920
ggagacagag tcttgctctt tcatccaggc tggaatgcag tgatgatatc aaagctcact    4980
gctgcctcaa actcctaggc tcataggctc gagtcatcct cccacttggg ctttggcatc    5040
ctgagtagct gggactgtag ttgtgtgcca ccacgcctgg ccagtttttt attgttttat    5100
ttttattttt tggtagagtc agggtctctc tttgttttca aagctgattg caaactcctg    5160
gcttcaagct atccttccac cttggcctcc caaagtgttg ggattttgtt gttgttgttt    5220
cccttctgtg ggcaggaccc agagtcccaa ctctcataaa tccatctttt tgccccccctt    5280
tagatggcca tgctgctgaa acttcaagaa gctgccaact acattgagtc tccagatcga    5340
gaaaccatcc tggaccccaa ccttcaggca acactttaag ggttcggcaa tcactgtcac    5400
ccccggacag cagaacgctg gcatcagcta tcttagctcc tcctctcccc tctcctcttt    5460
cagagcactg gctctccagc cccaggagga gaacaggagg gaggaggaga tgaaagagga    5520
```

```
gggacaggtt cttggtgctg tacctttgag aacttcctag gaaggaatgg tggggtggcg      5580
tttgggaact tgtgccccct aaacacattt actggcctcc tctaatgact ttggggaaaa      5640
gatgattctg ggtctttccc ttgacttctt gtttcaatta caaactcctg ggctttctgg      5700
ggaggggttc agaaaacatc aaaacactgc agcagttcct aaatgattct cacaagcaac      5760
cctgagagag acagtcttgt gagggagatc tgggggaggc aggaagctcc tcagattttc      5820
tcacagaccc ttcccaattc catcaccact gccaacaact cctcccccag agatctggct      5880
ggagcccaga aaagaagca tgtggtttaa aaaatgttta aatcaatctg taaaaggtaa       5940
aaatgaaaaa caaaaacaag caaacaaaca aaaacaatg gaaagatga agctggagag        6000 agaggaacca gttgccaagg tagagagctg cccgctcctg ccctctggat gacataggggg    6060 acatcaacaa gacggctgcc aacctgagaa gtcaccaaac cacaaaaata accttacagc     6120
cttcagggaa agactaccag ctctgtcttt ctaccctcta atttaacaat gcataagagt     6180
caataaaccc tactttttta ttttggttt ttatttgtt ttcatttttt tctcccattt        6240
gcctatttat tttttgttt ccctttttt tttcttttc cgttttcca tttcctcaca         6300 tgtccacgag atgcttgggt tgcttttcca ggggctagtt tggcttttcc aagtgggttt     6360
tctttggaga atctgatgcc atgcaattgg catgacacct gccatgccac tatctttggc     6420
atccatgggg cttatatgag acatgaagca ttggctcaga agtagaggga gaagaggaac    6480
ccagttccct tgacttccct tttgagagca cacgttctgc tgggtagctc aattgccagc    6540
ctctgtcatg agaaggtata gccccatctt gatagaagag ttactccgag ctttatcatg    6600
gaccagagga aaaccagaaa actgaaaaca ttcctctgtc ttgtggccag tttggccttt    6660
cactgcacta ttctgatggt gcctgactga atccaaatat cctagctggc tcttactatt    6720
tttcacaaat gagtattcac atataagaga tgaacatcca tgtgagatca tcccaatcag   6780
aatataagac tcaaggagtt tgacttggtg gccaatacct gccttccaaa gagatcctac   6840 cttttgcagat ttgctccttt cccattgcct tgaaggtctg gcaatccctg ttctttcatt   6900
tgacaagtac ttactgagta ctcactatat acaaatcatt aggttaaaac agacacacac    6960
acacacacac acacacacac acacacacac acacacacaa gacctgggcc cttaagttta    7020
cagtccagca ggaaatgtta acctccattc agctacgccc ccttgttatc tagaccttcg    7080
ggatcatcta agaaatgtag ctgaaaccca aggagccagc tagaaagaag cttttgatta    7140
gatgtacaat acattggggg cagaagatct gggatcaatt aagatggagc ctgaaggact    7200
atggaatctt gcttgtcagg aatgggcaag tctacttcct gccatttctg aaagccccgc    7260
gggaccagct tctaggctga gctgcctagt aggctgaagc ttcaggactc tgcaggtcaa    7320
ggatatgtga tgagcaccgg cctaagtgtt tgctcttcag attcctaagt agcacaagac    7380
tttatcagaa tctataggca taccaacctg gatcactctt ccacccaacc gaggagtaga    7440
tgcatctgaa tcttcatatc ggtatattaa gtccaaaaga tggtccgggc tgcccctcac    7500
aaaagcttct gcatccacgt ggtaagctcc catggatgac agggttctgt atgatggaga    7560
ctattattgc tattgctgct aattccatga gctgtgaaga tccctaacca actcagctgt    7620
aacatatgca attctgtggt gggaagaggc tgtgtgtcca aggatggtgc tgaaatcact    7680
gccttaaggt ctctgctgtg cagaatgagg aggcccccga gctggctgtt ctaacttaga    7740
aggaagagaa gactggatgg gcctgcttgg gatctaggcc tcttctaaac cctatcctaa    7800
gctccagttc catggcaagg ctcagacttt taatgccatc ttaatctgat ggttgagcgc    7860
ttcactctat tttctggtgc tgcccagcca gtgccttctg ccatggatgt tactggctac    7920
```

```
ttgagaaaaa ggagagggga gaacccttc tttcattcca actgcctccg accccaaagg    7980
gattcttggc tctctggtaa ccatggatac caccatgaat tttatttgga tcctcagcag    8040
gttgattctg gaggcctcat gctatgactt tttatttctc ttcctgggat ccaccaccct    8100
ctactctcag ctgactgctg catttaggcc aggtctccaa ttgctttcct ccagaaagtg    8160
tgttcccgtc tagtgaggta gtattgaagc ctcggctttc cctctggagc ctgggaccct    8220
gtttacagtt gcacatctgg gcccctcact gtggggattg atcattctca tgaaggaatc    8280
acagttatat ggcaactgca gaaggctgag cctcctcatg gtgctataac cccttgggac    8340
actcatccag acttctctga agcagaaaac ctgagctccc cactcactgc cctagaattt    8400
atggcaagga gcaaatctac agcattctct cccacctacg tcctgcttct tggttgagac    8460
tactgggatc cttcagaaaa gaaacactgg gtcccatagc taaattctca accgccaggc    8520
accttcagaa gaatccagcc taatactgga atttgtgcta ttatcttcct ctccagcccc    8580
ccaactccat ccctcaccac agttgtctag gaaatgacat gaattcaata tctaatgtca    8640
accaatgggg agagccacaa ctccaggaga ggttcctgag ctgagtccct taatttctgg    8700
atgaagaaga ccaacaagtt ttgtccaatg tatttgtttc tcagaccttg cctaggcact    8760
aaaaataaaa tactaggtca ttggaggcta atgtgggacc tgatgtctgc gtgtgtgtgt    8820
gtgtgtgtgt gtgtgtgtgt ctccctctct cacacacaca agagcagttt gctgttgctg    8880
tttcctacct tctgaggctt caaagtattt tttaaaatct atgctttgtg gcagctctac    8940
ggtgcttatc tctgtctttg tgtcaatcct aagtaccca tgtcttttc atgtctaacc     9000
attgggaagg tagaggctgg cagggaagac aaatctgcta caagtccatg ggaagaccct    9060
acaatgaaat gttcattggt tggtatactg ttttagtctt gaattgccaa ctttccaact    9120
gatctatcca tattccttaa gtactaaaga caaaatagag ggcttctttt tctctcttaa    9180
tgtcttgcct tctggttttc ctggtttgca agactaagtg tacctaatct caccatctct    9240
tcacttctag ctctctgaaa caagggtcac actactcaga gggataaccc cttacagtgg    9300
tctgaggagt aactatttcc taaagtattc taaaagagta ggaagagaga atggtagcc     9360
tgctgcttct cacagacacc tcacatcctc acttgggatg gcatccacat agaaaccctg    9420
catttaggta aaatttgcct gactgaaggg gactcagtcc tccaaatcaa ggtcaagaag    9480
atatctgcat gagaccttaa gaactcttta ttgccattat ttggagaggg cggggaatt     9540
gtcctaatca cacatttaac acagggaata agtgctgaag tgacccagat caccaagcgc    9600
agttcctcat catactttat ttttgctttc cttattcctt ggcactgact aagctaaagt    9660
taagaagccg acttcataag ccaaccctg tgatgggatg gaaaaatggg cttttgcaga    9720
gggtttatta atagagatgg atatactact cacaagttct ggctcatggc tccactgaga    9780
aggccatagt aataaaatga tcttatgaac actgttcccc aaaggccaaa gcctgaagat    9840
attgcccctt ataatccaat cagccttata ttttaataag tcctgaatca acctgactac    9900
ggatatatgg ggccaccagg gtgcatgggt gcatgtctgc tcagcctagc cctggaagtg    9960
agcactgccg gccacagatc ctgggaaagg tggtagtaac ccagaagatg tagccttgaa   10020
gggaggatac ctatcaaaat gccaaagctg cagggacacg aagacggttg aaaattcaac   10080
ctgtgtatac tagatccttc cagtttgatg gtttggtcat tcttcttcat gattatacca   10140
tggagaattt tctgtgacaa gggtggtcat ggaagtaagt gagtgatccc ctggtttctc   10200
attccttaaa gcagtggttc gcaaagtatg gcacaagacc agcagcatca gcagcctttg   10260
```

```
ggaacttgtt agaaacgaaa attctcaatc ccatcccaga tctgctgaat cagaaactct   10320
aatgagagga cccggcaatc cacgttttaa taagccctcc tggtgattct gatgcacact   10380
aaattcaact gttttaaagg gaaagccctt tatagtattg gagttcccac actgagaggc   10440 tttgggccc aaaataagaa ggttctaggt tgtcattcag actttaacat taatttcaaa   10500
gtcacctttc tcatgcttcc ttgtgtttct gttttttccat ttatgatttt aacaaagaaa   10560
ggtatgtgtg cttttgggtg gaagttagga gaatgtttgt gtctttccta gttgaataca   10620
accttcagag aaaaacctta tgccttggaa attactacct ggcacacaaa ggggcttcaa   10680
caaggaaaag cagttggagg tctcttccag attgctcttc tgccgaatta tttgtatcta   10740
ttccgagctg attatgtaat aggatggaaa aagtaaaaaa aaaaaaaaaa atctaatttg   10800
tatttccatg acaacgtgtt ctcccagcaa catccctctc ctttatttga gttataaagg   10860
gcactgctgg gcctgagaac caggccagaa cctccttctg tatggcagct aacagtgtag   10920
ggctccagta tcccaggaag gccccttatc cacactccac tcagctcata ggagagtctt   10980
gcataatgaa gacacagacc tgggcacttc agtccttgtg ctcctcctct cttttcccca   11040
cagcaggacc tggatacaga agtactcagc caaggtgaca gaataaaatc cttttttgt    11100 tgttttctgt ttgtttgttt gttttggaga aggagtctcg ctttgtcacc caggctggtg   11160
tgcagtggca cgatctcggc tcactgcaac ctccgcctcc caggttcaag cgattctcct   11220
gtctcagcct cctgagtagc tgggattaca acgtgcgcc atcacgccca gctaattttt   11280
gtatttttag tagatacgga gttttgcctt gttggccagg ctgtgctgga gctcctgacc   11340
tcaggtgatt cacctgccac agcctcccaa agtgctggga ttacaggcgt gagccacagc   11400
accctgccaa ataagatcct ttttaaaaaa tatctgaaaa aagcttcata tctttacaaa   11460
ctcataaaat agctgattgg gccatggagg agatgaggct gtttagaact ggttttgttt   11520
caagtttgtc aattttccct gtatgagaac ttgggtaaag cacaaagaaa catacagtgc   11580
tagtaacagg tctcctgcgc cctggaacta agtgttgga ggaaggacta aaccccgggg    11640
gaggtgagta taaataatt ccactaagat cacctcctca gtccccagaa ggctgatggt    11700
ggatcctctg gccatctcct gtggggtctt actgctcctc tgccatttct ctatgcctga   11760
agacacgaag atgatatcaa ggcagagcta ccatatcgca gccagtctct aggctactgc   11820
tgtgcagtgg ctcccacttt ctaatgcttt tttgttttg cttttctaa caaaacaatc     11880 ttttttcaaa atgaattcca acccctgcta gcttccttcc ccgcctccat actgttttag   11940
gcagcaccgt ttatgtgaca gagtccgtgt ttctcaaatg catggtgttc ctcaggtgga   12000
gagtgggcag aagttttgc aacactttt ttttaagtta ttgggtgcaa atcccaaac     12060 caggatatgt gtatgtctgt gtgtttatgt tttttatttg accctcccct ctttcaacct   12120
accccctttt atatctaatg tagaaaaagc gaaattgaat ctggaaagca aactgttgta   12180
tatagttgcg gtaacaatca tgaagagaga gccgggctgt cccctcagta attcatttta   12240
aataacaaat tatttaaaaa taaaattcat gccagagcca gctgaagagg ccttccttca   12300
tcaccactga ggccaccccc aatctgggcc ctctgtccat ctggcatgtc tcctcccagc   12360
aagattcatc tgttcaatgc catttgcgtt tcaataaagt tatctcctgt actgtccact   12420
ggttctctag ctccctctct gcctggtttc tgtctccatt tatcttgtgg cccattcctt   12480
gattggcaag gccagactgc ttgtggtcat ttgcctaacc cagaagtaac ctgaaaccct   12540
aagctagagt ctcctgactc ccatggttgg gggtgggagg aacccctgct cgcacattat   12600
ggacatagaa tccttcaccg gatctcaaaa catccagccc aaacatcaag gctccggagt   12660
```

```
cctccatctg ggttgctgca gtgtttgaaa acataccacc ctcttgactt tgctaaattt   12720
tcttcttggg gtaaaagtga actgacctat tagaagctgt tgtaatcaag ttcaacttct   12780
tttggccact tcaagaaagt aaataggctt actattcccc attgcaaaat tgaagggtcc   12840
aagaagcaat cttttcccta tgaaattgta gtaacataac tcatctctgc cctcttaaca   12900
tgggaggtga caagtgtgtt gagaactctc ttcaagccag ttgcagtggg tgtacctgta   12960
gttctagcta ctctggatgc tgaggtggga ggatcacctg tccagcctgg gcaacatagc   13020 aagaccccc caactcaaaa ataaataatt gagaaagctt tcttttgaag taatcttctg   13080
atgagatgac ttaatccctg attgttacca gtccagcatc cacagtcttg gaagtgacct   13140
aggatttggt aactcgtttc ctttgccatg tgagaatgaa ctcacttgat aagggttcct   13200
gggaaccatt ttgaaggcac ataacctgaa cagctcacta aaaataacct gtttctgttt   13260
gctctagaac ctcccattcc aacaacattc tatcctttct gccactacat gcttgccact   13320
ctgccctgca ttttttttaa tttttatttt tttttataga cagagtctgt atatcttgcc   13380
cagactggaa tgcagtagct attcataggt gtgatgacag cacactacag cctggaactc   13440
ctgggctcaa gtgatcctcc tgccttggct tacatcttgc ttttctcttct ttttctgaga   13500 caagatgtca ctctgtcgcc caggctggag tgcaatggcg caatcactgc tcactgcagc   13560
ctcctcctcc tgggctcaag tgatcttccc acctccacct cccgaacagc cgggactaca   13620
gggcgtacgc caccacgcct gggcaatttt tgtatttttt tgtagagacg aagtctcgct   13680
atgttgccca ggctgttctc gaaatcctgg gctcaagcga tcctcctgcc tcggcctccc   13740
aaagtgctag gattagaggc gtgagccact gcgcctcgcc caccctgca tttttaacac   13800 ctcactggag cgctcatcct ctccacctgc tccgctattc aggagcggct ctgcaccgta   13860
ggccatttcc cacgaccagc tgctgacaac catatcatca aactgctctt gttctcgcac   13920
cccttaaatg tccagccata atttctcagg gaaaaaaatt tatacatttt caacaaatag   13980
gattcattct caaatagtca catacaacac tcactctgga agaaactccc tttcacatgc   14040
cggtgtctcc cctgcccagc cacttcccag ctttgaggtt gggctcatct aggctggaaa   14100
accaagggac tgggccgtgg ttttcccact tccacttccc agtttgcttt agtttatttt   14160 ccccctctt tggattcctg aggctaagat gaagagagtc acttgagcca acttttttc   14220 agtgtttggg gggaaaagaa tgtggtttaa aataggggct atttgtgacc cagacctctc   14280
tccttaaagc cctctacatc tattcccatc ccgcctcctc tctcctaaca cctgaaagat   14340
gcatgaatat aaagtcatat atcatgaact ttattccaaa tgagattgct aacttactgt   14400
gcaactttag gaaagcccct taacctgtct ggggctcagt tttcacacaa atccagagat   14460
ccttgcagag aaaggtgcag ttctcgttca ggcagcagga ggcgctgtct ctggaggctt   14520
agattcattc cccgccctcc gcccgctccc gcccgcctct ggtgcgcagg cgcggcttcg   14580
cggattggcc gcgcgcgggg gccgtcattc ggtggcgggt cccggccgcg gggctggcgg   14640
gctgagggga gaaaagatgg cggcggcggc ggcagctggt gcggcctccg ggctgccggg   14700
tccagtggca caaggattaa aggaagcgtt agtggatacg ctcaccggga tcctatcccc   14760
agtacaggag gtgcgggcgg ctgctgaaga acagattaag gtgctggagg tgacggaggg   14820
tgagtgaggc gggaccgtca cgaggatggc tcagccgcac aatccgctga ccgcagctcc   14880
gtaccggctg gggacatggg gagcctgagc cagttggaga tgtgggcgcc gagaagtgga   14940
gcaggaagcg agagattgat gtcgctggtg gttgtgaaag tccgagagag gagaggcgcg   15000
```

-continued

```
cctgaaggat agggtcgggg gaggtggagc ctgggagtgg gggagggagg gtggagactt    15060
gaaaagatag atggagccta gaatctgcag gggacggaga tggagctaga cttggtgctg    15120
ttggaggaag tagcgcggtc ggggaaatat tttttgagtc caggaccaaa gtctttcgct    15180
gttctcttca ccagctggat tgtactggga taagagtagg gggagctatt agtaggagtg    15240
gtgaagggta gggcctcgaa aaggcggcta tcaaagctta atagatgtca tcaaacaagt    15300
ttctgcctct gagttataaa cctagctagt tgtttgtact cttcgtgttt tcccagaaat    15360
taaatgcata tgcgattgct tcactgtcct gaccatactt aacgtttatt ttaaaaataa    15420
tttgccctta ttaaatacct ttgtgcattt ctgtttggag gaactgatca tcctttgttt    15480
ttgattcttt gtctccgtcc tctattgtgt gctttaaagt gatggagaag aaaataaacc    15540
attggttcga gattttctat caatttcctg ccgcgtgagc ctttcaccgg gtccagtgta    15600
gctaccacaa agaacaattt aatccagaaa caggaggaga aatcttcttg gtctttgtgt    15660
aagaaatata tctggtcaga gcttcactgg aactccaaat cctcagaatc tcccaactca    15720
ggaatatttc caccaccact taaatacttc atcagagata tgggaaattg tcccatcaca    15780
cacccatcat attcaaaacc ttcagttagc tctcctactg gacgtatttc tattgaaaag    15840
aatttagaac aaatctctct taaatttagt ttacattctt tcacagtatg aaagagctgt    15900
tgaaaacaaa ttttcttctg ttggaaatat gttaagattt gggatctaac aggctaagga    15960
ccattttgaa ggcccacttg taattgtcat tgttttataa aatatcagat ctatacagga    16020
gaaaccactg gttaggagaa agctgtttga gaaccatgta taaactaatc taaaggaatt    16080
tttagcggct tctaaataaa attcgtttat gcacattaat gtctgtcccc cttgagtatg    16140
aggaaggaag agtgacaaag caaaggaacc tcatcacatt caagttgtca cctgaataaa    16200
acttgagagt ctggtgcaaa ttcatcttaa ctaaaccttc cctgagtggt acccagtgct    16260
cctggtgctc caaatgcatg tctggcacct ttgtatgaaa ggtggacctt gacttgtatt    16320
taaactgtct tacaacaact ccacttttgc tctgatcttt tcaactttag ccaaatgcca    16380
tggtctcatc tgggcaaagt caattataaa gttctcgagg tctttttga aactctgatt    16440
cctcacttta ttcatctttt ttttcttgag actgggtctc gctctatcgt gtagactttg    16500
gagcagtgat gccatcatgg ctcactgcag cctcaaactt ttggactcaa gcgatcctcc    16560
cacctaggcc tcccaaagtg ctgggattac aggcctcagc caccacacct ggcatctttt    16620
tgagccttta agtgaaaaat taaatttcag aagtacagaa ttttgatcta agtcactgat    16680
gagaaataga tcgactgccc cccgaccccc ataacttact ggtaatgtgc tgttgggcag    16740
actatgagaa tgaaaagtat ggaaaggcat cgatgcagtg acctgatatt ggtgatctag    16800
taatagagca tatgactcag gttttggatt tggttagagg gttggatcag tctctggagt    16860
ttagtgcaat gcttcggacc ctttggaggc tgcttgtgtc ttttaagtag tctggctcct    16920
taatgtctat caaaaaaact atagagattt accccccttct gtacctgttt taaggtggag    16980
aatggcggtc cattccctca gatgcggtct gctttcttcc tcttgtggcc tttaacaagt    17040
tatctttgac attgggttca gagtacctcc caccttaaac tctgtctgaa tctctcagat    17100
gttttctgaa catggtgcaa tatagtagct gcttctttac cagcctcaac ccttctttac    17160
atgaaaacat agaacccagc tttccagccg ggatttagcc aactatctgg cctgatgaaa    17220
ctggcaggac atggttcctc ctattagaat gccctacaga gcaagatgag ccattcttgc    17280
aaactacttt ccacttcttt ggtgttgctt cacattttag tgtttttgc ttttgttgtt    17340
gttgttgttg ttgttgttgt tgtttgaga cagagtctca gtctgtcgcc caggctggag    17400
```

```
tgcagtggtg cgatctcggc tcactgcaac ctccgcctcc tgggttcaag caattctcct   17460
gcctcagcct cccgagtagc tgggattaca ggcacctgcc accatgcctg gctaattttt   17520 gtattttag tagagacgag gtttcaccat gttggccagg ttgtctcgaa ctcctgacct    17580
caggtgatcc acccgcctcg gcctcccaaa gtgctgggat tacagccgtg agccactgca   17640
cccagcccac attttagttt taccctggta gaaggaacct tgttttctga ttctaggaaa   17700 cactttttt tttttttgaga ccgagtctca ctctgtggtc cagggccag gctggagtgc    17760 agtggcatga tctcagctca ctgcaacctc cacctcccag gttcaagcaa ttctcgtgcc   17820
tcagcctccc aagtagttgg gattacaggc atgcaccacc atgcctggct aattttttgta  17880 tttttagcag aggcggagtt tagccatgtt gcccaggctg atcttgaact cctgagctca   17940
agcagtctgc ccacctcagc ctcccaaaat gctgagatta caggcatgag ccaaccggcc   18000
aggccggaaa cactcttaaa acttgaagtt aatgagaaat ctgggatttg gtgtctatta   18060
ttatttgtgt tctggtaatc ttttgatcat ttttttggttc catggggccc aggatcaggt   18120
gacaaccaga tctagtcctc cctctgtcct ctcaaataac cacactgtct ttgtgagctg   18180
tttattagtc catcacatag gagactgatc ccacatggtc tttaagatta actggtccgt   18240 tcccttgcc aaaaacattt gttaccttcc ttggctacca ggtgatgatc ccttgtcttg    18300
aagattaaat ggaagaatat ctaatttatg gggaaggac acaggtcaat tgtcaactcc    18360
ctgttaaaag gacaggcaag agaagttgac atgctgtgac caaattgtac tatagatgag   18420
attttaagaa gcagttatct tagaaaataa agattgctgg agcctagagt agtcctgatc   18480
atttagtgta ccagctgata ttttctgata aataaataaa ttgcctataa ttaattatca   18540
cattttccag aatgggcacc tgttctctta agccaaggaa gtgtgtgtat gtgagagatc   18600
catttgattc atgtagcgtg tcaatctgaa aaggataaga taggttactt catcagcctg   18660
gtgtcctgga atgattttt ttttttttt aatttattt tttgagacag agtctcgctc      18720
tgtcacccag gctggagtgc attggcatga tctcggctca ctgcaacatc cgcctcctag   18780
attcaagtga ttctcatgcc taggcctccc aagtagctgg gattacaggc gcgtaccaac   18840
acgccaggct aattttgta ttttagtag agatggagtt tcaccatgtt agccaggctg     18900
gtctcgaact cctgacctca ggtgatccac ccaccttgcc ctcccaaagt gctaggatta   18960
caggcgtgag ccactgcgcc tggctggaat gattttcttg agcccctgtg cttgctattt   19020
ttgctagtca cttggaatct ggaagaaacc cagcaaacct ctctgaatat ttaaagtcta   19080
tttaacaggg ctaattagat aaggagatga tgccagtaac caccttcatc agatagcact   19140
cccatcctga attgagaaga acattgcttg aaagtttgga agttattatg gtgtacagta   19200
ttctgcagat aattgttaac ctttcatttt tctttctttc tttttttaa gatacagagt    19260 tttgctctgt cacccaggct agagtgcagt ggtgtgatca tagcttactg cagcttctaa   19320
ctcctgggct tacgcagtcc tcccaacctc agcctcccaa gtggctgtga ctacaagcac   19380
atgcccatac ttggctgatt tttttagttt ttttctggag atggggtctt gctgtgttga   19440
ccaggctggc cttgaactcc tgccctcaag tgatcctcct aaagtgctga gattataggc   19500
atgagcaacc acacctggcc cctttcattt ttcttaggag gattgagatt ttgagtttga   19560
tcaggtttgt aggaaattta cttctaccta aatagggtaa aaaaaatttt tttaagttt    19620 ttttattcgt tagagtaaaa aaactttct tttcttttt tttttgttg cactgctaag      19680 agtctaaagc atgctttcta attctgtttt gtttaatagg caggttcata ttaagcactt   19740
```

```
tacaaacata gtagttaaaa agactggaga ggttatgaac caccgaagat ctcttacgtc   19800
aaagtctcat attctgtact cagcttcatc aactcttttt cttttgtttt tgtctgactt   19860
acggtgagat catgagaatt accatctttt gagaatgtca gccttttatt tttggtgtat   19920
tcgtgcttta ttttttata tcttaaaatg aagttctttc cctcttttc tacttctttc   19980 tctactttc ctctaagaat ggcattatcc aagtggtgga atgggttgct ttcattcaga   20040
agctttaatt cttcgtgcca gcatgcacag actttcttac ataactagat ttagaccta   20100 ggacattttc ttctttgctt atttctttt tgcctattac aaatgatgac atttcccta   20160 tcatttggcc ttgtctagtt cccagtagat aagtcacaga aatacattt ttcttccctt   20220 ctaccaccat tatgttgaac aggggagggg ggaaattatc tctccctcac ctttcctggc   20280
attcagatgc tgccgagata cctgtattga tttccccatc ttagatgcct agagagatga   20340
tcctgctggc tggaagtttg ctttctggtt ctcatgggca cttttctggc tcttttgcag   20400
tatagcgtaa gcactgtcca cctgcgaagg gcgcccctca aggatccaga cgcactcctg   20460
ggcatgtggc gggcactgag ccgagcggaa ggcggccacg ctcggaaaaa ggccagtggt   20520
ggagttttct ttttccttc agctgtggtt ttgtggtgct taccaactcc catgagaaat   20580 aggggcttg tccaggggt ctactcaaaa ccgcatcctt ctccaacaat ccctgttcac   20640
aattcttatt agttgactgt caaagtactg ccaagtcttg tctctctagg agaccttca   20700 gaccaatagc atgtatttct taagtgatcc tttatcctcc atgctctcct ttgggttttc   20760
ccttctaaac caagttttag atagataatg ttttgccat atgggtgat aagagagaaa   20820 gggagcaag ataacgaga gggaagcaaa agactaaaag agaatgagac tagagaatga   20880
aagagggcag aggatttctt aggaagtcaa aggatgccat tttggatagg aataaaggta   20940
taattaagga gaatctagag tcagggtgaa aacccagatt aacagaatga actgtcctta   21000
tttcaccatg ggaaagggaa ctagagaaat taaatttcct aacaaaaata gctttagaaa   21060
acaacttcat atagccctct tggcagtgtt gcccctttggc tcaacttcat agattgaatg   21120
ttagtttaat cttaaacagt cgtttccaag caaagcaaaa taaagcggat atttatgtct   21180
gtgtttctta tatttccct gccttcatca tcccagagta agttattagg ctattctttc   21240
tcatattttt aaagacattg tgttaaagac accaggccgg gcacagtgtg gctcactcct   21300
gtaatcccag cactttggga ggccgaggag ggcggatcac aaggtcagga gatcaagacc   21360
atcctggcta acatggtgaa accccatctc tactaaaaat acaaaaaat tagccaggcg   21420 tggtggcggg cgcctgtagt cccagctatt ctggaggctg aggtaggaga atggcctgaa   21480
cccgggaggc agagcttgca gtgagccaag atcacaccac tgcactccag ccctccagcc   21540
tgggtgacag agcaagactc catctcaaaa aaaaaaaaa aaaaaaaaa cagacaccaa   21600 tcagtaaaac cagaagtccc ccaacacaca cacacgtact ttttttttaa caaatatact   21660
tagttgtatt tcaaaaaata ttgtatctct gttaagtgaa aaatctgtaa gtagggtttt   21720
actacgtaac agaaaccaat ggataggagc aaatgtgttg atcagattta aaataaggcc   21780
aagagcttta gaattatttt ctggctttc cttcttttgca ttagtttgtt tcttagtttg   21840
ttttttaatt gagacaaggt cttgctctgt catccaggct ggagtgcagt ggtgtgatca   21900
tagctcactg cagcctcaaa ctcctgggct caagtgatcc ttccatgtta gcctccttag   21960
tagctgggac tacaggtgtg catcaccaca cccagctaat tttgcatcgg ttttatagca   22020
cggagtttac catcaacatc atactccttg gaaacaatta tttatatagc ttttaagtaa   22080
actaaagtat tatgggtatg acactcttaa atggtgagtg atatccttgt atttctagta   22140
```

```
ggtatgtggt ctagacagaa taaattgggt taagtaaaag aattttgtat tttccctctt    22200
tcatccccct ataacctaat gcaaataagc tctttgtctt tgaattttg aggctttgaa    22260
acatgtggtc atgttggaca tgtggtcata atttttgaaa ctgtagggt ctgtagagaa    22320
ggaaatctgt tcatctattt tattttaaaa tttgtctta gttaacaatg atgatgttat    22380
ttgaagattt tctttgccat tatatatctg cttttgagca aatatatgtt acttgaactt    22440
taatgctgct tctttcatgc gtgaaagaaa ttagctttta gaaggagtcc atcttaaaat    22500
acttgttgta ggtacagatc ccttggctaa cttgggtttt tggcccctac gttggtctta    22560
atcttctgat gatctcttat tctccaccatc ccttccagtc tcagtgatgt gtgaagcaag    22620
gtggttagtg gaattttgta tatgatcttt gataggttac cagacatgat taacttatta    22680
ctgtattaga gtgaagagct tctagctact gtgatcatca ctggagtgca tccttctggc    22740
agggatatgg aaaaaatata ttcatgctaa gcttttctct gaagagaaaa gacttggaat    22800
tctctggttg atgagaaagg acccttaagc tgtgatagga cctatgtgta aagtttgcct    22860
ggtcttcatg ctctaatgac tcctgtgatc agtgccagag tgaactgatg gaaaatgtgt    22920
ggttcttttt ccctttgtg agctgtgagc ctcagtatta ccctacagct atatgaatat    22980
cagtgctttc attggaagga cagttgttca gatttgttta agcttaaagt cttaagtttc    23040
aaacccttct caaaagtct cattcctcag tatcttttca cactgtatat tgaagaattt    23100
cttcattttg atcttgtttt agtttgtccc tgtagtaatg atccaaaaat tatgctcttg    23160
ctaggaacat taaagtcca aatcataatg acctatggaa aaattattta aatcatgcct    23220
taaaagaaaa tactaggcca ggcacggggg ctcatgcctg taatcccagc actttgggag    23280
gctgaggcgg gcggatcact tgaggttggg agtttgagac cagcctgacc aacatggaga    23340
aaccacattt ctactcaaac tacaaaatta gctgggcgtg gtggcacatg cctgtaatcc    23400
cagccactcg ggaggctgag gcaggaggat cgcttgaacc cgggaggtgg aggttgcggt    23460
gagctgagat tgcgccattg cactccagtc tgggcaacaa gagtgcaact ctgtctcaaa    23520
agaaaaaaaa aggaaatgct gttatgtccc agataatttg tgaatgtgct tgtagattat    23580
tgtgaaggaa gttacataag gcacaccaga attggttcac catgtccagg gaggccaatc    23640
ctgggtggac agtgacattc taagcagact tgaagccatg aagtctaagt atcatccatt    23700
atcacactaa gtatctgaac tcaaaggaat tgtggatgcc cttactagtt gtctttctcc    23760
tttaaatgga tttcacatgt gcattttaga gtgcttttt ccattgaact ggaacattgc    23820
tatccaagag atgttcctga attatctgac tcatctgtgt tttagaatca gttctgatag    23880
ttgactccca tatcttcggg ttgtagatac ctgttgtttc ttctcttgct acaaatgggt    23940
tttatagatt taaccagagt ctgtactaac caaattaatc ctaagaatta gaatggattg    24000
cagtatctgt aggggattg tgcaagtttc aagtgtttgc ttgtgattta atcatttaat    24060
aactctttca gaaagaatgt ggcttcttct gtggcggtca tgccaaaaaa aaaaatccac    24120
tttcctgagt gaaacaatag gtgccatagg agtggatcaa aaactgcagc ttaaaggcat    24180
aataagaatg aattaagaat ctaagaattc agtaaaacag gacataaaat ataaaaatca    24240
atagctttca catacacaaa ccataaaagg ttagaggacg taatggtttt ttaaaaacca    24300
aaaccaattt acagtatcaa caaaaaagta aatgcttagg aaatgtgtaa gaacctatta    24360
gaggaaactt ttttttttt ttttgagatg gagccttgct gtgtcaccca ggctggagtg    24420
cagtggcatg atcttggctc actgcaacct ccgcctcctg gattcaagcg attctcctgc    24480
```

```
ctcagcctcc caagtagctg ggactacagg cgcccgccac cacgcccggc taattttttgt    24540
attttttagta gagatggggt ttcaccatgt tggccaagct ggtctcgaac tcctaacctc    24600
aggtgatcca cctgccttgt cctcccaaag tgttgggatt acaggcgtga gccactgcgc    24660
ccagcctaga ggaaactttt tgagacaaga ttttgctgtg tcacccaggc tggagtgcag    24720
tggctcagtc tcagctcact gcaacatctg cctcccaggc caagtgatt ctcgtgcctc     24780
agcctcccaa gtagctggga cttcagtcac gcaccaccac gcccagctga ttttgtatt     24840
tttcgtagag acggggtttc accatgttgc ccaggctggt gcctgtagtc ccaactactc    24900
gggaggctga ggcaggagaa tggcgggaac ctgggaggcg gagcttgcag tgatccgaga    24960
tcatgacact gcactccagc ctgggcgaca gagcaagact ccatctcaaa aaaaaaaaa    25020
aaaaaaaaaa agtgctgcta tgactgtgta gccatttgga attagaccca tatctcacac    25080
tagatttttt aaaaataaac tctaaaatga ttaggagtct aaacagaaaa aattaaatca    25140
tacaagtact agaggaaaac atgggtgatt ttgtctttaa acttgacata gggaaaggga    25200
ttctaaatat gactcaagat ccagagacaa taaaagaaaa tattttattg ataaatttga    25260
ctacataaaa ttttttttaca atttacatgg gaaaacacc acataaaaaa tcaagagaca    25320
actggcaaac tgggaggaat ttttttcccc acaatgtata ctacagacaa aaggataata    25380
cctttaatat ataaagaatt cttaaaaatt gaggaacaaa ggaccaaaac aacactcaga    25440
catacaaaaa gtgtttaaac tcacttgtgg ttagagaaat ataatctaaa acaacattga    25500
attaaccatt tatcacctgt caggctgaca aaaaaattta ttttatttac ttttgagaca    25560
gcgtgtcact ctgtcgccca ggctggagtg cagtggcaca gtccctcctc actatagcct    25620
caacctcctg ggctcaggtg accctcccac ctcagcctcc caagtagccg aggctacagg    25680
catgagccac cgtgcccagc tattttggtg tttcaccatg ttgcccaagc tggccttgaa    25740
ttcctgggct caagtgatct gcttgcctta gcctcccaaa gtgctggggt tgtaggtgtg    25800
agccaccaca cctggccaaa aaattttaaa tatgataaca cattctgttg gcaagactgg    25860
aaagatgctc ctatgtattg ctggtaggag tacaaattgg tgcaatcctt ctgaaggaaa    25920
atttgatcac acccagtagc tccacaaatg cacttacctc ttgacccaca atcccacttc    25980
tgaaaatcta tgctgaagac atcttcaaca tttcaaaaat acatattcac aatattattc    26040
actgcagcat ttttattaaa acaaaatatt agaaaaaaac taactgtcca tacagaggag    26100
agcacacgaa taacatatgg tatatctaca tatattatgc agctgtagag aagaacttca    26160
ggaatctctt tgaactgatt tggaaatccc aagatataat gttagctgaa aaaaagcaaa    26220
gtgcaaaaga gtgtctgtaa tatactcttt ttcatgtaaa caagaaggga atatttaaaa    26280
aaatgtgtct gctcatttgt gtaaaagaaa tacaggaaag aaaatcagaa actgattttg    26340
gttacctgcc tgcatgtagt gggtggggaa tagttgtaaa gaagtgggta atgaaaacaa    26400
ggtaataggg ttgaggaaga agtggcactt cttggaatat tccttttgt atagctttga    26460
ctctgagaat catggtaatg tttcacatac caaaaataaa taataatta aaattaaaat    26520
caaacaatag ggaggcacta aaaatggagc agaagtagta acaaatgaac ctaaatgttt    26580
tacaaatgaa taacataact ttttaggtga gaggaagaac taacctaagt aactttgtaa    26640
aatagtattt acaaatagta aaatagtatt tgactgcatc atgtaggtta cagttaaaaa    26700
aactatacac caaaattgta gttcaattaa taggtgtgtt tttcacaaag gtatggatta    26760
atacttctgt aattgctttta tattttaaga ttgaaaaaat aagtatagat gatgagagcc    26820
aagtgtatca ctgttagaga aagaagttac aaataaggga agagtagaat gaacctcgag    26880
```

-continued

```
gtttggattg gcatctgggc tatcagtcag tatgataaat ggatggatgg ctatatggtt   26940
aggtatactg tacttcctag ctctgttctc tgagaacgcc taggaatagt gatactcctg   27000
tagcaatgaa catacctagt gctcacatct tggtttctaa atataattct ccactaaaag   27060
acagcagggt tccttggagg agaagttgat atcttggctt ggacagagaa aatacaagat   27120
aagtatagaa tatcttgtgt attcaaaaaa taaggaagtg cttgataaag aatggggatg   27180
tatagaagta cacaggagtt aattggaagg agttccagtg gccaaagctg gaacaatttg   27240
agcaacaaaa aaataagat agtattggat taaaactcac agaataaaat aaatacttat    27300
gagttcatat aggtataaat aaatattagg aaaaacaaac catttttcct ctgctctcac   27360
actacaacag tcaacacaga agacttctgt gatctcaaaa atatgtggag atttctcccc   27420
accagcaaac aagcagtcag ttctgtagtg gacaccagct gggtgtcctc caattcaatt   27480
ccaacctgtc tacctggaga tagcatcaga tcctacagat tgaaagctca gtccccaaaa   27540
ctgcccccac ctgcttggat accagttgca agtctaggcc tctggaactt ctaacagacc   27600
agcttcaagt tggggttccc aggactcccc tctttgggtt tgattaattt gctagagcag   27660
ctcacagaac ttagggaaat gcttttacag attttctac aaaggatatt cgaaacgata    27720
caaatgaaca gccaggtgaa gagatacata ggatgaggtc tggaagggtg gaatgcagaa   27780
gtgtgttctt tggcattttt atggaggttt cattaccta ccatgattga ttgaaccact    27840
gaccattgat gatcaactta accttcagcc cctctaccct gtcagagggt gggatggggg   27900
gatgaaagtc ccaacccct aagcctgcct agatatttcc agtgaccagc ccccatcctg    27960
aagctaccta ggagctgcca gctatcaagt cagcttatta gcatacaaaa agacatcact   28020
ttggagtttc tgaggatttt aggagctgtt tgccaggaaa tgaagtagaa gaccaaaatac  28080 atatttcaca atatcacagt ccgcccttgg gtcttcgaac cctgatccct tatgtcaata   28140
ggatgtccaa ctcaaaagat actgccacat tactagaatc ccattcaata attaatagtc   28200
tagttcatca tattgtatga gtgtctccca gggtgaggct gctcagattg gcaggcttcc   28260
tttcattctt gtgaggttgc aaaagcagaa gtagtcttag caaacacaga actttaccat   28320
ttcatgagtt tgatataatt gagctaagaa gcaatgtcat ctcttgctct gagcctcttt   28380
tgaggtgtta atgtgatatt ggaatcctct cagttcataa tccacttatt catttctttc   28440
ctctgagcta ctgtttcttc tctcttaata agtacccaaa cttttccacc tttgaaggga   28500
gcattacaat cagccactgt gatggtctag attgcaggca acaatactag tctagcaagt   28560
acctcttcct cagtgcaccc ccttcagata gggttaggtt acagaggtgc agaactagtg   28620
ggctattttt actgtcaggc aatatagctg tattaactgt tagccccaat tttgctggat   28680
ggggtgaagg cacaacccat tcccatcagt ccattaggaa ttctgaccta agttacaata   28740
cgtagttaga atttcttgcc taggaatcat tcctgcttcc agcacatgta gttgcagccc   28800
tggtcctaag accattgcat caggtagggg aatggggaa aaaaaagaa aaggaaagtt     28860 gaggtgatgt gcgggaaaaa agacagaaag aagtatcttg taagtaagaa gagactgtct   28920
ttcaccttta tccttcagga gctacttcag gaaccaagga caaagccaa atacttttta    28980 agaaaatata ttcttggtcg ggtgtggtgg cccacacctg taatcccagc actttgggag   29040
gctgaggcag gcagacttga ggtcaagagt tcaagaccag cctggccaac atggcaaaac   29100
ccagtctcta cgaaaaatac aaaaattagc tgggcgtggt ggtacactcc tgcaattcca   29160
gctattccag aggctgaggc acaagaatcg cttgaaccca ggagacagag gttgcagtga   29220
```

```
actgagatag cgccactgca ctctagtctg ggtgacagag tgcgattctg tctcaaaaaa    29280
aaaaaaaaaa aagatattct tattactgta gtcagttagg aaagaataag cttacagga    29340 gctgagaacc aggaatcatg gatgaaaacc aaaatatata ttttataata ttgtaataaa    29400
taaaggagaa gggacagtac ttccttataa aagaattcca attaataaag tgaagagaat    29460
aaaagaaatg caaaatcacc attaggcagg taacacccac agatggatgc taaaatcagt    29520
gggtgagact ttgaaaagaa acaggataat agcaaaatgt caaatatttt ctccctagat    29580
ttggatcagt tacaaaggga aaaacagtac ctataagtag agaaacccag cagaccttgc    29640
catgtgatca aggttaccat aaccagtaat aaaattttta tcaacattat gtactcccta    29700
atatgatata ctgagaagga cacagcatca ctttctggta ttcttgccaa aaatgtataa    29760
cctcaatcta aaacatgagg aaactttagt caaacccaaa ttgagacacg ttctacaaaa    29820
taactgatcg atattcacca gaagtgttct ggtcacaaaa gacaaaaatg aagacctgtc    29880
acactttaga agaaactaag gagacatggc aaccagatac aatgtgggat cctgaaggaa    29940
aaaggacaat aaggaaaaaa actggtgaag ttcttatcaa gtctagttta gttaatagta    30000
ttatacccat gttaatttcc tgattttttga tcactgaacc gtggttatgt aagaggaaaa    30060
tggatgaatg atatccatga actctgtact gttcagcttt tctgtaagtc tttaaaaatt    30120
attttgtaaa atatggacat agatcatttt tagcagttat taacctggtt acttggataa    30180
gccctgaacc tgaaacattg catgtaacaa ctctttcttg gtattaagct tttctattgt    30240
ataaatgccc tttggatggc tatttcagta gaatccaatt aaggtggaac atagatggga    30300
aagccaaaca gtgtattcat gatagacaat aaaaaataat agcaaaataa cttatttttg    30360
ttttcaagtt tttaccagta tggcagatat tgtacaaagc attttacata tattatatta    30420
ttcagtctta aaaggattgc ttgatatatt gataccagta ttttttttgg gagggggggg    30480
cgtacagagt ttccctcttg ttgcccaggc tggagtgcaa tggcgcaatc tcggctcatc    30540
gcaacctctg cctcctgggt tcaattaatt ctcctgcctc agcctctcga gtagctggga    30600
ttacaggcat gtgccaccat atccggctaa ttttgtattt ttagtagaga cgggatttct    30660
ccatgttggt caggctggac tcgaactcca gacctcaggt gatccgccca ctcccacctc    30720
tcaaagttct gggattacag gcgtgagcca cctttcccgg ccctgatacc aatattctta    30780
ttttgtgggt gaggaagctg aggtttagaa aggaaactta cctaatgaca ggcatggtgg    30840
cttcaggatt tgaacctaaa cagcctgttc tcttaatcac accaatccat agctccctcc    30900
aaagggaagt gatgagccta ttgtgaccta tgtatctacc agtagtaagc aagtctagaa    30960
aactgctgtt cattctttag catagtgctg tacaacagaa atatagtatg agtcatgtgt    31020
gaaattttaa attttctagt ggctacatta aaaaggcaaa aagaaacata aaattaaatt    31080
ttaactctat attcatttaa cctgatatag acaaagtatt attgcaacat ttgatcaata    31140 taaaagata ttttcctctt ttttttcacac tgtttgaaat ctagtgagta ttacatttat    31200
aggcatctca agtctcacca gccacattac aggtacttag tagccattgt gactaatagc    31260
tactgcattg gatagcacag ccctacaatg tgagatgtaa aaattatgat gcactgttgg    31320
ttttacattc ttcctcctct tttcacaaag aaatatttga cagttgactc ctttgcaagt    31380
atatattaga tctaagttct aatttggagc caggcacagt ggcgtgcatc tgtagtctca    31440
gctactcggg agactgaagc aggaagtaca tttgagccta ggagtttgac actgcagtga    31500
gctattacta tgccactgca ctccagcctg gatgacagag tgagaccctg tctctaaaac    31560
aaaatttatt ttagtaatca tttttttaaaa ataaattttta atttggaagt aagagttact    31620
```

```
tacagcctcc caatgtgcag ttcaagttcc attgcttatt ggaaactact catttgtagg    31680
actaagtttg ttgaagccag gttttcttgg acttaatcag ctcataactg gtggcatata    31740
tctggacaac tcgtgaaatc tcaccttttα agttgtcctc aggaatagat ggtcccatga    31800
tattttgttt ttgttttgtt ttgtttgttt gttttttgag acggagtctc gctctgtagc    31860
ccaggctgaa atgcagtggc acgatctcag ctcactgcaa cctctgcctc ccaggttcaa    31920
acaattctct gcttcagcct cccaagtagc tgggattaca ggtgcccgct accatgcctg    31980
actaattttt ttgtgttttt agtagagacg gggttttcac catcttggcc aggctggtct    32040
taaactcctg accttgtgat ccacctgcct tggcctccca aagtgctagg attataggca    32100
tgagccactg cgcccagcct gttttgcttt tttgagatag agttttgctc ttgtctccca    32160
ggctggagta caatggtgcg atctcagctc actgcaacct cgtcctcctg ggttcaagcg    32220
attctcctgc ctctgcctcc cgagtagctg ggattacagc catgcatcac caagcctggc    32280
taattttgta tttttagtag agatggggtt tcaccatgtt ggccaaggtg atctcaaact    32340
cctgacctca agtgatccac ccacctcgac ctcccaaagt gctgggatta caggcgtgag    32400
ccaccacgcc aggctccatg tttcaattac cacattaatt ggtctaagag gaaggtgttg    32460
tcatcttgga agagaagatg gctggaaggt gctatgcagt gactggaaaa agtgtaaggg    32520
tgttgaaact tcattgtaac aaggcatgtc ctgcaagcca acttgtttct tttacttgga    32580
ggaatcagtc ttagcagtta tcagctcttt ttgaaacaac agattaagtt tctttctgga    32640
atcttgttgg catcagggtt agagcttagt aaatttctat ggctttccta ggtactctta    32700
gactcaataa aattttctct ttcagaattt ggtgttcact tggcagaact gactgtagat    32760
ccccaggggg cactggcaat ccgtcaggta agtccagact ggcccaattt ataaatagtt    32820
tcccttticct tggtaatgaa actttcttat aggaaagaaa aataaggcca gtgtataaat    32880
aacctaggat gttgtgccag atttagatat acttcagatg tatcaggcta tgtatatagt    32940
ttttatgtgt gaaaaaaatc tttttcttgc tgtactactt ggcttattct cttcacagct    33000
ggcatcagtc atcttgaaac aatatgtgga gactcactgg tgtgcccaat cagagaaatt    33060
taggcctcct gaaactacag aaagggtaag tcagttactt gattagtcta cctgaggaga    33120
tttgagggtc catttaaga gattagacta taacattctt tgacagcatg gagcaatcaa    33180
aagactaggc agaaaggag attggtggct ggcattgcgg gcatagggct atacattaaa    33240
gagctcaagt atcaggctgg tctgtgttca aattccagtt ttgcttttta caagctatga    33300
gatcattgga aatgtagtta acacctaagc ctcaatttcc taaatctcca aagtgagaat    33360
aaaaatacca actaagggtt taagaattaa atgaaataac atttgtactt agtgcagtac    33420
tgtgcagtca tcctgagtcc ccaagaaatt ttgaggtata aggtctggag gaatgttttc    33480
cactggagct ttatgcaatt atggaaatat tctgtgtctg tgctgcctaa acaatagct    33540
actagctgca tatggctgtt gagcacttaa aatggggcta gtgcaactga ggaactgaat    33600
tttaaatttt ttaaaatgtt aatagctatg tatagctagt ggctactgta atggactgca    33660
taagtttaga gatcacagat gaaccctcca aatgaattgt caagtttgtg tataggagtt    33720
ttctgtagac atgcagtacc ttgtactcat tgttttttcca acacagttcc caattgaact    33780
gggctctgcc agtcactttt aacctgatct aatagcaggt ggacttttat cccttacagg    33840
caaaaattgt tatccgggag ctattgccta atggggtgag agaatcgata agcaaagtgc    33900
gctccagtgt ggcctatgca gtgtcagcca ttgcccactg ggactggcct gaagcttggc    33960
```

```
cccaactctt caacctgctc atggagatgt tggtgagcgg agacttaaat gccgtccatg    34020
gagccatgcg tgtgctgaca ggtaccagaa gccctttttcc ctggtattgg tacttggatc   34080
tcaagcgaca ggagtattac cagaagctat gtgatataat ggcctggacc agtaggaatt    34140
gctgctgatg ttattcctcc ctcctagttt ttatctctcc atctaccctc cagctctatt    34200 gttttttttct agggaattaa gtttgtatag tattacttct actcccaaac ctaccactta   34260
cagatacagt attagcatag tgatggagta ttcagatttt ggattttgt agtggcttca    34320 ccttgatcct tcacttacct tctttgagcc tgagtttcct tttatataaa attaagatga    34380
tagtagtgtc tgcatcaaag gagcttttgg tatagtttaa atgttagcta atctatcttt    34440
attgacttgt tcagtaaagt ttagttacta tgattatcat tattactata tattatttgt    34500
ccacttagtt caaccaaggc aaagttaaga attgtaaaat ggattttat agaagtattt     34560 aaaaagaaga taaaaacagt atagccatgt aatcctgacc ttcatttagc cagttagaga    34620
atatgtagtc tcagtatctt ttccttctct ctgttctgag aagttgataa aaatacttca    34680 actttttagtt caaagagatt tgatggatat ctcttctaaa cctgattaag ctatcaatcc   34740
ctcccagaat ctgctttcat atatccttag ggatggcctg agtttcccag tcctttgcaa    34800
gttcctccct gcttcttatt ccctaaatga agtcactact ctgttttgcc ttcaagaaat    34860
tcttacctgg actttagtca tcctgtactg atcctttaga aatcatcttt ctcctttgtt    34920
catataggtt tgtagaagtc ccaccaatat cttatctctt tttctatgac ctgctagctt    34980
acctgatatg tattcttgct tagttgtgaa tgccaattct attctttctc aatctcagtt    35040
tactgaactt ggcacatagg cccaattttg ctagtccatg tgatgttaat ggtagataat    35100
atcaactctt tgtcaaatgc aaatcttttct tctccttttg tttcaaaatg acctcttctc   35160
agaccccagc tgccttttttg aattacccac tatattcgta ttgattgcct gtgacaaagc   35220
ttcagttttt agctcagata ccgaacagac ttaccaaaaa gatcagaatg ttccttgctc    35280
agattttgac ttctctgctt attgcccttt cttctgctta atgactcatt cattattcag    35340
gtgatttcac acacccctct gcatggaatt ggccttttag gattctttat tcaccacttc    35400
atagtgccag gatatcaatt aacagataca tgttctacca aggaaaggaa gcctgttccc    35460
tctcagtctt ccaagatgaa attcaggttc ttttgacaaa cctagagaga aaggttttgt    35520
acatttatct tgatttggat gctgaagagc tcttattgtg tttgactaag gaaattactg    35580
ttcagtgaga tcactttttct gccagccaca gggaaagaac tgttgggga aatttgtctc    35640 cttttgtaat ggagtcacca gacatggagt ggctagcagc caagcccat tcccaaatac     35700 ttgctccaaa tattttcaaa cgagagtaga ctgtactctg acaacaaaaa cttaggcatg    35760
catgaagata gcaggacatt ggtggttgga cagaggccca ttaggagaat gggactgatt    35820
cttttcagag ttttttcaaga tactatacca gtttcccttt aatgaggctt cctattaaac   35880 ttatctatttt atagatgaga accaactaag gctcatggtg taaaggaaat gcaaatatag   35940
cagctaagga ttagaagatt tgatccacca gatacagctt tttcttcgtt ctcaaagaag   36000
tttggagatt gagatgttgc tggagtccta gaattttttct gacttgctga atcacctcag  36060
aaaacttttg gaattaaacc tataaagtat taataaattg ataccaggga tgagtatagg    36120
agagtaaaaa gcagtcaagc actttattag cagaattaaa ttatactgta tttttcataa    36180
aacttgttat tatgccatct atcatatttg tttggactaa tttccttgaa tttctaaata    36240
aaatagaaca ctcaccattc aaagctcaga ctttatcctt gaggaggaaa ttacagctgt    36300
aaagaaaatt caaccttgag tatttgatct tcatttgact cgtggggatt gatattgttc    36360
```

```
aaaattgtgg agtaccttaa tcttgaaaat gccagcttgc gtttgtagct gtgtatcttc   36420
ccccaaaatg tcccaagtgg ttagctttat ttttagtttt atttatttat ttatttattt   36480
gagacatggt ctcactctgt cacccaggct caggtacagt ggcactgttg tagctcactg   36540
taaccttgac ctcctgggct caagcgagcc tcctgcctca gcatcctaag tagctgggac   36600
tgcagacaca tgccaccaca tgcagctttt tttttttttt ttttaaatgt actggcagat   36660
cttgctatgt tcaagctggt cttgaactcc tggcctcaag tgatcctcct gcctcaacct   36720
cccaaagctc tgggattaca ggtataagcc actgttcccg gcccatatgt ccatttctat   36780
agtgataacg tggaaaagca tcaggtaaag tggatagtta ctggaactca agagctttat   36840
tctgctgctt tgtaacatga atccagggtc ctttgtgctg tctcagtgcc ttgtgtgtgg   36900
tgtatttggt ttttttttt ttgagacgtg aagggaaaga tacgacccat atttccgtca   36960
ccttcgagtc tcattctgtg tataggttgc ttttttgtcac atttatatag aaaattccca   37020
tttgttccag ttagcagcag cctctgactt ttaggtcaat aaaatctgag aagagtaaca   37080
tatacaaaga ggagttgagg cctagtaagt ctgtacatat tttattacat gcatcaaacc   37140
agcttgccaa gcgaaagtac tgaaaacaga agcaaaggta agaaacctcg aagtgtaact   37200
gaatgttgac agatgggcac aagataaatt aatacagaat tttcccaagt tgacctcaca   37260
aggactttta tgcagttcta ttacagattt tctttcagta tttatattaa agttttcttt   37320
tttaatctct tgtattttc tttatttcca tattattctt tctccttcta acaaataatc   37380
agtaactctt gctacttttg ctttcacaga atgagaccac caggccagtg tctttacctg   37440
tgtgctgtct gtttgggaac tgccacctag aagcagttca gaaaatatca cacttaatat   37500
ctttatgaag cagtattttt tttttaacag tactacttt ttctttgtag aattcactcg   37560
tgaagtaaca gacacacaga tgccacttgt tgctcctgtc attctcccag agatgtataa   37620
gatcttcacc atggctgagg tatgaaatct cagctccaag attatagtga gttcaggctc   37680
tcttcagccc ccagcctttc aggtgggaga ttatggtgtt tgcaactgat ctcaatacct   37740
aaaaactaga actgacaaag atctggatct gaatctgcat taaccttaga cctttcactc   37800
aactacaagg gcaagccttt gataaaagtg tgaaatagct gaaatatttc ttcacatatc   37860
gtacttcctg gcatccagta gcccctaagt agataaatag tgccttcctt catgctactt   37920
ccagcctctt actgagttat cccacctacg cttgcctacc tcagctaagt aatgggaagc   37980
aatctatcac tgcattgcac ataatagacc cttaatatat tgcatatata tttgattagt   38040
gtgtatatga atgataactc atttatagta aggtataaat acctgatgga taatgtttta   38100
acttccctat tccctctgc ccccaaccaa tggtctgcat tttaaaggaa atatattggc   38160
tgtgttggga tttaagcac tacctagtct ggtatttttt aatcaaatga acccacagag   38220
gcccttatat aaggttcatt ccagtaagtt ccaacattat gattctgcta cctttcattc   38280
tctgaattac agaagtctgc ctcctggaca taaatgaatt acatttccca tttctcgagg   38340
gcatccaatc tcatgtgagg attcattagt catagtttta cttctagtct gagatacaca   38400
catacctaca cactccagtc tcgtggctat gctgttatgc tgtaaccttt cttccaggtg   38460
tatggtattc gaacccgttc ccgagccgtg gagattttta ccacttgtgc ccatatgatc   38520
tgtaacatgg aggagctgga aaaggtaagc aggtctttgg atcaataaca gacttcatgc   38580
ttaaaagttt tattcatgca gagcagtgag tcatttcatg atagcagcac gaaaaagcac   38640
actaaccagt attagagata gatttaacat ttttattaaa ttattgttgt tatttttcca   38700
```

```
gacagggtct tgctctgtca cccaggctgg actacagtgg tgcaatcatg gctcactaca   38760
gccttgaact cctgggctta agtgatcccc tgacccccag taggaactac aggtgtggtg   38820
tgcaccacca cacttggctg attttctttt ttaaatgttt gtagagatag ggtctcactg   38880
tattgcccag gctggtcttg aacttctggg ctcaagcagt cttccccct cagcctcca    38940 aagtgctggg gttataagca tgaaccacaa cactcagcta tatttgtatt ttttttattt   39000
atttgggttt tttttgagac aagatcttgc tctgtcaccc aggctggaat gcagtggcat   39060
gatcatagct cactgcagcc tcaacctccc aggttcaagc aatcctctca cctcagcctc   39120
ccgagtaggt gagatcacca gcatgtgcta ccactcctgg ctaatgaatg aatgagtgaa   39180
cgaatgaatt tatttattta tttagagatg gagtctcgct ctgtcaccag gctagagtgc   39240
agtggtgcaa tctcagctca ctgcaacgtc cgcctcccag gttcaagtga ttcttctgcc   39300
tcagcctccc gagtagctgg gactacaggc acgcgccatc atgcccagct aattttgtt    39360 ttgcagtaga cagggtttt caccatgttg gccaggatgg tctcaatatc ttgacctcgt    39420
gatccaccca cctcggcctc ccaaagtgct gggattacag gcatgagcca ccatgcccag   39480
cctaatgaat ttatatttgt agagacgggg tctctcccta tgttgcccag gctcatcttg   39540
aactccttgg ctcaagtgat cctcccacct tggcctccca agtgctagg attataggtg    39600 tgagccacca cacctggcct gattgaattt tcaacttgta aaaagcttag tcttcttttg   39660
agtcttactt cttcaaacac cttatcctat atccttttca tagtagtcat cccttagaac   39720
tttcctactc ttttatggcc tccttgtgtg aagcaaagct agctgaaaaa taccaatccc   39780
tgtgattcag aagcagttag gaggaaagtt ggtcttacat aatagttttt aagagggctt   39840
tgatgaagaa ctgcaagtgc tggttaagga aaatgaaat cttaggtaac accttcattg    39900
actttatagc tattctcttc tgatcaggct tggagcctga agagagcttt aggtgccttt   39960
caaatatcag tgtttgatat atatgtgttg aagccatgga ttaggggttt gtccagtatt   40020
gactttggtt tctgttatca gggtgcagcc aaagtcctga tctttcccgt ggtacagcag   40080
ttcacagagg cctttgttca ggccctccag ataccagatg gccccacatc tgacagtggg   40140
tttaagatgg aggtcctaaa ggtaaacact tactaccaat gaaatatttg gagtttgagg   40200
ggctggtctg aaatcattta tttcttatat atcactcata acttgggtcc ttttctctta   40260
acttcttagg cagtgacagc cctagtgaaa aacttcccaa agcacatggt gtcctccatg   40320
cagcagattc tgcctattgt ttggaacacc ctaaccgaga gtgcagcttt atatcctttc   40380
ttgaaagttt aagggagcta ctaccaccta tagttaggaa tctcgcactg ggtttcacat   40440
tcatatggtt ccactcttct tacacaggct ttttaaggt gtctactttt agtgttggaa    40500
tatgtaacat ttccatgtag attatatgta aagcagactc caaattctat ttctttactc   40560
ttcatcatac ttatgtgagg acagaagtaa attcacaga agaagtagaa gatcctgtgg    40620
attctgatgg tatgtagttt atttgatctt tatagaaata ccagttagtg ggaaaagaaa   40680
aagaagccag agatgggggc gggaaacagt aacttgagag gcttcactct attaagtgtt   40740
ttctaattca gtttattttc gatgtattcg atgtgggaa atgagaattg acaatcttta    40800
atctgttcca cataggtagt tgcataaatc tcataaaatc atagaatttc tgcattgaa    40860 gagatacttt taaggccatt taatctagcc tacttctggc attttgttgt gtttcatttg   40920
ggggtcccag atcatgaatc tttcgtttct gttttaacat ttctcattat ttcagattag   40980
aacaatagac atactggaaa atatatccag tgttctgat tcttttactt gaaaaccaa     41040 agaatattta atatcctcaa aattacgttt tgtgacctct gagccctctc tcccaattcc   41100
```

```
tcaggaatga tcattagcaa gtactttaaa tattcagtaa tttacaaagg ttatgtagtt   41160
cattttctgc atatatgctt tccttttgct ttcttgtcat taatttcttc tcttctgtat   41220
ttcctgcagg tgaagtcctg ggctttgaaa atctcgtctt tagcattttt gaatttgtcc   41280
atgctctact agaaaatagc aaattcaaaa gcactgttaa gaaagccttg cctgaattga   41340
tttattatat tatcctgtac atgcaaatca ctgaggagca ggtaaataat atttgagaga   41400
cagttaccat cttgtatttg gaaagtgcaa cttgaagaat atgaggtctt ggtcaggtga   41460
acactttatt tctaaaaata gacacaaaaa gaataatttc atgtgaagtt ctgggaaagg   41520
tttgacatca ttttattgcc aaatccaagg ttttggagtt caccaccata cctggctttt   41580
tttttttttt ttttcccag caaagtacta tactatgttg cccaggctag tagtctctaa   41640
ctcctgggct caagcaatcc acccaccttg gcctctcaaa gtgctgggat tacaggcatg   41700
agtgactgtg cctggcccac ttttgccatt agaaaatctc acaggaccac taacctaaga   41760
cactgatttt taggagaatc tgttccttcc ctaaagtaaa atgtaataat cagaccatta   41820
gcctgatggt gggtcatcaa aagcagcaaa gaacgttcaa aaattagata acgcctcgtt   41880
taaaacagca caagaattga cataatttc acaataaata gtctatcaga cttaatctat   41940
tcagaaaatc gatctatcaa agggtaacag caggttgaca ttggcagaga gctagtaatc   42000
agccagattc taaagagag caatagccat tgctacctac cttgctactt aatagtattt   42060
atttctctac atcaaaaaga aaagattttt ttaagctaga gttttgtttt cagtttttgt   42120
tgttgttgtt gttttgtttt gtttgctttt tgggacaggg tcttgctgtt ttgctcaggc   42180
tggagtgcag tggtgtagac aaagctcacg gcagccttga cctcccaggc tcaagccatc   42240
ctcctgcctc agcctcccga gtagctgaga ccacaggcat atgccaccat gcccagttga   42300
cttttttatt ttttgtagag gtggggtctc actatgttgc ccaggctggt ctcaaactcc   42360
tgggctcaag cagtcctccc accttggcct cccaaagtgt caggattaca gttgtgagcc   42420
attgcatcca gcaaaaggct agagtttttt caggataata ggttgaaatc ttcctgtatc   42480
tgttgatgaa aagctatgaa tcagattggc agcatcacaa agacataact tgatcttttc   42540
agattaaagt atggacagcc aacccccaac aatttgtaga agatgaagat gatgatacat   42600
tctcctatac tgttagaata gcagctcaag acttgttgct ggtaagttta ccttgatact   42660
tcagccacat aatttctatc agtcacttga gcatttcttc ttttttgtag acaactaatc   42720
caaggtgagc agtgttgttg ggtggcttta tctcagactt tattggggat gcaagagagt   42780
ttctgaaatg aaattcgaga ctcagaaatt ctaaaatcat tgctactggt tctaacttaa   42840
aactaaatat tagataaaag aattgtgcag accatagggc cggggtgcgg gggagaattg   42900
tatagaggat aaagtgttcc atggagtaag ggtagttgaa tcaagaacat ttcagtttat   42960
ggctgggcgt ggtgactcac acctgtaatc ccagcacttg gggaggccga ggcgggcaga   43020
tcacctgagg tccagagttc aagactagcc tgaccaacat ggagaaaccc catctctact   43080
aaacatacaa aattagccgg gcgtgatggc gcatgcctgt aatcccagct actcgggagg   43140
ctgacgcagg agaattgctt gaacccggga ggcggaggtt gtggtgagcc aagattacac   43200
cattgcgctc cagcctgggc gacaagagtg aaacttggtc tcaaaaaaaa aaaaaaagc   43260 catttcagtt taattcactc ttcaacaaga atctatagca cagacaaaag gttggcaaac   43320
ctagcaaaac aaaacagatt gctgaaagat taacatccaa atacctgctc atgttttctt   43380
tgcctcttct gactagagca tagagttgtc tctaggctga aatactaaga agaaactgcc   43440
```

```
acttgcttct tgttgggtag gagatttgtt ctctgttgat gaatcacttc tcattatcat    43500
ttagtatttc taaggagctg tgaaagatta tattcagttc caattagtag attagactta    43560
tttttctatc atcagtctcc aagagagcaa atatttggtc cattgtcatc caaagctaga    43620
tctattattg ctcacttatg ctctgctgaa tatagccaaa ggagccaact ggttagcctt    43680
acaatgccta ggcactaccg aaatacagat actactttaa tttcattaga gaccctgacc    43740
tactggtata acattttta tacaattagg ggtttgcaca tgtatgtgaa agagcttgaa    43800
ccaatcactt ctaacagtca tgactgaagc ggtttacaat taaaatgcat ttaatgggca    43860
caaacagatt tattagctct tctctctcta taggctgtgg ccacagattt ccagaatgaa    43920
agtgcagcag ccctggctgc tgcagccact cgacatttac aagaagctga gcaaaccaaa    43980
aacagtggca ctgagcactg gtaagagtga gccgctaatt ggttaagatg cttttgttta    44040 cccttctta aaaagtcttg aaaggatgga tttatttta tcttaatttg aaaatctggt    44100
tttaatttaa taacagattt taatctctta ttattaaaat ttcactcttt tcagctatag    44160
gttagaatgg aagggcttaa ggtaaatgac tcttttggaa gagattgtgc tggagtgccc    44220
ttttctgaat cttgttttcct caaatatttta tctctttttgg cagtttagta tgttttacta    44280
ggctgtagta tcctttcaca ggtggaagat ccatgaggca tgcatgcttg ccctaggctc    44340
agtgaaggcc atcatcactg acagtgtgaa aaatggcagg attcattttg acatgcatgg    44400
gttcctgacc aatgtcatcc ttgcagacct caacctctca ggtatgtttc agcacgtgcc    44460
aggattctag aaactcttta aacctgttgt ggggttgggg gagggatcag cattaggaga    44520
tatacctgat gtaagtgaca agttaatggg tgcagcacac caacatggca catgtataca    44580
tatgtaacct gcacattgtg tacatgtacc ctagaactca agtataata tatatatata    44640 tatatatata tataaaggaa actctttaaa cctgtcatta acttggttat attgttcact    44700
tagactggta ggccagatat tcttgtgtcc tttgagtgaa aattgtttgc accctacagc    44760
ttgaactcat ccgaacctct aaaacagccc agaggccgat tcaagcttca cctaatgaca    44820
atctaatatt gcctagttca taattcttcc gtgatgttta tgtttcttcc caaattggcg    44880
ttcccattca tggttgtttt tggcatttga atggaatcca aatctggttg ctgtaccttg    44940
agaattatcg agtactgctc ccattgttaa gtccagaatg ccctcaggca ttctgtatca    45000
ggcacattct tcctgtttgt ttcctgtcat ttttctcaaa ctttattttt ggccaatatc    45060
caaataatta aaatgttcca ttctcatacc catgttagcc atctgtctta aaagaaaaa    45120 agtaggccag gcgcgatggc tcatgcctct aatcccagca ctttgggagg ctaaggcagg    45180
tgactcacct gaggtcagga gttcaagacc agcctggcca acttggcgaa accccatctc    45240
tactaaaaat ataaaaatta gctgggtgtg gtagcaggag cctgtagtcc cagctactca    45300
agaggctgag gcaggagaat cacttgaacc aggaggcaga ggttgcagag aactgagatc    45360
acaccactgt attccacctt gggtgacaga gcgagacttg gttaaaaaa aaaaaaagg    45420 tagccctta ctattagacc gatttcttcc gcaatacaga gcagtagctg agaatcattg    45480
ttgtctatgt ggcatttct gctacttgct tctgccatgc catgcctttt ctcatccttg    45540
gagccagatc accatccgaa aacactgcct ttgctttctc tctcagtact taaatcatgg    45600
aacctttggt attgtttgct ccatttcgg tccatttact tcctctccat aggatagttc    45660
tgggagtagc ttatgtcatt tgaaaatgtt ctgctctgtg attttaaata ggtaatctat    45720
tatcgggtgt ctcagtccat cacttccatt ctctgaatca caaattaaaa tggttgtaca    45780
tccagagctc agatgcgttg ggaatatcct gtttcactct gtacttatca tatgctgcat    45840
```

```
tgttgaatat gttttcttac tcctactagt aaggtctctg agagtagaaa tcatgtctaa   45900
tctttgtatc ctacaagtgc cttgagtagg catcccatag ttacacattg aatgatttct   45960
gaagcccatc aacacatttc ttatagagtt taccctagca aagattttc aaaaactttg   46020
gaaattttag aatatttgtt atttagtctg gaaaaaggct caatatatat catttgttaa   46080
tcctacctgt agctaaaacc ttttctacac caaccattct gaaactttt ggttacaaat   46140
tatcaataat ttaaaagaca tttttatgtg gctttaattt attaatattt aacatactaa   46200
agattaaaac tgagttgttt ttaaaataaa agaaatggaa acatgttttc ccctggctgt   46260
cagagccatg atatcacata ccatataacc tctggaaaac tccactgtat acttgtgaaa   46320
gaatgaaagt gaggccgggc atggtggctt atgcctgtaa ccccagcact tgggaggct    46380
gaggtgggcg gatcatgagg tcaggagttc gagaccagcc tggctaacat ggcctaaccc   46440
catctctact aaaaatacaa aaattagctg ggcgtggtgg cacgcgtctg taatcccagc   46500
tactcaggag gctgaggtag aggaattgct tgaacccagg aggcggaggt tgcagtgagc   46560
cgagattgtg ccagtgcgct ccagcctggg caacagagcg agactctgtc tcaaaaaaaa   46620
gaaggaatga aagtgaaaaa aataatgttt ctgtattact gtgaaaatag ttttaacttt   46680
agggaatttc tggaccatcc tttgggaact gcttctgtac attatcagtt tctcacttac   46740
agtggttgga cttatgattt ttcatcttta cagtgatgcc aaagcaatat gcatttagta   46800
gaaattatac ttcaagtacc cttacaacca ttctgttttc acttacagta tagtattcaa   46860
taaattatat gagatattca acactttatt ataaaatagg ctttgtgtta cgtgagtttg   46920
cccaactta cgctaatgta agtgttctga gcatgtttaa ggtaggcccg gctaagctgt    46980
gatgttcagt attaaattta aatgcatttt taacttacag tattttcaac ttacgatgtg   47040
tttatcagga agtaaccca tcataagcag aggagcatct gtattgcgta atttgactgg    47100
cacagtttat taggttctgt tcagtgtttt ccgtcaacaa gatgtttatt gtgtgagtaa   47160
acaagttaag ccctgtgaca agctgaataa gaatagtctc tcctcagcag cttatagtaa   47220
acaagggtag taatccttac attagtggct agactatcaa acgaaatata taacatgtaa   47280
gaacactaaa gacagaatta ctgtggcata gagatagtta gaattgcttc agcctaagag   47340
atgaattagg taatgcaagg aggtgaatat gttggcttgc aatatgaaca aggcagagag   47400
ctgggagagt aagatgtaag ttgctaagga gggatgtgta cttgagtttg gaaaccataa   47460
agggaaatca taggtaatgc tagagtcact gatcttaggg agccttgaat aacgtgatga   47520
ctaaggtaat ctttatttgg tggactatgg aattaattga cagattttaa atagaagaat   47580
gacatgatca gagctataat ttatgtttta agagtggtcc aaggctgcac gcggtggctc   47640
atgcctgtaa tctcagcact tgggaggcc aagccgagtg gattgcttga gttcaggagt    47700
tcaagaccag cctggccaac atggtgaaac cccctctcta ctaaaaatac aaaaattagc   47760
caggcgtggt ggtacgcacc tgtaatccca gctgctcggg aggctgaggc aggagaatcg   47820
ctcgaacccg ggaagcagcg gttacagtga gctgagattg tgccactaca ctccagcctg   47880
ggcaacagag caagactcca tctcaaaaaa aagagtggt ccaaaagtgg gaataaacta    47940
gcaatggaga tggcaactta gaagattaag tgggcgggta ccatggctca cacctgtaat   48000
cccagcactt tggaggcca aggcaggcag atcacctaag gtcaggagtt tgagaccagc    48060
ctgaccaaca tggagaaagc ccatctctac taaaaataca aaattagctg ggcgtggtgg   48120
tgcatgcctg taatcccagc tactggggag gctgaggcag gagaatcact tgaaccaggg   48180
```

```
aggtggaggt tgtggtgagc cgagatcgca ctgttgcact ccagcctggg caacaagaat    48240
gaaacttcat ctcaaaaaaa aaaaaaaaaa gattaactag tagtacaggt aaggaataat    48300
gagagctggg ggtgaggact ggggtggtaa agtcttttta gtctaataat attcaagatc    48360
tactttgctc agaagagaca agggaaaact gggaaattga ttttgtacca caggtcacac    48420
atttgctttc atcatacaag gttatgcttt ttctctcaaa tgagttgtac atattatgta    48480
gcatctattt acttctaaaa aattgaggaa tggagggccg gatgcggtgg ctcatgcctg    48540
taatcccagc actttgggag gccgaggcag acagatcact tgaggtccag agtttgagac    48600
cagcctggcc aacatggcaa aacgccatct ctactaaaaa tacaaaaaat tagccgggca    48660
tggtggcagg cgcctgtgat cccaactact caggaggctg aggcaggaca gttgcttgaa    48720
cccgggggac ggaggttgca gtgagccgag atcacgccat cgcactccat cctgggtgac    48780
agagtgagac tccatctcaa aaaaaaaaaa ttgaggaatg aatgtgggaa agagaaagaa    48840
caagtaaaag gaattttcat tttccagccc ctaattgttc tgtctttctc ccagtgtctc    48900
ctttcctctt gggccgggca ctttgggctg ccagtcggtt cactgttgct atgtcccctg    48960
aactgatcca gcagttccta caggcaacag ttagtggtct tcacgagaca cagcccccat    49020
cagttcgaat ttctgcagtg agagccatct ggggtgagt atgctaccct agcgtgataa    49080
ttaagggaaa gttgctcagg ttagatataa caaatcacag ttttccagtg tattatgttg    49140
cttgaaaatc cctgctaatg atatccttca gggtgaatgt tggaaggaca gggaaagaaa    49200
ccatgctaga gacatggctt tgtgagtcc agaagatgtc ctgttccttt ctgctcctct    49260
tcctctttaa attcgctcca gttctggaat catctaggca actcccttc tctcaatggt    49320 gaagaacctg aggtttggag agaaaaatgt tttgcacagg gttgcacaat tgatgaatga    49380
tagaagcagg attagagtcc acatcatttt gttggttgat tatattagaa accaaatctg    49440
ggataatgtg acctagaaac actgcttatt ttttcccagt tttacctatc ttttttaagg    49500
ctagtgttac taatggatca aaagtcattt atttatattc ctacgcagac tagaaggacc    49560
attgttgttt taaggaatat cttaggctca aacttaaaca tctcaactga atcctataac    49620
taccaacaca aaatttattt tccatgtgcc tgccctgtct tatctttttga ggcagaggag    49680 tatctttga gatgccgtgt gttatatgtc attagaaagc attcaagaac tgcctgtttt    49740
aattaaatgg ttaatgttat gaccataaac accgtcccat ctttttctgc ttcaatctag    49800
gtgaagcaga tctttggctc taaaataatt agaagtatca tcttaagagg caaactaagt    49860
atagcttttt cagaaagctc taacaccatt ttaaatgtct gagaagagag agccctaagc    49920
tgcttaaggc atgaatgtta ttttaagggt ttttctgagt ttgtacctgt ggtcactgcc    49980
tgtttagctt ctgaccttag tgaaacttga tttcattgga gaattatcca ctttgtgttg    50040
tgattttatg gaaatgtttg cagctgcaag ctgtgagagg agtttggtat gaatgtgaaa    50100
gtactttggg taaaataagc ccattacttt ccagagtgtt ttaggtagac agcagtacct    50160
atcaggcata cttaccaaca ttgattctct ctgggggaga ttagagtaca aagaactttc    50220
attctctgtt atatatataa aatattttgt ttgtttgttt gtttcaacaa gtttatatta    50280
cttttataat cagaagaact gtgaagaaaa cttttatttt taatgttcat atctcttgga    50340
ccacatgggt agtggtttaa tagttttctt gagagatgta acagatatct ctgtaggatg    50400
acaaaagctg tggatatgtg ggccagagaa atggacactc atatatgttt acaaaatttt    50460
atattcattg tcaaacactg gattccttga agcctatctg tggatcccga ttaagaactg    50520
tcctatgaat ggatcattag ctatctttct ttcagtcaag agtttcccctt tggtcatttc    50580
```

```
ctatttagtt taccagccaa ttgcagactg gcttatgtcc gtgtcacact attggaacta    50640
tttttctttt ttttttttt ttttcttttc tgagacggag tcttgctgtc tgtcgcccag    50700
gctggagtgc agtggcgcga tctcggctca ccacaacctc tgcctcctgg gttcaagcaa    50760
ttctcctgct tcagcctccc cagcagctgg gattacaggc atgtgccacc acacccagct    50820
aattttgtat tttagtaga cagggtttt tccatgttg tcaggctgg tttcaaactc        50880 ctgacctcgg gtgatccgct cgcccccacc tcccaaagtg ctgggattac agacatgagc    50940
caccgcgccc ggcctgcagc tgtcttttct aatgtcacta gtaaccttt aatgatcagc     51000 attccaccgt tgcttttctt tttttcttta gccccagttt taatttattc cttcatgtca    51060
tagtttatgt atcattgcaa actcccttaa ataatctctg aaacaagata ctgattgaca    51120
aataattata cttgtttcac atttttcaac tcaaatttat gtcagactgt attcgcctca    51180
tttcaatcaa caaatattta ctgaatgttg cttatcatgt ccaatatgat acagttgtta    51240
aaaatacatt gtctaggacc agacacggtg gctcacacct gtgatcccag cactttgtgg    51300
ggccaaggca agtggatcac ctgaggtcag gagttcgctc catttcccac ttctattcta    51360
agggtttata gttactttgc ccctctaatg aacttgaaac tgtaccgtat ggtagattac    51420
agagtttgca tcatctatct acatcatgct ggatcttaaa tgccatgctg aaagaggttg    51480
gactttattt tggaagtcgg tgtttcttta acttgtgtta ctcctaacac ctaatcttct    51540
ctttaccctg aagtctccag gggaaactga tgtcccacga aaatattata tatatatcct    51600
gtggcttcct atactgcctg acataatatg actttcttct gaagtacctc tgtctcaagt    51660
tcgaagagaa caactgggcc acctgccttg gcccccaaa gtgctgggat cacaggtgtg     51720
agccaccgtg cctggtccta gacaatgtat ttttaacaat tgtatcatat tggacatgat    51780
aagcaacatt cagtaaatat tgttgattg aaaagaggct aatacagtaa aactatagag     51840
ggaactttaa atcctacagc taataggctg attttgaaag tgaaacataa aatgttata     51900 taaattaagc ttgtttcagg atgcaaaaaa aaaaaaacctc aagaaaaaaa gcagaagttt   51960
ttaaagaaaa tagcaaaagt caaagaaata aattacagaa catagaaatg gtggtgttga    52020
tgtttatata atacatccag aaagaagtag aaacttaaac ctaactttag aattagcttt    52080
ataaagctac acatacaaat gctataatat gtgagattga ttgggaaaac caggaattga    52140 attttttta ataattcttg cttatctatc tctctctagt tattgtgacc aactgaaagt      52200
ctcagagagt acccacgtgc tccagcccctt cctccccagc atccttgatg gcttaattca   52260
cctagcagcc cagttcagct cagaggtcct caacctggtg atggagaccc tgtgcatcgt    52320
ttgtacagta gaccccgaat tcacagcaag catggaaagc aaaatctgcc ccttcaccat    52380 cgccatttc ctaaagtaca gtaatggtat gctgccaggg aggatgtatt atgagggca      52440 ccaaagaaaa ggtggtggct ggtgaattta aatgaaagat tccctaggtc tggtcttagc    52500
tatgaagcta tggttttaac atcgtaagca agaatctgg ctttcaatta gcaaaaaata     52560
gaattgtgct gtaaatgtag cagcattaaa aaatagagta cctatttctg taacacttac    52620
tctctagtaa ggacttaggg ataaagataa taaataaagg gctaataagc aagagacata    52680
attcagaact ttgatgatag aataggaaat tgggcaaatg aaaagcctcc taaagaaaaa    52740
gggctaggac tataattag aaaaggagat actaagaaaa gatatatgga aagtttata      52800 aacaaaggta ttcactagat attttttaca gtagtaaaaa tttggaaatt ataaaaagac    52860
attagttaat tatatccata aaatgaaata ctgtgcagcc attaaaaatc aagcttaaaa    52920
```

```
ggaatatctg aaaccatggg aaagagctta cattataata aatgaaaaga tactttccc    52980 aaaaaatcca tagaatatga tcccaagttt tgattttct tttagaaaag catgtatgta    53040
tagataggta tgttttaaaa aaaaatacat caaaatgttg agtgtttagg tagtggaatt    53100
acaggtgttt tcattattac ttttctgcat tttaagtttt ttttttcctg tagtgaatgt    53160
atttattaat accttattac tagtaaaata ttaaggattc tttttttaaa gagagagctc    53220
caatattgaa gctcagaaag atgtacagga taaggattat ttatataatg tgatatactg    53280
aacatgttat ttgatagctt tttcactgaa aaatgtgtac tgaggagctt ccacattgt     53340 gttcttggat atatctcatt cttttcagcc attactaatg ttccataaaa tgggtatatc    53400
ataatttacc cattctgtta atggacatct agggtattcc caatttttt ctattacaaa     53460 caatgctgca gtgatctttt aaggtatact ttaatgcaca ttgcctatat ttttccatac    53520
taaatagagg aggatgtttt gttctataga taaagaagat tgagctaaag ttccctttct    53580
tcataaggct ctgcttttta ggagttttgc cttttgcccc agaagtagct ttgagagttc    53640
ttcatgtcta ccgtggctac cccataggag atatgtatga tttctctcat gcatcaaagc    53700
cagtgttttg gcaattttg cagctttcat gtcttcttaa agtatcagtt gggctttttt     53760
ttttttttta agcatttggt tttataacgt aggtttcaca agaataaaga ctttaaagat    53820
ttttctctag aaaagccac attttgtttt atgagtagct gttaatgact agtccctact     53880
ttaatgaagc catacaaagt gtacctcttg cagatttagg atctctcctg ttctttcagg    53940
ttattcatgt ggccccacta ggtcccgggt atgtgataag taatcaatgc agaagttgtt    54000
aacttaggtt agggccaaac aacaggcatc attaagcgag aagcagatgc agaccatcag    54060 gcaggggat tccgtgttgc cttatccact tcagatcccg tcgtcgcctc actggctcag      54120
gacatcttca aggagctgtc ccagattgaa gcctgtcagg gcccaatgca aatgaggctg    54180
attcccactc tggtcagcat aatgcaggcc ccagcagaca agattcctgc agggctttgt    54240
gcggtaagtg gccgtgtgtg tgtgtgtgtg tgtgtgagag agatctacaa gtgccaccca    54300
cagatgcatc tagctgacaa gaacctaata gcgttagaga ttcatggggt gattttgctg    54360 agctctttg cctgcaagga cagtgggtga ttctctgaag cttaagaaa atggcttggc       54420 ttggcgcggt ggctcatgcc tataattgca gcactttggg aggccgaggt gggtggatca    54480
caaggtcagg agttcgagac cagcctggcc aatgtggtga acccctatct ctactaaaaa    54540
tacaaaaatt agccgggcat ggtggcaggc atctgcagta ccagctactc aagaggctga    54600
ggcaggagaa tcacttgaac ccaggaggca gaggttgcag tgagtggaga tcgtgccact    54660
gcactccagc ctgggtgaca gagcgagact gcctcaaaaa gaaagaaaga aagaaatgg     54720 ctcttcttgt tccagaggta ccctcagtga attgaacaga gtgccacctt tacacagtgc    54780
cactaagtat gtcacctggt tatccaatcc actaccatgt actactgccc acccctatgg    54840
ctaatcaatt agtaagctat tatgagaagg ctgagagtac tacccattta attattcctt    54900
ttattttgga aacttgcctt tcattaataa gctttctctg ggttgctatg taatacccat    54960
ccagtaagga tcttggttgt tgggcaaccc ccaccccaga ggcaattctg acttttcttt    55020
ttcttctctc tttcagacag ccattgatat cctgacaaca gtagtacgaa atacaaagcc    55080 tccccttcc cagcttctca tctgccaagc tttccctgct gtggcacagt gtaccttca      55140 cacagatgac aatgccacca tgcaggtatc tgagacatgg agagtagaag agggaagata    55200 gctcccccagc catgggctta tactatgctg agaaatctga catggttta tgcttttgaa     55260 atacggaatt ctcaactcca tatttactta gcagattcag gaagggttca gtctgcaaaa    55320
```

```
gccaagcatt tctggtgctt tggagcatgt tacagttttt aaaaatatgg ataccaagca    55380
ccctgcccat ctgtattggg tattgctact gtgaaagagg ttacagacat ctagacttgg    55440
ggccataaga aagtctttct gcatatttct tctagtaata aagtcagcag agtgatgggc    55500
ctctagagag gggagacatg cctgaatatt ttttctcttt ttgtttcttg ggtgaattgg    55560
ttaccttttc aggtgtctgc tactgtgatt gattagaaag gttataggaa cttgccagtg    55620
aatattgatc agcttggaaa tccctaggca actagtggtt tgtgtaagac ctatataaag    55680
acctacagta tccccagtta ttccaagatt gtaagcatat ttttttagta ccagaggtag    55740
acctttatga ttaaaattca ttttgcttgg ccattgtccc ttgtgattaa aaaaatatat    55800
atacacattt gtgagatagc tgattaggta aaggggaat tatgtaatgc acgtctatgt    55860
ctgtaacagt aaatgtctta actccagtgg tatgagccca ccacaaacat tatagactca    55920
ccgcttttat gaggcatagg cctctgggaa catttgttta tacagactga gggccttctg    55980
gcatctgtcc ctcgattact aatcttgctt gccaccctg tctccccaga atggcggaga    56040
gtgcttgcgg gcctatgtgt cagtgaccct ggaacaagta gcccagtggc atgatgagca    56100
gggccacaat ggactgtggt atgtgatgca agtggtgagc cagctcctgg accccgcac    56160 ctcagagttc actgcggcct ttgtgggccg ccttgtttcc accctcatct ccaaggcagg    56220
gcgggaactc ggggagaatc tagaccagat tcttcgtgcc atcctcagta agatgcagca    56280
ggcagagacg ctcagtgtca tgcaggtaag agagcagtgg ggagtgggct tcctactccc    56340
tggctgataa aaatgaaaat tcgtattttg gtcctgagtt attttatttt accctcttac    56400
tagccttgta ggacagttaa gtaaaatggg acctgtctga tctgtttggc ctaagaaaca    56460
tggacaagga aatctcccat gttttcttgt cctgtggata ataccctcag tgtagactgt    56520
atttcttatc tgactggcca gttccctctc atctcctatg tctctgaaat tgatttccct    56580
gaagcaaatg tccttatttt ctcctagtcc ctgatcatgg tgttcgctca tctggtgcac    56640
actcagctag aacctctctt ggagttcctg tgtagcctcc caggacctac tggcaaacct    56700
gctctagagt ttgtgatggc tgagtggaca agccgacagc acctgttcta tggacagtat    56760
gaaggcaaag tcaggtagaa cctcatcttt cttttctggg cattctgcca ccactcatat    56820
ttcttttttt tttttttttt tttttttttt tttgagacag tctcgctctg tcgcccaggc    56880
tggagtgcag tggcacaatc ttggctcact gcaacctcca cctcctaggt tcaagcaatt    56940
ctcctgctcc tgcctcagcc gtccgaatat tacacacatg caccaccata cccagtgaat    57000
tctttgtgtg tgtgttttta gtagagagag ggtttcacca tgttggccag gctggtcttg    57060
aactcctgac ctcaagtgat ccacccactt cggcctccca cagtgctggg attacaggtg    57120
tgagccactg ctcctgacac atatttcttt tttttcctga tttgctccat tgattttgt    57180 ttgacatttc aaatggctct ctgtattccc ttttccctgt cttctttat tgctaacgca    57240 catatgtgaa tagctgccat cttgaaatcc ccaaaagaca gtcaacacag gtagactata    57300
tatttctggt ctctgtttac aagagatccc ttctctacca cagacttcac acagctaagt    57360
gctgctagtg gcttatttc ctttataagc ccaagccttg gccaggcaca gtggctcaca    57420
cctataatcc cagcacttta ggaggctgag gcgagcagat caccggaggt caggagttca    57480
agaccagcct ggcaaacatg gtgaaacact gtctctacta taaatacaaa aaatagctgg    57540
atgtggttgt gggtgcctgt aatcccagct actcggagg ctaaggcagg agaatcgctt    57600
gaaccaagga ggcagatcac gccattgcac ttcagcctgg gcgacgagcg aaattgtctc    57660
```

```
agaaaaataa aaataaaaaa cccaaccttc taaccctggc ttcctaactt tttatcctgg   57720 attttttatac cactgattct tatcacctcg ttgcacctta caatatggtg caaccttagc   57780
tttgttcaag aagaacaggt cacctgtaat cccggcactt tggaagactg aggtgggcga   57840
attgcttgag acccacccgg gcaacatggt gaaacctgtg tctaccaaaa aaatacaaaa   57900
attagccagg cacggtggcg catgcctata gtcccagcta cttgggaggc tgaggtggga   57960
ggatcacctg aacccaggga ggtcaaggct gcagtgaacc atgatcacac cactgcactc   58020
agcctgggtg acagaatgag accctatctc aaaaacaaca acaacaacaa caacaacaaa   58080
aaagcacaga tctcattaaa ccacctcatg aactctaaaa tctcattttc agctgaactc   58140
tcttagctct cctaattagt tgttaacgga attttcacta tcaaatagag ggtcttagga   58200
cataattgct tatctccttg gagtgaactc gagatgggcg gctgattgac ctttttttgg   58260
atcttccttg ccagctctgt ggcactctgt aagctgctcc agcatggcat caatgcagat   58320
gacaaacggc tacaggatat ccgtgtgaag ggagaggaga tctacagcat ggatgagggc   58380
atccgcaccc gctctaagtc agccaaaagt gggtgctgct gcgattcttc caatcctctc   58440
cctatacgaa ggggctaagg atacctgggt gaagggaagg aatgcactgt ggtgtatatt   58500
tttaaaacaa ttgttggtga tgggtttgat aagaagaag caggaaactt aggtaaaagg   58560
gatcagaaca tacggtttct tcctgttgtg gaaaatggac aaaaataggc cgggcatggt   58620
ggctcacgcc tgtaatccca gcacttggtg ggaggccaga gcggatggat cacttgaagt   58680
caggagtttg agactagcct gaccaacatg gtgaaatccc gtctttacta aaaatacaaa   58740
aattagccag gcatggtggt gggcgcctgt aatcccagct acttgggagg ctgaggcagg   58800
agaatcgctt gaacctggga ggcagaggtt gcggtgagca agatcgtgc cactgcattc   58860 cagcctggac aacaaaatga gactccgtct caaaaaaaaa aaaaaaaaa aaatgcaggc   58920 gtggtggctc acacctgtaa tcccagcact tgggaggcc gaggtgggtg gatcgcctga   58980
ggccgggagt cgagaccag cctgaccaac atagagaaac cccgtctcta ccaaaaatac   59040
aaagttagcc aggcatggtg gcgcatgcct gtaatcccag ctactcggga ggctgaggca   59100
ggagaatcgc ttgaacccgg gaggtggagg ttgcagtgag ccaagatcac gccattgcac   59160
tccagcctgg gcaataagag caaaactctg tctgaagaaa aaaaaagac aaaaatagtc   59220 tcaggcacca agcatcccag cttccagctt cattcagaag cgtgggcaca gatagtcagc   59280
atgtctttgt tactgagttg cctttggcct gtaactccaa tgatttgcag gtagggagta   59340
tagagctgct atctttaatg tagatttata attacctccg ctgtctctca aattctaagt   59400
cattgggact ggagtactgg ctctatacag ttccttggtt tcagagcttt attactaaca   59460
agactgtatc tcctttaatc cctgaactct catctctccc agcttctgaa ctgttacaat   59520
accaaacaat aaagttattt aactttaagt cactcttggg agactggata tagtcaggta   59580
cagtgaaagt ctgaggggtg gtgaactctg gtgagtggca ctgaggagag gacagggta   59640 cttccagaag taagctcagt gacactctga cttgaaacct ttttcttcct tcccagaccc   59700
agaacgctgg acaaacattc ctttgctggt caagatccta aagctgatca tcaacgagct   59760
ctccaacgtc atggaggcta atgccgctcg ccaggccact cctgcagagt ggagtcaagg   59820
tgcaccaggc ccttactccc aggagacttt tagcctggca gatcaagtta caaattgtca   59880
aattatcaac ttggttttgtt gagtcactaa ttgaaaaaaa aagttgatgg aatggctgct   59940
ctgtggctgg caccatgcta ggcactaggc atgtagagct gcttctccag tctgccatat   60000
gaaatctcac agaggctggg gtgggaggca gccaggaggc aagctaacat agcccttctt   60060
```

```
tggtttgatt cttcttaaga gcctgtcaac acttatatct ccaggttctt tcattgagac   60120
taaccaggag ggtttggcca tttctgattc tctttcactg gggactacaa gccacattgc   60180
agaagccttt ggggcccttc tattctggcc tatttggatt tggggaggga aaatgcatga   60240
atgtgctcta gctctagctg cttttcatct ccaagtagat gactccaatg atatgtggga   60300
ggaccaggag gaggaagagg aggaggagga ggatggttta gctggccaac ttttatctga   60360
cattcttgct acaagtaaat atggtaagct gtttgataag aggacagcca tggtaaatac   60420
cttttctttg cacactgatc ccaacagtgg ggtacccaag aaaggggaga ggtgggccca   60480
cagggacatt tcttgggctt ttgcaccttc cgcctcagtc atgtggtagt atatcaccac   60540
tcagggcctg atcatgggcc tttgtcctga cccgccctgt gttggctatg tctaacagag   60600
gaggattact acgaggatga tgaggaagat gaccctgatg ccctgaagga tcctctctat   60660
cagattgatc tgcaggtgag ggtgtccaga gatatcttgc aaatgacaat gtcccaggcc   60720
atggaaacag gaatatgggc tcaaatccat ttatagccag gcatggtggc tcatgcctgt   60780
aatcccaaca ctttgggagg tcaaggcggg aggattgctt aagcccagga gttcaagacc   60840
agtctgagca atgcagggac accctgtctc tacaaataat ttaaaaatta tctgggcata   60900
gtggcacacc cccgtggtcc cagctactcg ggaggctgag gtgggaggat cgcttgaggc   60960
caagaggtca aggctgcagt gagctgtgat cataccactg cactcgagcc tgggcgacaa   61020
agcaagaccc tgtgttcaaa aaaaaaaaaa aatccattta aatttaaca tgggagcctc   61080 atgggaaaga gttcctgtct tgttgagtgg tccagggttt tgggtgggct ggaactttgc   61140
acttgatgtg ttgtaattca tcttctagag gctatgttgt gaaggtcctt ggggtgatac   61200
agccttggaa aaatgttgtt tccctgtgga ttacctaaac tagatccaag aacatgaaag   61260
accatccctc agggagctgg catttgtcta aaaaccagca ttccctgtgc catttgattg   61320
tggttcttgc tccactgcaa atgggtgact tgcaatgtct cactaatgcc actcttgctc   61380
tttcctccag gcatatctca cagatttcct ctgccagttt gctcagcagc cctgctacat   61440
aatgttttca ggccacctta atgacaatga gaggcgagtt ctacagacca tcggcatcta   61500 aaaagggag cctttctaca tttgctcctt ctgggccagc cgcaaaccat tttgcagccc   61560
tcactggcct tgagatgcac tttcttctca acctaaagtg gcatcttgac ccttggccct   61620
tggcctcggc agtgacactg atgacaattc agaccaggct caccggtgcc gtcacttagg   61680
aatgctggaa caaaggacat ttctcaaagt tcccctgaag acatgccatc tctagaacct   61740 ttttctccc cgactctacc cccacctctg ttcctagagc cctctgctgg cgagtccaga   61800
aacattattg cccagaagga ttatgtgttt atggattatt ttgccccgcc tcaggagcgc   61860
aggaagtcac taccatttat attctaaaac agacctatct atgttcatag gacttctgat   61920
gtgttcagat aggaatcctc atgagagatc attatgcttt gtgccctgga ccactgctgc   61980
tctgggttct caggaggaac aggcaagagc agcttcattc taagcctttc cagtgacctc   62040
agccttgctt ctcttctaca acactaaggc tcctctgtca gaggaggtcg tcttgttttt   62100
gcttcattgc atgacataac ccttcccctc aagctgttcc tatatataca tgcacacaca   62160
aaataagcca gacagatggc aatttgatct tcctttttta gaaaaaaaaa aaaaatggg   62220 gaaaagggat ttttttaaa tccacctgac ccaactatat ttaatatgcc tctcccacac   62280
attaccacag agtctgatat tcaaaggtta tccccttttcc ctcaggaagc ctctaaagtg   62340
cttaagttgt agccctcaaa tttgcaacat gtattttttct aggacagtaa agtaatcttt   62400
```

```
acaaatgaat ttagttgcat ggtataaggt gtctcagcac ctgtttgcct tctattccct    62460
ttagaaggta agtaaaagta atgggggaaa ggattaggtg gagcctgtct aaacattcta    62520
gtgtgtcttg gcaaacatag cctgaaatga ttcttaaaga actggcattg tttaatcaaa    62580 tattttttaag ggagattcct taattgggaa gtttagtctg tttggggttc aaagagtaaa   62640
tgaggattag aaaatcatgg agagaggctg ggcgcggtgg ctaacgcctg taatcctagc    62700
actttgggag gctgagatgg gcggatcact tgagatcagg agtttgaggc tagcctggcc    62760
aacacagtga aacctgcatt tctactaaaa atacaaaaat tagctgggca tggtggtgca    62820
tgcctgtaat cccagttaac ttgagatgct gaggcaggag aatcgcttga acttgggaag    62880
cagaggttgc agtgaaccga tatcacaccg ttgcattcca aggcaagact caatcacaca    62940
cacacacaca cacacacaca aatcatgggg agaaagatga aacctgtgtt ccccttttt    63000 tggtagtgcc cacatctggt gccccatttt taataaccac aggatatttc tttagattga    63060
tattctcaca aagaagaaat agaatatagg ctgggcgtgg tgtgtcacac ctgtaatccc    63120
agcacttacg gaggccgaag ccagcggatc accagaggtc aggagttcga gaccagcctg    63180
accaacatga tgaaaccctg tctctactaa aaatacaaaa attagccagg catggtggca    63240
tgcacttgta atcccagcta ctcgggaggc tgagacagga gaatcgcttg aacctgggag    63300
gcagaggttg cagtaagcca agatcgcacc attgcactac agcctgggca acaagaggag    63360
cgaaactctg tctcaaaaaa aaaaaagaga agaatataaa agtgaatctg aatctccact    63420
caaggggatg gccccaagga tattgtagct ggtaatttct tcatgccact aggtgtcccc    63480
agtgttcaac ctccatgact gagattggaa gaagtagagt taaaagtttt tactacctt    63540 gagaagcctg cgggcatgtt cacagtcgtc ccatgccagc caggttctga ggctaactgc    63600
ttgtgcccct gctgcttcac atggcattgt gggagttgct gatactgggg aaatgatggc    63660
agatctgacc aagtggtgct gagaaaacca ccctcggcct tgcagactcc atagtttatc    63720
tcaaggcagt gccagtcgga tttggtgcta aaggcataag gccaagtcag cctctgatat    63780
tggcacaaaa gaatggtctc atgccagtag cattgaactg ctgagcttgg gaaggcttaa    63840
ggctcccaca cacagactga gaatgatggg ggtccctctg cgtctgctaa ttagacaaac    63900
attctatatc tagtgccaaa agtggtccta aatcctttgg caagggtcct ttctgctctc    63960
atgctgattt gggggaggac tgggcatcct gcctcaggag aacttgagtc ctgaggaaag    64020
ggccctagta acacttaagg gctaccctg gctaacagat actcggctgt gggtgagagc    64080
agaaggtctt ggaccctcg atgtgcaggt acttaattgt gtttccagtg catttcata    64140 tacattatcc catttaacct ttataacagg ttcacagagt ggatattccc attctgttga    64200
tgagaaaaag agtggagaga ctgtgtccag tgtcagcagg aagaaaaag atctgttgga    64260 ggccagtaca tgttgacaga aactctagac catattttgt ctcctgtctt tggccaaaga    64320
gaactagctt cagtctgaaa agggcagggc taagtggtta caaggaacta aaaagttcaa    64380
ggtaagacaa atgaggtaaa aataaaaaag agcacttagc tgctctgaga cattttagtc    64440
tcctgactgg taaacagcag ctggggcacc aaggggctcc caggagtttg tcgagctttt    64500
attggagtga actgaaagga aaatggaagg aatgctataa gactgaaaag aagttaaagc    64560
cctaggaagg aagctgataa cacaagttac agacgtatat gtgacattga tttgggagaa    64620
tgaacctaca acaaatgacc caaaagcacc taaataagag tgacgagagt ttaacagaca    64680
ttcattatgg acttcagaga aaatgatgct aaactggtct tagaatcttc tttaatttg    64740 ttaactaggt aaataatctg gacatttag tcaaagcatt agacagacag agaagttggt    64800
```

```
aactgaccac taactaacaa actataaatt cacccattgt gggttgacct ggtaagttcc    64860
cccagggctg tgtccttggc ccctcctttg atattagtga cagatgactt tttttatgcc    64920
ttacccattc cacaaaagaa tttgaagcca tttacacaag agatagtact agtaaattag    64980
gagtgctgat caaattttta gataataaga aacccttagg aaggatgaca atttagaatc    65040
caaatttagg atccaaacaa ataccattac aaactataaa aatgagcaga atctaaatgt    65100
aacatttcaa taaatgcaga ttgataataa catctgtgca gagttgagga ctatagagta    65160
ctgtgctgtc actaacagta ttgtgtgcta ctaagagttt aatggctggg tgtggtggct    65220
cacacctgta atcccaacac tttgggaggc ctaggtgggg aaatcagctg agatcaggag    65280
ttcgagacca gcctggccaa tgtggtgaaa ccccgcctct actaaaaata aaaaaattag    65340
ctgggcatgg tggcacgtgc ctgtaatccc agctactcgg gaggctgagg cgggagaatc    65400
acttgaacct gggagacaga ggttgcagtg agtcgagatc acaccattgc actccagcct    65460
gggcaacaga gcaagattct gtctcaaaaa ataaagttta ttatgccagg agggccaggt    65520
gtggtgccac acccatgtaa tcccagcact ttaggaggct gaggagggca gatcacttaa    65580
gcccaagagt ttgagaccag tctgggcaat gtggcaatac cttgtctctt aaaatttaaa    65640
ataaaaaaaa agtttattat gccaggaact gttaatgtgt ccaaaaaaac tccagtgtgg    65700
ttctaggatg agataataaa aacaggttgt ctagggtagt gtggaaggtc ctttcagtct    65760
tcctgtgcct atcagtgatc ctcattgcca tgttcccttc tggtgctcaa ccggaggctc    65820
cctgacagat gagtcctctg ccagaggaag gctaagatgt agaggacaaa tcgtgtcaag    65880 gaaagaagc ttgaaggagc taagaatgct tagcttagag aagacaagag gaaacaggac    65940
atggctttgg gaagttcaag gatggtccag tgaaatacat actatacttt tgcacccag    66000 ctaagctgac ccatgatcag taagtaggaa ataaaaggcc aatttctggc tactcttgcc    66060 cccaaccca tttcagtgaa ctatgaacct ctattagata tgcaaggccg gtgctaaatg    66120
ctggagggct ttggcccttt ccctcaagga gctagtctag taggggtca gaaatacaga    66180 tgggcctgaa cataatgatg gtttgacttc cagtttttca actttaggat tgtgcaaaag    66240
ctatacacat tcggtagaaa cagtacttca agtatccata caatcagtac agtattcaat    66300
aaattacatg agacattcaa cactttatta taaaataggc tttgtgttag atgagtttgc    66360
ccaactgtaa gctaatgtaa gtgatctgag taggtttaag gtagcctagg tgtattaaat    66420
gcatttttca cttaacggta ttttcaactt ttgttgggtt tattgggatg tagccccatt    66480
ataagctgaa aagcatctgt agtataataa atgtggggag tgctgtgaga gaataagtg    66540 tactgggttt agttcccact gcccaaaaaa ggaactggct aatggtaacc tgggggagga    66600
agtcgggtaa gttgcatgga gaaggcaacc cttgaacact tgcaaggagc taacaatacc    66660
tgcttctgga gtatttaaac gccagtgggt atgctaaata cttttacctc agaccaccta    66720
ctaaccttac aaagtagtcc actttgctca cccagttta cagattgatg aaactgaagc    66780
agacagatat tgttaaccta tcaaaggtca ccctgcaagt gtgtgattat agtccaagca    66840
gcttgtactt gttgcctatt tgttttgcct ttcctgtgca tttgccaggc agatgagagt    66900
ggggtaagac attgcagaga aaagtaaga aaaggccgtc atgaaacaat tcattttca    66960 gaccttataa gcacgttaca agtactgata tttatgctta agttcacggg agtcctggcc    67020
agaaataaag ctggaaggac aagtgggggg cagattgtga aggatccttc aagacctgct    67080
tcctctagag aatgggagac tacccaagat aactaaacag ggaagtgatc aggttttgtg    67140
```

```
tcttagaaaa gtgttgcagt gttgatgcaa atgtgactag aagggtgact tggaacctgg    67200
attgaagggg tgggagatgg gagaaaggaa tgcagtctgg cagcagctac agcagtccag    67260
gtgggaaaac ccagagcctg aactaaggtt gtaactagag gggatagggt ggaagagctg    67320
gattagagat gttgacaaga taaagtcagt aggacttaaa gactgacaag taaggatttt    67380
ccaaaagtga gagctgtgga atgaattgtc ttaaaatgtt gcagtgagtt cctcctcatc    67440
aatccaagtg ctcgatcaga ggctagacct ttagttagca gtcacgggaa aattccccat    67500
tctcacgggg atttagacta ggtcttaacc atactttacc aagattccag tagcaaagca    67560
cccaaaagta atcgcaataa aattccaatt tttgtaggcc gggcatagtg gctcacacct    67620
gtaatcccag cactttggga ggccgaggca ggcggaccac gacatcaaga gttcaagagc    67680
agcctggcca gcatggtgaa accccgtctc tactaaaaat acaaaaaaat tagctgggca    67740
tggtggcgca tgcctataat cctagctact caggcagctg aagcaggaga attgcttgaa    67800
cccgggaggc agaggttgca gtgagccaag atcatgccac tacactccag cctgggcgac    67860
agagcgacac tctgcctcaa aaaaaaaaaa aaacaaaaaa aaaacaagt tttgtgaatt     67920 taagtttccc taatggatgg tacaggtcaa catttgccat ctaatgacac ttacattcca    67980
gttttttcct tttttgagta actgggaaaa gggtggcatt actgctggct tcctaaaatt    68040
gaaaagtata ctagggtttt taaacctgtg tagaatacat gatatggtag caaatgtgct    68100
gtaggaagaa aagcaatgag gaactactgg cctgactagg aggcctagaa gtccctccca    68160
ggcttgagtt gttctgactt ggcatgatta catagctgcg gcaagtgacg tttccttcaa    68220
gccttggttc cctcatctgt aaaatagggc actaataccct acctcacagg attgtagtta    68280
gaattaagga tgacttcatt aaagcacctc tagtggtgga agatgtccca tcctatcccc    68340
cacccatagc tgggagctat gtttggctca ttcttcctga ctcactggat tacactgtga    68400
ctcagttcaa tttcacacat gctgctgcta aattagggtc ttggtgagcc tttgggagga    68460
cagctctgag gaatgaattg tagcactgca gccctgcctg aggaacatga tagaaacagg    68520
tggtaggccc agctcttgcc ttccacctac taagcagttt ttctgtggtt agctgtgtga    68580
cataaactat cggtgtatta atttgctttc actagattcc ccccccccca acaacttagt    68640
ccaagaacat acctgaattc tttgcatttc cttgccttag ttgcttttgt agggtggaca    68700
gcaggactgc atgagaatag ctgtgcttct ggacccctatg gtgaaagctc tagtgaactg    68760
caattaggcc cagggtcccg gaggaagaag gggagagaaa aagggggggta gttttccaaa    68820 agataagtag gggacaaaaa agtccacggg gcctatgagc ggtgagactc ctgccctgat    68880
tgtggcaaag cacctggaga tgatagaact tcctagggaa aaggctgcat ggagtcccca    68940
gggatgctgg gccctggtca ccaaggctcc ctgggaaggt ctcttgtacc tggggcacac    69000
agaccaacac ttctgaattt gcaagcttaa gagcatgtat gagcagaacc tgtgcagacc    69060
aaggcttaga gggctcacct caatgttttg cactgtgtga gaccccagga ccttttcgtg    69120
attctggaga ggggaacaaa ccataataac aacaaaccag gtagcaggat agagactcat    69180
tctcatctat tttggttaaa agaaaataaa tgtatttctt ccacacctga ttttgtgatt    69240
gcaaattcat aactaatatc cctcgtcagc tccgctgact catccctgcc acagggaggt    69300
tcacagcaag agcacagaaa ctagggccag tgcccggttg tgtgaccttg agtaagttct    69360
ttttcccttg aacagggaga gagacacaat ggatcagagt gtctctgcca gttctaactt    69420
ggggattcta gtgggttgaa ccgaacggta gtccgtttcc aaaagaggaa gccaagacca    69480 gaggggggagt ggttccttca agtttgcaga accagtaagt ggcagagcag gactcatatc    69540
```

```
tagttagtgg ttcagagcat gggctccgga gctagactgc ctggatttga accctggctt    69600
tgccacttgc ctgttgggtg actttggaca agctgcttaa attatgtctc catttcctaa    69660
tccacagaac aagtgtaata ctagttatct gtttcatgga gtgattgtga ggattaaata    69720
aagttaatat aacacaaagc acttcgtagt gctgcctcat agtaagtgtt aatgttacct    69780
attattagtc tgatcccaag tctaatgcag ttgtcaccac ctaaacctgc ctttacagag    69840
ctggcctttc tgagaaaccc tgtgcctctg tagattcaac actcccatct gtgcagatgg    69900
ctaacagcta ggctgaaaac agaaacctta ggttggaaag ggtcagctgg agggctgagg    69960
cccatggccc caaatcctcc ccaggagaga gagtaggttc agaaggaga gagctataaa    70020 cagagccttc ctcccttgcc ctcagatccc aaaataacac ttgtctaccg ccatcctgcc    70080
caactggcag agtggcaggc tgagtaaggt gccatttaaa gataacctgg ccctcaccat    70140
ctgccccact ggctgggctg ggctcctgag gccaggcctt ggctgcctgg gactgctgct    70200
gctcccacag ccacccagag tgtgcctgag taggggctg ctcacagctg ccatccaagc    70260
cagcctggct acaccctctt ctttcctgag gcccaggctg tcctgggctc tctacaaaca    70320
agcagaagcc tggcgttctg ggagaggcaa tcctacaaag gcattggtag aaagtccttc    70380
tggagaagag tgctccatat atatatatat aaatgtatag gatacttgtg caactttgtt    70440
acatggaaga gtacaccttc ttaccagtag cttggcagca gtgaggctca tcctcactgt    70500
ccttcaccca ccctccactt gctagtccct cccaccaaga ggacaaacag gagacagtct    70560
ttcatttaca gcaagaaaga ttaaagctgg atgccaagaa aagcattctg atttaagaga    70620
gatgtttgtt tattccgggg cagtgagagc caaaagacct ggttcccaa ctaagccatg    70680 agacttggcc aagtcctggt gctgtcctag gccttactct tcctagctgt ggactgcaag    70740
gagaattaat gtgtccaaga ccctccagga aggatctgac attaaatcag agtaaagaac    70800
tcagggtcct atggagtggg ggaatgtata attacctgtc tgcaggagtt gggttgccag    70860
aggctgggca aggaggaata gaaaaaagga gggcagagta atgtagagtg cattcctgga    70920
gagcactgac tgaccagagg caggaattag gaaaggaatg gagtttccct tatcttggaa    70980
tggttcaaca aaccactggc cagacaaaag tggaggcagg agcctccacg gccaaacagc    71040
atgggtgggg taggaccagg gtgggatgga gcctccaggg ctcatggccc aggaaagtaa    71100
ggaaggcctc aggaatgcct gtgttagtct gctctgatag aggagcatgg aagaggttgg    71160
gaggagccct gggctggtca ttcagcccag gagtgaggtg actcagcaga gcactcctac    71220 cacagccct agccaagccc aaactgggtc acaggcaggg tcccagccct tcccctcctc    71280
ctgcctttcc ccacttcaga tatccctggc taccttctca ccacatgcag aggcctgcta    71340
gagataaggc ctgggcatca aagtttccct gaatacatgc ttttatgcc aggcatagca    71400 ctgaacattt tagacttgtt tttttgtttg tttgagacgg agtttcgctc ttgttgccca    71460
ggctggaatg caatggcgat tcccgggttc aagcctcccg ggttcaagtg attctcctgc    71520
ctcagcctcc cgagcagcta ggattacagt catgtgccac cacacccagc taattttgta    71580
tttttagtag agacggggtt tctacatgtt gatcaggctg gtctccaact cccgacctca    71640
ggtgatctgc ctgccttggc ctcccaaagt gttgggatta caagcgtgag ccaccgtgcc    71700 tggccctta gacttgttta aagagaagca ggtggtgaag ctgaagggcc tgggctttga    71760
agccacaaaa gtccaactgc aaatcccagc agtgtgagct gggggaattg aagttcttcc    71820
aacttcagtt tcctcatctg tacaatggga tgagctcatc agcaatgttc gctgctggtg    71880
```

```
gtatcattac catcatattc cagacaccct gaggagaacc tcctactggc aaagcctatg    71940
ttttgtctca tctgatcaca aattactctg cctcctcttt tccaggaaag cgtttctttc    72000
ccttgctggg gattaagaga ccagcttggt gagcgggggg tattcctgcc tgcccttacc    72060
tagagaaggt gtagtgaagc ccttccaggc ctgaagattt agacaacttc ttccagggcc    72120
cccagtcctc ccacccaagc ccctcctcac tcctggccaa tctacagact cttttcaagac   72180 ccaggttcat tatggcgaca taagctagcc ccagctctcc atctccgagc tccagcatcc    72240
cttgtcaagg taagaagtgc cagttctccc agtgcagcca gttctcccct ctggttggcc    72300
cacagccccc tctcttcact ctctgtccta gtctagtcac ctcccatccc atgaactgaa    72360
acacattctt agaattttgc aattagaaaa tcactgatga tgttggtgcg tgctaggtgt    72420
cattgcaagc tggaagtgtc aactaggggt atacactttg aggagggcgt gtcaactagg    72480
ggtatacact ttgaggaagg ctagttggag aaaaaagcag gaaagtagct agagagggat    72540
gagttttagg aaggatgtgg tttggtttgg tttgctttgc tttgctttgc tttaaatagg    72600
agagacttga gatttcctag ggaaaagaag ctggtaaggt gtgagaagct aaagacacta    72660
aagagatggg ataatgaaga gacaaatcag caggggtcaa gggtacacat gggagattca    72720
gctctgggca ggaaagacag tcccttatct gaagatgatt caaccaacaa tgacaacact    72780
gatggctagg gctggatggc cacattgaac acagccacgt ggtccctgca gtcatggagc    72840
ttttagtgta ggaaagagga gatggatggc aatgggcaca ctgagtaggt ggtgctggat    72900
tcagaggcgt ttctctttgt ccctgctgct gcatttatga ctgtgtcctg cgtgaggaca    72960
tactcttgcc catcaggcta ccagcaactt tctgggcag gagcctatcc tctcctattc    73020
cagctctctt gggtaggtgt gccagcaccc acaggggccc aggatgggt agctcctctt    73080 tcggctgtcc ttccctaacc tactaagatt ctactgggcc ttccatggac ctgtcctgat    73140
tctctcaccc cagaacacaa gaaatactca ctgtctacac tgtctgctgt tgcggctggg    73200
gatcaaccct gatttagatt tgggtcttcc tgatgcctct accatttact ggctgtatta    73260
ccttgaacaa gttctttaac ctccatgagt cctagtttct cagtctgtga aatgcgattg    73320
ataacactga tgaaccttgc ttagttcatg gagttgtgga aagattccag tgaggtagat    73380
gtggaagccc agaagtgtgt gaaagggtgt acatggcagg ggattaaggt aggcttttga    73440
tgatctccct ggcttaattt gcagttcctc ggagggtacc tcatgtagca tgggcatag    73500 tcactggcac tcagtataaa cctgtgaaga ctgacctctc ccatcctaaa acactgtctc    73560
cacctggaat taactgttgc ccacctgaaa ttaactgttg ccctccctat gctccggtgg    73620
ctattgcagt acaggcttgc tctgtgaagg ctttcactg tgaagagtgt ttaactggat    73680
gggccccagg tggccccagc agcctgcctt ccctgctagt gaggccatgg gctggtgcat    73740
gccagctctg tccacttgaa gggggaaggg tccatcgtag ggagccagtg cagctggcag    73800
ggttcaggcc tgtgggcacc gctggggaca aagccactct gaatgcctct caatgagtgc    73860
ttgtgttctg ggaatggggg cggggtgaca tccagcctct ttccctctcc gcccccgaca    73920
ggatgtccca ggctggacgc ggcagaggag gtcccccaca agtgaaggtc cagccctgct    73980
cctccagggt tggcccatgt gtctgggcat tcggaggtgg caccaggatc agggcttctg    74040
gagtccagca tagtgattgg gcccaggccg ggggcgggtc caggacacag ccaggcttcc    74100
ctggccgcag tgcccaactg cccgcagtgc ccatggtggc tcggatggga ggaaccaccg    74160
cggagccggg gacaggggga gcagggcagt gctctgctgg gtgaggggca cccagctcca    74220
gaggctaggt gggcgtcgct ggtgggtgga ctcctgggcg ctgcgcggag ccgcgccggc    74280
```

```
tgggttagcg cgggcggggc gcttagtccc accccccagag gaggcggaag aggagcccga   74340
gcctggccgc gggctgggcc ccgccgcagc tccagctggc cggcttggtc ctgcggtccc   74400
ttctctggga ggcccgaccc cggccgcgcc cagcccccac catgccaccc gcggggctcc   74460
gccggccgc gccgctcacc gcaatcgctc tgttggtgct gggggctccc ctgggtaagg   74520
ggatggggag agatgcggca ggagtgggat ggggcggag aaggggagg gaccgatccg   74580
aggggcttgg gctcggggct tctccgagac cctccggctg ccacgggagc cttgggtgtt   74640
gctgggtcct caagaagcgg gaagagggag ctccaggatg ctgggccatg ggaggctgat   74700
cccgggtgc agggtcagct tcaggcagag gcctcggggg ctctgggct gagaccctca   74760
gggtggagac aaggggcaac cctcagtgtt cgggagccgt caggctgggg accgccgggg   74820
gagtggggcc gagcgcggct ggggatgaac tggcctggtg gccactgggc acccccaatc   74880
cctgcccgca gtgctggccg gcgaggactg cctgtggtac ctggaccgga atggctcctg   74940
gcatccgggg tttaactgcg agttcttcac cttctgctgc gggacctgct accatcggta   75000
ctgctgcagg gacctgacct tgcttatcac cgagaggcag cagaagcact gcctggcctt   75060
caggtggggtt cctgcctcct caccctcacc acctcctcta tccttttctc cagaggcctc   75120
ctcttcctcc ctcccggact cctgcctcct ccgttgtcga cctccacatt cttagctgaa   75180
tagagtcacc aggactcaag cctggcggca gagctaggtg cttaggtgct ggtgcctggg   75240
agttccagaa aaggcatgtt agttaccttc ataggctttg actgggcccg gggtttccag   75300
gttcttctg gagccctccc tttggtcctg ccaggtcatg gggagggagg gttcaaggtt   75360
aacacccgga cgacagtgta gctttgtgga agaagctctg gcacaaaggc aggagacttg   75420
ggtttgattc ccaggtccac ttcttactag ctgtgtgatc ttggagaaga cacttgcctt   75480
ctatgggtca ttgcttgcca aattagtggt tgtcaaactt ttttttaata tatcatatat   75540
aaaatagata tagagacttc tgattgaagc ggggtttgga aaaatggct ctagattatt   75600
tctaaggctc ctttcagtgt tatgctgtat gtctaatcat ttaagttgta gatataaaag   75660
caatggtttgg gggcgcactg caaatccccg tatgcttcac actagccagc caggcagcat   75720
agccttctgg gaagtggagg tcctctaaga tctccttcac agggactggg cagagcccca   75780
caaggaaccc caaatctcag catgccatgg ccccccctgct ggccaggagt tggagccagc   75840
ataatgagga ctccgtccta tgagtgttgg aaggtgagag gacctgttct ttgtctaaag   75900
ccccaagacc atagcaggca tcgcctcagc tgtgatcctc tttgttgctg tggttgccac   75960
caccatctgc tgcttcctct gttcctgttg ctacctgtac cgccggcgcc agcagctcca   76020
gagcccattt gaaggtacac ccagtactgg gcaagaaggg cctcagatgg gctgggctaa   76080
gtccaataat gggcagcaga gagttcatgg attgggtaaa ttctgtagta gtatgtgctt   76140
ctgtatacac acacctgcca gcatgaaaac ccagaaaaat gcttgtaaac ccgtgaatat   76200
tagaatgtgc ctgggatata tggaacatca gactttgtgt gcatttctgt gcatacacat   76260
gaagattcaa atgtgtacag gagtgcagtc tgtcaacaat agtgggtgca gtgggtgtat   76320
gcatacatat gactcttagt aagtacacgg ggtcaggtct gtagtgatga acattaattg   76380
agtgtgctcc agtggatggc aaaatatgtg cctgagtgtt ggcatgtgat gcacatatgc   76440
cacaacctga tggacatggg gacagtgatg ccatacggga gatcagtgtg ggagggaagg   76500
gctaggagaa gaccctctta gtggcagctc tgctggatta caggatacca gccctgagct   76560
gtccccttct tgcccaagtg agatattccc tgggctgtgc tccctggttc atgaggtctc   76620
```

```
tgaaacctgc tgaggggagc aaacttgctc aacacagatt gaccagctgg ggccacgtgc    76680
acagctccct gcttaactct gccaagcagg gtgtgggagg caaagatggc cagcctggag    76740
cttgccagag gccagcacca gggtgcttac cttggtttcc tgggcaggag gaggaggctt    76800
cccataggag atgggtctct gaatgctgat ccttctcccc catctaggcc aggagattcc    76860
aatgacaggc atcccagtgc agccagtata cccatacccc caggacccca aagctggccc    76920
tgcaccccca cagcctggct tcata                                         76945

<210> SEQ ID NO 3
<211> LENGTH: 68637
<212> TYPE: DNA
<213> ORGANISM: Homo sapiens

<400> SEQUENCE: 3
gcgcaagggg agaggccgag aggtctcatt cccattctcc cctgtagggc tgactctctg       60
acttcaagat aggaataaaa ggaggaggag tctgctacac ccaccatcaa gtgcgctcac      120
agtatttact caaccagtga caaggagggc caaacaagg gaaaaatcct agaactgcag       180
caagacagat gggaatcaca ctagaggagg gacttcccag ggcatctgag gtaaggtgta      240
aaatctctgc cttctcctcc ctaaatgtcc ccacaactga gtccagtgca atacagcctg      300
aagatgatag atgggtgaga tggcatatgg aagccccatt gcaggcctct gatgatgggg      360
gtcctcctgg ctgagtagct tttcccattc tggaagggag gtcctgaatg tgctaggagt      420
tgtgagagat gactggaatt ccagtaactt ttggcaggat ttactactgt atctggatct      480
ttgggattga gagaggagca agaagctgac actgcctact gcaagtggct ataaagccat      540
tctcacggtc ctgatgcaat gctcaagata aaagcaagt gagtaattaa taactaggtt       600
gtgaactaac ctcttgctcc aaggcatagt accatttgc acaatccatc caggcctgcg       660
ggaaggagag acactggcct gagtccaggt gtctgagcag gaacaccagc cccagactcc      720
aaatgaagct ccagaggaac agaaggagtt ggtgggaagg gcccctctgc tgggcttcag      780
ggccagaaaa gggagaagga acaaacacaa gtagtggcag agcaccatcc agtcatgttg      840
gccaaatgat gcctcctttg ttcagtaaga agtgaagaga gaatgctaga accgcagccg      900
ggcgtggtgg ttcacgcctg tatcccagca ctttgggaag ccaggcggga ggatcacttg      960
aggtcaggag ttagagacca gccaggccaa catggtgaaa ccccatctct actattaata     1020
aaaatacaaa aattagccag gcgtggtggc atgtgtctat aatcccagct acttgggagg     1080
ctgaggcagg agaattgctt gaacccagga ggcggaggtt gcagtgagct aagattgcac     1140
cattgcactc cagcctgggt gatagagtga gactctctct cagaaaaaaa aaaaaagaa     1200 tgctggaaca tcccatttgt tccctggctg tccagagctg ttggtgcagc agatgaaaca     1260
gcacttgcaa gcagtcacac caaggtgtgc ttatcatgtg tactgagtct agaggacctg     1320
cagaaggcac ttggtctgca tttggagcaa agagcgccct ccctctacct cccttcttca     1380 caatacccg ccccctgcga cactcctctt cccatttgta tatccttttt tgttttttgt      1440 tttttgaga tggagtgtca ctctgtcgcc caggctggag tgcagtggtg cgatctcggc     1500
tcactgcaac ctctgcctcc caggttcaag cgattcttct gcctcagcct cctgagtagc     1560
tgggtctaca ggtacacacc accacgccca gctaattttt gtattttgg tacagacagg     1620 gtttcaccat gttggccagg ctggtctcaa actcctgatc tcgtgatccg cccacctcgg     1680
cctcccaaag tgctgggatt acaggcatga gccaccgtgc ccggcctcca tttatatatt     1740
ctttcccacg tttttttct tcttctttcc cattcccagt tactctttat tgtttaacgc      1800
```

```
cctcttttcc tagactttt  tcttttctcc tttaattaat tagttaatta ataaatgaat   1860
taatttcagt ctctcccagg gcttccatgt acagttgtac atgtgattca cttcccaagc   1920
acaaataggc atgcctcatg gttgcatcta ccttgttcta agctgcataa aagcactata   1980
tggaccagca gtagccctgg cactttctgt gggccaggta ttgtgccagg cacatagaaa   2040
tacttcctgt ctctcacttc ctgtattcca gtggactctt ctcctcctat ctccatttta   2100
ctcttatgcc taccccagga ataggttttc tggaaacttg gtggagtgca agatcacag    2160
actctggagt cagacagatt tgggcttgct ggtcaactct gcccttacta gccttaaact   2220
ttgggcaaat tgctgaactt cgctgagcct aggttgcttc ctctgtaaaa tggatattac   2280
agtgtccata tcacgggctg tgagaggatc agagaatgct tggtttagtg ttggacatac   2340
agcactaaat catcattttc cccctgcccc ccagtccctc cacacctttc ccctctgtc    2400
ccccagcccc tggctaaggc ctgctgcctg tttctgtccc cattatccca ccagtctgtg   2460
tccgcttccc catttcccac tctttgaaaa tagccgtccc ttgcatggaa atggagccat   2520
tttcaaagca cttccataag cgcctcacat ttgctcctcg gcactgagag tgggcaggaa   2580
gggaatcgat tctgcaattt atgggaggag gttcaagcag tggagattaa gtgacttcca   2640
agagctccat ggctaccgag tgcaggcct  ggactagagc ttggggccca ctccccttca   2700
caccgagctc cccttccaag gataaaagag aagaaagaga gtggcacctg aagtccacca   2760
cattcagaac ctcacctcca ccattcctgc cttgagcagc tgagcagcag aggagggcca   2820
agaccctgga gaagctgcag caccagagtg ggtgggcagc agaccgctat cacggtccaa   2880
ctgccagggt cgaacaggaa ggctgcgccc tgtcagagat gctgagatca gaccacaagc   2940
atgatagcat ctccaaggcc tcctagctgt tggaagggcc ttcctcttct cactcacttc   3000
tcctagattg gatacaacac cttggtgata gaagcctcat cccatggct  gggcacagtg   3060
tctcacgcct gtaattccaa cactgtgagg ccagaagttc gagatcagcc tgggcaataa   3120
catagcaaga ccccagctct ataaatatat ttttttaatt agccaggcat gatgtcatgc   3180
ctataatctc aactgcttgg gaggctgaag tgggaggatc acttgagccc aggaggtaga   3240
ggctgcagtg atctatgatt gtgccactgc actccagcct gggtgactat gcttaggtgt   3300
gtgcacatag attgtagctt gttcacatga atattccttc ctgggcttta tagttttaaa   3360
agtggtttca tgtgcagcat gtcattttgt cctcacaatg accttgggag acaggtatca   3420
ttatatgagg gaaatgtaaa cttagagaag tagtggctcg cccacgaagc cactcagtgt   3480
tggaacacgt cctcaacttc tagttatcca tccagatcta ctcctaagga agatgaccca   3540
aggggggaaga ggctgctgga tgcttggaac tggggatgct gagaaaggac aatgttctac   3600
ctttgttacc tgagaagtct ggtaaaacag gacttttctt ccctgcaggg agcagggcag   3660
tggtgggggc tcggcccagc cctccagact tcccagagat ggtggaggaa ggacaagggg   3720
aaagaaggaa gcattcaagt ggtgggctgg ctgcacggcc acactcctgc actgcactgc   3780
actgtgccct agccccgca  cttaggaggg cagccggtgt ttcctcctac tttcaacttc   3840
ctgttcatcc ccagtaccct ggcctttgca aggacagagc ctttgcgttt gcatttaaat   3900
tcctgtccct tctctgcaca gccctgtgaa tttgcacaca tacccccacc cccaaggcca   3960
cacagcagcc ttcttcaatg tcgttggctc catcagccct ggtgtctctg ccacacgaag   4020
ggggagcctc ccacggtgat tataagctcc ctagagagag agacctgtca ttaggagcag   4080
actttccacc tccctgaagc ggctggctct cctgcttttc ctaagaataa tctaccaggg   4140
```

```
ctctcgcaga ctgcccgcct acatggggcc tgcagtgcgg atgtgcaaca gcctctggga    4200
ggagagaggg ttcccagggc tcccacttgg ggtgggtcgc ctctgtcttg gagagctgat    4260
gtctggaagt ccagctactt taaccatgcc accctcccta ccttctggag aaaactaagc    4320
ccaggaaaaa gggaggtcag aggagctgcc acagggcaag tggctcctgg gggggcttcc    4380
ctctgtgggg gcttccctct gggggctcct tccctaaaac gcttaggagg tgtacagctc    4440
cctcaagctc tctctgggct ccaggaggct ggcagtgcct ctgcagccag aggtaaaaca    4500
gaaccttctg aagcatgcag cagagagccc tgaaagagaa acagtcccct gaggttggcc    4560
tgtcctctcc ttgccaccat gcagtctctt agacaagctc cttattagaa tccgtaaaga    4620
gtcagatggg aaatattgca ggggctatat ggtctccatc gcaactactc acctctgtgc    4680
ttgtagcaca gagcagccac agataataca gaaatgaatg ggtgttgctg tgttctaatg    4740
aaactttatt tatgcacact gaaatttaaa ttcatacaat tttcatgtgt catgaaatat    4800
tcttcttctt ttgattttttt tcaaccactt aaaaatgtaa aaccattcat cgctcaggga    4860
ccatacaaaa cccagcagtg tggctgggcg tggtggctca cgcctatgat cccagcactt    4920
tgggagaccg aggcgggtgg atcatgaggt caggagatcg agaccatcct ggccaacatg    4980
gtgaaaccte atctctaata aaaatacaaa aattagctgg gcgtggtggc atgcgcctgt    5040
agtaccagct actcaggagg ctgaggcagg agaatcgcta gaacccagga ggcagaggtc    5100
acagtgagcc aagatcacgc cactgcactc cagcaagact ctgcctaaaa aaaccaacca    5160
accaaacaaa aaacaaaaac agaaaacaaa acaaaacaaa acctggcggt ggcctggatt    5220
tagtctgtgg atggtggcat tctgtttatc cctccatcag ggttgcctcg tattgcagcc    5280
tccttaaatg aagagcatga tacagttgat taaaggaatg gaggcaagat tattgtgtaa    5340
cggcacccag actctgttttt actatctctg gataaccacg tggattattt ttaatccata    5400
tctattttgc actttcatgt aattctctcc tcctcaccac aatcttagaa gctaagcgat    5460
agcatttctg ttttacagat ggggaaaatt aaattcaaag aagtaaagta acttgtctgg    5520
gattacacag ctaatatatg gcaaacctag gatgcaaacc taaacttgtc tggtttatttt    5580
tgttcctata cttggttttc tagtctccga ggccagcgtt ctgcccacaa atgggccttc    5640
tccaatctca ctgcaatatc agagggattc atttatcacc cagtgaaata tttggctggg    5700
tgcagtggct cacgcctgta atcccagcac tttgggaggc tgaggcgggc agatcacgag    5760
gtcaggagtt caaggccagc ctgaccaaca tggagaaacc ccgcctctac taaaatacaa    5820
aaaaaaaaaa aaaaaaaaaa tagctgggca tggtggcgtg cgcctgtaat cccagctact    5880
cgggaagctg aggcagaaga gttgcttgaa tcccggaggc agaggttgca gtgagctgag    5940
attgcaccac tgcactccag cctgggcgac agagtgagac tgcgtctcaa aaaaaaaaa    6000
aagaaagcca gagtacgaga ggcgtaaatg gggtgagata agtgggcaga aactagacca    6060
tatgtatttc attctcacac aacaggaaga cattagaagg agtcaagcag aggagtaaca    6120
tgatgtaatt gacttaaaaa aaatttttttt tgagacagtg gcttcctctg ttgtccaggc    6180
tggagtgcag tggcgccatc atggctcact gtagcctcaa cctccctggc tcaagtgaat    6240
ctcctgcctt agcctcccta agtgctggga cttataggtg ggagccactg cacctggcca    6300
taatgtacat ttttattttt attatttatt tatttatttt tttagacaga gtctctctct    6360
gttgcccctg ctggagtgca gtggcgtgat cttggctcac tgcaacctcc gcctcccaga    6420
ttcaagcaat tctcctcaac ctcccgagta gctgggacta caggcacacg ccaacatgcc    6480
cggctaatct tttgtatttt tagtagagac agggtttcac catgctggcc aggctggtct    6540
```

```
caaacttctg aacttgtgac ctgcctgcct cggcctccca aagtgctggg attacaggca    6600
tgagccacca cgcccggtct acccataatg tactttttt ttttttttga gagggaatct    6660
cgctttgttg cccatgctgg agcgcagtgg catgatctag gctcactgca acctctgcct    6720
cttgggttca agagattatc ctgcctcagc ctcctgagca gctgggatta caggcatgcg    6780
ccaccatacc cagctaattt ttttgttgt tgtattgtta gtagagacag gttttgtcc     6840
tgttggccag gctggtctcg aactcctgac ctcaggggat cctcccacct tggcgtccca    6900
aagtgcaagg attacaggcg tgagccacca tgcccagccc cataatgtac atttttaaag    6960
gtcattttgg gaggtataaa tttggctcca gttaggacct gagaggtgcc agaggcagga    7020
agagtagatg agagcaggaa acagagactc gagagcctat aagcccgact ttttttttt    7080
ttttttgag acagggtctt gctctgtcac ccaggctgga gtgcagtggc acaatcataa    7140
ctcactgcag ccttgaactc ccaggctcaa gtgatcctcc tgcctcagga gggatcaata    7200
aaaccagtga aaaagtaat gattggcaca agaagtttg aatagaaca gaaaatgtgc      7260
tgtgaccact agagtggtgg ggagggcctt gaatgaggtg aagggctct tttagactgg    7320
ccacatccaa agcaaactct gtctctatcc tcctccttct atctcccta ccccatgccc    7380
actctggagg aggcaagacc ggaggcccaa agggcgatgg gagagagaac tggcagacca    7440
cgcatccagg agcacagtgg cctgttgccc ctggtcacca ccaccactgg cttcaaaggc    7500
cagggctct tcccagccac atctctggct ccaggggaa gcaggaggaa gtcaggagct     7560
gggaggtgcc agaggcagga agagtagatg acagcagaaa acagagactc aagagcttat    7620
gatcccttc tgttccaaaa gacgcgaagg gaggtaaccc atgttcaaaa gaaacaagag    7680
tgggaacaag gaaaggaggg ttctatttcc ccccattcca gtggcctagg gctggggaac    7740
agtcccatga tgggatcaaa aggtcaagtg tcttcgtgag atcaaaggta gccctgggag    7800
gagggctgtg cagggccagg cactttctgg aaggcgttgg agggaccaag gactttggct    7860
gcttggggtt tggaatctga agaggggtg gtttggtgga tggtttgcat ttgctgggct    7920
ggaggagagg ggcaggcgag catcttgtcc aacacaccct ggtagctgct ccaaagaggg    7980
atgcacactg tctgtgtcag gccttaata aagtaaggag aagctcacct tgaaagcaga    8040
aaaaacagag tgtggagtac ccagccaagc agtaactgaa ctagtgaccc cttgggccaa    8100
accctatttg tgaattcctg ctctgctttg aggcaatccc tatgctccaa agaggggcc    8160
tgcatctaat tcagtccact tctgagtcca gtctccctgc ctgagttcag tctgtcctct    8220
gtcttactcg tatgccccct acaagctttc tttaaaccaa actccttttc agaggtcttt    8280
cctgactagc cagccccaaa atctttttct tttttttctt tttttgaga tggagtcttg    8340
ctctgtcgcc aggcaggagt gcagtggcac aatcttggct cactgcaacc tccgcccccc    8400
aggttcaagc gattctcctg cctcagcctc ctagtagct gggactacag gcgcaagcca    8460
ccatgcctgg ctaattttg tatttttagt agagacaggg tttcaccaca ttggccaggc    8520
tggtctcaaa ctactaacct caggtgatcc gcctgcctca gcctcccaaa gtgctaggat    8580
tacaggtgtg agctaccaag cccgactttt tttttttttt tttttttgag acagggtctt    8640
gctctgtcac ccaggctgga gtgctgtggc acaatcataa ctcactgcag ccttgaactc    8700
ccaggctcaa gcgatcctcc tgcctcagcc tcctaaattg ctgggactgc agacatgagt    8760
cactgcaccc ctaatatcta ttacttcttt acttgccatt agggtgggga ggcagaaagg    8820
aaactaatat tcattcaggg actactgtga gtcaagaact ttatgtatcc tattttactc    8880
```

| | |
|---|---|
| attgctcagg actcttatga gaaagatact attatatctt cattttacag gttagaaaat | 8940 |
| gtagtctcag agagattaag taatttgcgc agaacacaca gctaaaaagt ggtggaggcg | 9000 |
| gggtttgaat aaggtgttcc caaagcccct gctgtcatca ctgttagagc tgcttcagga | 9060 |
| ttcctgtaac ctgcatgtat atcatttcac acactgtccc atgccatgtc cactgtcact | 9120 |
| ctcacccata tattatcatt tgttcactat atgtaatttt ggcctcctgt agtcccaact | 9180 |
| gcttaatact aatcatgacc atgcgtcctt tgatcaatcc tttcatcaga ctgagccttg | 9240 |
| attttttggct cattgttcgt ggaaatgacc accccccacc gtcattcttg ctttcttccc | 9300 |
| tactcccacc tggactacag tgctagagca gattgtcctg agtcatttcc aaggaacact | 9360 |
| gactgaggat ctgatgtgtg cccggcacga tactggcact ggatagacaa gcatgtaaaa | 9420 |
| acttgatgtt catataaaaa tgaactgtca cataaatgtc catagcagcc ttatttgtat | 9480 |
| agctccaaat ggaaaacaac ccaaatgtcc tttgacaggt gaatgttcaa acaaactctg | 9540 |
| gtactaatat accacagatt actactcagc aataaaaagg aatgaactat atcttttttt | 9600 |
| tttttttttt tttttttttt tggacagagt cttgctctgt tgcctaggct ggagtgcagt | 9660 |
| ggcatgatct cggctcactg caacctctgc cttctggttt taagcaatta tcctgcctca | 9720 |
| gcctcccgag tggctgggac tacaggtaca caccaccacg cccagctaat ttttgtatat | 9780 |
| tttgtagaga tgaggttttg ccatgttgcc cagcctggtc ttgaaccccct gagctcaagc | 9840 |
| aatttgccca cctggcctcc aaagggctg ggattacatg tgtgaaccac cgtgcccagc | 9900 |
| caggaatgaa ctattgattt atgccatgac ttggatgaat ctgtagggaa ttatgccaag | 9960 |
| agaaaagcca atccctaaaa gtcacatgcc atatgattcc ctttatataa ggttttttgaa | 10020 |
| agaaaatttta gaattggagg gcagaatagt agttgccagg aatcaggtac agaaagggga | 10080 |
| atgggaaggg aggaagtgtg gttttaagac ggcaacataa gggacctctt catgttataa | 10140 |
| ctgttcagaa tctggattga ggtggtggat actcacatgt gggtgatgaa attgtataaa | 10200 |
| actcaacaca cacacacata caggtacaaa taaaacagga atctgaata aggttgttgg | 10260 |
| attgtatcag cgtcaatatc ctggttgtga tatttttactg tagttttgca aaatgtcatc | 10320 |
| aatgggggaa actgggcaag tatacaaggg atctctctgt attgtttctt ataactgcat | 10380 |
| gtgaatctac aatgatctta ataaaaagtt taattcaaaa aaagacttga ggccggtgcg | 10440 |
| gtggttcagg cctgtaatcc cagcactttg ggaggccaag gtgggcagat cacttaaagt | 10500 |
| caagagtttg agatcagcct ggccaacatg gtgaaaccct gtctttacta aaaataaaaa | 10560 |
| aattagcctg gctggtggt gcacacttgt aatcccagct actcaggagg ctgaggcaga | 10620 |
| attgcttgaa catgggaggc agaggtggca tgatccctca gtgagctgag atcacgccac | 10680 |
| tgcactccag cctgggcgac agagcaaggc tccatctcaa aaacaaaaca aaacaaaaca | 10740 |
| aaataaaaca aaacaaaaca aaaaccaaa cacaaaagac ttgaaaggtc tcctgccctc | 10800 |
| aaagggcttg tactctcaac tgtgtttccg gtttctttct tctgcctgtt tctcttatct | 10860 |
| agctgaatgc catcgatgca caacaaatga ctgtcctgat tttcttccgg gaagacattg | 10920 |
| ctaaatgatt ggtgaaggac catatattca ggttactcct cttcctgatt tccccaatcc | 10980 |
| cagtctcttc aactttggca ttttattttt ttaaaggaga attgggaggt gggaagctct | 11040 |
| tagaaccttc aggataaccc tgtttcttgt ttgtgtttga cctgttcatg tgtatgatag | 11100 |
| agaaatagag aggcagagta tgaaattttt gtgttttttg gagggtgggt ggctgaaaga | 11160 |
| gaagaggcca gagattttct cttgtgtaat cccacattgc caggctccca gctgaccagc | 11220 |
| ttccatctca ctgtaggtgt tgaagagacc atggaaccac tgtgggtctc tctctctctc | 11280 |

```
tctctctctc tctctccttt ccagtagtgg aaagaggaaa ggtgcccaga accctcacat    11340
cctggaatct gctccatgag taacctctct agggaaacag cagcccagct gtttcctgga    11400
ccggtaactt ctctccccag ccccctcac ctatagtccc caactgactg ttttctgaaa     11460
ccacctccca gagactgtgc tgactgaggg aggccctgga gggagaggaa gatcttgcag    11520
ccttgtcctg ggacttcagc caatctcccc tgcctccccc actgtgtccc tgccccaac     11580 cccagccaag cttagagcag ccggctctgt ccccagcagc tgtacacagc aggggtgggg    11640
gacagtcaca ctccctcact cctaggctgc agctgagggg ctgtgaataa aaagcttggc    11700
ttcctcaggg gtctggttga catccagcct gtatccacca cctaatccca tcctttgctt    11760
gggttttctc aacgtatcca tgtcctggcc atgcccagtg gcaggtctgg aggctcctgc    11820
tggcagaagg aaatggttcc tgtctccagg tggggccggg cacccctcaa gagggttggg    11880
aaggcaagaa gtagaagcag ctgcttcctt ttttgtcctt cccagatacc catgatgagg    11940
gggcaccagg gacttgggtt tcccagctta gctgagaaac tatttccttt cattaaagag    12000
gcatgtaatt agctggggga aatgggagga ccctggagag tgaacacatc ctttggtgca    12060
ttgacaagag aggggctcca gagtgatgag aagcccctgt ttcagccccc caccctccca    12120
aacacacaaa aattccacac tctgcctctc tgtttctcta tcatacacat gaacaggcca    12180
aacacaaaca agaaacacta ggtgtgccct agggtacata gaattccaaa aatcttgctg    12240
cattaggagc actgtgcggc aggaggcagg cagatgcaag cccagcccca gctgtaagtc    12300
ctagttgtgc gttcctagag gtgctgtgcc tcctcgtgat ccttttcttc ctgcttctag    12360
tccaggtctg ggttgccaga tggactgcag tggtcaaggt gaaaaagcag aggtttcctg    12420
gggctcctta agctaggcag ggcaagtggg gccaagggtt gggcttcttc tcttgaaggc    12480
agctttgtcc ctcgctcttt gataagacct atagaatgaa aaactcaaga ccaaatcact    12540
agaaaaaaaa ttgtaggaaa cacttagatc agtgttgtca attgaggcaa ttttattccc    12600
cagtggacat gtggcagtgt ctgaacactt ttcttttat tttttttaat aacaactaga     12660
aggctgggcg tggtggctca cggctgtaat cccagcactt tgggaggctg aggtgggcag    12720
atcacaaggt caggagttcg agaccagcct ggccaacatg gtgaaaccca tctctattaa    12780
aattacaaaa attagcagcg cgtgatggcg cacgcctgta atctcagcta cttgggaggc    12840
tgaggaagca gaattgcttg aaaccgggag gtggaggttt cagtgagccg agatcctgcc    12900
actgcactcc agcctgggaa aaagagtgaa actctatctc aaaaaaacaa aacaaagcaa    12960
aacaaaacaa aacaaaatga ctagggaaga gagtgctatt ggcatctgat aggtagaggc    13020
cagggttgct ggtaaacatc ctacaatgca caggacagct ccccaaaaca aagaattatc    13080
tgtcaattcg tgctaaggtt acaaaatcct gatttcggct ggggtggtgg ctcactctat    13140
tgcactccag ccttggtgac aagagtgaaa ttctgtctca aaaaaaaaa aaaagaaat     13200 cctgatttag ataaaccaac atttgtctga ctccttatga taaaaatttc tcttcctcc    13260 ccatcctaca ggaaacaaaa aaaagcccc acaaaactgt ccacttaaca atatattact     13320
tcctgatcac tttgggtcaa tttttcttct ctcaagaaaa aaaaaaaat ggaagcaaag     13380 ctccccacta acaaaaaatt tgtcctccac ctagctggca gatcagcttg catccccttc    13440
cacagtggca cattaaaaaa aaaaaaaaa aaaggagaaa cacagccaaa taataaaaca     13500
atatcttctg taagtaaaga gtacacccct gtttacctgg tcgccactgt ttattctgaa    13560
agactacact aagcaaatac tgagcctgac agctaggctg gaggggaggg gtctctaggc    13620
```

```
cacaaaggtg caaagccctc tttcagatcc atctccacca tttcccttca ggatggtggg    13680
tgcaggacca cccctagcca tgagcaactt gagttcctag agggaggtgg tccttttctt    13740
catgcttcat gcttcttgtt cactttctat tcaccatcag ctcttcccta cctccccgca    13800
agactgagag cctgtagttc tacaaggctg acaatcaaga gtctatccac ctatgtgtgg    13860
atgtggatgt gaattccagg cctccccacc acactctgac tctgctaagc ccctgtaggg    13920
aggcggaggt gagccaaaag ctgactggtg ggaaataccc agtgtggcct gtcttcctct    13980
ccaaggctca aataaactca agtcatctgc accaagggag caagggaaaa ggaacaagaa    14040
agctgtgtgg ggttattctg catctcacct gcccaccacc tgcccttccc tccttttag     14100 gaatccactg cagcattgga gagagaggcc taagagggag ctcactgtac tcccaaccca    14160
tccctctgcc cagctcttat tattatggtc ccatttccta gggtagagct tccacattca    14220
gtgtctcaca aggggtacta gttacctatc atttccatca tgccctccac ccaccaccta    14280
accagggaga tctgaccagg caagagaatg ttgtgaggcc gacctgattg ttgcccttct    14340
gaatgttagg gcattccaac agagacctct gcctggctcc atccacaagt atcagaatgt    14400
cataagaagt gtgttgtttg ccagatagtt cacagaacaa gtataagtta acagatagcg    14460
tctgaagcaa ggcacccagg gaggcacaga ggaacgcagg agcgctgaga catggtggat    14520
ggtaggattc caacctgccc tccttttccc ttatttaccc agtttgcgcc atcatcccac    14580
cctccagaga aaatacggag acaggaacg tccctcggca gcaagaatga aaggtacggt     14640
ggctcagcaa ccaaggctgc tccttgtttc tgctactgat gtcctattaa cttcttatct    14700
tccagggtga agatattact gcaaggcctt ttgccaggca gttcatgta tgatccttac      14760 tacaaccctg agaagtagat gttactgacc tggttaacag tctcagaaac tgagactcag    14820
agagattgtg ttcccaaaga cccagctggt tagcagagag ccagaactca gacctaggtc    14880
cctgactttc tgtctagagt tttccccact gtttctcttt tcatctattt ttggtcaatt    14940
cactgctccc tgatgcttct gctggaggct ctatattctg ggaaacaagc gaaggcaagc    15000
aaaatgcagc caatcagtgc tgaccttagt caataaaaag gttgcagaca gttgtggttg    15060
tcaggctttg ttgcttaacc atctctagac ctctgtttct ttctctgtag attggggaca    15120
gtaatattac ctgtatctca tgggactgtg gtgaggattc aatgataaaa ggcaggacaa    15180
gtgctcaaga ggatgccttg aacatagtaa gccctcaata aagggagct gcggttacta      15240 ctaagacagt gttggagaaa gtacaagagc cacagttttt ccagggtaag aggtagatta    15300
ttaaaggctg atactgtata tgttctctta gctcctctct tgaacataaa catctgtggt    15360
ttgtcaaaga cattttcagg atccggtttt cttttagaa agaggaagga aaaaaaccc      15420 aaggcctgaa tctataggaa gtccaaatgc acccaggatt cttaagtcac aagataaaaa    15480
gtggagatgc ttgaagaggc atctgatagt ggaattcatg gaagaggaaa aggtcagttc    15540
catctctagt gactccaaca gagggatgaa acatccaaga atgaagaaaa ttatttccag    15600
gaatggcaaa tgaggatgga accataggat atagttatta ttgttaaacc aaacccagtg    15660
caataattgg tctgtctcaa taacatcact ccggccaagt tgccgtttcc aagaaggaaa    15720
gaataagaat ttagtccagc tgattcttcg gcatgattta aaccagcagt ggttgtcaaa    15780
ccttagtgtg cctcagaatc aactggaggg cttgttaaat ccaaactgcg aagtctcatc    15840
ccgagtttct catttaatgg attgggggtg ggacccgagt ttgcattttg aacaagctac    15900
cagctgatgc tgagactgct ggtccatcca gggaccacat ttcgagaacc actgatttaa    15960
agcacttttc tatgggcaat caaagaatat caaattgcat aattctttt tatttttatt     16020
```

```
tttgagacgt agtctggctg tcgcccaggc tggagcgcag tggtgcgatc tcggctcact   16080
gcaagctccg cctcccgggt tcacgccatt ctcccgcctc agcctcgcga gtagctggga   16140
ctacaggcgc ccgccaccac gcccggctaa ttttttttgt attttttagta gagacggggt   16200 ttcaccgtgt tagccaggat ggtctcgatc tcctgacctc atgatccgcc cacctcggcc   16260
tcccaaagtg ttgggattac aggcgtgagc caccgcccca gcctcaaatt gtagaattct   16320
taataccttg cttctcaata tgtataacag ttgcatttac ttattagcct ctctcctctc   16380
ttcagtcaca ttgattagaa aatgaatacg tgtttctcaa ttaagaatct tatggtaagg   16440
ccgggcgtgg ttcctcacgc cagtaatccc agcactttgg gaggccgagg cgggtggatc   16500
acgaggtcag gagactgaga ccatcctgtc taacacggtg aaaccccgta tctactaaaa   16560
atacaaaaaa ttagccgggc gtggtggcgg gcgcctgtag tcccagctag tcgagaggct   16620
gaggcaggag aatggcgtga acccgggaag cggagcttgc agtgagtcga gatcgcacca   16680
ctgcactcca ttcctgggag agagagtgag actctgtctc aaaaaaaaaa aaaaaaaaaa   16740
aaattatggt aaaacaggaa aaatcaagag caaaaaaccc aaaacaaaga aacttcctgt   16800
gcaagtctga ctgacataac aagaactaac ttggcttgtc aagtaggtag acacaggggg   16860
ctccagaagc agaggtgctt atttctcact ctactccttc accattgaac accttcagac   16920
tgagaattgg ccttgcctat gtttatctcc aactaagtta gcattctgac tccacaagaa   16980
tgttgtgaaa gcgaagcctg gggaaagaat gctatcctag ttttcagcta agttttctta   17040
atatcatact cttcagaggg aacaaaatcc agttctcacg accttaaatg ctgacacttg   17100
tccaaaaggc ctaatgaggg agaagcatgc gtcatgcaca ttaacagaac tcagtgatag   17160
aaattgggtt gagacaagtg aaaatttac caaagccaaa tgactagttc tatctccttc   17220
agcaagataa catgacaaga ggaacttcag acttctgaga gttatcttat caatccaaga   17280
agcacaaatg atgatcttag caatctagag gaagagggta ttacaagata acaggctcct   17340
gaccaaaatt tcagtattta tacagtctgt tactcaactt acataaatca aacttttaaa   17400
aacggcctct tcactatgtt gaaattgggt cttctttccc caaagattga agagaatttg   17460
cgggggatga gggcggtgtc tatcttatag cttgtccctg gggttcaatt gccaaaatgt   17520
tatcagtcta tgtaagggtc tcatgatagg ggccacccac aaaaagcatt ctagtgagac   17580
ttcagtattg tgagaacaca ggatgtcaca tttcatcagt aaaacagccc agctgagccc   17640
caggattctg tccccaatca tggctccagt aagttttgtg gcttcctttc tggtattgaa   17700
cttgaaagat caaggacaca aaaataggat gatttcatag actgaaaata tgctattgac   17760
aagtatttgt aataggtttc cagtccaaaa tgaatgttct ctcacttgta atatatatcc   17820
cataactaga aatacagttt gaaaccattg gataaaatta tttttttcct aggagaagct   17880
aaagaagcat tcaagatcca atcaataatt ctgtgtacgt acactgggaa aaaacaaaac   17940
aaaacaaaac aaaacttta ctagtgcagg tgacttggaa gttactgtca ctcttccctc   18000
ccctctaaaa ccatcctata ctgtgagctg gttaaagttt acctttctgc aagagtaagt   18060
gttcttacta ataaataact catttatact tcagagacaa agctaaaagg atttcagttc   18120
tgcaggaatg aggttttcag cccccataaa ccttgcctgg aggtacatcg ctgcttttgt   18180
ttgaggctag ttggtctaca gtgccaatag caacatatgt gcatagacag cctgtgttct   18240
aggcattaag tacccatggc ctcacttatt ctcataatgt ccttttggtt tgttttttt    18300 ttttagatgg actctcactt tgtcacccag gctggagtgc aatggcgcaa tcttggctca   18360
```

```
ctgcaacttc catctcccgg gttcaagcaa ttctcatgcc tcagcctccc gagtagttgg    18420
gattacaggc gcctgccacc acacctagct aattttttgta tttttagtag agacaggttt   18480
caccatgttg gccaggctgg tctcgaactc ctgatctcag gcgatccgcc tgcctttgtc    18540
tcccaaagtg ctgggattac aggcatgagc cacagtgccc ggcccataa tgtccctttg     18600 aagcagagga gaatcagtcc cttataatcc tcattatata aaaagaagaa acgagcatag    18660
agtgggaggt aggcggataa gctgacttgc ccaagatcac cctgtcgatt gatctgactt    18720
catctgcaac cagccacata gcttctccaa agcaggtcgc cagacaagga aaagtgattg    18780
ggggttcaaa taaaacaaat gactactcat gctatagtta gcacgatgtg ctgttctgaa    18840
ctctgctgtg gaacacctgt tgcacttttt atactattca catacattac ctggaatact    18900
ccagttttca acattgtctg cttcagtccc ttaaaccata gaagtatcca gacatgccaa    18960
tatcatgaga accaaactat accttaaact gttttttcctg ttgaggaata tgaaagaact   19020
cttcattgta gcacagatcc caattttttgg tggaatatag tcaccacaat tttcattgtc   19080
aataaatatt gctggctaat tcagaggtga cctgtggaag caacacgtgc tctaagaact    19140 cctgttttcca ctgtctggta ttattagtgt gtccttactt agacttagct ctcccagaga  19200
gagagccatc tgcttctctc attgcacagt gactgtgcaa tggtgttgac ttctagagaa    19260
gagtagccca agagctaaat attagaggtc ttattgcttc ccttaagtgc atggcaagag    19320
aaaggaaagc aaggtgagaa aaggactgac ttgctttgcc aatggcccag gactggtgat    19380
tttataaggt ttagcacaaa aaccactctt ttgaactaga tactgtgtat atcctgtgta    19440
cttcaagtca caccagcatt ccctacaaca gagcttagga atgctattta tcttgtactc    19500
aggccaactg tgtggctctc taccgaacag ctggttcccc atccacctct aggactatct    19560
agttgatgta taaacaatat ttttgcctca aaaacgctaa ccccatggaa actaactgtt    19620
catccacaca cacacacaca cacacacaca cgcacacata cacacacgaa ggaaaagaaa    19680
gatggggtta attaggtcag aagcaggagg aaaagacaaa acaggggag cttgggggttt    19740 gtaactgaga tgtggcatgc attagatttg aagtcaggtt actgaagccc cagattatgt    19800
tccaaggtct aaacagaacg tccattgagt ctttgattcc taaagacatt tagtgcctta   19860
taaaagagct tagctatatc attattcctg attaccttag aagtaaaacg atattttttaa  19920 agtgtttagt atttgtattc ctctaggctg aattagtgaa ccacaagaga cccaattttat  19980 agccacaaaa tgaggatcca gtgtgggtca ctgtctacac acttcttggt aaacaccagt    20040
gtttcacaat ctattttttcg ttatttcttt ttatctttta agagacaggg tctcattctg   20100
tcacccaggc tggagtgcag tggtgcgatc atagctcact gcagccttga actcctgggc    20160
tcaggtgatt cttcctccta agcctcccca gtagctggga ttataggtgc atgccactat    20220
acacagctaa cttgtttatt tgttttttgt agagacagga tctcactgtt ttccaggctg    20280
gtatgaactc ctggcctcaa gcaatcctcc tgcctcagct tctgaaaatg ttgagattac    20340
aggtgtgagc cactgcacct tatttttttgt taattatatt actacacacg ttcagttctt   20400
tatggatgag acacttctta ccagataacc aatcagctag ggttaccaaa ttggtagtta    20460
tcatatccta aaatttaggc tatcatttttt cttggatcaa tgactttcta tctccttcag   20520
agccttactt tacccatcta ccctaatctc ttataatcag gagagccctg actacatata    20580
gactgtgtat ttgtgtttct tcccaagatg gaaaaagtat aactattaca cacattgctt    20640
tgtacatcag ccaaggaggt ggtcttacac attctaataa aagggtttgt gtattcaact    20700
taatagctaa aacattacca ataataatat atatgtgtac tcttccttga tcaacctgtt    20760
```

```
ccttaaagtt agattttttaa acaaatccct tctgggtgcc agcttactgc taaatcaagg    20820
caaacaatta tttccaacat tttgttatca tagtttaaag taattatttg ctttattagg    20880
atgggaactc tggctgtacc ctctcactcc ctgaccccag aattaacaca gcatttattt    20940
cacaatattt gtgcagggtt tactattgaa ccagggggca cacccatgaa taatactgat    21000
ttctcttggt ggtgacccag ccaaagcatg tcaaaatgag tacctatcta ttctagtaag    21060
ataatggagg aaaagagaag caagtcatca agataaagga acacaaacta ccatattacc    21120
ttgaaaacaa atctaagtat ttgttgtgtg tgaacacata tcagtgctga ttgtacaaga    21180
aacaaggctt ttgagctgga aggcaatttc aaagacaaca cctgtttcaa aatagggcaa    21240
agagttcaca gctgcatttt gaaatttcag tctgcacttc tatttcggga tgttatccac    21300
ataggcttag gagatataaa gagggaacaa cacaagaaga cagatgtgca tgaatcaaga    21360
aattctattt cctatttaaa attcagaaaa gattgctgct acatacatta ggatgttaac    21420
tgggtacact gatcacaggg cttcgataac ccaagtaagt ggcaaggtgt tgatacactt    21480
gcagaatatc aactgagcct agccgacagt atctaaaaat gtcctgagcc tagtctgata    21540
gtatctaaaa atgagatggg gagagcaagc attccactac ctatggagga caaacactgc    21600
cctctactgg cagactgtaa ctgctataca gtcaacatga cgaacatttt cctcaacagt    21660
cactatcatg agacataatc agaaaataaa agcttttaaa taatttgagg ctttgtgtct    21720
aggggtcacc aggattttca agcaaaccga agtattcaat gagaaatctc cttactcatt    21780
gaagtttccg actttccccca ttaaatcttt gatgtaactc attggactgg ttcaagtatc    21840
actgttactg ggagatgtga gagaacagca aaatgctcaa aagctcaata ccaggaagaa    21900
ggcttaaggg acccatgtat accaaaggga gctggcttta gaacgaacaa ctgtgataac    21960
ttaaagcaca cagcactgat tcaaacccttt gttgtactac atactagcta catcaggtac    22020
cacataaaac ctcatcttac ctgaaccagg ttattctttta caatattgga agaacaaaca    22080
cttgccgatc tcacagttgt tggaaaaatt aaatgaggta atatgtgttg cacaactaca    22140
gtgtagtact gtataccgat gttcatggat aggagtctag gtagctccaa gtgtgtttta    22200
acctctcttc atctgtttat ccacttgttg gttttttgaaa tcctttaaat cagactgcat    22260
ttcttcagca ctgtcctgaa acataaaatt gtctatgtta tccataaaat acttaaggat    22320
tatgaggaaa agtagatggt taatgctcat ccaaattcaa ctttaacctg agacaactca    22380
ttatattaag aaataaatgt atgtgggcag tgtgcctgca cctgtaatct gagctactgg    22440
gggagctgaa gcaggaggat cccttgagtc caggaatttg agaccagccc aggcaacata    22500
gcaagactct catatctccg aaaaagaata aaatggccgg gaggggtggc tcacgcctat    22560
aatcctagaa ctttgggagg ccgaggtggg cagatcactt gagatcagga gttcaagacc    22620
agcctggcca acatagtgaa accccgtctg tactaaaaat acaaaaatta gccaggtgtg    22680
gtggtgtatg cctgtaatcc cagctacttg ggaggctgag gcaggagaat cacttgaacc    22740
cgggaggtgg agtttgcagt gagctgagat catgtcattg cactccagcc tgggcgacaa    22800
gagcaagact ccatctcaaa aaaaaaaaa aaaaaagaa agaaagaaat ttaaaaagtt    22860
agctagtcac tgacgaataa caggatgcac aaagcattta atttcaaagc caaatttgca    22920
tttcaattat agtatttggc tgacaaggca agtatgtaaa caagaggaaa agttaaaaag    22980
aaaaaagccc taatagctac aatatcagcc cagttctaaa gagggatctt gtaccacatt    23040
gtccacctaa caagtaatct ttaattcaaa attcagcgta gttcttatgg gtatttggaa    23100
```

```
ttgaatgcaa gtgtgttctg tgagtataaa cattatcttt tattatatat gattgttaaa    23160
ctttgctttc cacaacactt cataaccttg gatgtaaaca tgagaaaaaa tgctaattaa    23220
gaatccttac gcacccagtc cagtgctccc ttaattaatc aaactggtaa gtctactgct    23280
tcttgattcc atcctgaggt attaactttt gaaccaagac atgtttatct tttaccaaca    23340
acagggatgg tcactgttaa agtttctaaa taatttatta gggaaataag ttcccacaaa    23400
gtcaggctga actgggagct gattaacaaa gctgtgtaag ttagtgtgtt tgctttaagg    23460
tattacaaga agtacacaga gcacacatct gggttataaa agccctttta taaagccatt    23520
tttaaacaaa acaaaaaaaa agtttacaaa agaaaaaaag atacagaaaa agaataactt    23580
gcttcatatg tcccaaaaag agaaaaaaat aaaggggaca atgccaacat gctcaacaat    23640
aaaggcttct ttttcttatt tttttaatac aaaatacaag caaaggatac acatacttaa    23700
aacagagctc aggagcagac acgcagtcct ggaaaccctt caataaaagc aaagcaggag    23760
tttgtttttt ctttgtctat gcagatacat acagagactg ggatatgtaa aaattaagta    23820
tcacaaaaga ccatcacacg attctaccaa tgcatgttgc atctgtaatt cacgaacatg    23880
gtcaacaaaa tcatgttcac ttcaacccca tttcatttaa attaaagaaa aaacctttt    23940 aaataaagtg gttacattca aactttaact tccttagtac catgctgcag atttcagcac    24000
tgttaaggta ttgcaagaat gcccaaccct ctggtgtctg atcatgtatc tagcaacatt    24060
gcagtatgaa gaaagagat gccccggtct cagcccatgg actagttaat acagtgaagc    24120
aggttcctgt cttttaccct tcctgctcag aacataaaag attaaggact aaaatcaagg    24180
aagactggga gttttagagc tggcaaaatg aagtctaaaa gataaatcaa ggcaaacaat    24240
tactgagaac ttggctgttg cttaacctgg caagtctaaa agcctttctt taaccttgta    24300
ggaattagat gcataaggtt tgctgcaaca tgttcatggt aaacaaacta agtagagctc    24360
ttatttacaa atcttgtaac aaatacttct ggaggaaaaa gagaaaagaa ttcactaagt    24420
tccagaagac aaagctttaa ttgccagatg tatacaaaca cactcaca cgtacacacc    24480 cacacaatac ttcaggggtt tttatacatg ttattttagg gcataagctg agtactatac    24540
ccccacaccc catcaaaaaa ggaacaacaa aaaaatccca attttaccct cccccaataa    24600
tctagaaaac cctcccttca cccctgatgt acaaagtgta tgcacaacgg tggcattcta    24660
ccagccacac aaagcatgct caaacagatg tcaccagttc agtcactcca ttggcatggc    24720
aacaggcagg tttacgggat gtttcccaat agtggttatt acacagtcag caccactgtg    24780
aattttgtga atttgaaaaa aaaagtgta atttatggat tcaggattca aaaagaatca    24840
ttttgtatcg aatттaccccc agacaaaggg aaaactggtt gcgactgaaa cttggctata    24900
gatagcttga tgtcccaata ttcaaacaat aagccaactc tccattttca agtaaatcca    24960
gcttcatcca cagagaaaca gacaattttc taacctcaag agcaaccagc ttgttacatt    25020
ttccctatcc tatggcagga aatgcgtatt acttctgttc tgtttaagca tctcagtcta    25080
aatgccatga agaccagagc ccaggtttct tccttttcaa attcttaagg tgaaagtttt    25140
ttcctttcag tgcagctacc aatgatgcag gcaaagaact gttcaagcca gcactcattc    25200
ttcaaagctg caacagtggc caccatgatc ttttataaag ctttccccgt tgctcctgat    25260
atttatttct gcttttgcct aacgctctca agcatctcg taaactgaag tttaaagaaa    25320
agcacgattc ccatccccaa ccagtacttg aaaatccact tatctgaatg ttcacagata    25380
aaaaagccat taaaaaaaag agtcaagttt agtctagctg accatattca caagtgttaa    25440
aaactttact ggagtataac ctcaaatttc actcttgatt tgttatctgt aagaaaatgc    25500
```

```
tatttgagcc agtaccaaat taagtattaa aatgaggatt gaactggggc aaacaggtta   25560
ttgtgaaaac agtcaatatg taagctcctt caagggaaat caactactgt tcctcaagat   25620
tagaagatgt ccacactctt tgcattacct ccctaaagga ggaaacaccc attaattttc   25680
ccttatggaa tcaatatgga gtggaaatat gaaatgagga gatgttttag aaagcaggac   25740
aaatctacct accattactg gaattaaaat gtatcctctg ggcccactcc attgattccg   25800
atctgaggtg aggaggacta aaagcagcag caggttacag aaagactgaa taagatgaaa   25860
gtatgctacg tatgtctagc tggggaaggg gggatctgga aaaaaatct taagaactag    25920 aatgtagtgt cagtcagcat agctgctgaa atctacgttg tagaggtaaa cctagcagag   25980
ctaatacaaa caagcaccct caaagttaac gtcccacttc ctgagcactg caaaatacga   26040
cagtgaatgc tattgccatt tcaccatagg cacactagaa aaaagagga aggttagtca    26100 aggatggtgc caatggccag tcagtatcgg cttacagctt gtaatgcgtc ctgacatcac   26160
tatcaagcct gactattgag cacctgtatc cagttgagtc accaccactg tcctcctatt   26220
tgcatgcatg atttgagggg aagactagag tgttttaaat catcaataaa aagtggagaa   26280
aacaaaggtt attcagagcc tgtctcactt ggggacacag atccttctgt ccagtctatc   26340
agaaatatag aatacatttt tcaatctaat gaattaattt taaaagggac cctaaacaag   26400
aagcccaatc aaatgcacac aagtaatcta gaagacatga ttacctctaa aatatgtgca   26460
tatatcacag agatgttagt gcagattaat atattaaaga gactgttaaa caactgaggc   26520
tgaagtttta aaagagccct ccccccaaat cttcacgaaa cataacctaa gaaaagccca   26580
aatgttacta ggaatgtaag acttaaaatt ataaactcct aaaaaataga agtgcatggt   26640
ggaaacactg ataggtcttt tactatatga acacaaactt ctttgttaaa aatggatacc   26700
tgaacaaacc catttaggca aatagattaa tctttaacac cctcattaca aagttcacac   26760
ctctgaattt aaccgtcatg aaagagaatg atccaactgc tatttatgtt caagtcctgt   26820
atttttggcc atgtaactga aaactcctta ttcattcttt aacacacagt gcaatagtga   26880
aatgactctg ccactgtgtg tttttaaaa aaagatcaga gtaagcatgt tcctagtaaa    26940
ccacaaagta ggatattgag gaagcaaatc tagattaaaa ggcaggaaaa aaaggcagaa   27000
gtttaaattt cactaatttt tcaatttatt agcataccag gacccttaa accttgttcc    27060 cattagcgcc tggtattaga tgtgaaggat caaacctacg gatctatctc ctgactgctt   27120
ttataaggcg tgtaaaagtc ggttttcaac tgcacacagg cctcctaaaa tgccttgttt   27180
ctctagtccc tcctgcttta agcagcatga gcagtaaagc aggggttgga ccaaataaaa   27240
agacaagagc taactgaatt gtatgggagc agcatttaac atattcctag tcaaggacag   27300
gatgggaagt aagtgaagaa tagggccagg aaaatagtgt cctatagcag aggtggttgg   27360
cactcggggt agggtgtgca gtggtgctct acgaagcagc aggatcacag ggatgtactt   27420 cttatccacat ttctatgaag aaatgggaag atcgggatat gaaaagaaa atgttctatc    27480 cccaaataaa agcagagcat ggttaatggg acctgaatgc acatttatag cataaaagaa   27540
tgtcaattct atttcataaa ggaaaaatct caactctttg tgactgagtt tcacattaac   27600
tggaacttta tttgcttaaa acctaaacat tgtcagtttg aaaagaaatc cactgtgacc   27660
tgtagactga tcttgttgat taaattctag ggtttttttt ttttggatt cttggtaaaa    27720 ttttatccaa aaaacaggat acatatatat ttagagaagg aaatatgaaa tcaagagttt   27780
tggcagcccc tgcttttttt ttttttttag ctccctaaag actgtagcag gataaaagga   27840
```

```
tcactggctc cgagtctctt tgagataaca agtgatgaaa taaaaaagaa agcccatacc    27900
ctcaaataag gtcaggtaac cccattgccc accctcccta caaggtaaaa aatgagtact    27960
tttagtaaca gttcagaatt catctttatc tcctacctgc ctcatcggtg gaagtttaaa    28020
gtcatgattt tttttagaca ttgatacttg tgtctataga caaataaact catattagat    28080
gacaattgat tttttaaaag tccaggtaga gaaaggagca atcattttga actaaaatct    28140
ttctatgttt tttgattact attcaacttg ctattttta gcaaaaagcg aagtttcaat     28200
agtgttcatc tcaaatctta ttgctttaca accgtggtac acctttcatt aaaaataaaa    28260
agatgaagca gtcaatccag tgattaattt gacatggctt tcattgggaa aggggagggc    28320
tggcaaagag accaatagac aaaaaggtaa cttaaacact tacacataca atggtttgct    28380
ttaaaaaaaa aaaaaaaaa agagagagag agagaaatgt tactttcaac aaatggaaaa    28440
aagcactgaa agcccatgag tcaagccata gccaaaacca tgttctatct taagtaggtt    28500 ctttttttc ctccctcttt tttctttttt tttctttttt tttttaataa aatctctccc     28560
cagaccatca tcacttttaa tcctccccag aagggcttc atcttcagac ccttcatccc     28620
cagatttctc gggtggggg cttgtagatg ttttctttc tggcgggctt tccggttcct      28680
catcttcttc tttgggagaa ggagtctttt cctttgatgc ctttgaagct gtggggcgac    28740
ccactttccc tttgccttc actggacttg gcgtcactga aaatagaaaa ataatttggg     28800
gaagggaaga gaaaaaatg tctttaataa aagtcagcta caaatacaa caatctgtaa      28860 gaataaaatc tataaagaca atatgcaact tactaaaaac caaggtgggc acaagggagc    28920
acatatatcc ctaggtaaat ctatctcagt ttctaaactg gtcataagtt actacactat    28980
gctacagtat ttcccatcag ttttaccaa cactctatga tgttagcagt aatacctgta    29040
aagaagaagc accatgctat agaatatgca caacatcctt aattgcttgg taaactaaca   29100
gttgtttatg ataaagttg tttataaaaa gcaggtcaaa aagacggaag gaaaagaatt    29160
aatctgatca gaaactaaag ccatcaaata acatttgata gttccatcat tcctaacagt    29220
aggaagtgat aaacagaagt ttaacaatga ctagttctac ctaacagaat aaaaccacct   29280
acacaaaaag caaattgatt tctgatttag ttaacaaact agctccaacg aggagaaacc   29340
attagggctc agaaaaaaat caactcatgt catcaagtgt ggttttattc tgatagcaca   29400
gaggatgggg tagagttcag aacgtggaac ttaaacgtat tactctaggt ttgtgcatt    29460 tcacaattaa gtctttgctg gctgctgaga ctgtgatacc agtgaggaaa aaagagcagt   29520
aacaactatg atgacacagt gtttctacca ctgtgtctga aacaaataga tcattctgaa   29580
atcttgctca agtactggca gtagttgaag aacatggcta agcccactag actcttaaac   29640
aggctagtgt ctttattaat aagagatact tccagttgca gaatacaaga cccttttaga   29700
tttcttgtat tcctgctaaa catcaggcca atgccaaatc ctaatgagga atttctgtat   29760
tgaaaataat gattctcaaa atttttaaag cagtaaattt aatttcactt ctgcagaaat   29820
tacctgtagc ctttagtctg ggtttgggca ttttcttttc ttttctttca ggtttggact   29880
tcttaaccat ctttttgttt ttcttttttcg aactgccata gtcactatcg tcatcatctt   29940
ccattaggaa atcttcatcg ctgccggaat cttctgagaa gaaagaagaa tttcaacatc    30000
taacttaatg tacacatcct tccaagtaaa aaaggaagag agtgctaaga atgactagag   30060
gatgggattt gggagtcaaa cacccttgga ttctatttgg agctgtacta ccaatttgac   30120
tggagtcatc actggcctca tttgtcaaat ggattttgca tgcaccttac atgagagagt   30180
tacatgagtg atgtgtttga aaagtagatt gaaaacagga agggtaagag ttaatctgaa   30240
```

```
taaaaactga aactatcaaa taacttttgg tagttccatc acttccaagt agtactggtt    30300
gagaccaggg aaacaaaact gaactgacag ggccttttg gtccaattat gaataagtga    30360
aacaagaaaa ccaaacacaa aacaaaaata cataggatta actaatctga ataacctgtg    30420
aaacacctaa attttattat taacatgttt ttttctgtga aaagaggtct acaacctcct    30480
ccaccagggc aaaatacaaa tctcaatcac aatgcctaat gtgactgtta cttaagcaaa    30540
ttgttcattc agtgtttgaa cacagacatc attaaataaa gggtgcaacc attacaaatg    30600
gtgggcaatc gtgagaatct ctgaaccttt aaaaatatta acaggaacca atacagtcat    30660
ctcttttaac acgagtatc tacccaattt aagggactgg ttgtaacatt tagcatccta    30720
gaaaatgcca aagtaaccaa ggtcacaaac tacaattatg accaaacaac caaagtacac    30780
aaaacaactt cacatactct cctggaatgg tgcctcatcc tcctcttctt gttcttcctc    30840
actgcccaca tcttccatga gcatctctct ctgtttagaa gctgctttag atgccgcctg    30900
ccgttgttgg cgcacatttt tatgatcttc ttttcatct tcactatcct ctgcaatatc    30960
agaattacca tgatataatg attaaagaat tttatatttg acaagatagt gcaaaagatt    31020
aataattgac tgaaaacata actgactgaa aaggccaaca cagtggccaa tataggatat    31080
aatctgcagc tttatttcat tgtaaaaggg caaattctat ccttcaacat ttctgcaaaa    31140
tgatggaatc aactcaaatg cccatcaatg atagactgga taagaaaat gtggtacata    31200 cacaccatgg aatactatgc agccataaaa agggaaggag atcatgctct ttgcagggac    31260
atggatggag ctggaggcca ttatcctcag caaactaatg caggcacaaa agaccaaaca    31320
ctgccatgtt ctcgcttata agtgggagct gaacaatgag aacacatgga cacagggagg    31380
ggaacaacac acactggggc ctgtggcgag ggaggggca gggtgggggg atggagaggg    31440
agagcattaa aaattagcta atgcatgctg ggcttaatac ctaggtgatg ggttgatggg    31500
tgcagcaaat caccatggca cacatttacg tatgtaacaa acctgcacat cctgcacatg    31560
tatcccacaa cataaaaaaa aaaaaattc tacaaaatgt ataagggga cctaaattca    31620 caaagaatga acttggacaa gactatgtaa ccactattac atataaagta acaagggaat    31680
gtaattttaa gcagtagaca agctgaatta aagcgtgaat acatgactcc tatactttaa    31740
agttacatca ttgctttgct ctacaattct caattacatt caaatctatg ttcactgttt    31800
ttgaaagcta aagttagaaa aatatcttaa catagtatga gagagaaaga atgtcttcca    31860
ataatcttta ttctaagaca taaaacacga aaaccctaaa ataatgtcaa actgttaccc    31920
tttacaatga atggcttgtg accatttcaa tttagagggg attgtggaaa acctttttt    31980 tttttttgag atggagtttt gctcttgttg cccaggctgg agtgcaatat agcgcaatct    32040
cgcctcactg caacctcacc tcccaggttc aagcgattct cctgcctcac cctcccgagt    32100
agctgggatt acaggtgcgc accaccactc ctggctaatt ttgtattttt agtagagaca    32160
gggtttcacc atgttggtca ggctggtctc gaactcccga cctcaggtga tccaccctcc    32220
ttggcctccc aaagtgctgg aattacaggc gtgagccact gcgcccagct ggaaaatctt    32280
taaaatacat atttgatta attagtgaaa gacatttgga gaagcctata aaaaatttac    32340
tttcacatat tcttagagtc tattaatgaa aaaaaaattt tttttttttt aatttggagt    32400
ctcactctgt cgcccagatt ggagtgcagt ggtgcaatct tggctcattg cagcctgtgc    32460
ctcctgggtt caagctattc tcctgtctca tcctcccgag tagctaggac tccaggcaca    32520
tgcagccatg cccggctaat ttcttgttgt tgtttgcttg tttgttttt gagatggagt    32580
```

```
tttgctcttc ttgcttaggc tggagtacaa cagtgggatc tcagctcact gcaacctctg    32640
cctcccaggt tcaagtgatt ctcctgcctc ggcctcccga gtagctggga ttacaggcac    32700
ccaccaccac acccggctaa ttttttttatt tttagtagag aaggagtttt gccatgttgg   32760
ccaggctggt ctcgaactcc tgacctcagg tgatccacct gccttggcct cccaaagtgc    32820
tgggattaca ggcatgagcc accgggctca gccaattttt tgtattttg atagagacag    32880
ggttttgcca tgttggccag gctggtcttg aacccttgac ctcaggtgat ccacccacct    32940
tggcctccca aagtgctggg atggcgggtg ggagccacca tgctcagcct aaaaaaaatt    33000
tttttaacac acagttgtgt ttgtgaataa atttggttaa agggtaggct gccagcctac    33060
tgcctctaga ctaaaccata tttgccttag tctctaccta cagccctttt ctgaaaacac    33120
ttctagtccc atgagccttg ccatagtcag tgttcaagtc atctctttca cttttaaaaa    33180
tctcatctag agacaaacag aataaagctg acatggccga cccaaaacta aacccacttg    33240
gtagaagctt agcttaatac tagtacagag ttatttatct agaagtgctc aataaactag    33300
caagtgtaag agattcaaac taggatttac aaggcaaatg actgaaagca tatactctat    33360
tatcacagga tcaccagata gtgcaaaaga ttaatacagt ttcttttcaa cttaggtagc    33420
cagatagtat acttgaatag gagggaaagc aaaacagcta agcagagtga atttagcaga    33480
actttgtctc tccccttttgt attagctaaa cagcagtctc atttaagggg agatccaggg   33540
agacaacagc aagggaatgt aggtcaaaac taaagtggct ggaagtaata tggattaaaa    33600
atctcaattc ttagaagatt aaatttaaaa ataaatacca acaacaagta gaatcatcag    33660
gactgaacat tttatttggc catggagact ccccattaat tcatattaat ttaagttaaa    33720
atttttacaa aaaaaacttt ctctatggct actgttacaa aaggctatgt ctccactaaa    33780
aagagtggga atgaaacttt catttgcttt tccacccaga gtccaccact ccccttttt    33840
atgcccctat tttaccaagt tttatattta tatattattc tatttagttt gatgtctttt    33900
gtttacgtaa atgatttcca atattgactg tgcataagaa taatgtatag atacttaaag    33960
aaaaccaagc cccaacatcc cacttagatc tatttaatca gaaattttgg gacaggaccc    34020
agaatatgca ttttaaaaaa gattcataga tgactgtaat aagccaccag gactgacaat    34080
cattaggagc tctttgaaga tggaaacgtc tttgtaatcc cagatttgca acagtgcctg    34140
gcatagaaat cacttattaa aacatctaat aaaataatat acaaatataa ttatacctct    34200
tacatttaaa atagtttact acctgctgag tgagaatcat ccttcttggt cttcacatct    34260
ttgtcttctg agtcctcact ataaaggag gcaaaaaagc aaatgcataa aagtcttagc    34320
tcaaaatcta agtgaacata gatctctgat ttctgacttg agaagaagtg aaaaatacct    34380
cttctatata aaatcttcaa acaaatgcta aggagtactt tatttcctta tttacaggga    34440
tgctggtgaa taagcacaat tttatttacg ttacaaaaca ctgcttccaa agactcaaag    34500
gaaaaaaga agctgtctca acacaggctg gaattttttc acctatggat aaagcttggt    34560
tcacaagaat atttaataag aaaaatattc tcgaacagag gcagagtata aaaatactaa    34620
aaatacatag tgttgatggc aaataaagat cactaaatat acacaagaaa aactgctaaa    34680
atatctaaaa ttattaaaag gaactgtagt ccgggcgtgg tggctcacgc ctgtaatctc    34740
agcagtttgg gtggctgagg taggcagatt gctgaggcc aggagttcaa gaccagcctg    34800
gctaacatgg tgaaaccctg tctctactaa aaatacaaat attagccagg cgtggtggtg    34860
catggttgta atctcagcta ctcgggaggc tgagagagga gaatcacttg aacccaggag    34920
gcagaggttg cagtgagcta ggattgcacc gctgcactcc agcttgggtg gcagagcaag    34980
```

```
actccatccc cacccccccc aaaaaaagga attgtagttc agttatctta cctaacttat    35040
aatatgccta aaaatttacc tagaacaaaa tggaaaataa attgattgaa ttatccccta    35100
ttaatatttc cttccaatat ttctttgcat cagaaacatc aacatatagt cctgcctggt    35160
ggtaccatga agaaaataaa atgagctcaa aatcactcca caaagtaaaa taagaagtta    35220
aggagcttca aagttcaatg gaaagttttt aaaaacaatt tttagttaca accaaacaca    35280
ttatgtcttc ataagtctta actccagaat ctggattcta gtatcctatc tctctttgtt    35340
aatttccata ttttttaaaaa tagagatggg gtttcaccat gttgcccagg ctggtgatga    35400
actcctgagc tcaagtgatc cacctgtcct ggcatcccaa agtgctggga ttacaagcgt    35460
gagccaccat atccagcacc tagtagtctg tttgtcatta gttagttgta tgatcttagg    35520
caaatcactt ggtattcttc aatgctacaa ttttacgatt ccatgaaaaa ttctgaagaa    35580
caaaaaccaa aaactcgcac ataaaaactg ccttcaaagc tttcctttct caaatagcag    35640
gtcttataaa tcacttttgg tattctccat aatctagacc acactcaaat gagaaattac    35700
tgaacccatg attcctaagc aaagagaatg accaaacata ttcctttact aagcaacctg    35760
agtccaagac actttataat tctgaaacct gtgactgttc tgtataaatg ttttttatgc    35820
aaaataagca ccaaattcat aattctaaca caatgatgaa ttatattatt ttttccagct    35880
cttttatcga gttatagac tacattaatc tttaagtacc actacagcaa agttaagtga    35940
aggctgaact ttgaaaacag aaaaatcaac agagcactgg tctgagaata aatacacaag    36000
gcatacagat agcaataaaa cctgtattta tttcaatcct tccagcactc agaataataa    36060
aatcaaatga ctgcaacaag aaaaactgta agctagatgt taattatgtc aatgagacat    36120
tataacatgc cacaaagcag gtctttccta ggagaaataa gataatgaat ataatgaaaa    36180
atagttctga gttgggctgc catctaaaac tgtttggccc ggcgcggtgg ctcatgcctg    36240
taattccaac actttgggag gccgaggtgg gctgatcacg aggtcaggag ttcaagacca    36300
gcctagccaa cactgtgaaa ccccatctct actaaaaata caaaaattag ccaggtgtgg    36360
tggtgggtgc ccatagtccc agctactcag gaggctgagg caagagaatc acttgaaccc    36420
agaaggcaga ggttgcagtg agctgagacc ataccattgc actccagcct gggtgacaag    36480
agtgagactg cctcaaaaaa caaacaaaca aacaaacaaa aaactgtttt aggccaggca    36540
tggtggctca cactgtaatc cctgcacttt gggacgctga gatgggagga tcgcttgagc    36600
ccaggagttt gaaactagcc tgggcaacat ggcgagagcc catctctatt aaaaacaaac    36660
aacaacaact atgttagaca tataccaaga agctctagaa gacttgtttc ccaacagtat    36720
aattctgtat tattttttcct taaaagcaca cttctgaaat gctccagcaa aaaaagtatt    36780
agaggttgtc aacataaata aaactactag gtaaatacat gaatttaata atgatttttgg    36840 tgctccaaga ttcttagaag aagcagtgag aaatatttca tttatttgaa ctgctcattt    36900
gtaatagtat tatttggaag tggtatagag ctccaatggt taaacaatgt actttggagt    36960
ccaacagaca tggtttcata acctgtttgt ccatttgctg gataactttg gttaaatcac    37020
agaacccctc taagaagtta atatttaccc aaatagagat gatgtaagaa ttaaatgata    37080
gtgtacgtaa aacacataat agagattgtc acataataaa cagtagccat caccatcact    37140
ataatcacca ttatcaccaa gaaggtcttg ttacaccaag tgtaacaagt tcatgttaca    37200
tcaagtgtga gagtgtgtat aactttacta acaaggcaga aattacaata tcctcgtctt    37260
gttgttgttt tttttttccca agacagtcct ggctctgtca cctaggctgg agtgcagtgg    37320
```

```
tgcaatcata gctcactgca gccttgaact cctgggctca aggatcctc ctgcctcgga   37380 ctcctgagta gctgggacta caggcaagtg ccaccattcc cggccaattt ttaaatttt   37440 atgtagagat gtggtctcct tatattgccc aggctggtct caaactcccg ggctcaagcg   37500
atcctcctac ctaggcctcc caaagtcctg ggattacaag catgagccac catgtactcc   37560
taatatcctg gtcttatgag gcaaaattat agttaaaatc acaactcatt tgtaaaacta   37620
agggaaaaga aactctccaa aatggttaaa ttatttaaac aaaggagaat tgattatgag   37680
acagcaaaag gcagcaggct atacaactta agattctaca agctttagtt gtaattaatt   37740
gtgccagtga tttgtgactg aatgagatat atcacttatt ttttgttatc actacaatga   37800
aagtgtcagt attaacctta gataacaaat tgtatactcg agcacagcct gagataatat   37860
gaaatatgca aaatattaag tggacagtaa gtacttttca aaagtatatg agattccaac   37920
aatttagaga tcagagactg ctctcatctc agagtggtaa cagtgtaagc aggaacagaa   37980
aaacaatgcc tcttacctat cttcctgtga attctttcca gatcgcctct tatttttagc   38040
ttctcgggga gatgatcgaa ttttcttagt gggagggccc gaatctcttc cataatcttc   38100
atctaaacag tgttttttcaa acttaattaa ctatgatttt tacatgttaa aatcaccact   38160
atatttactg acataattat ctctcatgct gtttaaatgg tgagaggagc aggatttccc   38220
aaatagtttc tttcatcttt aaaaaactaa attatttccc aacgcagtcc tatcaccttc   38280
acttcgtttt tgcatattac cctctagtcc ttatgatata tatttcatct ttctatagct   38340
aaacctctct catcatttta taccctcccc ttttgatttc aacatcttca cacttatttg   38400
aaaattattg taatatggtt atattacaaa cattttagga agtaaacaca attactatta   38460
ctaagcaaat tactttttaaa ctaaagcatt aaatacaaca taatcttgca cttgaagaaa   38520
atatctccaa tttcaaaagc cctataaaac taaggaaaat gactctacct taaaaggaaa   38580
ttatttccaa aactgtttac tgcaccattt gcacacacac acatgcacac acacacacac   38640
acgatggcga gatgctggaa gtagtctgga gcgtcagcaa ttattaagtg gtcagaaaca   38700
ttataaattc cattatggga tattatataa ccattgatag gaattttca aataccttt   38760 attaacaaga tactcaaaat agaaataata atagtatatc acacattaac agattattct   38820
aagtaaatat taaatacaaa catttgaaac aattcctgac atgtagcaag catttaataa   38880
atattagtgc tacatattat ttttttttctc ttcttcatat ctttcagtat tttctaagtc   38940
ttcccaaagg gcacatatta tctttataaa gaaaagttag aataaaaaga aagaaaaaag   39000
aatagtaaac atacctggaa agtaatgaga ttaaggagac aactctgaaa aaacctctta   39060
tggctaagac ttagctatac aacactcatt ccttgatgaa ttagttcata aatataagtt   39120
gtttcacaaa acagactctc atcttagttg ctttattatg taaaaacata atacaaggca   39180
caagttttat tgtagtaaca gcaggagatt tttttccc tgcaaagtgc tgggattcat   39240
aggcgtgagc cactgcgcct ggctgtagtg gattttttt tttgagacag gtctctttc   39300 tgttgcccag gctggagtgc agtggcgcca tctcggctca ctgcaacctc cgcctccga   39360 gttcaagcga ttctcttgcc tcagcctcca gagtagctgg gattacaggt gcatgccaac   39420
actcccggct aatttttgta ttttagcag agatgggtt tcaccatgtt ggccaggatg   39480
gtctggaact cttgacctca gtggtccgc ccaccttggc ctcccaaagt gctgggatta   39540
caggcatgag ccatggcgac tggctgacag caggagatat tttaagcaat gaacactgta   39600
tcagaattac tggacattta aactttggac tccaaaacca ggtaagaaaa agcttttta   39660 atgtttatta tcaatgattt accaaggaaa agttaaaatc catgtaagtt caacttttgc   39720
```

```
tttggttgac acagatcatg acatggtttt ggtaaatgat ctaaaaataa aaaagtaaaa   39780
cttattccaa aagcataata aaactatata agctggtaac ctccactggt cagtccaact   39840
taaaatttgt tgaaaccaca aaacttacct gcatcatcag attcctgaaa ctgtgagtaa   39900
tcaacaacct tcctatttct gtagaaagaa gagactctaa ttaaaatcat aaaactgtag   39960
gatttttcta agacatcaga acacacattt ctctttcata aacagaactg aactagcact   40020
ttgaaaatta tttaattgct ggacgtggtg gctcacacct gtaatcccag cactttggga   40080
ggccaaggct ggtggatcat ctgaggttgg gagtttgaga tcagcctaac caacatagag   40140
aaaccttgtc tctactaaaa acacaaaatt agccaagcgt ggtggtgcat gcctgtaatc   40200
cctgctactt gggaagctga ggtaggagaa tcacttgaac ccaggggtca gaggttgtgg   40260
tgagccgaga tacctccatt gcactccagc ctgggcaaca aaagtgaaac tccatctcaa   40320
aaaaaaaaaa gaaaagaaaa aaaaagaaaa ttatttaatt aatttttttga dacagggtgt   40380
cactctgtcg cctaggctgg agagcagtga cacaatcatg gctcactgca accttgacct   40440
actgggccca agtaatccgc ctgcctcagc ctcctgagta gctgggacta cagacgcatg   40500
ctggctaatt ttttttcatt ttttgtagag acagggtctc ctggtgttgc ccaggctggt   40560
ctcaaactcc tgagctcagg tagtcatcct gcctcagcct cccgaagtgc tgggattaca   40620
ggcacgagcc actgcaccca gccaaaaatt attttttaaa ggcccccact taagcctaag   40680
tacttaacat tctgttataa gaaagcatag cataaaccac aagtatgtca agctacaatt   40740
ctcatactgc tcatctcagt gataattcaa ataccattct tttctctctc ttttttttt   40800
tttgagatga agtcttgccc tgtcgcccag gctagagtgc aatggcgaga tcttggctca   40860
ctgcaacctc tgcctcccaa gttcaagcga ttctcctgct tcagcctccc gagtagctga   40920
gattacaggc gtgtgccacc acgcctggct aatatttgta tctttagtag agacgggtt   40980
tcaccatgtt ggccaggctg gtctcccctg atctcgtgat ccgcccgtct tggcctccca   41040
aagtgctggg attacaggcg tgagccaccg tgcccggtct caaataccat tctttctac   41100
aaaacaatct cccgtctctc aaaacaaata tacataaaac agcaaaatga gccaaatcac   41160
catgtaccta tgtattcatt atatacaaag atgcccatt tataagctaa agttgtaaat   41220
gatattttac tcttactgct acacacatat atatgtatac ttgataaaca aggttattac   41280
taagcttttc aaggcaaaag caattttag gtatagtaca gttacattat aatgcacaaa   41340
aattatggta atgttaagct ttatacagaa ggggaaggaa acaaattaat tggtccagtc   41400
aaaagatgct ttatttaaaa aactatgaaa gcctcacaga tttatgtaca tctatgtatt   41460
tgactctatt cttttgtttc taaacttttt ttttccttt ccaattttac agacctggtt   41520
tatcagcaac atttataaaa ctagacctca ggaaagaact agttctgggg atatatgcat   41580
ggtcttaata aagtgaatgg ttagcctgtc ctgactatta caaaatcaaa acagtgagaa   41640
tatctgcaga atctatttga ctctaaatga ctttaagtac tccctatcaa gtaacgtatc   41700
tttaacatct caaacaaatc ttcatttcta tttttgtact ctgcactcta aatctaaaag   41760
tttaatactt cttctctaga gatatacatg taagcttcca tgttagtacc caaacagcct   41820
acctggcaaa agagccttag attaaaaaat gcactgttac tgtaggccta aattgatcaa   41880
gtgaacttaa aaaattaaga gaaataggcc aggcgcagtg gctcacgcct ataatttcac   41940
cactttggga ggccgaggcg ggcagatcac gaggtcagga gattgagacc atcctggcca   42000
acgtggtgaa accccgtctc cactaaaaat actaaaaaat tagctgggtg tggtggcggg   42060
```

```
cgcctgtagt cccagctact cgggaggctg aggcaggaga atggcttgaa cccgggaggc   42120
agagctcgca gtgagtgagc caacatcacg ccactgcact ccagcctggg cgaaagagag   42180
agactccgtc tcaaaaaaaa aaaaaaaatt taagataaat atacattacc acctatactt   42240
aaacctgagc agagggatat tcttggctgt atagattaag acaccattta aattcaaaga   42300
caggatggtc agactgcaaa cactggtcca ccttctagta tagtatgtgg agatggtatg   42360
gatggaggtg aattctggaa aaaaggctt gggcttatat gtagaggaat atatagttac   42420
atactcagca ttagaaagag aaaaaacaag gctcttaagg agttccacct tctgtttttc   42480
tttagtttaa caaaactata aaatatactc caactatata ttttattgta agaagctgag   42540
tttatattac caaagatact atattattag gaaagctaac tttaaatatg actattaatt   42600
ccatgtacat gagggaccta gagtagatga attcagagag acagaaagta gagtggtggt   42660
tgccagaggc tggaagagtg gggatgagga gctgttgttt agtgggttta gtttcagttt   42720
tgcaagatta agagttcttt acaacaatgt caagtactta acaatactga actatacact   42780
taaaaatggt taacatgggc cgggcacagt ggctcatgcc tgtaatccca gcactttggg   42840
aggccaaggt gggcggatca tgaggtcaaa agatcgagac catcctggcc aacatggtga   42900
aaacccgtct ctagtaaaag tacaaaaatt agctgggcgt ggtggtgcgt gcctgtagtg   42960
ccagctactt gggagactga tgcaggagaa ttgcttgaac ctgggagaca gaggttgcag   43020
tgagcaggga tcgcaccact gcactccagc ctggcaacag agcaagactc tgtctcaaaa   43080
aaaaaaaaaa aagttaagat ggtaaatttt atgctaagca tattttatta caataaaaat   43140
atattttctt tcttaaaaat atgactatga aaaatctaa tattttttggg ctactatgga   43200 aatgcctgcc atgttctggc aaaacagtga tttttttaatg acaaatgcca tgaaaaatag   43260
tatgatgatc ataatgcaaa cacgaccatt ttctgtatta tttaggataa aaaaaatggg   43320
tcatagaacc aggggaagaa aggtatctag aagaggaact cttacatctt atcctctaat   43380
aattaaaata caggttccga acttgtaggt ataattctag cttatcccat gcttgtgggg   43440
tggcaactaa catattatta ccccatttct gggtacgacg tagcaatgga tatatcctat   43500
gaaactacat aaggatggac aaccagaatg gtaaacggta tatcatatga agaacaaatg   43560
aataaattga gaatatttaa cttgtaaaat gggaaaacat gttagctact ttagggcttt   43620
gatgtgaaag gagtagtaga ggtacagctt agctttagca atcacattaa gtgtaggttc   43680
aacataaaga gctttaactg tctgctaaca atggctactt ccttactcta tcactagaaa   43740
cactcaagaa aggaattagt atggactctt tgtactagga atcctgggtt ctggttctag   43800
aatgtcaaga aaatcatgta atttctctgg gccttagttc ttcctctgtt ggaactgata   43860
acctaaattg cttgacagat ctaaaagata ttctataaaa ttaaatgttt aaataataaa   43920
ttaaataata aataaaatat ttaataaata acataaatgg caggcattat attaaaatat   43980
aatatagaaa atggtcactg caaatgatca tattgcatta tgatcacaat actgtttttc   44040
atggcatttg tcattaaaaa ttaactgccc tccacaacag aagaaaactt aatctcctcc   44100
tccttccctg tatatctatc tgtatctatc tagacagacc tacctaccta tcttccatct   44160
gtccgtccac ccatccatcc atccaacaat tgagacaggg tcttgttctg tcatccaggc   44220
tggagtgcag tggcagtcat agctcactgc agtctccaac tcctgagctc aagtgatcct   44280
cccaccttag cttgtggaac tacagaaagg cacacagcca ccatgcctgg ctaattaaaa   44340
acaatttttt ttttttgtag agacggggcc tttctatgtt tcccatgctg gtctcaaact   44400
cctggcctca agcaatcctc tcaccttaat ctcccaaaat gctgggatta caggtgtgag   44460
```

```
ccaccaggcc tggcctgtaa cttgttactt taaacctaag acactaaaaa ggatactttt   44520
tatttagtac atatttttct atcctacttt tcaacaaaca gaactacaga aatgccatgt   44580
agactatatt ggcattatat aaacaattaa attttaaaat taaattgaaa gactatccct   44640
tccgttgaaa tatgaagtat tttaactttc aatgatctga aaacagccag aatgatctca   44700
tatgccattt atcacaaata ccataaaatc agtgtaaagc aaaatatgaa tatagaagca   44760
attctgcctt attaagggca accagtcaga aacaaatata gtcatccata aatgctaaag   44820
agggaaaaga taaataaat aaataaaaga tctgtgataa caagggccat tcatgatgac   44880
tcataatgac tcataataat ttggttcagg ccgggcttgg tggctcacgc ctgtaatccc   44940
agcactttgg gaggccaagg tgggtggatc acctgaagtc aggagttcaa gaccagcctg   45000
gccaacatgg tgaaacccca tctccactaa aaatacaaaa aattagccag gcgtggtggc   45060
ggtcacctgt aatcccagct actcgggagg ctgaggcaca agaatcgctt gaacccggaa   45120
ggtggaggtt acagtgggcc aagattgtgc cactgcactc cagcctgggt gatagagcaa   45180
gactccatct caaaaaaaaa ataaaaaagt ttatttccca aacaatgtcc tgcctcctaa   45240
agatgcttat tcaaaataat ataataaca tactatttcc accacttaaa ggcttgcttt   45300
gtctggggtt gaaatacatt tttgatgaat ttgttcctaa tgagatgata ggacagaaat   45360
ccagcattta agaatttcat ttaagtccca gggcatgaga ggttctattt ctaggtgaaa   45420
acaaagaaac attctaattt cttcaaaata caatcatgtg ctgcatgaca ttatggtgaa   45480
ctgcatacat gacaatggtc tcacaagatt attatagcat atttttactg tacttttct   45540 atgtttagat atataaatac ctaccattgt gttacaattg cttacagtat tcagtacagt   45600
aacatgctat acatgtttgt agtctaggag caataggcta taccatacag cctaggtgtg   45660
caggagacta caccatctgg ttttgtggaa atacatgcaa atcacctaaa aatgcagttc   45720
tcagaatgta tccctggtgc tatgtgcacac atgatagtta aatgccaaag ctaaactaac   45780
tcttcaatgt aaaatgagta tcaataacta gaactggagg acagcataaa atttcaatat   45840
agcagagagg ttaaaaacac agattcttga atttacgtcc tgactcttac tagttgtata   45900
tcctcaagca agttacttcc cctgactgaa cttcagtctc atcatctgta aaacaggaat   45960 aacaataacct gttacaggaa taacaagagt gttgagaaca tttcagaaca tttgtgcaag   46020
gtatataaat atcaataaca gctattatta cttataagta ttaacttgtt ccacccagaa   46080
taccactgta attttgaaca cataactaac tcttatttgg atatgatgat taagtcacttt   46140 tgttgaaaaa tatgtaagtc ttaaaagtat tggttctagt atcattcaga aagattgtct   46200
ttgttttctt gttcatctca ctaaaatgta ataccaaaat atctcttttt ttttttgga   46260 gacagggtct gctctgtcat ccaggttgga gtgcatgaag tgcagtggtg tgaccatagc   46320
tcactatagc ctcaaactcc tggactcaag caattctccc aactcagcct cctggggagt   46380
tgagattaca ggtgtgtgtc acaacagcca gtaaattaaa aattttttt tgtagagacc   46440 aagtcttgct gtttcccagg ctggttttga actcctggcc tcaagtgatc ctcccttctc   46500
ggcctctcaa agtgctagga ttacaagcat gagccaccac atccagccct ccctattttt   46560
atttctgact ttatggcaaa gttcaggtta ccatttagat caaaaatttt taaatcatttt   46620 tttaagttta aagcattcat aaaacctatc aaagtctgat ggtcgtgggg gtgggagata   46680
tggtggtgct gagagtatta tatgtagtag agctactgga ccctagacaa tctaattcaa   46740
cctttagctt gtatcctgtt aacaaatatc cctagaagag aatgactgag aacttctcat   46800
```

```
gatctccaag gcagcctatg ctaagaaaat tccagtaatt gccaggtgtg gtggctcacc   46860
cctgtaatcc cagcactttg agaggccgag gcagtggatc acctgaggtc aggagttcaa   46920
gaccagcctg gccaacatgg caaaactcca tctctactaa aaaataaaaa ataaaaaatt   46980
agcccggcgt ggttgtaggc gcctgtaatc ccaggtactt gggaggttga ggcaggagaa   47040
tagcttgaac ccggggaacg gagtttgcag tgagccgaga tcacgccact gcactccagc   47100
ctgggtgaca gagcaaaact ccttctaaaa aaaaaaaaa aaaattccaa taattaaata   47160
gttctttaca aggagatgaa tctgcctcta gtgtccactc actggttcta tctagttcca   47220
cctcctggga ttagcatggt ctaaatctaa cccctcctct tcagagcatt ccttaaattt   47280
atatgactat tcccactttt tctctgaagc taaatactag ggctcctttt taacacttcc   47340
tcatatttca agtactcgct tcatgctcta gctgctttcc tccataccac cttggattta   47400
gtaaatacta aagcagcacc caggatgaaa cataatgatg ttataaaaag atggggaatg   47460
gggagcaaat caggattatg accctcctct tcctattcta ctctatactt caatgcaatc   47520
caagatttca gttccctttt ggactgttcc atcattcagt ggactatata ttgtaattcc   47580
aatgactaaa acctcctttt ccataatcta agaccgtttg gtatcctgat cctgccattt   47640
cagcatatta tttatcttcc ccaacttctt aacatctgca aatttaatca gcacaccatc   47700
agtgtcctca tctatatcat taattagaag atatgccaag aacagaatcc tttcaggcaa   47760
cagtgcaaac agtcttccag ggtaacaatc tatttatttg tcagccctct ccgggtaagg   47820
ctgctcaggc aaagtccctc acactgagct atcattctgc ctgtatttct ccatcttaca   47880
aggacctatg tgaagctgtc aaaatccttg ttgaaataaa acctcggtat tttcacagaa   47940
ttcttttgct ctaataaatt tttaaaaaag gaaattagtt catttaaatc agtgacagtt   48000
aaacttttta gcagtaaaca ctttttgttc aaataaaatc ttcccaggaa tcataaaatt   48060
aaacacagct aatcaaaagt attttaaaag tatacatttg tcttatagta tcgtattta   48120
aaaattatct cattacagaa ttgtccaacc tgtgttgtca aaataggttt tctaaagatt   48180
tactggtaat tatcagttgg atattatcag tattaccacc ccaataaaca ttcaaaatga   48240
atttaatgt gaaaagcttt gaaagttcca cattaaagaa aactgctaaa ctttacctcc   48300
aaaattatat ttatctattt ttatcttta tttatttttt gagacggagt ctcgctttgt   48360
ttcccaggct ggagtgcagt ggcgtgatct cggctcactg caacctctac ctcccgggtt   48420
caagcaattc tcctgcctca gcctccccaa tagctgagat tacaggtatc caccaccatg   48480
cccggctact ttttttgtat ttttagtaga gacagggttc catcatgttg gccaggctgg   48540
tttcaaaccg ctgacctcaa gtgatctgcc cgccttggcc tcccaacgtg ctaggattac   48600
aggcatgagc caccatgccc agcctattta ttttaaaag acaggttttt actctgtcac   48660
ccaggctgga ctgcagtggc tcactgtagc ctccagagta cccaggacta gagtggaca   48720
ctaccatgcc cagctaattt ttttttttt ttttgtagac aggttgccca ggctggtctc   48780
caactcctgg gctcatgcaa tcctcccacc atgctgagat tacaggcagg aatcactacg   48840
actggcccaa aattatactt aaaaatttga acaggcatg ctcgctttgg cagcacatat   48900
actaaaattt gagccaggtg tggtggccca cacctgtaat cccagcactg tgggaggccg   48960
aggtgggcgg atggcttcag cccataaatt caagatcagc ctaggcatca tggagaaatt   49020
ccatctctac aaaataaat aaataaaat aaattagctg ggtgtggtgg catgcacctg   49080
tgaagtccca gccactccag gggctgaggt gggagaatag cttgagcctg ggaggcgag   49140
gttgcagtgc gagtcgagat caccacactg cactctggcc tgggtgagag agggagaacc   49200
```

```
tgtctcaaat gaataactac ataaaattta aatcaaatgt ttaagacacc tccaaaagca   49260
aacattatga agactcctga cctatatgac atttttgtg tgtgaatcca cggcgacttt    49320
tagtaataat tataacagca gttacttcag atatttgata tgttctagtt actttgccta   49380
aattctcatt taattctcac cctaatgtca caagaggagc taattaactg aggaaactat   49440
gctcaaaagg ccaagtaact ttattgcaag ccattaagtg gtaaaaacca ttttccaacc   49500
caagtccttc caaacctata atccacacat gctactgttg atgcagcttc tcaaaccttc   49560 cttcctaag tctttacaaa tctaactctt ccaagaact gatgcaatta aagttgctgc     49620
acaccaagta ctgctgcttt ccctttaaaa tttggaagat ttacctcttt ccactcttcc   49680
tgcctcaaag atgattaaga aatctcacat gcaagatttt ctcaacataa aaaaatattg   49740
agggcagaat gcctgaacac aactcaaatt ttttttttc tttttttgag acggggtctc    49800
actctgctgc ccaggctgga gtgccatggc acaatgacac ctaacagcaa tgtggacctc   49860
ctgggctcaa gcgatcttcc cacctcagcc cctaccccag tagctgggac tacaggcact   49920
ggctaatttt tttgtaaaga tggggtttca gcatattgcc caggttagtc tcaaactcct   49980
gagctcaagc aatcttctgc ctcagcctct taagtagctg ggactacagt tgtgcaacac   50040
catgtctggc tgattttgtt tatttttgt agagatgagg tctccctatt gctcaggctg     50100
gtctcaaatt ccttgactca agcgatctgc cctcctcggc ctcccaaagt gttgggatta   50160
taggtgtgag ccactgtgtg gccaactcca ggtaatttct tacagtagct tcatttatct   50220
tgaccttcaa gttccttttg cctaaaatac attgttttca ctgtattta catcatcctg    50280 ctatttactt taggttttt tttttttttt ttttgagag acagtgtctc cctctgttgt     50340
ccagactgga gtacagtggc atgatgatgg ctcactacaa cctctgcctc ccaggttcca   50400
gcgattctcc tgcctcagcc accccagtag ctgggattac agttgtgcac caccacagct   50460
ggctaatttt ttttaagtt tagtagagaa ggggtttcac catgttggcc aggctgccct    50520
caaactccag gactcaagca atccacccac ctcggcctcc caaagtgctg ggattatagg   50580
cgtaaaccac cacacctggc ccatcctatt tacaatttaa aatatcaaat tccctctggt   50640
tgtggtagct cacgcctgta atcccagcac tctgggaggc agagatggca ggattgcttg   50700
agtcccagga gttcaagacc agcctgaacc acacagcaat aacctgtctc ttctaaaaaa   50760
aattagccag gtgtggtggc gcacgcctgt agtctcagat acttgggaga ctgaggtggg   50820
aggatcgctt gagcccagga ggctgatgtt gcaatgagat caggccactg cactctagcc   50880
tgagcgacag attgagaccc catctcaaaa aaataaataa aataaatata aaattcacaa   50940
caaagccaca agatatgaga aagcaaaaat aaaaccaaaa tccccaatag cattatagaa   51000
aagagctcct aatttttca aatcagatgt ttctaatttc tgcagaaaac ggaggtgggg    51060
aaaggtgttc tgaatgactg agccagacac atttactaga tcacaatctc ctactaagta   51120
tatatatata tatatactta gtatgtatat atatataaaa ccaatatatt accaacttgt   51180
taatggttta gccccatgaa caagtattaa ctcttataag gcactcctta ttcccaggac   51240
tcaagttact ttatttcaca acttaccatg ttcagtttca ccatatagga aaatgttttc   51300
ttttaaagtc acacacggcc gggcgcggtg gctcacgcct gtaatcccgc ctcaggaggc   51360
cgaggcgggc ggatcacttg aggtcaggag atgcagacca tcctggctaa cacggtgaaa   51420
gcccgtctct actaaaaata caaaaaatta gccgggcgtg gtggcgggcg cctgtagtcc   51480
cagctactcg ggaggctgag gcaggagaat ggcgtgaacc cgggaggcgg agcttgcagt   51540
```

```
gagccgagat cgcgccactg cactccagcc tgggcgacag agcgagactg tctcaaaaaa   51600
aaaaaaaaaa aaaaaagaaa agaaaagaaa gaaaaagtca catacaaatt tcaatgagca   51660
taagataaag tatttgataa ataaagtcag ctaggttaga ttttcccag tggaagttta    51720 gtgtaaaacc tatgcaactg gggacagaga aacctctaat gtgtgagact gaagggtct    51780 cagatgcgaa attactgagt agagtcccat ggtcttggaa acctcggtgg tgtcttccaa   51840
actgtgtaac tcaatcgcta gggacaaacc tgtagcctga caaatttagg tttattgact   51900
gaatacaatg aaggacaagc acatcagaga agtgtgaagc atctcatgta acagaaaaaa   51960
ttacagaatt ttggagaagg gtagaactaa gataaatgaa gcagtatctt gatagactat   52020
aagcacagaa ctgtgttaaa gggatcaata tcaggtctgg actgcagagt ggaactaggg   52080
tcctatttcc tgggaaagaa gttagggtag atgcagagtt ttgtgtttaa caaccccta    52140 tccaaagctc tgaagttgta aatcaaagct agttctctgt gtcaaaatga cttagatctt   52200
cctgacaaaa gtgtgacgtt catttttact cagagaattc caaacagtaa agtttctgat   52260
agtctctgat tttatagaac caagtttctc tgtaagagag cagtagtcac tcaaggaaga   52320
ggggttgtta agaatctcta gagctgcagc aagtccttgg aagacaagca gctgtatgtt   52380
atcccagtgt aagagatagc agcaccgact tttactcttt cagtggagct aatatttagt   52440
ttcttgagta gttcatttc taagtcattt tattgtgacc tagaacactc caaccaaagg    52500
tagctggaag ggaaatctcc ctgaagatcg ccttgcttag cacagaactg aacagataca   52560
caattcaaat aatagtaaca cctaagaagc acctgaaaac tgcaatacct agttgaaaca   52620
ctcttaagca gcctgtgatc tcttcatcta aagtgtttca aagacctaca attaagacca   52680
tttaaatagt agttatttta aaacatggca atataactgt ataacgatta gtttcacttc   52740
ctagaatcta gacagcaata atttttccc aacaaaataa aggggcgccc agtttgaccg     52800
aagtggtctt gtgctaaaaa ataaaaggtt tcctcctggg gccggacgct gtggctcacg   52860
cctgtaatcc cagcactttg ggaggccgag gtgggcggat cacaaggtca ggggatcgag   52920
accatcctgg ccaacacggt gaaaccccgt ctctactaaa aatactaaaa aattagccgg   52980
gcgtggtggc gggcgcctgt agtcccagct actcgcgagg ctgaggcggg agaatggcgt   53040
gaacccggga ggcggagctt gcagtgagcc gagatcgctc cactgcattc cagcctggag   53100
gacagagcga gactcggtct caaagaaaaa aaataaata aataaacaaa caataaata     53160 aaaggtttcc tcctattgtc cacaacatgt gagtctccta ggtgcagtct ccagtctcaa   53220
caatccaaaa agctacttct gaatttagag taatacggtc acattccttt tacagctagg   53280
aattgttttt aaaatgcaaa tttaacactt ttcagcatgc tcaatacttt ttaagttcaa   53340
agtttgcaaa gtaacccatt tggccatgca gactgtaagt catacaactc tagagggaca   53400
accttcatgt agaatgcgta ggcgcagtat cccagcgtta cacagtatgg tgactgttac   53460
atttttggga aaaacaggc caaaaaaacc ccaaaaacca aaacttttta ttcaaaatta    53520
gctttctttc ttaactaacg gtgttttttg ggctggagga agccagtgag aaaaagtttt   53580
gaaaattgta aatgctttg tgactgcaag atactattac tccaatggag ttcaacatct    53640
ccactatata aacccagaag aggctgaaat ccgttcctg atacccaggg cttcttttgt    53700
tgtgccagga ttatctctcc ccaataatta atcactaatc gacttaaaac actaaaaact   53760
caaccactta acctatttgt aacctcagtc aagttaatca tttccttcta attttaatgc   53820
attaagtttt acaataggcg ttaaaccttt ttcaaatgca atggttttc ctttagtctt    53880 ttaatacatt gactcacaga aagattgttt tgttcttggg acaaacccta cttgatcaca   53940
```

```
tatattttta atacagttct cacttaacgt cactgatagg ctcttggaaa gtggagcctt   54000
aagtgaaatg ttgcagtaga cctttctcat cgaccttgta acacaacatt attaaaaaac   54060
ctgtttactg tatatcatgt tgcttaaagt tagaagtttc caagagccta ctgatgacag   54120
tgagttagtg tactcattgg tttcagttag ctaattgtct gtttagcatt tttgcatcca   54180
tatttttatg taaaatgagc ccctcattcc cttttgtcc tttaggtggc tttggaatca    54240
cctagttaag gggaaacgcc ctcatatttt gaaacgtata aacttaaaac aatgccacct   54300
ttttctcggc aaaggttcac actaaatact ccactggttt ttcctcctgt caggtgtatc   54360
tccccttaat ctcttcacat tttctcctct tcctccctag aaaattaggc ctccccacaa   54420
caaaagttct attatgaact gtaacttgct ccaagaaga caaaatgtgc taacaccgtg    54480
acaaagtgta ccctgtgaca atgtcacatt gaaaagatca cgaactggct ttgggttgtt   54540
cacagtggga tacaaattcc tgcttcatct cttaatagtt aggtgaactg tgtagttact   54600
ttttttatcc taacctcagg cctaacatat gaaatgagga taacatatgc ctttaagagt   54660
tgtgcatgat tttgaaatat gtataaagta cctggtggaa ttatttggca tctaagagtt   54720
gctcagtaat tgctaattct actaagtgag gaagtgattt tttttcagct catgctgtta   54780
aatgtcctca atccaccaac ccacaattta gaaatccaaa aagttctgaa aattaagtat   54840
tttcataact tacatggtgg caaaatatga tgacctaaat gtgaggcctt tcatatctca   54900
gtgtgaaaat tcctaagttc actagagttt ttttttttt tttttgaga cggagtttcg     54960 cccttgttgc ccaggctcca gtgcaatggc gtggtctcgg ctcactgcaa cctccgcctc   55020
ctgggttcaa gcgattctcc tgcctcagcc tcctaagtag ctgagattat aggcatgcgc   55080
caccacgcct ggctaatttt gtattttcag tagagacggg gtttctccat gttggtcagg   55140
ctggtctcga actcccgacc ttaggtgatc tgcccgcctc agcctcccaa agtgctggga   55200
ttacaggcat gagccaccgc gcctggccct cacgagagat attaatgtga ttgtttacag   55260
gagtactacc ctaaactagt gatggtacat tactatacag tacatgcatc ctgttacctt   55320
ttgggaattc cacattttc aaaaatttta aaccacatat ggccccaatg gtttcaaact    55380
aggaatgtgg acttctaata cactctctgt aaaatcaaat actgtatata caaatagtaa   55440
aaaggagaat gactaagatt tatgcagtct aaatccagcc ttgatattat ctctacacta   55500
actccttggg ttcaaagtca tcactggtaa actgaaggaa cgggacttaa gttctttcta   55560 gcttatttt ttaatttagt acttttaact atctctctca gcctgagcaa catggtgaaa    55620
ccctgtctac aaaaaattag ccaggcgtgg tgggccacac ctatagtccc agctacctga   55680
aaggctgagg tgggaggatc acctgagcct gaaaggttga ggatgcagtg agcctgtgat   55740
cgcaccagtg cactcccgcc tgggtgacag tgagatcctg tctccaaaaa aaaaagtat    55800 ctctgaaaat tattttaaat attgagttga gcaaaacgc taagttaaac attttggctg    55860 ttttcctaa aatgttttaa acagctaaaa atcaatgtgt atggaatgta ttcaccattg    55920
aggagatatt aaaaaaaacc tgaccatctt cacactgaat actaggcaag aaagattagt   55980
accatggaaa aaaaatgcta gttttgtatt cagatctgag ctcaaacctt agctctgcta   56040
tcatagctct gtaactgtaa catattcttt aagcttgttt tgtcatgtta catggtgata   56100
aagaaaaata cttgttacag ggttgtaata aggataaaac aaagtgaaaa cctctagcac   56160
agttcctgac tgcattttt ctcaatgttt gttgaaaatg aaaacatttt aaacatttaa    56220
aatgaaaatt ttaaacactg taattttcag gtaattaatt acatgtatgt tgagcaaaag   56280
```

```
tgaatacttt tcttataaaa gtaactttcc ggccgggcgc ggtagttcac gcctgtaatc    56340
ccagcacttt gggaggctga agtgggtgga tcgcctgagg tcaagagttc gagaccagcc    56400
tggccaacat ggtgaaaccc tgtccctact aaaaatacaa aagttagctg ggtgtggtag    56460
tgggcacctg taattccagc tactctgagg ctgaggcagg agaatcactt gaacccggga    56520
ggtggaggtt gcaatgagcc gagattgcac cattgcactc ccgcctgggc aacaagaggg    56580
aaatcccatc tcaaataaat aaataactcc cccattattc aggcattgta aattatgtat    56640
ctttgatggc atgtctttga aggaattatg tcttttttaga ggaaactgac aggtaatttt   56700
aaaaagtata gatccaaggt taataaactc acttctctct ctctctctct cacacacaca    56760
cacacacaca cacacacaca cacactagag aataagagaa tgagccagtc tcatctacaa    56820
ccatattaaa cttgtgtctt catgtgcaca tttggtaaca cattttgaac taccttgaat    56880
tttcaagttt ctagttttc tctttagctg aggacttctt gaaaccaatt gttttggggg     56940
agagaatatt tttagaatcc aggcatggcc caaacaattc tctttgaaaa gaaagcaaac    57000
tggaatcctg ggaaagccgt taattctcaa cactacttat aaacatgaca aacaataaaa    57060
taaattctat aacaacttgt aagagcttat gttttcacat ctaaattttc aatggtaagg    57120
ttccttacaa tctcaagtgt taaacaaaag gtatcaagca cacttaggtt acaaggagaa    57180
gcaaaaagat tggtttgagc aacctggatc actttcaata agggaggagg atctctggag    57240
agtgtaacag ctgaatttca agaaatctgg tttctagttt gggcaagtca gtaaatctga    57300
gctttctttc tcacctctta caagtaatgg cattttcctt ccttcctcac aaagttgact    57360
catgaaagca cttaaaaaag ttaaaaatgt tacatactat gttctttaat cagcactaat    57420
aacattaata ttgatcgggc agaaggtaca gcgatcatgc gggtggggac cagaattggg    57480
aattgggaat tgggaaatct aggttctcag cccaacattt gcacctgcta gttcgtgatg    57540
caaggcacct cacttatcca ggtccccatt aaactaggtt taataaagtg agtttgccta    57600
aacctcttcc tagctccaag gctaatttta agctattaat ttgaatccaa ggcctaaaat    57660
atttgagctc tcatttaaca gtcggccact gcaagggta aagacagcaa tcttgtatga     57720
acaaagttaa acataacgtg ctagacacag gtctttgcaa aaccatgcag tagccaatag    57780
gtccaccata ccacccttca tttggaaatt gatgctaagg tgccataggt acatttccaa    57840
atgctcttaa aatgtttagg ttcatattaa aataaaaatg gatatttatg gtacaatgag    57900
aaccagaaaa actgcaaaat tatacacagg cctaagggca gaaatacccc aaaagacgac    57960
acagtgacaa tattttccaa cttgtgcttt tttgttttta aaacaaggct gatgattctg    58020
aaatcaggtc aatgtctatc acttttttcg ttgatgttaa atgcactaag ggaatataga    58080
ttcttcaatt atactttgaa acaacatcat ttccctaagt caggactttt ttattgcaaa    58140
atttaacaaa ccaccaaact caagtttaat tatttctgct ttattattgg tcatgaataa    58200
agacttcttt taaaaaataa ttacaaagaa tttatgacta aaatatactc cgtaaccaac    58260
ttgctctgaa attaataatt tgaaaatggc aagaaaaaa aaaacagcc cacaacatat     58320 taacttcact cttcaattag gggaaataaa caaggtcaaa attagtttaa acaacatact    58380
gagtaataaa aaagttgtgc agaagtccca atgcctccaa aaaactgata gaatgtgctt    58440
aatatatata tccccacatg gtaacataaa aaatccaagt tttccagtaa aatgttctg    58500 ttcatgttcc aatacctaaa tctgggaaaa caaattcagg cagatgagat aagaacgtca    58560
ccacaataaa ataaagtcat caaaacttag tgaactaaaa tttaaaaggt agaggaatta    58620
tttttcctaa tttgacctaa tttgaccaca cagtaattac ttccagaaga caaaagatcc    58680
```

```
aatccaggta aaataaatct ttattttatt attttacctg atcctaaaga aaatattcta   58740
cgtgagttga tggatacatt ggtcaagttt tatgccaaaa aaattacgca aactatactc   58800
tgaaagagct atccagactc cttgccaaaa ggccagcata actttcagag tagagatcgt   58860
gagttaccac agatgctgat tgaaacagag ctaacagcag ctttctcctc attcccaccc   58920
cgtgtgtagg agtacgcagt ctcataccac caccagttgg aggatgatct agtctggaga   58980
cagaacggtg tagaacaaaa cccttgccag ggtcccaaac ctctctttag aactctaatt   59040
aaaggtactt ccgtttccca cacaacttgg aatgaagggg aagcaacgac tgttaaaaca   59100
tttaaaaact aagcctttat ctatttattt agaaaacaca ctatgcaaag aagccaattc   59160
cttacattaa aaatatttat ttgcaacagc tctccttttt aaggcctcaa cagattggac   59220
taaaccacac ccctccataa atggcacatt ccatacaata gcctggagaa tggcatagga   59280
cgattccacc gacagctggg ggaatagcaa acttgttgaa attccgagaa tgaagtctga   59340
tggttacccg aacctagccc ttttattact aaagtcactc ggggacaaga gggttacaaa   59400
aatatcccga gacgcgtacg cgggtgagag tggaacgaga accacacggg atttgggccg   59460
tgctgttaac ccgcacctcc ctgagtacgg acatttcccc gaggaaggac atttctagtc   59520
ggagagaaag agcgaacttt ggggttaact ctctcaaaac tctgaggtgg ggagagaggc   59580
agcagcccat tattttccag gatccagtcc cgaactctca cttttgcccg ggggaaaaa    59640 aacgggtccc gcccacgctc ggcccgatcc gggaggcggg gcctgcagcg accccgaagg   59700
acagaggcgg ggccggttgg cagtgctgcc cctcccccct tgccaggaac accccgtcc    59760 gctacagaga gggctcaggg cccccacccc cgcgccagtc gctggggaa ggggcaatac     59820 gggtgcctcc gcccctcctc gctgaaggtg gggagtggag ctcgagtccg cccgcctccc   59880
cgcgctggct ccaaggggac ggccccgagg aggtggggcc tcttgggggc gctgacttca   59940
caccctcccc cctccggccg ctggcggctc agggacaccc cgcccgctct agtgcggtgg   60000
gtgggggagg cagctgagca gaccggagcc ctgcagcggc gcggggcggg gagggcgcg    60060 cgcacgggcg cgcagccacc accccgcgc gccagcaggg cccccacgc tcaagggtgc      60120 gcgcgggccc cgaaagggag gaggccgcgc gcggcaccgg ggatggcgga ctctagcctt   60180
ctgtccccca ctcttttcac cactcgcccc catcccccct caacccgctc caggcctcag   60240
actccgcact gacctgacag gccgcgacat gttcgctgtc gaaacaggac cgagtcgaga   60300
agccaaagac caggaccccc cccaccccgc gcgctcggcg ccccaccccc ccgaacttc    60360 agccgatggg accgctgctg ccgaacccg agctgctggc ttctcaaact ccgctgctct    60420
ttggttcagg gctcctggaa cagacgagcc ccccgctccc ccgtctcttc aaaatggatg   60480
aatcaaacca gccgaaaatg cgccaaagcc gccgtgcaac caaacccact agggtttgtg   60540
cgctcctccc caacacgcct gctcattgga gacttctgcc agatgcgccc agatcattag   60600
tccgtttgaa tcatcacgtc ttccaggccc gccctgctc tctgataggc tccaccttca    60660 ccgtggggt cctgttagtc aagatgctct gagagcgcac ggccgcaaaa caaaaatggt     60720
cgctgcttag cccgcccct ggtttccact ccagagttgc agattcgtct ggggtcgtat     60780
cttagaaaga ctagaaaaaa agatttatgt agggttcagc gttgctcagt gttagtttaa   60840
tggtgtttca tctcgtctgc cttgatcacc ttgaaaatcc tctaatagca aaacccgtgg   60900
gagaggcagc agattcgtca ctgcggggct gctacagaat tggagggaaa ttccttaggt   60960
tcaaaaaatt tgaccttaaa cctacaagcc ccttaccctg gcttcggcat taaccctcag   61020
```

```
ggaccaaatg aggctgctgg agtagagagg caggatcata atcaaggaat atcttcaccc   61080
ccaattacca ttctccattc tggacctcga gatccacttc agggtcatta aagtcccagt   61140
ctggtgcatt actattttaa gaaaagagtc aggtgtacaa taactaagag catgagctca   61200
ggggccacaa ggtatttcag gtggaatccc aggtccacta cttaatggtg gtataacttt   61260
ccttctctgt gcctcagttt tctcatctgt aaaatgggaa acaagggtac ctaactgcat   61320
aggcttatta gtattaaatg agttgatata tctatcaaaa gtctttagga tagtctctgg   61380
ctcacagtaa gtgctacgta agtgttaaat ccaagtttta aaagatgatt ccgtccctgg   61440
gtagagatgg gtggagctgg ctcaagaccc tatgaattct attgatttac ccttgcactt   61500
tgaaaaacaa aacaaagact cttcgaagtc atataactga aagtaacgca catcatttca   61560
cttaaatccg tgagcatttg ttggatgcct aatactctca aaggcagagc tcaggattcc   61620
tatgtgaatg gctaaggctg agtctgctat cgaaaataga cgtcaatccc tgtcacagtc   61680
aaagcgatca ttttgtttg gtggctgtgc gctctcagag catcttgact aacaggaccc   61740
cacggtgaag gtggggccta tcagagagta gggtggggcc tggaagacgt gatgattcaa   61800
acggactaat gatctgggcg catctggcag aagtctccaa tgagcagtca gttaacaacc   61860
aattgaagat acactttcca aacaacaaca acaaaaaaca caccacatct gcctcctgaa   61920
agtctccctt tgtaaaatct ggcttcccaa aaagaagaga atagcacagt ccaccagtga   61980
agcattaaac aaattaatat cttttgtctc ttccatgtca ttccaccctc tgtccctctt   62040
attttatttt ttaattttta ttttttcgag acggagtctc actcactatg ctccccaggc   62100
tggattgcag tggcacgatc tctgcacact gaaacttcca ccacccgggt tcaagcgatt   62160
ctcctgcctc agcctcccaa gtagctggga ttacaggcgt gctccaccat gcccagctaa   62220
ttttggtatt ttattgtgga gatggggttt caccatgttg gccaggctgg tcttgaactc   62280
ttgacctcaa gtgatctgcc tgccttggcc tcccaaagtg ctggcattac aggagtgagc   62340
caccgcaccc gtcccccgca atttttttaa attgtggtta aaaaaaaaat acataacata   62400
aatgtaccac tttaactgtc tctaagtgta cagttaagtg gcgttaagta cattcacatt   62460
gttatgcaac catcaccacg attcaacacc agaactttct cattttccca aactgaaact   62520
ctgtgcccat taaacactaa ctccccactt tccccttcc ccatagccgc tggcaaccac   62580
cattttactt tctgtctgta tgaacctgac tgctctagga atctcatgtt agtgtaatca   62640
tacagtattt gtccttttgt gactggctta tttcacttag cataatggca tccaggttta   62700
tccatgttgt agcaagtgtc aaaatttcct ttctcttaaa ggccaaataa tattccactg   62760
tatgtatatg ccacatttg tttatccact catccatcaa tggacacttg ggttgcttcc   62820
accttatggc tattgtgaat gatgttgctg ggcaagtggg agtacaaata tgtttgagta   62880
cctgctttcc tttctggata tacccagaa atggaattg ctagatcata cagctattct   62940
gtttaatttt tgaagaatt gccgtatgga ttctccatca gctgtatcat tttacactcc   63000
taccagcaat gtgcaagtgt tccaatttcc ccatgtcctt gccaacagta agtttttac   63060 aatagccatc ctaatgagtg tccatatacg gttttttttt tttttttga aacggagtct   63120 cgctctgttg cccaggctgg agtgcagtgg tgcgatctct gctcactgca aactccgcct   63180
cccaggttca cgccattctc ctgcctcagc ctcccaagta gctgagacta cagatgcccg   63240
ccaccacgcc tggctaattt ttgtattttt agtacagacg gagtttcatt acgttggcca   63300
ggctggtctc aaactcctga cctcaggtga tccaccgcc tcggcctccc aaagtgctgg   63360
gattacaggc atgagccacc acgcccagcc tttttttttt ttttagatag agtctagccc   63420
```

-continued

```
tgtcacctgg tctggctcac tgcagcctct acctcccggg ttcaagcaat tctcctgcct   63480
tagcctcaga gtagctggga ttacaggcat gcgccaccac acctggcttt ttgtattttt   63540
agtagagacg gggtttcact atgtttgcca ggctggtctc gaactcctga cctcaagtga   63600
tccacccacc tcagcctccc aaagtgctgg gattacaggc gtgagccacc gcgcccggct   63660
ccatatatgt tttgactaag tgtattacca tccccactat tgtcagaatg ccagggcaga   63720
aacttgggtg gcagagtgat caccaagtgg ctttggtgga ggctctttta ttaggccaaa   63780
ttgttattat tttagtaaac atcattattt ggtattgtga gatggggcag aggaattctt   63840
gttactcatt tattaggtag tgaacagaaa tgaccatagt caacatttgc aggcaggtgg   63900
aaagttcaga ataggtcttc aggttgttgg cctgatagtg tagtgcaagg ccagtataca   63960
aatggccact gagtgaagac tctcctcctt ccaagttcag cctcatatcc tacctttctc   64020
ttcactgcag cttcagctaa catcttcctt ccatttgctc atttattcac ttagtattgc   64080
aatcaacatc gtctctcagg gaagaaataa cttaagactt gaacttcgag tttacttttt   64140
agtggacaag tacagaacta tggccagtag tgccaaaaga acgtggaatg cagtctccaa   64200
ggtcagttcc ctctaatctg tacccagtg atctgccctg tgtacctgtt ttaaccacaa   64260
tcagtttgct ggaaactgaa gaaggacact gatcatagga taggtcaggt tttagaagca   64320
ctatctgata accccgaagg gacaatatgt gtaataaaac taggagaaac tatgaaaaca   64380
gaaaagcctc aggagacaga aaaggcggaa ttattccttt tccctggaaa tgaaatctca   64440
tggcctttta aacacagtgc ttaattttcc cctgtgattt ttagttatgt tttgagaagt   64500 accatttttcc ttctccttca catatgttag acagtaagaa ctggcagtgc tgggatggta   64560
agactgatgg gttttccaca tacccaacaa aaacccattt ccatcaaggg ctacactata   64620
gcagctgaga gcttcataaa aattttttcag cattgtgtgc tgggcacttc cagttctgtg   64680
atctcatgaa agtcaaccaa ccaggtctaa agacagagac tgcttccaca gagaacagga   64740
ccacagaagg gtaccactct ttggagatgc tgccaggaag ttaaagaaac ctccaactct   64800 tttttttaaaa attttttatt tttaaatctt ctacctccaa cctgctggct ctctctgtac   64860
taccactcta gaagacagga tgggatagaa gaactgtgtg tattaggtct gtctctctac   64920
aaccccagag actgagtagc ctgcttggag atagatccgt gattagagga aattttccct   64980
tgtcttcttt ttctcaagtg tgtatttctt tgctccagat tcccatcttc ctctctactt   65040
tgaatattaa gagctaagct taggtgattt tgtactacta aaacaataaa gatgtacaac   65100
tcaatatcca gtttaaattg aagaaaaata caacaagact aacttactgt tttgctggac   65160
acaaaatcca tagaaaactt gtcattgtaa cactgaggga gagacagctt tatctatgca   65220
aaccactgac aaatattgtg aggtgaacac tgctgaaaag cgaggcccca aggtagaaca   65280
aaaagagcac tgaacttgta atcaagatta tctgtctctg agcttgtaat ttactaccta   65340 tgtccttttag caaatttcaa actccctgtg cctcagctcc ttcatctgtg aaatggagat   65400
aattatactg gtccttaccc acttcacaag gttagcataa taacaagaaa aaaaaaaagg   65460
gatcacttgc gaaagtagtt tgtagactgt gaagcactat gagcggtaga atgggatcac   65520
attcgcttca ctaaaggaaa accccaaatt ccgatagctg acttattcct ccaacagaat   65580
acaaccatcc ctgaatactg gtaacagtta aaaaaactgc tcagcagggc gcggtggctc   65640
atgcctgtaa tccagcacct tgggagacc aaggtgggcg gatcacgagg tcaggagttc   65700
gagaccagcc tggctaacat ggtgaaatcc cgtctctact aaaaatacaa aaattagctg   65760
```

```
ggtgttgtgg tgcacacctg taatcccagc taccagggag gctgaggcag gagaatgact   65820
tgaacccagg aggtggagat tgcagtgagc cgagatggtg ctactgcact ccagcctgga   65880
tgtcagagca agactccatc tcaaaaaaac aaaacaaaac aaaactgctt acagcttcca   65940
gatgagatga agaaaaggtg cagtaatgag gagtgatgac catcagcttg cagcactgcg   66000
atacactttc tgtttcatat agagagacaa tgacattctc tacctcccaa ctattcctag   66060
gagaattaag ctgctccaac catgaccata taggcatgat ttcaccaact agtgccagcc   66120
tttctacttc tgtattggtt ccagctcggt atccctaact gcctaacagg tatttccact   66180
tggatgtcca caagctcaat ttatttatgt caaaaaaaat catctttccc acccacatta   66240
ttttcctgac tctattcctg tcctctgtat cattttcccc tgtcagtttt attgaggtat   66300
aattgacaaa taaaaattgt atatatttaa gttgtacatt gtgatgtttt gatacattat   66360
gaaatgatta tccaatcaag ctaattaaca tgtccatggc ctcagttatc ttttttttggt   66420
gtagtgagaa tacttaagat ctactctcca agcaaatttc aagtatataa aatattaact   66480
atagtcacca tgctgtacat taggtctcca aaacctgttc atcttataac tgcaagtttg   66540
tgccctttga ccatcatctc ctcattttc ccatcctctg accctggta gccatcctct     66600
actctctttt tctatgagat ccacttttct gagattccac acactggata aacgagatca   66660
tgcagtattt gtcttctat gcctggctta tttcacttag tataatgtct tccaggttca    66720
tccatgtggt tgcaaatagc agaacttcaa gaaggctgaa taatattctg tcgtgtgtat   66780
gtaggtatat aaacacacat atcacatttt ctttatccat tcatccactg acaatctgat   66840
tccatatcgt ggctattgca ataatgctg tgatgaacat gggcatgcag atacctcttt    66900
gagataccaa tttcattttc tttggatata tatccagaag tggggctgct ggatcatatg   66960
gtagttctat tttttaaattt tttgaggaac ctctatactg ttctccacaa tggctgtacc   67020
aatttacatc ccactaatga tgtataaggg ttccctttt tccacctcct caccaacact    67080
tgttatcgtt tgacttttg agaatagcca tcctaccagg cgtgaggtgg tatctcattg    67140
tgttttgttt ttttttgttt ttgttttttg agatggagtt tcactcttgt ccctcagggt   67200
ggagtgcaat ggtgtgatct cggctcactg gttcaagaga gtttcctccc tcagcctccc   67260
aaggtagctg agattacagg tgcacaccac cacatctggc taatttttgt attttagta    67320
gagacgggat tttattacgt tggccaggct ggtctgaaac tcctgacctc aggtgatcca   67380
cccaccttgg cttcccaaag tgtgcccggc tcattgtggt tttgatttgc atttccctga   67440
tgactgtgat gttgagcacc ttttcatat acctgctggg tgtttgttgg gtgtttgtat    67500
gtctcctttg gaaaaatgtc tattcaggtc ctttgtccat ttttatttg ggttatttgg    67560
gttttttttt tttttttttt gctattgagt tgtatgagtt ccttatatat tttggatatt   67620
aatgccttac tgaaaacatg gtttgcaaat atttttctccc attctgtagg ctgccttttc   67680
attttgtaga ttgttttctt tgctgtgcgt tatcaccttc ctcttagcta tctgtattca   67740
aatcttggta ctactgactc cgtcttatgc ctcactgtta gtcttcaaag tggaaacctc   67800
ttgattcctt cttcattgca tttgtcaaat tcatttttca cttgccattt acattgtcac   67860
cattcatgct taaactacta taacagtctt tcttctttcc tttttctgta atctgtagta   67920
gacacaacag gcaatactac cttcctgtgg tttacagtac tcatatcatt ctcatactca   67980
aattttcaat aagtccatac agcttccaca ataaaggcta aactgtgcta gcatttaagc   68040
taccatcaga cagatttctc aagcccaaat ctaatattac tctacttaaa atacctccac   68100
gggccaggca caatggctca cgcctgtaat cccagcactt cgggaggctg aggcaagcgg   68160
```

```
atcacttgag gtcaggagtt cgaggccagc cggaccaaca tggtgaaacc caatctctac    68220
taaaaataca aaaaaaaaaa aaaaaattag ctggtcatgg tggtatgcgc ctgtaatccc    68280
agctactgag gaggctgagg catgagaatc aaatcgcttg taccctggag gtagaggttg    68340
cagtgagctg agatggcgcc actgcactcc agcctgggag acagagtgag actccgtctc    68400
aataaaaaat aaataaaatc cctccatgaa ctggggaaaa tatttgcaat atgtgtgaca    68460
aaaggttaat gttcataata taaaagaac ttttaaaag tcacaagaaa aagacaaaat     68520
gaaaacagac ataggacaca aataggtgat tcatacaata aaaatgacta atacatttaa    68580
aaatatgatc acttgtaaca aaaacaaat taaaaacatt ttctagcatg cacactg       68637
```

<210> SEQ ID NO 4
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 4
agcacatagc aggcactagc    20

<210> SEQ ID NO 5
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 5
cgattgtgcc actacacagt    20

<210> SEQ ID NO 6
<211> LENGTH: 23
<212> TYPE: DNA
<213> ORGANISM: Artificial sequence
<220> FEATURE:
<223> OTHER INFORMATION: Oligonucleotide as PCR primer

<400> SEQUENCE: 6
aaaaatgagt ccagtagaag cct    23

<210> SEQ ID NO 7
<211> LENGTH: 19
<212> TYPE: DNA
<213> ORGANISM: Artificial sequence
<220> FEATURE:
<223> OTHER INFORMATION: Oligonucleotide as PCR primer

<400> SEQUENCE: 7
agccagattt acatcccag    19

<210> SEQ ID NO 8
<211> LENGTH: 16
<212> TYPE: DNA
<213> ORGANISM: Artificial sequence
<220> FEATURE:
<223> OTHER INFORMATION: Oligonucleotide as PCR primer

<400> SEQUENCE: 8
tatcttgccc tgcacc    16

<210> SEQ ID NO 9

```
<211> LENGTH: 16
<212> TYPE: DNA
<213> ORGANISM: Artificial sequence
<220> FEATURE:
<223> OTHER INFORMATION: Oligonucleotide as PCR primer

<400> SEQUENCE: 9
aagtgggtct ccccag                                                        16

<210> SEQ ID NO 10
<211> LENGTH: 17
<212> TYPE: DNA
<213> ORGANISM: Artificial sequence
<220> FEATURE:
<223> OTHER INFORMATION: Oligonucleotide as PCR primer

<400> SEQUENCE: 10
ttgctcggcc agagtct                                                       17

<210> SEQ ID NO 11
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 11
acgcatcaca cctggctagt                                                    20

<210> SEQ ID NO 12
<211> LENGTH: 16
<212> TYPE: DNA
<213> ORGANISM: Artificial sequence
<220> FEATURE:
<223> OTHER INFORMATION: Oligonucleotide as PCR primer

<400> SEQUENCE: 12
gggcctatgg ctggaa                                                        16

<210> SEQ ID NO 13
<211> LENGTH: 16
<212> TYPE: DNA
<213> ORGANISM: Artificial sequence
<220> FEATURE:
<223> OTHER INFORMATION: Oligonucleotide as PCR primer

<400> SEQUENCE: 13
ggctatgctg gggcaa                                                        16

<210> SEQ ID NO 14
<211> LENGTH: 19
<212> TYPE: DNA
<213> ORGANISM: Artificial sequence
<220> FEATURE:
<223> OTHER INFORMATION: Oligonucleotide as PCR primer

<400> SEQUENCE: 14
tcagttccat aggctgacg                                                     19

<210> SEQ ID NO 15
<211> LENGTH: 18
<212> TYPE: DNA
<213> ORGANISM: Artificial sequence
<220> FEATURE:
<223> OTHER INFORMATION: Oligonucleotide as PCR primer

<400> SEQUENCE: 15
```

```
cattgctgat gctggagg                                                    18

<210> SEQ ID NO 16
<211> LENGTH: 19
<212> TYPE: DNA
<213> ORGANISM: Artificial sequence
<220> FEATURE:
<223> OTHER INFORMATION: Oligonucleotide as PCR primer

<400> SEQUENCE: 16
ccttaattgt ggtgttggt                                                   19

<210> SEQ ID NO 17
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 17
aaaaatctgg aaggcataaa                                                  20

<210> SEQ ID NO 18
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 18
agcaagaccc tgtctcaaaa                                                  20

<210> SEQ ID NO 19
<211> LENGTH: 19
<212> TYPE: DNA
<213> ORGANISM: Artificial sequence
<220> FEATURE:
<223> OTHER INFORMATION: Oligonucleotide as PCR primer

<400> SEQUENCE: 19
tggatagctt tccaccact                                                   19

<210> SEQ ID NO 20
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 20
acaaggtgac cggaaagacc                                                  20

<210> SEQ ID NO 21
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 21
agctctggca agttgaagga                                                  20

<210> SEQ ID NO 22
<211> LENGTH: 25
<212> TYPE: DNA
```

```
<213> ORGANISM: Artificial sequence
<220> FEATURE:
<223> OTHER INFORMATION: Oligonucleotide as PCR primer

<400> SEQUENCE: 22
atctgggttc actattaaac agagt                                         25

<210> SEQ ID NO 23
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 23
tgggcaaggt agaatatgtg                                               20

<210> SEQ ID NO 24
<211> LENGTH: 19
<212> TYPE: DNA
<213> ORGANISM: Artificial sequence
<220> FEATURE:
<223> OTHER INFORMATION: Oligonucleotide as PCR primer

<400> SEQUENCE: 24
gggtgacaga gcaagactc                                                19

<210> SEQ ID NO 25
<211> LENGTH: 19
<212> TYPE: DNA
<213> ORGANISM: Artificial sequence
<220> FEATURE:
<223> OTHER INFORMATION: Oligonucleotide as PCR primer

<400> SEQUENCE: 25
ccctgacctc ccttacaga                                                19

<210> SEQ ID NO 26
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 26
aactgtgtcc agcagcaact                                               20

<210> SEQ ID NO 27
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 27
tatgtgcctg ttgtgtgcat                                               20

<210> SEQ ID NO 28
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 28
agggtcccca aagagccttc                                               20
```

<210> SEQ ID NO 29
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 29
atggcagcac atcctgcttc                                                    20

<210> SEQ ID NO 30
<211> LENGTH: 19
<212> TYPE: DNA
<213> ORGANISM: Artificial sequence
<220> FEATURE:
<223> OTHER INFORMATION: Oligonucleotide as PCR primer

<400> SEQUENCE: 30
aatcacttga acctgggag                                                     19

<210> SEQ ID NO 31
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 31
actgactggc tgtttctgag                                                    20

<210> SEQ ID NO 32
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 32
actgcttatt cggagttgga                                                    20

<210> SEQ ID NO 33
<211> LENGTH: 24
<212> TYPE: DNA
<213> ORGANISM: Artificial sequence
<220> FEATURE:
<223> OTHER INFORMATION: Oligonucleotide as PCR primer

<400> SEQUENCE: 33
ccaagagttt tcttagcaaa tcac                                               24

<210> SEQ ID NO 34
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 34
ctgagcacag cagtggtctc                                                    20

<210> SEQ ID NO 35
<211> LENGTH: 20
<212> TYPE: DNA
<213> ORGANISM: Artificial sequence
<220> FEATURE:

```
<223> OTHER INFORMATION: Oligonucleotide as PCR primer

<400> SEQUENCE: 35
aaggcttatc aagagcgagg                                                    20

<210> SEQ ID NO 36
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 36
agacttacag cactggctgc                                                    20

<210> SEQ ID NO 37
<211> LENGTH: 20
<212> TYPE: DNA
<213> ORGANISM: Artificial sequence
<220> FEATURE:
<223> OTHER INFORMATION: Oligonucleotide as PCR primer

<400> SEQUENCE: 37
tgctcctagg aaaggaaaca                                                    20

<210> SEQ ID NO 38
<211> LENGTH: 17
<212> TYPE: DNA
<213> ORGANISM: Artificial sequence
<220> FEATURE:
<223> OTHER INFORMATION: Oligonucleotide as PCR primer

<400> SEQUENCE: 38
gcttctggcc tctgtca                                                       17

<210> SEQ ID NO 39
<211> LENGTH: 18
<212> TYPE: DNA
<213> ORGANISM: Artificial sequence
<220> FEATURE:
<223> OTHER INFORMATION: Oligonucleotide as PCR primer

<400> SEQUENCE: 39
aattttgcgt gtgtgtgc                                                      18

<210> SEQ ID NO 40
<211> LENGTH: 23
<212> TYPE: DNA
<213> ORGANISM: Artificial sequence
<220> FEATURE:
<223> OTHER INFORMATION: Oligonucleotide as PCR primer
<220> FEATURE:
<221> NAME/KEY: misc_feature
<222> LOCATION: (16)..(16)
<223> OTHER INFORMATION: n

<400> SEQUENCE: 40
tgaagtgtgc attctntaca tca                                                23

<210> SEQ ID NO 41
<211> LENGTH: 19
<212> TYPE: DNA
<213> ORGANISM: Artificial sequence
<220> FEATURE:
<223> OTHER INFORMATION: Oligonucleotide as PCR primer

<400> SEQUENCE: 41
```

```
cgagacattt gcatcatca                                                  19

<210> SEQ ID NO 42
<211> LENGTH: 1817
<212> TYPE: DNA
<213> ORGANISM: Homo sapiens
<220> FEATURE:
<221> NAME/KEY: CDS
<222> LOCATION: (55)..(636)
<223> OTHER INFORMATION: CDS

<400> SEQUENCE: 42
gccgccactt ccgagagcgc ctgccgcccc tgcgccgccg agccagctgc caga atg      57
                                                              Met
                                                              1 ccg aac tgg gga gga ggc aag aaa tgt ggg gtg tgt cag aag acg gtt     105
Pro Asn Trp Gly Gly Gly Lys Lys Cys Gly Val Cys Gln Lys Thr Val
        5                   10                  15 tac ttt gcc gaa gag gtt cag tgc gaa ggc aac agc ttc cat aaa tcc     153
Tyr Phe Ala Glu Glu Val Gln Cys Glu Gly Asn Ser Phe His Lys Ser
                20                  25                  30 tgc ttc ctg tgc atg gtc tgc aag aag aat ctg gac agt acc act gtg     201
Cys Phe Leu Cys Met Val Cys Lys Lys Asn Leu Asp Ser Thr Thr Val
    35                  40                  45 gcc gtg cat ggt gag gag att tac tgc aag tcc tgc tac ggc aag aag     249
Ala Val His Gly Glu Glu Ile Tyr Cys Lys Ser Cys Tyr Gly Lys Lys
50                  55                  60                  65 tat ggg ccc aaa ggc tat ggc tac ggg cag ggc gca ggc acc ctc agc     297
Tyr Gly Pro Lys Gly Tyr Gly Tyr Gly Gln Gly Ala Gly Thr Leu Ser
                70                  75                  80 act gac aag ggg gag tcg ctg ggt atc aag cac gag gaa gcc cct ggc     345
Thr Asp Lys Gly Glu Ser Leu Gly Ile Lys His Glu Glu Ala Pro Gly
                85                  90                  95 cac agg ccc acc acc aac ccc aat gca tcc aaa ttt gcc cag aag att     393
His Arg Pro Thr Thr Asn Pro Asn Ala Ser Lys Phe Ala Gln Lys Ile
            100                 105                 110 ggt ggc tcc gag cgc tgc ccc cga tgc agc cag gca gtc tat gct gcg     441
Gly Gly Ser Glu Arg Cys Pro Arg Cys Ser Gln Ala Val Tyr Ala Ala
        115                 120                 125 gag aag gtg att ggt gct ggg aag tcc tgg cat aag gcc tgc ttt cga     489
Glu Lys Val Ile Gly Ala Gly Lys Ser Trp His Lys Ala Cys Phe Arg
130                 135                 140                 145 tgt gcc aag tgt ggc aaa ggc ctt gag tca acc acc ctg gca gac aag     537
Cys Ala Lys Cys Gly Lys Gly Leu Glu Ser Thr Thr Leu Ala Asp Lys
                150                 155                 160 gat ggc gag att tac tgc aaa gga tgt tat gct aaa aac ttc ggg ccc     585
Asp Gly Glu Ile Tyr Cys Lys Gly Cys Tyr Ala Lys Asn Phe Gly Pro
                165                 170                 175 aag ggc ttt ggt ttt ggg caa gga gct ggg gcc ttg gtc cac tct gag     633
Lys Gly Phe Gly Phe Gly Gln Gly Ala Gly Ala Leu Val His Ser Glu
            180                 185                 190 tga ggccaccatc acccaccaca ccctgcccac tcctgcgctt ttcatcgcca          686
ttccattccc agcagctttg gagacctcca ggattattc tctgtcagcc ctgccacata    746
tcactaatga cttgaacttg gcatctggc tccctttggt ttgggggtct gcctgaggtc    806
ccaccccact aaagggctcc ccaggcctgg gatctgacac catcaccagt aggagacctc   866
agtgttttgg gtctaggtga gagcaggcc ctctccccac acctcgcccc acagagctct    926
gttcttagcc tcctgtgctg cgtgtccatc atcagctgac caagacacct gaggacacat   986
```

| | |
|---|---|
| cttggcaccc agaggagcag cagcaacagg ctgagggag agggaagcaa gaccaagatg | 1046 |
| aggaggggg aaggctgggt tttttggatc tcagagattc tcctctgtgg gaaagaggtt | 1106 |
| gagcttcctg gtgtccctca gagtaagcct gaggagtccc agcttaggga gtcactattg | 1166 |
| gaggcagaga ggcatgcagg cagggtccta ggagcccctg cttctccagg cctcttgcct | 1226 |
| ttgagtcttt gtggaatgga tagcctccca ctaggactgg gaggagaata acccaggtct | 1286 |
| taaggacccc aaagtcagga tgttgtttga tcttctcaaa catctagttc cctgcttgat | 1346 |
| gggaggatcc taatgaaata cctgaaacat atattggcat ttatcaatgg ctcaaatctt | 1406 |
| catttatctc tggccttaac cctggctcct gaggctgcgg ccagcagagc ccaggccagg | 1466 |
| gctctgttct tgccacacct gcttgatcct cagatgtgga gggaggtagg cactgcctca | 1526 |
| gtcttcatcc aaacaccttt ccctttgccc tgagacctca gaatcttccc tttaacccaa | 1586 |
| gaccctgcct cttccactcc acccttctcc agggacccctt agatcacatc actccacccc | 1646 |
| tgccaggccc caggttagga atagtggtgg gaggaagggg aaagggctgg gcctcaccgc | 1706 |
| tcccagcaac tgaaaggaca acactatctg gagccaccca ctgaaagggc tgcaggcatg | 1766 |
| ggctgtaccc aagctgattt ctcatctggt caataaagct gtttagacca g | 1817 |

<210> SEQ ID NO 43
<211> LENGTH: 193
<212> TYPE: PRT
<213> ORGANISM: Homo sapiens

<400> SEQUENCE: 43

```
Met Pro Asn Trp Gly Gly Gly Lys Lys Cys Gly Val Cys Gln Lys Thr
 1               5                  10                  15

Val Tyr Phe Ala Glu Glu Val Gln Cys Glu Gly Asn Ser Phe His Lys
            20                  25                  30

Ser Cys Phe Leu Cys Met Val Cys Lys Lys Asn Leu Asp Ser Thr Thr
        35                  40                  45

Val Ala Val His Gly Glu Glu Ile Tyr Cys Lys Ser Cys Tyr Gly Lys
    50                  55                  60

Lys Tyr Gly Pro Lys Gly Tyr Gly Tyr Gly Gln Gly Ala Gly Thr Leu
65                  70                  75                  80

Ser Thr Asp Lys Gly Glu Ser Leu Gly Ile Lys His Glu Glu Ala Pro
                85                  90                  95

Gly His Arg Pro Thr Thr Asn Pro Asn Ala Ser Lys Phe Ala Gln Lys
            100                 105                 110

Ile Gly Gly Ser Glu Arg Cys Pro Arg Cys Ser Gln Ala Val Tyr Ala
        115                 120                 125

Ala Glu Lys Val Ile Gly Ala Gly Lys Ser Trp His Lys Ala Cys Phe
    130                 135                 140

Arg Cys Ala Lys Cys Gly Lys Gly Leu Glu Ser Thr Thr Leu Ala Asp
145                 150                 155                 160

Lys Asp Gly Glu Ile Tyr Cys Lys Gly Cys Tyr Ala Lys Asn Phe Gly
                165                 170                 175

Pro Lys Gly Phe Gly Phe Gly Gln Gly Ala Gly Ala Leu Val His Ser
            180                 185                 190

Glu
```

<210> SEQ ID NO 44
<211> LENGTH: 11416
<212> TYPE: DNA
<213> ORGANISM: Homo sapiens

```
<220> FEATURE:
<221> NAME/KEY: CDS
<222> LOCATION: (51)..(3176)
<223> OTHER INFORMATION: CDS

<400> SEQUENCE: 44
attcggtggc gggtcccggc cgcggggctg gcgggctgag gggagaaaag atg gcg      56
                                                        Met Ala
                                                         1 gcg gcg gcg gca gct ggt gcg gcc tcc ggg ctg ccg ggt cca gtg gca    104
Ala Ala Ala Ala Ala Gly Ala Ala Ser Gly Leu Pro Gly Pro Val Ala
      5                  10                  15 caa gga tta aag gaa gcg tta gtg gat acg ctc acc ggg atc cta tcc    152
Gln Gly Leu Lys Glu Ala Leu Val Asp Thr Leu Thr Gly Ile Leu Ser
 20                  25                  30 cca gta cag gag gtg cgg gcg gct gct gaa gaa cag att aag gtg ctg    200
Pro Val Gln Glu Val Arg Ala Ala Ala Glu Glu Gln Ile Lys Val Leu
 35                  40                  45                  50 gag gtg acg gag gaa ttt ggt gtt cac ttg gca gaa ctg act gta gat    248
Glu Val Thr Glu Glu Phe Gly Val His Leu Ala Glu Leu Thr Val Asp
                 55                  60                  65 ccc cag ggg gca ctg gca atc cgt cag ctg gca tca gtc atc ttg aaa    296
Pro Gln Gly Ala Leu Ala Ile Arg Gln Leu Ala Ser Val Ile Leu Lys
                 70                  75                  80 caa tat gtg gag act cac tgg tgt gcc caa tca gag aaa ttt agg cct    344
Gln Tyr Val Glu Thr His Trp Cys Ala Gln Ser Glu Lys Phe Arg Pro
             85                  90                  95 cct gaa act aca gaa agg gca aaa att gtt atc cgg gag cta ttg cct    392
Pro Glu Thr Thr Glu Arg Ala Lys Ile Val Ile Arg Glu Leu Leu Pro
100                 105                 110 aat ggg ttg aga gaa tcg ata agc aaa gtg cgc tcc agt gtg gcc tat    440
Asn Gly Leu Arg Glu Ser Ile Ser Lys Val Arg Ser Ser Val Ala Tyr
115                 120                 125                 130 gca gtg tca gcc att gcc cac tgg gac tgg cct gaa gct tgg ccc caa    488
Ala Val Ser Ala Ile Ala His Trp Asp Trp Pro Glu Ala Trp Pro Gln
                135                 140                 145 ctc ttc aac ctg ctc atg gag atg ttg gtg agc gga gac tta aat gcc    536
Leu Phe Asn Leu Leu Met Glu Met Leu Val Ser Gly Asp Leu Asn Ala
            150                 155                 160 gtc cat gga gcc atg cgt gtg ctg aca gaa ttc act cgt gaa gta aca    584
Val His Gly Ala Met Arg Val Leu Thr Glu Phe Thr Arg Glu Val Thr
            165                 170                 175 gac aca cag atg cca ctt gtt gct cct gtc att ctc cca gag atg tat    632
Asp Thr Gln Met Pro Leu Val Ala Pro Val Ile Leu Pro Glu Met Tyr
        180                 185                 190 aag atc ttc acc atg gct gag gtg tat ggt att cga acc cgt tcc cga    680
Lys Ile Phe Thr Met Ala Glu Val Tyr Gly Ile Arg Thr Arg Ser Arg
195                 200                 205                 210 gcc gtg gag att ttt acc act tgt gcc cat atg atc tgt aac atg gag    728
Ala Val Glu Ile Phe Thr Thr Cys Ala His Met Ile Cys Asn Met Glu
                215                 220                 225 gag ctg gaa aag ggt gca gcc aaa gtc ctg atc ttt ccc gtg gta cag    776
Glu Leu Glu Lys Gly Ala Ala Lys Val Leu Ile Phe Pro Val Val Gln
                230                 235                 240 cag ttc aca gag gcc ttt gtt cag gcc ctc cag ata cca gat ggc ccc    824
Gln Phe Thr Glu Ala Phe Val Gln Ala Leu Gln Ile Pro Asp Gly Pro
            245                 250                 255 aca tct gac agt ggg ttt aag atg gag gtc cta aag gca gtg aca gcc    872
Thr Ser Asp Ser Gly Phe Lys Met Glu Val Leu Lys Ala Val Thr Ala
        260                 265                 270
```

```
cta gtg aaa aac ttc cca aag cac atg gtg tcc tcc atg cag cag att    920
Leu Val Lys Asn Phe Pro Lys His Met Val Ser Ser Met Gln Gln Ile
275             280                 285                 290 ctg cct att gtt tgg aac acc cta acc gag agt gca gct ttt tat gtg    968
Leu Pro Ile Val Trp Asn Thr Leu Thr Glu Ser Ala Ala Phe Tyr Val
            295                 300                 305 agg aca gaa gta aat tac aca gaa gaa gta gaa gat cct gtg gat tct   1016
Arg Thr Glu Val Asn Tyr Thr Glu Glu Val Glu Asp Pro Val Asp Ser
                310                 315                 320 gat ggt gaa gtc ctg ggc ttt gaa aat ctc gtc ttt agc att ttt gaa   1064
Asp Gly Glu Val Leu Gly Phe Glu Asn Leu Val Phe Ser Ile Phe Glu
        325                 330                 335 ttt gtc cat gct cta cta gaa aat agc aaa ttc aaa agc act gtt aag   1112
Phe Val His Ala Leu Leu Glu Asn Ser Lys Phe Lys Ser Thr Val Lys
        340                 345                 350 aaa gcc ttg cct gaa ttg att tat tat att atc ctg tac atg caa atc   1160
Lys Ala Leu Pro Glu Leu Ile Tyr Tyr Ile Ile Leu Tyr Met Gln Ile
355                 360                 365                 370 act gag gag cag att aaa gta tgg aca gcc aac ccc caa caa ttt gta   1208
Thr Glu Glu Gln Ile Lys Val Trp Thr Ala Asn Pro Gln Gln Phe Val
                375                 380                 385 gaa gat gaa gat gat gat aca ttc tcc tat act gtt aga ata gca gct   1256
Glu Asp Glu Asp Asp Asp Thr Phe Ser Tyr Thr Val Arg Ile Ala Ala
                390                 395                 400 caa gac ttg ttg ctg gct gtg gcc aca gat ttc cag aat gaa agt gca   1304
Gln Asp Leu Leu Leu Ala Val Ala Thr Asp Phe Gln Asn Glu Ser Ala
        405                 410                 415 gca gcc ctg gct gct gca gcc act cga cat tta caa gaa gct gag caa   1352
Ala Ala Leu Ala Ala Ala Ala Thr Arg His Leu Gln Glu Ala Glu Gln
        420                 425                 430 acc aaa aac agt ggc act gag cac tgg tgg aag atc cat gag gca tgc   1400
Thr Lys Asn Ser Gly Thr Glu His Trp Trp Lys Ile His Glu Ala Cys
435                 440                 445                 450 atg ctt gcc cta ggc tca gtg aag gcc atc atc act gac agt gtg aaa   1448
Met Leu Ala Leu Gly Ser Val Lys Ala Ile Ile Thr Asp Ser Val Lys
                455                 460                 465 aat ggc agg att cat ttt gac atg cat ggg ttc ctg acc aat gtc atc   1496
Asn Gly Arg Ile His Phe Asp Met His Gly Phe Leu Thr Asn Val Ile
            470                 475                 480 ctt gca gac ctc aac ctc tca gtg tct cct ttc ctc ttg ggc cgg gca   1544
Leu Ala Asp Leu Asn Leu Ser Val Ser Pro Phe Leu Leu Gly Arg Ala
        485                 490                 495 ctt tgg gct gcc agt cgg ttc act gtt gct atg tcc cct gaa ctg atc   1592
Leu Trp Ala Ala Ser Arg Phe Thr Val Ala Met Ser Pro Glu Leu Ile
500                 505                 510 cag cag ttc cta cag gca aca gtt agt ggt ctt cac gag aca cag ccc   1640
Gln Gln Phe Leu Gln Ala Thr Val Ser Gly Leu His Glu Thr Gln Pro
515                 520                 525                 530 cca tca gtt cga att tct gca gtg aga gcc atc tgg ggt tat tgt gac   1688
Pro Ser Val Arg Ile Ser Ala Val Arg Ala Ile Trp Gly Tyr Cys Asp
                535                 540                 545 caa ctg aaa gtc tca gag agt acc cac gtg ctc cag ccc ttc ctc ccc   1736
Gln Leu Lys Val Ser Glu Ser Thr His Val Leu Gln Pro Phe Leu Pro
            550                 555                 560 agc atc ctt gat ggc tta att cac cta gca gcc cag ttc agc tca gag   1784
Ser Ile Leu Asp Gly Leu Ile His Leu Ala Ala Gln Phe Ser Ser Glu
        565                 570                 575 gtc ctc aac ctg gtg atg gag acc ctg tgc atc gtt tgt aca gta gac   1832
Val Leu Asn Leu Val Met Glu Thr Leu Cys Ile Val Cys Thr Val Asp
580                 585                 590
```

```
ccc gaa ttc aca gca agc atg gaa agc aaa atc tgc ccc ttc acc atc     1880
Pro Glu Phe Thr Ala Ser Met Glu Ser Lys Ile Cys Pro Phe Thr Ile
595                 600                 605                 610 gcc att ttc cta aag tac agt aat gat ccc gtc gtc gcc tca ctg gct     1928
Ala Ile Phe Leu Lys Tyr Ser Asn Asp Pro Val Val Ala Ser Leu Ala
                615                 620                 625 cag gac atc ttc aag gag ctg tcc cag att gaa gcc tgt cag ggc cca     1976
Gln Asp Ile Phe Lys Glu Leu Ser Gln Ile Glu Ala Cys Gln Gly Pro
        630                 635                 640 atg caa atg agg ctg att ccc act ctg gtc agc ata atg cag gcc cca     2024
Met Gln Met Arg Leu Ile Pro Thr Leu Val Ser Ile Met Gln Ala Pro
            645                 650                 655 gca gac aag att cct gca ggg ctt tgt gcg aca gcc att gat atc ctg     2072
Ala Asp Lys Ile Pro Ala Gly Leu Cys Ala Thr Ala Ile Asp Ile Leu
660                 665                 670 aca aca gta gta cga aat aca aag cct ccc ctt tcc cag ctt ctc atc     2120
Thr Thr Val Val Arg Asn Thr Lys Pro Pro Leu Ser Gln Leu Leu Ile
675                 680                 685                 690 tgc caa gct ttc cct gct gtg gca cag tgt acc ctt cac aca gat gac     2168
Cys Gln Ala Phe Pro Ala Val Ala Gln Cys Thr Leu His Thr Asp Asp
                695                 700                 705 aat gcc acc atg cag aat ggc gga gag tgc ttg cgg gcc tat gtg tca     2216
Asn Ala Thr Met Gln Asn Gly Gly Glu Cys Leu Arg Ala Tyr Val Ser
        710                 715                 720 gtg acc ctg gaa caa gta gcc cag tgg cat gat gag cag ggc cac aat     2264
Val Thr Leu Glu Gln Val Ala Gln Trp His Asp Glu Gln Gly His Asn
            725                 730                 735 gga ctg tgg tat gtg atg caa gtg gtg agc cag ctc ctg gac ccc cgc     2312
Gly Leu Trp Tyr Val Met Gln Val Val Ser Gln Leu Leu Asp Pro Arg
740                 745                 750 acc tca gag ttc act gcg gcc ttt gtg ggc cgc ctt gtt tcc acc ctc     2360
Thr Ser Glu Phe Thr Ala Ala Phe Val Gly Arg Leu Val Ser Thr Leu
755                 760                 765                 770 atc tcc aag gca ggg cgg gaa ctc ggg gag aat cta gac cag att ctt     2408
Ile Ser Lys Ala Gly Arg Glu Leu Gly Glu Asn Leu Asp Gln Ile Leu
                775                 780                 785 cgt gcc atc ctc agt aag atg cag cag gca gag acg ctc agt gtc atg     2456
Arg Ala Ile Leu Ser Lys Met Gln Gln Ala Glu Thr Leu Ser Val Met
        790                 795                 800 cag tcc ctg atc atg gtg ttc gct cat ctg gtg cac act cag cta gaa     2504
Gln Ser Leu Ile Met Val Phe Ala His Leu Val His Thr Gln Leu Glu
            805                 810                 815 cct ctc ttg gag ttc ctg tgt agc ctc cca gga cct act ggc aaa cct     2552
Pro Leu Leu Glu Phe Leu Cys Ser Leu Pro Gly Pro Thr Gly Lys Pro
820                 825                 830 gct cta gag ttt gtg atg gct gag tgg aca agc cga cag cac ctg ttc     2600
Ala Leu Glu Phe Val Met Ala Glu Trp Thr Ser Arg Gln His Leu Phe
835                 840                 845                 850 tat gga cag tat gaa ggc aaa gtc agc tct gtg gca ctc tgt aag ctg     2648
Tyr Gly Gln Tyr Glu Gly Lys Val Ser Ser Val Ala Leu Cys Lys Leu
                855                 860                 865 ctc cag cat ggc atc aat gca gat gac aaa cgg cta cag gat atc cgt     2696
Leu Gln His Gly Ile Asn Ala Asp Asp Lys Arg Leu Gln Asp Ile Arg
        870                 875                 880 gtg aag gga gag gag atc tac agc atg gat gag ggc atc cgc acc cgc     2744
Val Lys Gly Glu Glu Ile Tyr Ser Met Asp Glu Gly Ile Arg Thr Arg
            885                 890                 895 tct aag tca gcc aaa aac cca gaa cgc tgg aca aac att cct ttg ctg     2792
Ser Lys Ser Ala Lys Asn Pro Glu Arg Trp Thr Asn Ile Pro Leu Leu
```

-continued

```
             900                 905                 910
gtc aag atc cta aag ctg atc atc aac gag ctc tcc aac gtc atg gag    2840
Val Lys Ile Leu Lys Leu Ile Ile Asn Glu Leu Ser Asn Val Met Glu
915                 920                 925                 930 gct aat gcc gct cgc cag gcc act cct gca gag tgg agt caa gat gac    2888
Ala Asn Ala Ala Arg Gln Ala Thr Pro Ala Glu Trp Ser Gln Asp Asp
                935                 940                 945 tcc aat gat atg tgg gag gac cag gag gag gaa gag gag gag gag gag    2936
Ser Asn Asp Met Trp Glu Asp Gln Glu Glu Glu Glu Glu Glu Glu Glu
            950                 955                 960 gat ggt tta gct ggc caa ctt tta tct gac att ctt gct aca agt aaa    2984
Asp Gly Leu Ala Gly Gln Leu Leu Ser Asp Ile Leu Ala Thr Ser Lys
            965                 970                 975 tat gag gag gat tac tac gag gat gat gag gaa gat gac cct gat gcc    3032
Tyr Glu Glu Asp Tyr Tyr Glu Asp Asp Glu Glu Asp Asp Pro Asp Ala
        980                 985                 990 ctg aag gat cct ctc tat  cag att gat ctg cag  gca tat ctc aca      3077
Leu Lys Asp Pro Leu Tyr  Gln Ile Asp Leu Gln  Ala Tyr Leu Thr
995                 1000                 1005 gat  ttc ctc tgc cag ttt  gct cag cag ccc tgc  tac ata atg ttt     3122
Asp  Phe Leu Cys Gln Phe  Ala Gln Gln Pro Cys  Tyr Ile Met Phe
1010                 1015                 1020 tca  ggc cac ctt aat gac  aat gag agg cga gtt  cta cag acc atc     3167
Ser  Gly His Leu Asn Asp  Asn Glu Arg Arg Val  Leu Gln Thr Ile
1025                 1030                 1035 ggc  atc taa aaaggggagc ctttctacat ttgctccttc tgggccagcc           3216
Gly  Ile
1040 gcaaaccatt ttgcagccct cactggcctt gagatgcact ttcttctcaa cctaaagtgg   3276 catcttgacc cttggccctt ggcctcggca gtgacactga tgacaattca gaccaggctc   3336 accggtgccg tcacttagga atgctggaac aaaggacatt tctcaaagtt ccctgaaga    3396 catgccatct ctagaacctt ttttctcccc gactctaccc ccacctctgt tcctagagcc   3456 ctctgctggc gagtccagaa acattattgc ccagaaggat tatgtgttta tggattattt   3516 tgccccgcct caggagcgca ggaagtcact accatttata ttctaaaaca gacctatcta   3576 tgttcatagg acttctgatg tgttcagata ggaatcctca tgagagatca ttatgctttg   3636 tgccctggac cactgctgct ctgggttctc aggaggaaca ggcaagagca gcttcattct   3696 aagcctttcc agtgacctca gccttgcttc tcttctacaa cactaaggct cctctgtcag   3756 aggaggtcgt cttgttttg cttcattgca tgacataacc cttcccctca agctgttcct    3816 atatatacat gcacacacaa aataagccag acagatggca atttgatctt ccttttttag   3876 aaaaaaaaaa aaaatggggg aaagggatt ttttttaaat ccacctgacc caactatatt    3936 taatatgcct ctcccacaca ttaccacaga gtctgatatt caaaggttat ccccttccc    3996 tcaggaagcc tctaaagtgc ttaagttgta gccctcaaat ttgcaacatg tatttttcta   4056 ggacagtaaa gtaatcttta caaatgaatt tagttgcatg gtataaggtg tctcagcacc   4116 tgtttgcctt ctattccctt tagaaggtaa gtaaaagtaa tgggggaaag gattaggtgg   4176 agcctgtcta acattctag tgtgtcttgg caaacatagc ctgaaatgat tcttaaagaa    4236 ctggcattgt ttaatcaaat attttaagg gagattcctt aattgggaag tttagtctgt    4296 ttggggttca aagagtaaat gaggattaga aaatcatgga gagaggctgg gcgcggtggc   4356 taacgcctgt aatcctagca ctttgggagg ctgagtgggg cggatcactt gagatcagga   4416 gtttgaggct agcctggcca acacagtgaa acctgcattt ctactaaaaa tacaaaaatt   4476
```

```
agctgggcat ggtggtgcat gcctgtaatc ccagttaact tgagatgctg aggcaggaga    4536
atcgcttgaa cttgggaagc agaggttgca gtgaaccgat atcacaccgt tgcattccaa    4596
ggcaagactc aatcacacac acacacacac acacacacaa atcatgggga gaaagatgaa    4656
acctgtgttc cccttttttt ggtagtgccc acatctggtg ccccattttt aataaccaca    4716
ggatatttct ttagattgat attctcacaa agaagaaata gaatataggc tgggcgtggt    4776
gtgtcacacc tgtaatccca gcacttacgg aggccgaagc agcggatca ccagaggtca     4836
ggagttcgag accagcctga ccaacatgat gaaaccctgt ctctactaaa aatacaaaaa    4896
ttagccaggc atggtggcat gcacttgtaa tcccagctac tcgggaggct gagacaggag    4956
aatcgcttga acctgggagg cagaggttgc agtaagccaa gatcgcacca ttgcactaca    5016
gcctgggcaa caagaggagc gaaactctgt ctcaaaaaaa aaaagagaa agaatataaa     5076
gtgaatctga atctccactc aaggggatgg ccccaaggat attgtagctg gtaatttctt    5136
catgccacta ggtgtcccca gtgttcaacc tccatgactg agattggaag aagtagagtt    5196
aaaagttttt actacctttg agaagcctgc gggcatgttc acagtcgtcc catgccagcc    5256
aggttctgag gctaactgct tgtgcccctg ctgcttcaca tggcattgtg ggagttgctg    5316
atactgggga aatgatggca gatctgacca gtggtgctg agaaaaccac cctcggcctt     5376
gcagactcca tagtttatct caaggcagtg ccagtcggat ttggtgctaa aggcataagg    5436
ccaagtcagc ctctgatatt ggcacaaaag aatggtctca tgccagtagc attgaactgc    5496
tgagcttggg aaggcttaag gctcccacac acagactgag aatgatgggg gtccctctgc    5556
gtctgctaat tagacaaaca ttctatatct agtgccaaaa gtggtcctaa atcctttggc    5616
aagggtcctt tctgctctca tgctgatttg ggggaggact gggcatcctg cctcaggaga    5676
acttgagtcc tgaggaaagg gccctagtaa cacttaaggg ctaccctgg ctaacagata    5736
ctcggctgtg ggtgagagca gaaggtcttg gaccctcga tgtgcaggta cttaattgtg    5796
tttccagtgc attttcatat acattatccc atttaacctt tataacaggt tcacagagtg    5856
gatattccca ttctgttgat gagaaaaaga gtggagagac tgtgtccagt gtcagcagga    5916
agaaaaaaga tctgttggag gccagtacat gttgacagaa actctagacc atattttgtc    5976
tcctgtctt ggccaaagag aactagcttc agtctgaaaa gggcagggct aagtggttac     6036
aaggaactaa aaagttcaag gtaagacaaa tgaggtaaaa ataaaaaaga gcacttagct    6096
gctctgagac attttagtct cctgactggt aaacagcagc tggggcacca aggggctccc    6156
aggagtttgt cgagcttta ttggagtgaa ctgaaaggaa aatggaagga atgctataag     6216
actgaaaaga agttaaagcc ctaggaagga agctgataac acaagttaca gacgtatatg    6276
tgacattgat ttgggagaat gaacctacaa caaatgaccc aaaagcacct aaataagagt    6336
gacgagagtt taacagacat tcattatgga cttcagagaa aatgatgcta aactggtctt    6396
agaatcttct ttaattttgt taactaggta aataatctgg acattttagt caaagcatta    6456
gacagacaga gaagttggta actgaccact aactaacaaa ctataaattc acccattgtg    6516
ggttgacctg gtaagttccc ccagggctgt gtccttggcc cctcctttga tattagtgac    6576
agatgacttt ttttatgcct tacccattcc acaaaagaat ttgaagccat ttacacaaga    6636
gatagtacta gtaaattagg agtgctgatc aaatttttag ataataagaa acccttagga    6696
aggatgacaa tttagaatcc aaattttagga tccaaacaaa taccattaca aactataaaa   6756
atgagcagaa tctaaatgta acatttcaat aaatgcagat tgataataac atctgtgcag    6816
```

```
agttgaggac tatagagtac tgtgctgtca ctaacagtat tgtgtgctac taagagttta    6876
atggctgggt gtggtggctc acacctgtaa tcccaacact tgggaggcc  taggtgggta    6936
aatcagctga gatcaggagt tcgagaccag cctggccaat gtggtgaaac cccgcctcta    6996
ctaaaaataa aaaaattagc tgggcatggt ggcacgtgcc tgtaatccca gctactcggg    7056
aggctgaggc gggagaatca cttgaacctg ggagacagag gttgcagtga gtcgagatca    7116
caccattgca ctccagcctg gcaacagag  caagattctg tctcaaaaaa taaagtttat    7176
tatgccagga gggccaggtg tggtgccaca cccatgtaat cccagcactt taggaggctg    7236
aggagggcag atcacttaag cccaagagtt tgagaccagt ctgggcaatg tggcaatacc    7296
ttgtctctta aaatttaaaa taaaaaaaaa gtttattatg ccaggaactg ttaatgtgtc    7356
caaaaaaact ccagtgtggt tctaggatga gataataaaa acaggttgtc tagggtagtg    7416
tggaaggtcc tttcagtctt cctgtgccta tcagtgatcc tcattgccat gttcccttct    7476
ggtgctcaac cggaggctcc ctgacagatg agtcctctgc cagaggaagg ctaagatgta    7536
gaggacaaat cgtgtcaagg aaaagaagct tgaaggagct aagaatgctt agcttagaga    7596
agacaagagg aaacaggaca tggctttggg aagttcaagg atggtccagt gaaatacata    7656
ctatactttt gcaccccagc taagctgacc catgatcagt aagtaggaaa taaaaggcca    7716
atttctggct actcttgccc ccaaccccat ttcagtgaac tatgaacctc tattagatat    7776
gcaaggccgg tgctaaatgc tggagggctt tggccctttc cctcaaggag ctagtctagt    7836
agggggtcag aaatacagat gggcctgaac ataatgatgg tttgacttcc agttttttcaa   7896
ctttaggatt gtgcaaaagc tatacacatt cggtagaaac agtacttcaa gtatccatac    7956
aatcagtaca gtattcaata aattacatga gacattcaac actttattat aaaataggct    8016
ttgtgttaga tgagtttgcc caactgtaag ctaatgtaag tgatctgagt aggtttaagg    8076
tagcctaggt gtattaaatg catttttcac ttaacggtat tttcaacttt tgttgggttt    8136
attgggatgt agccccatta taagctgaaa agcatctgta gtataataaa tgtggggagt    8196
gctgtgagag aaataagtgt actgggttta gttcccactg cccaaaaaag gaactggcta    8256
atggtaacct gggggaggaa gtcgggtaag ttgcatggag aaggcaaccc ttgaacactt    8316
gcaaggagct aacaatacct gcttctggag tatttaaacg ccagtgggta tgctaaatac    8376
ttttacctca gaccacctac taaccttaca agtagtccca cttttgctcac ccagttttac   8436
agattgatga aactgaagca gacagatatt gttaacctat caaaggtcac cctgcaagtg    8496
tgtgattata gtccaagcag cttgtacttg ttgcctattt gttttgcctt tcctgtgcat    8556
ttgccaggca gatgagagtg gggtaagaca ttgcagagaa aaagtaagaa aaggccgtca    8616
tgaaacaatt tcattttcag acctataag  cacgttacaa gtactgatat ttatgcttaa    8676
gttcacggga gtcctggcca gaaataaagc tggaaggaca agtgggggc  agattgtgaa    8736
ggatccttca agacctgctt cctctagaga atgggagact acccaagata actaaacagg    8796
gaagtgatca ggttttgtgt cttagaaaag tgttgcagtg ttgatgcaaa tgtgactaga    8856
agggtgactt ggaacctgga ttgaaggggt gggagatggg agaaaggaat gcagtctggc    8916
agcagctaca gcagtccagg tgggaaaacc cagagcctga actaaggttg taactagagg    8976
ggatagggtg gaagagctgg attagagatg ttgacaagat aaagtcagta ggacttaaag    9036
actgacaagt aaggatttc  caaaagtgag agctgtggaa tgaattgtct taaaatgttg    9096
cagtgagttc ctcctcatca atccaagtgc tcgatcagag gctagacctt tagttagcag    9156
tcacgggaaa attccccatt ctcacgggga tttagactag gtcttaacca tactttacca    9216
```

```
agattccagt agcaaagcac ccaaaagtaa tcgcaataaa attccaattt ttgtaggccg    9276
ggcatagtgg ctcacacctg taatcccagc actttgggag gccgaggcag gcggaccacg    9336
acatcaagag ttcaagagca gcctggccag catggtgaaa ccccgtctct actaaaaata    9396
caaaaaaatt agctgggcat ggtggcgcat gcctataatc ctagctactc aggcagctga    9456
agcaggagaa ttgcttgaac ccgggaggca gaggttgcag tgagccaaga tcatgccact    9516
acactccagc ctgggcgaca gagcgacact ctgcctcaaa aaaaaaaaa aacaaaaaaa    9576
aaaacaagtt ttgtgaattt aagtttccct aatggatggt acaggtcaac atttgccatc    9636
taatgacact tacattccag ttttttcctt ttttgagtaa ctgggaaaag ggtggcatta    9696
ctgctggctt cctaaaattg aaaagtatac taggggttttt aaacctgtgt agaatacatg    9756
atatggtagc aaatgtgctg taggaagaaa agcaatgagg aactactggc ctgactagga    9816
ggcctagaag tccctcccag gcttgagttg ttctgacttg gcatgattac atagctgcgg    9876
caagtgacgt ttccttcaag ccttggttcc ctcatctgta aaatagggaa ctaataccta    9936
cctcacagga ttgtagttag aattaaggat gacttcatta aagcacctct agtggtggaa    9996
gatgtcccat cctatccccc acccatagct gggagctatg tttggctcat cttcctgac   10056
tcactggatt acactgtgac tcagttcaat ttcacacatg ctgctgctaa attagggtct   10116
tggtgagcct tgggaggac agctctgagg aatgaattgt agcactgcag ccctgcctga   10176
ggaacatgat agaaacaggt ggtaggccca gctcttgcct tccacctact aagcagtttt   10236
tctgtggtta gctgtgtgac ataaactatc ggtgtattaa tttgctttca ctagattccc   10296
cccccccaa caacttagtc caagaacata cctgaattct ttgcatttcc ttgccttagt   10356
tgcttttgta gggtggacag caggactgca tgagaatagc tgtgcttctg gaccctatgg   10416
tgaaagctct agtgaactgc aattaggccc agggtcccgg aggaagaagg ggagagaaaa   10476
aggggggtag ttttccaaaa gataagtagg ggacaaaaaa gtccacgggg cctatgagcg   10536
gtgagactcc tgccctgatt gtggcaaagc acctggagat gatagaactt cctagggaaa   10596
aggctgcatg gagtccccag ggatgctggg ccctggtcac caaggctccc tgggaaggtc   10656
tcttgtacct gggggcacaca gaccaacact tctgaatttg caagcttaag agcatgtatg   10716
agcagaacct gtgcagacca aggcttagag ggctcacctc aatgttttgc actgtgtgag   10776
accccaggac cttttcgtga ttctggagag gggaacaaac cataataaca acaaaccagg   10836
tagcaggata gagactcatt ctcatctatt ttggttaaaa gaaatataat gtatttcttc   10896
cacacctgat tttgtgattg caaattcata actaatatcc ctcgtcagct ccgctgactc   10956
atccctgcca cagggaggtt cacagcaaga gcacagaaac tagggccagt gcccggttgt   11016
gtgaccttga gtaagttctt ttttcccttga acagggagag agacacaatg gatcagagtg   11076
tctctgccag ttctaacttg gggattctag tgggttgaac cgaacggtag tccgtttcca   11136
aaagaggaag ccaagaccag aggggagtg gttccttcaa gtttgcagaa ccagtaagtg   11196
gcagagcagg actcatatct agttagtggt tcagagcatg ggctccggag ctagactgcc   11256
tggatttgaa ccctggcttt gccacttgcc tgttgggtga cttggacaa gctgcttaaa   11316
ttatgtctcc atttcctaat ccacagaaca agtgtaaac tagttatctg tttcatggag   11376
tgattgtgag gattaaataa agttaatata acacaaagca                         11416
```

<210> SEQ ID NO 45
<211> LENGTH: 1041
<212> TYPE: PRT

<213> ORGANISM: Homo sapiens

<400> SEQUENCE: 45

```
Met Ala Ala Ala Ala Ala Gly Ala Ala Ser Gly Leu Pro Gly Pro
1               5                   10                  15

Val Ala Gln Gly Leu Lys Glu Ala Leu Val Asp Thr Leu Thr Gly Ile
            20                  25                  30

Leu Ser Pro Val Gln Glu Val Arg Ala Ala Glu Glu Gln Ile Lys
        35                  40                  45

Val Leu Glu Val Thr Glu Glu Phe Gly Val His Leu Ala Glu Leu Thr
50                  55                  60

Val Asp Pro Gln Gly Ala Leu Ala Ile Arg Gln Leu Ala Ser Val Ile
65                  70                  75                  80

Leu Lys Gln Tyr Val Glu Thr His Trp Cys Ala Gln Ser Glu Lys Phe
            85                  90                  95

Arg Pro Pro Glu Thr Thr Glu Arg Ala Lys Ile Val Ile Arg Glu Leu
            100                 105                 110

Leu Pro Asn Gly Leu Arg Glu Ser Ile Ser Lys Val Arg Ser Ser Val
            115                 120                 125

Ala Tyr Ala Val Ser Ala Ile His Trp Asp Trp Pro Glu Ala Trp
130                 135                 140

Pro Gln Leu Phe Asn Leu Leu Met Glu Met Leu Val Ser Gly Asp Leu
145                 150                 155                 160

Asn Ala Val His Gly Ala Met Arg Val Leu Thr Glu Phe Thr Arg Glu
            165                 170                 175

Val Thr Asp Thr Gln Met Pro Leu Val Ala Pro Val Ile Leu Pro Glu
            180                 185                 190

Met Tyr Lys Ile Phe Thr Met Ala Glu Val Tyr Gly Ile Arg Thr Arg
            195                 200                 205

Ser Arg Ala Val Glu Ile Phe Thr Thr Cys Ala His Met Ile Cys Asn
210                 215                 220

Met Glu Glu Leu Glu Lys Gly Ala Ala Lys Val Leu Ile Phe Pro Val
225                 230                 235                 240

Val Gln Gln Phe Thr Glu Ala Phe Val Gln Ala Leu Gln Ile Pro Asp
            245                 250                 255

Gly Pro Thr Ser Asp Ser Gly Phe Lys Met Glu Val Leu Lys Ala Val
            260                 265                 270

Thr Ala Leu Val Lys Asn Phe Pro Lys His Met Val Ser Ser Met Gln
            275                 280                 285

Gln Ile Leu Pro Ile Val Trp Asn Thr Leu Thr Glu Ser Ala Ala Phe
            290                 295                 300

Tyr Val Arg Thr Glu Val Asn Tyr Thr Glu Val Glu Asp Pro Val
305                 310                 315                 320

Asp Ser Asp Gly Glu Val Leu Gly Phe Glu Asn Leu Val Phe Ser Ile
            325                 330                 335

Phe Glu Phe Val His Ala Leu Leu Glu Asn Ser Lys Phe Lys Ser Thr
            340                 345                 350

Val Lys Lys Ala Leu Pro Glu Leu Ile Tyr Tyr Ile Ile Leu Tyr Met
            355                 360                 365

Gln Ile Thr Glu Glu Gln Ile Lys Val Trp Thr Ala Asn Pro Gln Gln
            370                 375                 380

Phe Val Glu Asp Glu Asp Asp Thr Phe Ser Tyr Thr Val Arg Ile
385                 390                 395                 400
```

-continued

```
Ala Ala Gln Asp Leu Leu Ala Val Ala Thr Asp Phe Gln Asn Glu
            405                 410                 415

Ser Ala Ala Ala Leu Ala Ala Ala Thr Arg His Leu Gln Glu Ala
        420                 425                 430

Glu Gln Thr Lys Asn Ser Gly Thr Glu His Trp Trp Lys Ile His Glu
        435                 440                 445

Ala Cys Met Leu Ala Leu Gly Ser Val Lys Ala Ile Thr Asp Ser
    450                 455                 460

Val Lys Asn Gly Arg Ile His Phe Asp Met His Gly Phe Leu Thr Asn
465                 470                 475                 480

Val Ile Leu Ala Asp Leu Asn Leu Ser Val Ser Pro Phe Leu Leu Gly
            485                 490                 495

Arg Ala Leu Trp Ala Ala Ser Arg Phe Thr Val Ala Met Ser Pro Glu
                500                 505                 510

Leu Ile Gln Gln Phe Leu Gln Ala Thr Val Ser Gly Leu His Glu Thr
            515                 520                 525

Gln Pro Pro Ser Val Arg Ile Ser Ala Val Arg Ala Ile Trp Gly Tyr
            530                 535                 540

Cys Asp Gln Leu Lys Val Ser Glu Ser Thr His Val Leu Gln Pro Phe
545                 550                 555                 560

Leu Pro Ser Ile Leu Asp Gly Leu Ile His Leu Ala Ala Gln Phe Ser
                565                 570                 575

Ser Glu Val Leu Asn Leu Val Met Glu Thr Leu Cys Ile Val Cys Thr
            580                 585                 590

Val Asp Pro Glu Phe Thr Ala Ser Met Glu Ser Lys Ile Cys Pro Phe
            595                 600                 605

Thr Ile Ala Ile Phe Leu Lys Tyr Ser Asn Asp Pro Val Val Ala Ser
            610                 615                 620

Leu Ala Gln Asp Ile Phe Lys Glu Leu Ser Gln Ile Glu Ala Cys Gln
625                 630                 635                 640

Gly Pro Met Gln Met Arg Leu Ile Pro Thr Leu Val Ser Ile Met Gln
                645                 650                 655

Ala Pro Ala Asp Lys Ile Pro Ala Gly Leu Cys Ala Thr Ala Ile Asp
            660                 665                 670

Ile Leu Thr Thr Val Val Arg Asn Thr Lys Pro Pro Leu Ser Gln Leu
            675                 680                 685

Leu Ile Cys Gln Ala Phe Pro Ala Val Ala Gln Cys Thr Leu His Thr
            690                 695                 700

Asp Asp Asn Ala Thr Met Gln Asn Gly Gly Glu Cys Leu Arg Ala Tyr
705                 710                 715                 720

Val Ser Val Thr Leu Glu Gln Val Ala Gln Trp His Asp Gln Gly
            725                 730                 735

His Asn Gly Leu Trp Tyr Val Met Gln Val Ser Gln Leu Leu Asp
                740                 745                 750

Pro Arg Thr Ser Glu Phe Thr Ala Ala Phe Val Gly Arg Leu Val Ser
            755                 760                 765

Thr Leu Ile Ser Lys Ala Gly Arg Glu Leu Gly Glu Asn Leu Asp Gln
            770                 775                 780

Ile Leu Arg Ala Ile Leu Ser Lys Met Gln Gln Ala Glu Thr Leu Ser
785                 790                 795                 800

Val Met Gln Ser Leu Ile Met Val Phe Ala His Leu Val His Thr Gln
            805                 810                 815

Leu Glu Pro Leu Leu Glu Phe Leu Cys Ser Leu Pro Gly Pro Thr Gly
```

```
                 820                 825                 830
Lys Pro Ala Leu Glu Phe Val Met Ala Glu Trp Thr Ser Arg Gln His
            835                 840                 845
Leu Phe Tyr Gly Gln Tyr Glu Gly Lys Val Ser Ser Val Ala Leu Cys
        850                 855                 860
Lys Leu Leu Gln His Gly Ile Asn Ala Asp Asp Lys Arg Leu Gln Asp
865                 870                 875                 880
Ile Arg Val Lys Gly Glu Glu Ile Tyr Ser Met Asp Glu Gly Ile Arg
                885                 890                 895
Thr Arg Ser Lys Ser Ala Lys Asn Pro Glu Arg Trp Thr Asn Ile Pro
            900                 905                 910
Leu Leu Val Lys Ile Leu Lys Leu Ile Ile Asn Glu Leu Ser Asn Val
        915                 920                 925
Met Glu Ala Asn Ala Ala Arg Gln Ala Thr Pro Ala Glu Trp Ser Gln
    930                 935                 940
Asp Asp Ser Asn Asp Met Trp Glu Asp Gln Glu Glu Glu Glu Glu Glu
945                 950                 955                 960
Glu Glu Asp Gly Leu Ala Gly Gln Leu Leu Ser Asp Ile Leu Ala Thr
                965                 970                 975
Ser Lys Tyr Glu Glu Asp Tyr Tyr Glu Asp Asp Glu Glu Asp Asp Pro
            980                 985                 990
Asp Ala Leu Lys Asp Pro Leu Tyr  Gln Ile Asp Leu Gln  Ala Tyr Leu
        995                 1000                1005
Thr Asp  Phe Leu Cys Gln Phe  Ala Gln Gln Pro Cys  Tyr Ile Met
    1010                1015                1020
Phe Ser  Gly His Leu Asn Asp  Asn Glu Arg Arg Val  Leu Gln Thr
    1025                1030                1035
Ile Gly  Ile
    1040

<210> SEQ ID NO 46
<211> LENGTH: 1223
<212> TYPE: DNA
<213> ORGANISM: Homo sapiens
<220> FEATURE:
<221> NAME/KEY: CDS
<222> LOCATION: (193)..(924)
<223> OTHER INFORMATION: CDS

<400> SEQUENCE: 46
gggggagcgg ggggctcgtc tgttccagga gccctgaacc aaagagcagc ggagtttgag      60
aagccagcag ctcggggttc ggcagcagcg gtcccatcgg ctgaagttcg ggggggtgg      120 ggcgccgagc gcgcggggtg gggggggtcc tggtctttgg cttctcgact cggtcctgtt     180
tcgacagcga ac atg tcg cgg cct gtc aga aat agg aag gtt gtt gat tac     231
              Met Ser Arg Pro Val Arg Asn Arg Lys Val Val Asp Tyr
                1               5                  10 tca cag ttt cag gaa tct gat gat gca gat gaa gat tat gga aga gat     279
Ser Gln Phe Gln Glu Ser Asp Asp Ala Asp Glu Asp Tyr Gly Arg Asp
    15                  20                  25 tcg ggc cct ccc act aag aaa att cga tca tct ccc cga gaa gct aaa     327
Ser Gly Pro Pro Thr Lys Lys Ile Arg Ser Ser Pro Arg Glu Ala Lys
30                  35                  40                  45 aat aag agg cga tct gga aag aat tca cag gaa gat agt gag gac tca     375
Asn Lys Arg Arg Ser Gly Lys Asn Ser Gln Glu Asp Ser Glu Asp Ser
                50                  55                  60 gaa gac aaa gat gtg aag acc aag aag gat gat tct cac tca gca gag     423
```

```
Glu Asp Lys Asp Val Lys Thr Lys Lys Asp Asp Ser His Ser Ala Glu
            65                  70                  75 gat agt gaa gat gaa aaa gaa gat cat aaa aat gtg cgc caa caa cgg       471
Asp Ser Glu Asp Glu Lys Glu Asp His Lys Asn Val Arg Gln Gln Arg
        80                  85                  90 cag gcg gca tct aaa gca gct tct aaa cag aga gag atg ctc atg gaa       519
Gln Ala Ala Ser Lys Ala Ala Ser Lys Gln Arg Glu Met Leu Met Glu
    95                  100                 105 gat gtg ggc agt gag gaa gaa caa gaa gag gag gat gag gca cca ttc       567
Asp Val Gly Ser Glu Glu Glu Gln Glu Glu Glu Asp Glu Ala Pro Phe
110                 115                 120                 125 cag gag aaa gat tcc ggc agc gat gaa gat ttc cta atg gaa gat gat       615
Gln Glu Lys Asp Ser Gly Ser Asp Glu Asp Phe Leu Met Glu Asp Asp
                130                 135                 140 gac gat agt gac tat ggc agt tcg aaa aag aaa aac aaa aag atg gtt       663
Asp Asp Ser Asp Tyr Gly Ser Ser Lys Lys Lys Asn Lys Lys Met Val
                    145                 150                 155 aag aag tcc aaa cct gaa aga aaa gaa aag aaa atg ccc aaa ccc aga       711
Lys Lys Ser Lys Pro Glu Arg Lys Glu Lys Lys Met Pro Lys Pro Arg
                160                 165                 170 cta aag gct aca gtg acg cca agt cca gtg aaa ggc aaa ggg aaa gtg       759
Leu Lys Ala Thr Val Thr Pro Ser Pro Val Lys Gly Lys Gly Lys Val
    175                 180                 185 ggt cgc ccc aca gct tca aag gca tca aag gaa aag act cct tct ccc       807
Gly Arg Pro Thr Ala Ser Lys Ala Ser Lys Glu Lys Thr Pro Ser Pro
190                 195                 200                 205 aaa gaa gaa gat gag gaa ccg gaa agc ccg cca gaa aag aaa aca tct       855
Lys Glu Glu Asp Glu Glu Pro Glu Ser Pro Pro Glu Lys Lys Thr Ser
                    210                 215                 220 aca agc ccc cca ccc gag aaa tct ggg gat gaa ggg tct gaa gat gaa       903
Thr Ser Pro Pro Pro Glu Lys Ser Gly Asp Glu Gly Ser Glu Asp Glu
                225                 230                 235 gcc cct tct ggg gag gat taa aagtgatgat ggtctgggga gagattttat         954
Ala Pro Ser Gly Glu Asp
                240 taaaaaaaaa aagaaaaaaa aagaaaaaag agggaggaaa aaaaagaacc tacttaagat    1014 agaacatggt tttggctatg gcttgactca tgggctttca gtgctttttt ccatttgttg    1074 aaagtaacat ttctctctct ctctcttttt tttttttttt ttttaaagca aaccattgta    1134 tgtgtaagtg tttaagttac cttttttgtct attggtctct ttgccagccc tccccttttcc  1194 caatgaaagc catgtcaaat taatcactg                                       1223

<210> SEQ ID NO 47
<211> LENGTH: 243
<212> TYPE: PRT
<213> ORGANISM: Homo sapiens

<400> SEQUENCE: 47

Met Ser Arg Pro Val Arg Asn Arg Lys Val Val Asp Tyr Ser Gln Phe
1               5                   10                  15

Gln Glu Ser Asp Asp Ala Asp Glu Asp Tyr Gly Arg Asp Ser Gly Pro
            20                  25                  30

Pro Thr Lys Lys Ile Arg Ser Ser Pro Arg Glu Ala Lys Asn Lys Arg
        35                  40                  45

Arg Ser Gly Lys Asn Ser Gln Glu Asp Ser Glu Asp Ser Glu Asp Lys
    50                  55                  60

Asp Val Lys Thr Lys Lys Asp Asp Ser His Ser Ala Glu Asp Ser Glu
65                  70                  75                  80
```

```
Asp Glu Lys Glu Asp His Lys Asn Val Arg Gln Gln Arg Gln Ala Ala
                85                  90                  95
Ser Lys Ala Ala Ser Lys Gln Arg Glu Met Leu Met Glu Asp Val Gly
            100                 105                 110
Ser Glu Glu Glu Gln Glu Glu Asp Glu Ala Pro Phe Gln Glu Lys
        115                 120                 125
Asp Ser Gly Ser Asp Glu Asp Phe Leu Met Glu Asp Asp Asp Ser
    130                 135                 140
Asp Tyr Gly Ser Ser Lys Lys Asn Lys Lys Met Val Lys Lys Ser
145                 150                 155                 160
Lys Pro Glu Arg Lys Glu Lys Lys Met Pro Lys Pro Arg Leu Lys Ala
                165                 170                 175
Thr Val Thr Pro Ser Pro Val Lys Gly Lys Gly Lys Val Gly Arg Pro
                180                 185                 190
Thr Ala Ser Lys Ala Ser Lys Glu Lys Thr Pro Ser Pro Lys Glu Glu
                195                 200                 205
Asp Glu Glu Pro Glu Ser Pro Glu Lys Lys Thr Ser Thr Ser Pro
    210                 215                 220
Pro Pro Glu Lys Ser Gly Asp Gly Ser Glu Asp Glu Ala Pro Ser
225                 230                 235                 240
Gly Glu Asp

<210> SEQ ID NO 48
<211> LENGTH: 7334
<212> TYPE: DNA
<213> ORGANISM: Homo sapiens

<400> SEQUENCE: 48
agcctccagc cacaggagta agggagactc agtgaagaat ccagccagct ctcatttgac      60
tgtaatcaca ggagagatcc cagcaagaac aatcggctga gcttgggaaa accctaaaac     120
catgagagag aaaaacaaat gaccgctctg ttacactacc aagtttgggg tggtttgttg     180
cagagcaata ggtaaccaga atgctgtcca tctccataca ttatgagcct aaccacccett     240
tatggcccag ctcattagcc tgtcatctcc catgtaagcc ttctctgatc cccacaatgg     300
agttctctcc ctgtctgaac tcccggtgct cttcctgtgc cagtctcctc tcccacatct     360
gggtgcacac ttcagctctc ccctccctgt aaagtctcca ttctccattc atatctctcg     420
gcacctagcc cagtgcttgg cacatagtgg gtgctcaata caggctttct ctgtctggat     480
gcgtgaagga tagggaaagg gatcttgggg agagaacatc taccagtgga gaagagaggg     540
tcctgagttg caaaacagct tccagggctt tcaaggcct ttttcactga ctagtgtcct     600
aggacatttt tggcttctct gctaagaatg taggatatga gttagagtca aaaggattta     660
tgaataagta tcaagttgtc agaggtgttt gagctggagc aactccatct tgtgtagggg     720
atgtgtaaaa taaggctgag acctactggg ctgcattccc agacggttaa ggcattctaa     780
gtcacaggat gagataggag gtcagcacca gatacacatc ataaagacct tgctgataaa     840
acagcttgca gtaaagaagg atgccaaaac ccaccaaaac caagatggcg acgagagtga     900
cctgtcctca ctgctacact cccaccagtg ccatgacagt ttacaaatgc atgggaacg      960
tcaggaagtt accttatatg gtctaaaagg ggaggcatga ataatccacc ccttgtttag    1020
cacataatca agaaataagc ataaacatgg gcaaaaagca gccctcaggg ctgctccgtc    1080
tatggagtag ccattctttc attccttac tttcctaata aacttgcttt cactttactc     1140
```

```
tatggacttg ccctgaattc cttcttgcgt gagatccaag aaccctctct tggggtctgg    1200
attgggactt cctgtaacaa agggctcctt ggaaagaaag gattgtccaa gctgagggtt    1260
ttcttaggat tacagtgtat ggccacttgg gggagccgag gtgcggcgag gtgtctttca    1320
caagttcacc agcaggtggc aagcttattc gtggtttctt gcaaactatg gatttatcca    1380
cgcacacatt cataaaatac tgagcaccta ctccatgtaa ggctctgtgt ggctacaaag    1440
gagggtaagc tacaattcct gccctccaag accttccagg tgagtgaact caatgttttcc   1500 ttagcttgtc tttgggttga aatagttctt caaaagtcat ccaatccttt cttctgtcag    1560
tgtaatttaa tataatcgac cctgatggag gagaggagtc aagagtcttg ccaaggccgg    1620
gtgcagtggc tgacgcctgt aatcccagca ctttgggagg ccgaagtgca cggatcacct    1680
gaggccagga gtttgagacc agcctggcca acatggtgaa acgccgtgtt gcagggtttc    1740
tactaaaaat acaaaaatta gctgggtgtg gtggcgcatg cctgtagtcc caggctggga    1800
ggctgaggca ggagaatcgc ttgaccccag gaggtggagg ttgcagtaag catagatcgc    1860
cccactgcac tccagcctgg gcaacagact gaaactccgt ctcaaaaaaa aaaaaaaaa    1920 aaaaaagag ttttgccgaa agtctggtta ttttcagtct acttcactgc tttaagtaga    1980
ttggccaggt gatcatagat aagatcagag cagtgaaggt ggtgtggcta gggaccagga    2040
gaacagggag aaagagattt taaagcagga ggaaagcaaa ctgatcagta gattaggagc    2100
tggcgtgatt ggaactgggc ctgtcagaaa agcctctcct gagccttcag ccagctccct    2160
gtggccacac ttccctagag cctgtcaggc tcggaacagt ggagccatgc acagccagct    2220
gcccgggagc tccctgccgc ctgctcccgc cctgagtccc cagctcctcc tgctttcccc    2280
tccccacact ttggctgtga gagccactcc acagttttgc ctgtttggga cagaggcagt    2340
ggctgcagag ggagcaggag ggaagtgacc ttacatcaat tcaggccaa ggggagggga    2400 agaggaagtg gtcatttaaa aacctatcta gactgtttca cagtgttctt aaggacccaa    2460
ccctgagcca ccccagtgca tttctgaata tcacctttca agctcccctg gagcttcaca    2520
gtgtaaattt cagcctgaaa atcagaagag atttctggat caggaacccc ctagagtttt    2580 tatttgttc ctttctaaat ggatttctcc ttttcttgcc tctaagcatt ttattcttat    2640
aacatgtata cactgccttt tccgattttc atttgcctct ggctgccaag ctcatttctc    2700
cagcaaaccc tgagagattc taggaatctt ccttagaaaa catgaataca gggactgaaa    2760
gcaaatgctg ggccttattc cacaagcccc ctttgacttg cctcatccta gcctaggcac    2820
agccgaacag tgccagagcc agggagagcc ttgcagatca cccacgtggg taggcgggcc    2880
tagtcatatt cccaggggcc cacagagata ctacccacca agcacgatac atttcctaag    2940
aactccattt ctctgaacag taagtaattt tatttattta ttcatttatt ttttgagaca    3000
gggtctcact ttatcaccca ggctggagta cagtggagta tagtacggct cactgcaacc    3060
tctacctcct gggctcaagc gatcctccca cctcagcgtc cctagtagct gggactacaa    3120
gcatgccacc atgtccagct aattttgta tattttgtag agactgggtt ttaccatgtt    3180
gccaaacttg gtctcaaact tctggactca aatgatccac ctgcctcagc cttccaaagg    3240
gttgggatta caggtgtgag ccaccgtgcc tggccagtga gtcattttaa acattatctt    3300
tttatgaaga caaatacagt tatgtgccaa ggagaatgca aaattcaaat aaattttgc    3360 aataaacccc aagacttcaa ggactgggag tggattgatt ctgacaacac tgtgggttcc    3420
ttacatttac ttctttgctg tcagaggtac ctcagtggaa attttggaga atactgagtt    3480
agtccaacct cccatttcac acatgaggaa aactgaggcc taggccatgg tcacaaagct    3540
```

```
actaagttag ctactgctgt aagccctggt ctcctcacat gcaaagcagg gggtaaaaat    3600
agtccttact tcatacagct actgcgaaga ttaaagggga caattgtgta aagtacctga    3660
caggtagtaa atgcttaata attataatta ttcctcatta tcaacagtat tttatttgtt    3720
ttttgttttt ttgagacaca gtttcactct gtcacccagg ctggagtgca gtggttggat    3780
ctcgcctcac tgcaacctcc acctcccagg ttcaagcgat tctcttgtct cagcttccac    3840
agtagttggg attacaggca catgccacca tacccggcta ttttttctat ttttagtaga    3900
aatgggtttt caccatgttg accaggctgg tcttgaactc ctgacctcaa gtgatctgct    3960
ggccttggcc tcccaaagtg ctgggattaa ggcatgagcc actgcgccag ccatcattag    4020
tattttaaat catagatgac agagctgaga ctcaaactgc aagtttaggg ctggattttt    4080
ttttttctttt tttagaccat tagatgagta aacttcttga ggtcaggatc caaattatag    4140
gcttccttgt attcccagaa cctagagacc agcacagagt ggggcccccaa taaatgtctt    4200
ctgagtgaat ggttggatgg atacatggat gaacaggtgg atggacggat ggatggatgg    4260
atggatggag ggagggatgg atggatggag agacagatgg atgaacaaat ggatggatgg    4320
gtgaatgaat gaatggatgg atggacagat ggatggaagg atggacaaga agatctccag    4380
cccagactgg atctctaatt tctctgggat gatgagcaga gctaagccag acacattccc    4440
ttactctttc ctcagcctca cactcaggtc ctcttcactt gggatcaatg cggaaaagaa    4500
gggtttcacc acaggagagg agagagaaga tgtagcatca ggatgctgat gagggaggaa    4560
agagaagaaa agatgccaga ggaagcagca gacaaagttg gaagctggag gacaggggcc    4620
ctacttcctg cctgtaacag gccccacttc attcctagca gccatcaaat accaacccag    4680
aagtgttggg aaatagagtg cacagagaga acataaagat actgaaaagg ttagacattt    4740
gtgagagtcc tgagaagcag gtaagcccct aagtgtgcca agcctccttc tagaacccct    4800
agcagataat ttattggtga tgagctctga ctgcattgtc tctgcagatg tgggtgctgc    4860
tgaccagctc gggccagtct agatatggtt atataaatga ggtcagccag aatgagaacc    4920
tctgcagaat gagaatctct gccttaagga tgtcccaagt attgatgatg tttactgatt    4980
tttctgtcat ttcaacatca ggcttgttcc tgtttgcatg gtgggtaacc ccagcatcac    5040
ctttgactca actcaatccc aaagcccttc ctcatccctc aagtcttctt tatctgcaaa    5100
tgtgctatct aagaccaagc ccaagtaact ggcagcaggc tggagaata atatagtcag    5160
aaggtgagag gttctggaaa aacaccaaac aaggcaggtc ctacttggct tcatctgtag    5220
ctctgcgtag acagctccta agacaagtga cctgacagtc tttgggtgga aaagagggt    5280
gaccatctgc cctggactgc ctgagatagt cctgttgcct tagtgtagtt acgaatacta    5340
ccacatacca cttactatcc aaagcattct ggtttagatg acacattgta cagccattct    5400
gtttataagg tgctttaaga tctgggagaa atccaagtgt gactgcagtg actgctcttc    5460
tttttctgga tctaccctaa agccatttca cagcacaggt tggcatgtcc tcacagggaa    5520
atctatcaac agtcccatga ctccagagag acaaaccca gaccaaagaa ggtaatgtag    5580
gagtttgccc ttttgtaaaa tcctgggcaa aactccgagg ctcatctctc caagatactg    5640
agaattgaaa ggagaggggg aaatcccatg ggatcgccat ctttgggcgg aagcccttgg    5700
tctctgacac tgatggtggt tctgcagttt aatggacctg tttaactatt gcttagtcag    5760
tgcagccgtg accagaaatt cttctggttt ctcctcctc atcttggttg ggtcagatga    5820
agatggccca atctgcaaga aacactggtt gtgtgcttct agacatttta atcttggagg    5880
```

```
gccttgttta taggatggac ctggccaaag gaaagatgtt acttatggta gaaagcaaga   5940
aaaacctaga taaacacttt ttttttgag aaacactctt gctctgtcgc ccaggctgga    6000
gtgcagtggt gcaatcttgg ctcactgcaa cctctgcctc ctgagttcaa gtgatccttc   6060
cacctcagcc tctcgagtag cttggattac aggcacacac caccacgcct ggctaatttt   6120
tttaattttt ttgtagaaac agggtttcac caggtctcga actcctgggt ttaagcaatc   6180
tgcctgcctc ggcctcccaa agtgttggga ttacaggcgt gagccacagt gcctggccaa   6240
atacttcatt ttctagatca taagatgctt aactttattc ctggcaaaaa gttgattcag   6300
caaaccaggg ctttaagtga agccggttgg ggcctgaacc cttgacacct gcccagggtg   6360
gaagacatag cagctgcatc tatgggccac ctggggtgta gggtgaccag ctggaggctg   6420
tgagcttctc tgctccctga aatgcctgca cggggcactc aggaagggct ggggactggg   6480
tgaggaggtg tggacagaat gtcccctgga aactgcccca ggggcagctt gagtggcctg   6540
agcctgtgtc tgtcctactg aaggttggag ccccagagaa aagcctctat ggaggcaccc   6600
acttttcaga actgctgctt tgcgggagaa cacctttttt ccaggtgttg tccttagggt   6660
agcagggaag actgggaaaa actgaggggc aagagctgtt ggagggggga gttacattta   6720
ttgagtgtct attacatgcc gggtgctgct gaaggtctgc gggtcctacc ggatctcctt   6780
ttagcccctc acatccctgt agattacacg ccgttcacag atgaccctga acccagaagg   6840
gctgtctagg cccagggccc agctagtgag tggatgggca gaatcagacc tgccctggaa   6900
gggtctgtct taccctggcg cccaaaatgt gtccctcacc ctctgccacc aggacaagta   6960
aattcgagac acccttttcgt tagggctca agtttatcat gggtctgacc tctaaggtca   7020
tatctccgcc ttctcacctg acagacagga aactcctgaa atgcccctcg cacgtgcaag   7080
acgttttccg cggtggcggc gacagggcgc acagtgggac cgcagcacga gctcggagca   7140
cccccagagt cggcgactcc tgccccgcc cctgccggcc ggccttcccg gggcctagga    7200
gggcagcacc gccgggcttc gcgccatgac atcagccctg gagtggtgca gtgtgcaaag   7260
cccactggtt ggcgtggccc gggacacgcc ttccgcggag cggaacaaaa cggcgcgcag   7320
gccgggcgca ccca                                                      7334
```

<210> SEQ ID NO 49
<211> LENGTH: 5000
<212> TYPE: DNA
<213> ORGANISM: Homo sapiens

<400> SEQUENCE: 49

```
tcatcatact ttattttgc tttccttatt ccttggcact gactaagcta aagttaagaa      60
gccgacttca taagccaacc cctgtgatgg gatggaaaaa tgggcttttg cagagggttt    120
attaatagag atggatatac tactcacaag ttctggctca tggctccact gagaaggcca    180
tagtaataaa atgatcttat gaacactgtt ccccaaaggc caaagcctga agatattgcc    240
ccttataatc caatcagcct tatattttaa taagtcctga atcaacctga ctacggatat    300
atggggccac cagggtgcat gggtgcatgt ctgctcagcc tagccctgga agtgagcact    360 gccgccaca gatcctggga aaggtggtag taacccagaa gatgtagcct tgaagggagg     420 ataccctatca aaatgccaaa gctgcaggga cacgaagacg gttgaaaatt caacctgtgt   480
atactagatc cttccagttt gatggtttgg tcattcttct tcatgattat accatggaga    540 atttctgtg acaagggtgg tcatggaagt aagtgagtga tccccctggtt tctcattcct    600 taaagcagtg gttcgcaaag tatggcacaa gaccagcagc atcagcagcc tttgggaact    660
```

-continued

```
tgttagaaac gaaaattctc aatcccatcc cagatctgct gaatcagaaa ctctaatgag       720
aggacccggc aatccacgtt ttaataagcc ctcctggtga ttctgatgca cactaaattc       780
aactgtttta aagggaaagc cctttatagt attggagttc ccacactgag aggctttggg       840
gcccaaaata agaaggttct aggttgtcat tcagacttta acattaattt caaagtcacc       900
tttctcatgc ttccttgtgt ttctgttttt ccatttatga ttttaacaaa gaaaggtatg       960
tgtgcttttg ggtggaagtt aggagaatgt ttgtgtcttt cctagttgaa tacaaccttc      1020
agagaaaaac cttatgcctt ggaaattact acctggcaca caagggggct tcaacaagga      1080
aaagcagttg gaggtctctt ccagattgct cttctgccga attatttgta tctattccga      1140
gctgattatg taataggatg gaaaagtaa aaaaaaaaaa aaaatctaa tttgtatttc        1200 catgacaacg tgttctccca gcaacatccc tctcctttat ttgagttata aagggcactg      1260
ctgggcctga gaaccaggcc agaacctcct tctgtatggc agctaacagt gtagggctcc      1320
agtatcccag gaaggcccct tatccacact ccactcagct cataggagag tcttgcataa      1380
tgaagacaca gacctgggca cttcagtcct tgtgctcctc ctctcttttc cccacagcag      1440
gacctggata cagaagtact cagccaaggt gacagaataa aatccttttt ttgttgtttt      1500
ctgtttgttt gtttgttttg gagaaggagt ctcgctttgt cacccaggct ggtgtgcagt      1560
ggcacgatct cggctcactg caacctccgc ctcccaggtt caagcgattc tcctgtctca      1620
gcctcctgag tagctgggat tacagacgtg cgccatcacg cccagctaat ttttgtattt      1680
ttagtagata cggagttttg ccttgttggc caggctgtgc tggagctcct gacctcaggt      1740
gattcacctg ccacagcctc ccaaagtgct gggattacag gcgtgagcca cagcaccctg      1800
ccaaataaga tccttttta aaaatatctg aaaaaagctt catatcttta caaactcata      1860
aaatagctga ttgggccatg gaggagatga ggctgtttag aactggtttt gtttcaagtt      1920
tgtcaatttt ccctgtatga gaacttgggt aaagcacaaa gaaacataca gtgctagtaa      1980
caggtctcct gcgccctgga actaagtgtt tggaggaagg actaaacccc ggggaggtg      2040 agtataaaat aattccacta agatcacctc ctcagtcccc agaaggctga tggtggatcc      2100
tctggccatc tcctgtgggg tcttactgct cctctgccat ttctctatgc ctgaagacac      2160
gaagatgata tcaaggcaga gctaccatat cgcagccagt ctctaggcta ctgctgtgca      2220
gtggctccca ctttctaatg cttttttgtt tttgcttttt ctaacaaaac aatctttttt      2280
caaaatgaat tccaaccct gctagcttcc ttccccgcct ccatactgtt ttaggcagca      2340
ccgtttatgt gacagagtcc gtgttttctca aatgcatggt gttcctcagg tggagagtgg      2400
gcagaagttt ttgcaacact ttttttttaa gttattgggt gcaaaatccc aaaccaggat      2460
atgtgtatgt ctgtgtgttt atgttttta tttgacccct ccctcttca acctacccc        2520 ttttatatct aatgtagaaa aagcgaaatt gaatctggaa agcaaactgt tgtatatagt      2580
tgcggtaaca atcatgaaga gagagccggg ctgtcccctc agtaattcat tttaaataac      2640
aaattattta aaaataaaat tcatgccaga gccagctgaa gaggccttcc ttcatcacca      2700
ctgaggccac ccccaatctg ggccctctgt ccatctggca tgtctcctcc cagcaagatt      2760
catctgttca atgccatttg cgtttcaata aagttatctc ctgtactgtc cactggttct      2820
ctagctccct ctctgcctgg tttctgtctc catttatctt gtgggccatt ccttgattgg      2880
caaggccaga ctgcttgtgg tcatttgcct aacccagaag taacctgaaa ccctaagcta      2940
gagtctcctg actcccatgg ttgggggtgg gaggaacccc tgctcgcaca ttatggacat      3000
```

| | |
|---|---|
| agaatccttc accggatctc aaaacatcca gcccaaacat caaggctccg gagtcctcca | 3060 |
| tctgggttgc tgcagtgttt gaaaacatac caccctcttg actttgctaa attttcttct | 3120 |
| tggggtaaaa gtgaactgac ctattagaag ctgttgtaat caagttcaac ttcttttggc | 3180 |
| cacttcaaga aagtaaatag gcttactatt ccccattgca aaattgaagg gtccaagaag | 3240 |
| caatcttttc cctatgaaat tgtagtaaca taactcatct ctgccctctt aacatgggag | 3300 |
| gtgacaagtg tgttgagaac tctcttcaag ccagttgcag tgggtgtacc tgtagttcta | 3360 |
| gctactctgg atgctgaggt gggaggatca cctgtccagc ctgggcaaca tagcaagacc | 3420 |
| cccccaactc aaaaataaat aattgagaaa gctttctttt gaagtaatct tctgatgaga | 3480 |
| tgacttaatc cctgattgtt accagtccag catccacagt cttggaagtg acctaggatt | 3540 |
| tggtaactcg tttcctttgc catgtgagaa tgaactcact tgataagggt tcctgggaac | 3600 |
| cattttgaag gcacataacc tgaacagctc actaaaaaat acctgtttct gtttgctcta | 3660 |
| gaacctccca ttccaacaac attctatcct ttctgccact acatgcttgc cactctgccc | 3720 |
| tgcattttt ttaattttta tttttttta tagacagagt ctgtatatct tgcccagact | 3780 |
| ggaatgcagt agctattcat aggtgtgatg acagcacact acagcctgga actcctgggc | 3840 |
| tcaagtgatc ctcctgcctt ggcttacatc ttgctttttc ttcttttttct gagacaagat | 3900 |
| gtcactctgt cgcccaggct ggagtgcaat ggcgcaatca ctgctcactg cagcctcctc | 3960 |
| ctcctgggct caagtgatct tcccacctcc acctcccgaa cagccgggac tacagggcgt | 4020 |
| acgccaccac gcctgggcaa ttttttgtatt ttttttgtaga gacgaagtct cgctatgttg | 4080 |
| cccaggctgt tctcgaaatc ctgggctcaa gcgatcctcc tgcctcggcc tcccaaagtg | 4140 |
| ctaggattag aggcgtgagc cactgcgcct cgccacaccc tgcattttta acacctcact | 4200 |
| ggagcgctca tcctctccac ctgctccgct attcaggagc ggctctgcac cgtaggccat | 4260 |
| ttcccacgac cagctgctga caaccatatc atcaaactgc tcttgttctc gcacccctta | 4320 |
| aatgtccagc cataatttct cagggaaaaa aatttataca ttttcaacaa ataggattca | 4380 |
| ttctcaaata gtcacataca acactcactc tggaagaaac tcccttcac atgccggtgt | 4440 |
| ctccctgcc cagccacttc ccagctttga ggttgggctc atctaggctg aaaaccaag | 4500 |
| ggactgggcc gtggttttcc cacttccact tcccagtttg ctttagttta ttttcccccc | 4560 |
| tctttggatt cctgaggcta agatgaagag agtcacttga ccaactttt tttcagtgtt | 4620 |
| tgggggaaa agaatgtggt ttaaaatagg ggctatttgt gacccagacc tctctcctta | 4680 |
| aagccctcta catctattcc catcccgcct cctctctcct aacacctgaa agatgcatga | 4740 |
| atataaagtc atatatcatg aactttattc caaatgagat tgctaactta ctgtgcaact | 4800 |
| ttaggaaagc cccttaacct gtctggggct cagttttcac acaaatccag agatccttgc | 4860 |
| agagaaaggt gcagttctcg ttcaggcagc aggaggcgct gtctctggag cttagattc | 4920 |
| attccccgcc ctccgcccgc tcccgcccgc ctctggtgcg caggcgcggc ttcgcggatt | 4980 |
| ggccgcgcgc gggggccgtc | 5000 |

<210> SEQ ID NO 50
<211> LENGTH: 5004
<212> TYPE: DNA
<213> ORGANISM: Homo sapiens

<400> SEQUENCE: 50

| | |
|---|---|
| gtgatcccctt tttttttttc ttgttattat gctaaccttg tgaagtgggt aaggaccagt | 60 |
| ataattatct ccatttcaca gatgaaggag ctgaggcaca gggagtttga aatttgctaa | 120 |

```
aggacatagg tagtaaatta caagctcaga gacagataat cttgattaca agttcagtgc    180 tcttttgtt ctaccttggg gcctcgcttt tcagcagtgt tcacctcaca atatttgtca    240
gtggtttgca tagataaagc tgtctctccc tcagtgttac aatgacaagt tttctatgga    300
ttttgtgtcc agcaaaacag taagttagtc ttgttgtatt tttcttcaat ttaaactgga    360
tattgagttg tacatcttta ttgttttagt agtacaaaat cacctaagct tagctcttaa    420
tattcaaagt agagaggaag atgggaatct ggagcaaaga aatacacact tgagaaaaag    480
aagacaaggg aaaatttcct ctaatcacgg atctatctcc aagcaggcta ctcagtctct    540
ggggttgtag agagacagac ctaatacaca cagttcttct atcccatcct gtcttctaga    600
gtggtagtac agagagagcc agcaggttgg aggtagaaga tttaaaaata aaaaattttt    660
aaaaaaagag ttggaggttt ctttaacttc ctggcagcat ctccaaagag tggtacccttt    720 ctgtggtcct gttctctgtg gaagcagtct ctgtctttag acctggttgg ttgactttca    780
tgagatcaca gaactggaag tgcccagcac acaatgctga aaaatttta tgaagctctc    840 agctgctata gtgtagccct tgatggaaat gggtttttgt tgggtatgtg gaaaacccat    900
cagtcttacc atcccagcac tgccagttct tactgtctaa catatgtgaa ggagaaggaa    960
aatggtactt ctcaaaacat aactaaaaat cacaggggaa aattaagcac tgtgtttaaa   1020
aggccatgag atttcatttc cagggaaaag gaataattcc gccttttctg tctcctgagg   1080
cttttctgtt ttcatagttt ctcctagttt tattacacat attgtccctt cggggttatc   1140
agatagtgct tctaaaacct gacctatcct atgatcagtg tccttcttca gtttccagca   1200
aactgattgt ggttaaaaca ggtacacagg gcagatcact ggggtacaga ttagagggaa   1260
ctgaccttgg agactgcatt ccacgttctt ttggcactac tggccatagt tctgtacttg   1320
tccactaaaa agtaaactcg aagttcaagt cttaagttat ttcttccctg agagacgatg   1380
ttgattgcaa tactaagtga ataaatgagc aaatggaagg aagatgttag ctgaagctgc   1440
agtgaagaga aaggtaggat atgaggctga acttggaagg aggagagtct tcactcagtg   1500
gccatttgta tactggcctt gcactacact atcaggccaa caacctgaag acctattctg   1560
aactttccac ctgcctgcaa atgttgacta tggtcatttc tgttcactac ctaataaatg   1620
agtaacaaga attcctctgc cccatctcac aataccaaat aatgatgttt actaaaataa   1680
taacaatttg gcctaataaa agagcctcca ccaaagccac ttggtgatca ctctgccacc   1740
caagtttctg ccctggcatt ctgacaatag tggggatggt aatacactta gtcaaaacat   1800
atatggagcc gggcgcggtg gctcacgcct gtaatcccag cactttggga ggctgaggtg   1860
ggtggatcac ttgaggtcag gagttcgaga ccagcctggc aaacatagtg aaaccccgtc   1920
tctactaaaa atacaaaaag ccaggtgtgg tggcgcatgc ctgtaatccc agctactctg   1980
aggctaaggc aggagaattg cttgaacccg ggaggtagag gctgcagtga gccagaccag   2040
gtgacagggc tagactctat ctaaaaaaaa aaaaaggct gggcgtggtg gctcatgcct   2100
gtaatcccag cactttggga ggccgaggcg ggtggatcac ctgaggtcag gagtttgaga   2160
ccagcctggc caacgtaatg aaactccgtc tgtactaaaa atacaaaaat tagccaggcg   2220
tggtggcggg catctgtagt ctcagctact gggaggctg aggcaggaga atggcgtgaa   2280
cctgggaggc ggagtttgca gtgagcagag atcgcaccac tgcactccag cctgggcaac   2340
agagcgagac tccgtttcaa aaaaaaaaa aaaaaccgta tatggacact cattaggatg   2400
gctattgtaa aaaacttact gttggcaagg acatgggaa attggaacac ttgcacattg   2460
```

```
ctggtaggag tgtaaaatga tacagctgat ggagaatcca tacggcaatt cttcaaaaaa    2520
ttaaacagaa tagctgtatg atctagcaat tccatttctg ggtatatatc cagaaaggaa    2580
agcaggtact caaacatatt tgtactccca cttgcccagc aacatcattc acaatagcca    2640
taaggtggaa gcaacccaag tgtccattga tggatgagtg gataaacaaa atgtggcata    2700
tacatacagt ggaatattat ttggccttta agagaaagga aattttgaca cttgctacaa    2760
catggataaa cctggatgcc attatgctaa gtgaaataag ccagtcacaa aaggacaaat    2820
actgtatgat tacactaaca tgagattcct agagcagtca ggttcataca gacagaaagt    2880
aaaatggtgg ttgccagcgg ctatggggaa ggggaaagt ggggagttag tgtttaatgg    2940
gcacagagtt tcagtttggg aaaatgagaa agttctggtg ttgaatcgtg gtgatggttg    3000
cataacaatg tgaatgtact taacgccact taactgtaca cttagagaca gttaaagtgg    3060
tacatttatg ttatgtattt ttttttttaac cacaatttaa aaaaattgcg ggggacgggt    3120
gcggtggctc actcctgtaa tgccagcact ttgggaggcc aaggcaggca gatcacttga    3180
ggtcaagagt tcaagaccag cctggccaac atggtgaaac cccatctcca caataaaata    3240
ccaaaattag ctgggcatgg tggagcacgc ctgtaatccc agctacttgg gaggctgagg    3300
caggagaatc gcttgaaccc gggtggtgga agtttcagtg tgcagagatc gtgccactgc    3360
aatccagcct ggggagcata gtgagtgaga ctccgtctcg aaaaaataaa aattaaaaat    3420
aaaaataaga gggacagagg gtggaatgac atggaagaga caaagatat taatttgttt    3480 aatgcttcac tggtggactg tgctattctc ttcttttttgg gaagccagat tttacaaagg    3540
gagactttca ggaggcagat gtggtgtgtt ttttgttgtt gttgtttgga aagtgtatct    3600
tcaattggtt gttaactgac tgctcattgg agacttctgc cagatgcgcc cagatcatta    3660
gtccgtttga atcatcacgt cttccaggcc ccaccctact ctctgatagg ccccaccttc    3720
accgtggggt cctgttagtc aagatgctct gagagcgcac agccaccaaa caaaaatgat    3780
cgctttgact gtgacaggga ttgacgtcta ttttcgatag cagactcagc cttagccatt    3840
cacataggaa tcctgagctc tgcctttgag agtattaggc atccaacaaa tgctcacgga    3900
tttaagtgaa atgatgtgcg ttactttcag ttatatgact tcgaagagtc tttgttttgt    3960
ttttcaaagt gcaagggtaa atcaatagaa ttcatagggt cttgagccag ctccacccat    4020
ctctacccag ggacggaatc atcttttaaa acttggattt aacacttacg tagcacttac    4080
tgtgagccag agactatcct aaagactttt gatagatata tcaactcatt taatactaat    4140
aagcctatgc agttaggtac ccttgtttcc cattttacag atgagaaaac tgaggcacag    4200
agaaggaaag ttataccacc attaagtagt ggacctggga ttccacctga aatacttgt     4260 ggccctgag ctcatgctct tagttattgt acacctgact cttttcttaa aatagtaatg    4320
caccagactg ggactttaat gaccctgaag tggatctcaa ggtccagaat ggagaatggt    4380
aattgggggt gaagatattc cttgattatg atcctgcctc tctactccag cagcctcatt    4440
tggtccctga gggttaatgc cgaagccagg gtaagggggct tgtaggttta aggtcaaatt    4500
ttttgaacct aaggaatttc cctccaattc tgtagcagcc ccgcagtgac gaatctgctg    4560
cctctcccac gggttttgct attagaggat tttcaaggtg atcaaggcag acgagatgaa    4620
acaccattaa actaacactg agcaacgctg aaccctacat aaatcttttt ttctagtctt    4680
tctaagatac gaccccagac gaatctgcaa ctctggagtg gaaaccaggg ggcgggctaa    4740
gcagcgacca ttttttgtttt gcggccgtgc gctctcagag catcttgact aacaggaccc    4800
ccacggtgaa ggtggagcct atcagagagc agggcggggc ctggaagacg tgatgattca    4860
```

```
aacggactaa tgatctgggc gcatctggca gaagtctcca atgagcaggc gtgttgggga    4920
ggagcgcaca aaccctagtg ggtttggttg cacggcggct ttggcgcatt ttcggctggt    4980
ttgattcatc cattttgaag agac                                           5004
```

HAIR SHAPE SUSCEPTIBILITY GENE

REFERENCE TO SEQUENCE LISTING SUBMITTED ELECTRONICALLY

The content of the electronically submitted substitute sequence listing, file name 2537_0680004SequenceListing_ascii.txt; size 267,388 bytes; and date of creation Apr. 4, 2012, filed herewith, is incorporated herein by reference in its entirety.

FIELD OF THE INVENTION

The present invention relates to a gene related to hair shape, determination of genetic susceptibility to hair shape, detection and/or determination of the type of hair shape, a marker for screening an ingredient effective for the regulation of hair shape, and a use of the marker.

BACKGROUND OF THE INVENTION

The natural shape of human hair is generally classified into straight hair, wavy hair (wave hair), curled hair, and kinky hair (or coiled hair), depending on the degree of curl of the hair. Since the shape of hair and hairstyle constitutes one of the traits that can be easily recognized as physical features of human being, and also serve as an important factor that determines the first impression of a person, the shape of hair and hairstyle is a matter of great interest from a cosmetic viewpoint, irrespective of gender and age. In the case of kinky hair or curled hair with a high degree of curl, the person has trouble that the degree of freedom in hairstyle is limited so that desired styling cannot be achieved. On the other hand, even in the case of straight hair, the person also has trouble that the hair cannot be volumized, and bare skin is easily shown through.

As methods for changing the shape of hair and hairstyle, hairdressing using various hairstyling agents or hair dryers/hair irons, wave/straight permanent treatments, and the like are being extensively carried out. However, although these operations can effectively modify the shape of hair, the operations have no effect on the causative factor that determines the hair shape. These operations, which are the solutions to the above described troubles, are not fundamental solutions but are merely temporary, and in order to maintain the shape of hair and hairstyle, these operations must be repeated frequently. However, on the contrary, these operations cause increased damage to hair, and consequently impair the cosmetic value. For this reason, there is a demand for the development of a method for the intrinsic regulation of hair shape, by which the hair shape can be changed from the beginning of hair growth.

Searching for a causative factor that determines the hair shape and identifying a causative gene thereof are expected to provide useful information in the development of a method for the intrinsic regulation of hair shape. In regard to the factors or genes related to hair shape, there have been reports on the genetic diseases that bring changes to the shape of hair (Non-Patent Documents 1 to 3), acquired kinky hair caused by drugs (Non-Patent Document 4), curly hair model animals (Non-Patent Documents 5 and 6), an the like. However, the factors or genes disclosed in these documents are merely a special example which affect the hair shape, and are not adequate to be considered as causative factors that determine the natural shape of human hair.

Meanwhile, along with the rapid progress in the genome analysis technology in recent years, the correlation between diseases and genes is being gradually clarified. Particularly, not only for so-called genetic diseases that are defined by variation or abnormality of a single gene, but also for polygenic diseases characterized by low penetrance (the ratio of onset of a certain disease in an individual having a variation in a certain gene), such as highly frequent common diseases including lifestyle diseases such as diabetes and hypertension, search for causative genes using non-parametric linkage analysis techniques such as affected sib-pair linkage analysis is frequently carried out (see, for example, Non-Patent Document 7). Further, based on the hypothesis that the variation of a disease-associated gene for a common disease is a highly frequent genetic polymorphism (common variant), and that although the variation is present in healthy persons as well, the prevalence is significantly high inpatients (Common Disease-Common Variant), search for causative genes by means of linkage disequilibrium analysis using a genetic polymorphism (for example, SNP (Single Nucleotide Polymorphism)) is also actively carried out throughout the world (see, for example, Non-Patent Document 8).

More recently, with the progress in the international HapMap Project, a database of general polymorphisms (SNP) of high frequencies such as one million loci or more in four human populations has been established, and research is being conducted on common diseases as well as on general traits in which the phenotype varies with the human race or population, for example, skin color, hair color, and eye color (see, for example, Non-Patent Documents 9 and 10).

Similarly, also in regard to the natural shape of human hair, it can be contemplated that the natural hair shape is a general trait in which the phenotype varies with the human race or population. In general, many Asian people have straight hair, while African people predominantly have kinky hair (or curled hair). Indo-European people have a high ratio of having a trait of wavy hair (wave hair), which is intermediate of the two. The mode of inheritance was first observed by Rostand, J., et al., and they reported that curly hair is an autosomal (semi) dominant trait over straight hair (Non-Patent Document 11). Furthermore, descriptions on the curly hair trait may also be found in the human Mendelian inheritance database of the NCBI (OMIM, http://www.ncbi.nlm.nih.gov/omim/). However, in regard to causative genes that determine the natural shape of human hair, systematic research on genome analysis has not been completed, and no such genes have been found yet.

PRIOR ART DOCUMENTS

Non-Patent Document

Non-Patent Document 1: Norgett E E et al., Hum. Mol. Genet. 9(18), p. 2761-2766, 2000
Non-Patent Document 2: Moller L B et al., Hum. Mutat. 26 (2), p. 84-93, 2005
Non-Patent Document 3: Kjaer K W et al., Am. J. Med. Genet. A. 127A(2), p. 152-157, 2004
Non-Patent Document 4: Cullen S I et al., Arch. Dermatol. 125(2), p. 252-255, 1989
Non-Patent Document 5: Du X et al. Genetics. 166(1), p. 331-340, 2004
Non-Patent Document 6: Mann G B et al., Cell. 73(2), p. 249-61, 1993
Non-Patent Document 7: Hanis C L et al., Nat. Genet. 13(2), p 161-166, 1996
Non-Patent Document 8: Altshuler D et al., Nat. Genet. 26(1), p. 76-80, 2000

Non-Patent Document 9: Sulem P et al., Nat. Genet. 39(12), p. 1443-1452, 2007

Non-Patent Document 10: Sabeti P C et al., Nature. 449 (7164), p. 913-918, 2007

Non-Patent Document 11: Rostand J et al., "An Atlas of Human Genetics", Hutchinson Scientific & Technical, London, pp. 26-29, 1964

SUMMARY OF THE INVENTION

The invention provides a hair shape susceptibility gene, which overlaps with a haplotype block in the 1q32.1 to 1832.2 region (D1S249 to D1S2891) of human chromosome 1 and includes a portion or the entirety of the base sequence of the haplotype block, wherein the haplotype block is determined by a linkage disequilibrium analysis conducted on a single nucleotide polymorphism (SNP) marker whose allele frequency differs statistically significantly between a group having a curly hair trait and a group having a non-curly hair trait, and consists of a base sequence set forth in any one of SEQ ID NO:1 to NO:3.

The present invention also provides a hair shape determining marker, which is an oligo- or polynucleotide containing a partial base sequence of the base sequence of the haplotype block described above, or a complementary strand thereof, wherein the partial base sequence consists of a contiguous base sequence containing one or more single nucleotide polymorphisms (SNPs), wherein the SNPs include an SNP whose allele frequency differs statistically significantly between a group having a curly hair trait and a group having a non-curly hair trait, and an SNPs linked to the SNP.

Furthermore, the present invention provides a method for determining the genetic susceptibility of a test subject to hair shape, the method including the following steps (a) to (c):

(a) preparing a genomic DNA derived from a test subject;

(b) detecting, from the genomic DNA, in the haplotype block, a single nucleotide polymorphism (SNP) which exists in the haplotype block described above and whose allele frequency differs statistically significantly between a group having a curly hair trait and a group having a non-curly hair trait, and a single nucleotide polymorphism (SNP) that is linked to the SNP; and (c) determining, if the allele frequency of the detected relevant SNP is statistically significantly higher in the group of curly hair people than in the group of non-curly hair people, that the test subject has a genetic predisposition to curly hair, and if the allele frequency of the detected SNP is statistically significantly higher in an arbitrary group of non-curly hair people than in the group of curly hair people, that the test subject does not have a genetic predisposition to curly hair.

The present invention also provides a method for determining the genetic susceptibility of a test subject to hair shape, the method including identifying, for any one or more nucleotides of the nucleotide numbers as indicated in the following table that are present in the base sequences set forth in SEQ ID NO: 1 to NO: 3 in the genomic DNA derived from a test subject, whether the nucleotide is nucleotide (i) or nucleotide (ii); and determining, when the nucleotide is nucleotide (i), that the test subject has a predisposition to curly hair, and when the nucleotide is nucleotide (ii), that the test subject does not have a predisposition to curly hair.

TABLE 1

| SEQ ID NO. | Nucleotide Number | Nucleotide (i) (having predisposition) | Nucleotide (ii) (no predisposition) |
|---|---|---|---|
| 1 | 1 | C | T |
|   | 1635 | A | G |
|   | 2527 | A | G |
|   | 3766 | A | C |
| 2 | 7519 | A | G |
|   | 16901 | G | T |
|   | 30270 | G | A |
|   | 31333 | G | C |
|   | 50038 | A | T |
|   | 63008 | T | G |
| 3 | 24524 | G | T |
|   | 60701 | A | G |

Furthermore, the present invention provides a reagent for the determination of the genetic susceptibility of a test subject to hair shape, the reagent including a probe and/or a primer, which hybridizes with the hair shape determining marker of the present invention under stringent conditions.

The present invention also provides a kit for the determination of the genetic susceptibility of a test subject to hair shape, the kit including the reagent described above.

Furthermore, the present invention provides a method for screening a hair shape regulating agent, the method including the following steps (a) and (b):

(a) administering a test substance to a cell containing the hair shape susceptibility gene of the present invention; and (b) selecting, among the administered test substances, a substance which converts the type of polymorphism of the nucleotide in a marker with a single nucleotide polymorphism (SNP) that is present on the hair shape susceptibility gene or in the vicinity thereof, and the allele frequency of which differs statistically significantly between a group having a curly hair trait and a group having a non-curly hair trait, or a single nucleotide polymorphism (SNP) that is linked to the SNP, to another polymorphisms, as a hair shape regulating agent.

Furthermore, the invention provides a marker for the type of hair shape, consisting of a polynucleotide consisting of a base sequence set forth in SEQ ID NO:42, SEQ ID NO:44, or SEQ ID NO:46, or a base sequence complementary thereto, or a partial polynucleotide of these polynucleotides, or consisting of a polypeptide consisting of an amino acid sequence set forth in SEQ ID NO:43, SEQ ID NO:45, or SEQ ID NO:47, or a partial polypeptide thereof.

The invention also provides a primer for amplifying the marker for the type of hair shape of the present invention, the primer consisting of a partial polynucleotide of a polynucleotide consisting of a base sequence set forth in SEQ ID NO:42, SEQ ID NO:44, or SEQ ID NO:46, or a base sequence complementary thereto.

Furthermore, the invention also provides a probe for detecting the marker for the type of hair shape of the present invention, the probe consisting of a polynucleotide consisting of a base sequence set forth in SEQ ID NO:42, SEQ ID NO:44, or SEQ ID NO:46, or a base sequence complementary thereto, or a partial polynucleotide of these polynucleotides.

The invention also provides an antibody for detecting the marker for the type of hair shape of the present invention, the antibody being capable of specifically recognizing a polypeptide consisting of an amino acid sequence set forth in SEQ ID NO:43, SEQ ID NO:45, or SEQ ID NO:47, or a partial polypeptide thereof.

Furthermore, the present invention provides a method for detecting and/or determining the type of hair shape, the method including the following steps (a) to (c):

(a) measuring the amount of expression of the marker for the type of hair shape of the invention in a sample derived from a test subject;

(b) comparing the results in the measurement obtained from step (a) with the results of non-curly hair people; and (c) determining the type of hair shape based on the results obtained from (b).

The invention also provides a method for evaluating or selecting a hair shape regulating agent, the method including the following steps (a) to (d):

(a) contacting a test substance with a cell capable of expressing the hair shape susceptibility gene of the invention or a protein encoded by the gene;

(b) measuring the amount of expression of the gene or the protein in the cell contacted a with test sample;

(c) comparing the amount of expression measured in step (b) with the amount of expression of the gene or the protein in a control cell that has not been contacted with the test substance; and (d) selecting, based on the results obtained in step (c), a test substance which increases or decreases the amount of expression of the gene or the protein, as a hair shape regulating agent.

The invention also provides a method for evaluating or selecting a hair shape regulating agent, the method including the following steps (a) to (c):

(a) introducing, to a cell capable of expressing the hair shape susceptibility gene for the type of hair shape of the present invention, a fusion gene of the regulatory region of the hair shape susceptibility gene and a reporter gene, and culturing the cell in the presence and in the absence of a test substance;

(b) measuring the amount of expression of reporter gene expression product in the cell culture cultured in the presence of the test substance, and comparing the amount with the amount of expression of an expression product of the reporter gene expression product in the cell culture cultured in the absence of the test substance; and (c) selecting, based on the comparison results obtained from step (b), a test substance which increases or decreases the amount of expression of the reporter gene expression product, as a hair shape regulating agent.

The invention also provides a method for evaluating or selecting a hair shape regulating agent, the method including the following steps (a) to (c):

(a) contacting a test subject with an aqueous solution, a cell or a cell fraction prepared from the cell, which contains all contain a protein encoded by the hair shape susceptibility gene of the present invention;

(b) measuring the function or activity of the protein in the aqueous solution, cell or cell fraction that has been contacted with the test substance, and comparing the function or activity with that in a control aqueous solution, a control cell or a control cell fraction, which all have not been contacted with the test substance; and (c) selecting, based on the comparison results obtained from step (b), a test substance which increases or decreases the function or activity of the protein, as a hair shape regulating agent.

The present invention also provides a method for regulating the type of hair shape, the method including controlling the expression of the hair shape susceptibility gene of the present invention in the human hair root area.

According to an embodiment, the hair shape susceptibility gene of the invention is selected from CSRP1, NAV1, IPO9, TMEM58, and NUCKS1.

According to an embodiment of the hair shape determining marker of the present invention, the SNPs include a SNP in a nucleotide selected from the group consisting of the following bases:

(1) in the base sequence set forth in SEQ ID NO:1, nucleotides represented by Nucleotide Numbers 1 (dbSNP database ID: rs576697, T or C), 1635 (rs645390, G or A), 2527 (rs3767542, G or A), and 3766 (rs675508, C or A);

(2) in the base sequence set forth in SEQ ID NO:2, nucleotides represented by Nucleotide Numbers 7519 (rs2271763, G or A), 16901 (rs10920260, T or G), 30270 (rs16849387, A or G), 31333 (rs12127375, C or G), 50038 (rs1495840, T or A), and 63008 (rs10920269, G or T); and (3) in the base sequence set forth in SEQ ID NO:3, nucleotides represented by Nucleotide Numbers 24524 (rs3805, T or G), and 60701 (rs823114, G or A).

According to another embodiment, the hair shape determining marker consists of a contiguous base sequence having a length of 10 to 601 nucleotides.

According to the embodiment of the reagent of the invention for the determination of the genetic susceptibility of a test subject to hair shape, the probe and/or the primer is hybridized with a region containing SNPs of the nucleotides described in the items (1) to (3) above.

According to an embodiment of the marker for the type of hair shape of the present invention, the partial polynucleotide is a polynucleotide of 15 bases or more.

According to an embodiment of the method of the present invention for detecting and/or determining the type of hair shape, the sample derived from a test subject is an RNA prepared from a biological sample collected from the test subject, or a complementary polynucleotide transcribed from the RNA.

According to another embodiment of the method of the present invention for detecting and/or determining the type of hair shape, the step (a) is a step for contacting a biological sample collected from a test subject with an antibody for detecting the marker for the type of hair shape of the present invention, and measuring the amount of the marker for the type of hair shape of the present invention in the biological sample that has been bound with the antibody.

According to another embodiment of the method of the present invention for detecting and/or determining the type of hair shape, the biological sample collected from the test subject is derived from an epithelial tissue or epithelial cell.

BRIEF DESCRIPTION OF THE DRAWINGS

FIG. 8-1 is a graph showing the amounts of expression of the hair shape susceptibility gene in the scalp hair roots of a curly hair group and a straight hair group, A: CSRP1 gene, B: IPO9 gene;

FIG. 8-2 is a graph showing the amounts of expression of the hair shape susceptibility gene in the scalp hair roots of a curly hair group and a straight hair group, C: NUCKS1 gene;

DETAILED DESCRIPTION OF THE INVENTION

Figure 1:
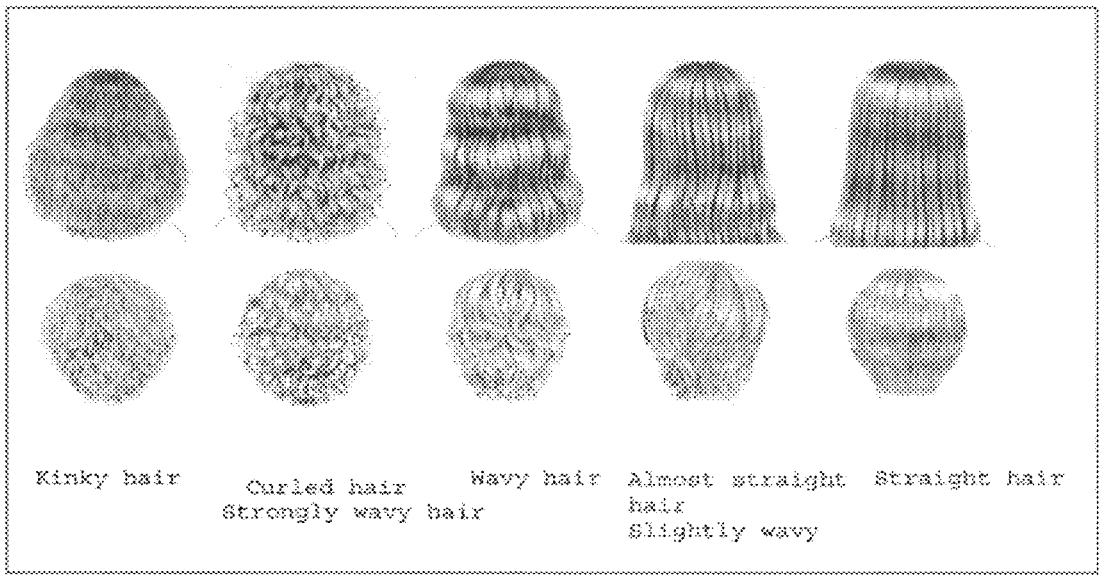
FIG. 1 is a set of images of the phenotypes of hair shape.

The present invention relates to the provision of a genetic polymorphism and a hair shape susceptibility gene that are related to the natural shape of human hair such as curly hair or straight hair, and the provision of a method for determining the genetic susceptibility of individual test subjects to hair shape based on this information. Furthermore, the present invention relates to the provision of a reagent and a reagent kit, which are useful for conveniently carrying out the method. In addition, the present invention relates to the provision of a marker (polynucleotide or polypeptide) for detecting and determining the natural shape of human hair such as curly hair or straight hair, and to the use of the marker, such as the detection and/or determination of the type of hair shape, or the evaluation and selection of a ingredient effective for the regulation of hair shape using the marker.

The inventors of the invention set a goal of finding a causative gene that determines the natural shape of human hair, and conducted a genome analysis directed to Japanese family lines having curly hair, a group of Japanese curly hair people, and a group of Japanese non-curly hair people. As a result, the inventors identified genetic polymorphisms related to hair shape, that is, hair shape susceptibility SNP markers, and also identified hair shape susceptibility genes in the 1q32.1 to 1q32.2 region of chromosome 1. The inventors of the present invention also investigated the relations between hair shape and the gene expression of various genes in the hair root area, and found that the amount of expression of the hair shape susceptibility genes in the hair root area differs significantly between non-curly hair people and curly hair people. These genes are hair shape susceptibility genes, and can serve as markers for detecting and/or determining the type of hair shape. Based on these findings, the inventors of the present invention finally completed the present invention.

According to the present invention, a hair shape susceptibility gene related to the natural shape of human hair such as curly hair or straight hair, a hair shape susceptibility SNP marker, and a hair shape determining marker utilizing these are provided. When the hair shape susceptibility gene, the SNP marker, and the hair shape determining marker of the present invention are analyzed in detail, research on the mechanism of the hair formation related to the hair shape, and application research such as the development of an adequate method for promoting the regulation of hair shape are made available.

According to the method for determining the genetic susceptibility to hair shape of a test subject, search for a gene that serves as a main factor that determines the hair shape of individual test subjects, and determination of the susceptibility of individual test subjects to the acquired changes of hair shape, that is, the degree of risk of the future change in the hair shape, can be more conveniently and rapidly carried out. Furthermore, based on the results, an adequate method for regulating the hair shape for individual persons can be provided. Further, the determination method can be carried out more conveniently and rapidly, by the reagent for the determination of genetic susceptibility of a test subject to hair shape of the present invention and the kit including the reagent.

According to the present invention, the shape or nature of hair such as curly hair or kinky hair can be detected and determined without damaging the hair. Furthermore, a substance selected according to the method of the present invention for screening an ingredient effective for the regulation of hair shape can be used as a hair shape regulating agent that is effective for the regulation of hair shape, and can also be used for the preparation of a pharmaceutical product, a quasi-drugs, cosmetic materials, health foods and the like, which all contain the agent. Further, according to the present invention, a method for regulating the hair shape using the hair shape susceptibility SNP marker obtained by the present invention can be provided.

1. DEFINITIONS OF TERMS USED IN PRESENT INVENTION

The indication of base sequences (nucleotide sequences), nucleic acids and the like by means of abbreviations in the present specification is as recommended by the specifications of IUPAC-IUB (IUPAC-IUB Communication on Biological Nomenclature (Eur. J. Biochem. 138, 9, 1984), "Guidelines for the preparation of specifications containing base sequences or amino acid sequences" (edited by the Japanese Patent Office), and the symbols conventionally used in the art.

The term "DNA" as used in the present specification encompasses not only a double-strand DNA, but also single-strand DNAs such as a sense strand, and an anti-sense strand constituting the double-strand DNA. Unless particularly stated otherwise, the term "gene" as used herein encompasses all of a double-stranded DNA including human genome DNA, a single-stranded DNA (sense strand) and a single-stranded DNA having a sequence complementary to the sense strand (anti-sense strand), and fragments thereof. Unless particularly stated otherwise, the term "gene" as used herein is intended to indicate any of a regulatory region, a coding region, an exon and an intron without discrimination. Further, the "gene" or "DNA" encompasses a "gene" or "DNA" represented by a specific base sequence, as well as a "gene" or "DNA" which encodes a homologue, a derivative or a variant of a protein encoded by the "gene" or "DNA" represented by a specific base sequence, provided that they have a biological function equivalent to that of the protein.

Furthermore, according to the present invention, the terms "nucleotide", "oligonucleotide" and "polynucleotide" have the same meanings as nucleic acid, and they are intended to encompass both DNA and RNA. The DNA encompasses all of cDNA, genomic DNA and synthetic DNA. The RNA encompasses all of total RNA, mRNA, rRNA and synthetic RNA. Further, the "nucleotide", "oligonucleotide" and "polynucleotide" may be double-stranded or single-stranded, and in the case of a "nucleotide" (or an "oligonucleotide" or "polynucleotide") having a certain sequence, unless particularly stated otherwise, the "nucleotide" is intended to collectively mean "nucleotide" (or an "oligonucleotide" or "polynucleotide") having a sequence complementary to the sequence. Furthermore, when the "nucleotide" (or "oligonucleotide" or "polynucleotide") is RNA, the nucleotide symbol "T" indicated in the base sequence may be replaced with "U".

The term "polynucleotide having a complementary base sequence" means a polynucleotide that is in a complementary relation in terms of nucleotide (i.e., complementary strand or anti-sense strand), to a polynucleotide having an arbitrary base sequence (sense strand). A complementary base sequence encompasses a sequence that is completely complementary to the subject base sequence, as well as a base sequence that can be hybridized with the subject base sequence under stringent conditions. Here, the stringent conditions may conventionally refer to washing conditions of approximately "1×SSC, 0.1% SDS, 37° C.", and more stringent hybridization conditions may be approximately "0.5× SSC, 0.1% SDS, 42° C.", and even more stringent hybridization conditions may be approximately "0.1×SSC, 0.1% SDS, 65° C.". Furthermore, a person having ordinary skill in the art can determine stringent hybridization conditions according to general textbooks (for example, Sambrook, J. & Russell, D., 2001, Molecular Cloning: a Laboratory Manual, $3^{rd}$ edition, Cold Spring Harbor, N.Y.: cold Spring Harbor Laboratory). An example of a base sequence that can be hybridized with a subject base sequence under stringent conditions may be a base sequence having a homology of 90% or higher, and preferably 95% or higher, with the subject base sequence.

The term "protein" or "polypeptide" encompasses a "protein" or "polypeptide" represented by a specific base sequence or amino acid sequence, as well as a fragment, a homologue, a derivative and a variant thereof, provided that they all have a biological function equivalent to that of the "protein" or "polypeptide". Meanwhile, the variant encompasses a naturally occurring allele variant, a variant that does not occur naturally, and a variant having an amino acid sequence modified by artificial deletion, substitution, addition and insertion. In addition, examples of the variant include those having a homology in the amino acid sequence of 80% or higher, preferably 90% or higher, more preferably 95% or higher, and even more preferably 98% or higher, with a protein or polypeptide having no variation.

According to the present specification, the homology of amino acid sequences and base sequences is calculated by the Lipman-Pearson method (Science, 227, 1435, 1985). Specifically, the homology is calculated by performing an analysis using a homology analysis (Search homology) program in the genetic information processing software Genetyx-Win (Software Development Co., Ltd.), and by setting the parameter, Unit size to compare (ktup), at 2.

The term "antibody" encompasses a polyclonal antibody, a monoclonal antibody, a chimeric antibody, a single-chain antibody, and portions of the antibodies described above, which have antigen-binding properties, such as Fab fragments, and fragments produced by a Fab expression library.

In regard to the term "genetic polymorphism" as used herein, when there are two or more genetically determined alleles, the term refers to such an allele gene. Specifically, in a human population, when variations such as substitution, deletion, insertion, dislocation, and inversion of one or plural nucleotides exist at a specific region in the genome of one or plural individuals, with respect to the genomic sequence of one certain individual, the variation is called "genetic polymorphism" if it is statistically ensured that the variation is not a mutation occurring in the one or plural individuals, or if it can be genetically demonstrated that the variation is not a specific variation in the individuals but occurs in the population at a frequency of 1% or greater. Examples of the "genetic polymorphism" as used herein include substitution of one nucleotide with another nucleotide, that is, a single nucleotide polymorphism (SNP); deletion or insertion of one to several tens of nucleotides (DIP); a region includes repetition units of sequence consisting of 2 to several tens of nucleotides as one unit, where the number of the repetition is different (when the unit repeated in the consist of 2 to 4 nucleotides, it is referred to as a microsatellite polymorphism, and when the unit repeated in the region consists of several to several tens of nucleotides, it is referred to as a VNTR (Variable Number of Tandem Repeat); and the like.

The term "hair shape" as used herein refers to the tendency of the overall shape of hair in the head area, which attributes to the shape of individual hairs, such as straight hair, wavy hair or wave hair, curled hair, or kinky hair or coiled hair.

The term "curly hair" as used herein is, unless particularly stated otherwise, a term which collectively refers to the shape other than straight hair in the case of contrasting with straight hair. Therefore, according to the present specification, in the case of contrasting with the "curly hair", unless particularly stated otherwise, the "straight hair" and the "non-curly hair" are considered to have the same meaning. The "curly hair", "non-curly hair" and "straight hair" are of relative nature, and can be defined by various methods that will be described below. The "curly hair trait", "non-curly hair trait", and "straight hair trait" refer to the phenotypes representing the "curly hair", "non-curly hair" and "straight hair", respectively.

The term "hair shape susceptibility gene" as used herein refers to a causative gene that determines the hair shape which is a polygenic trait, and the term "hair shape susceptibility SNP marker" refers to the nucleotide at a site which represents an SNP associated with the trait of hair shape of the individual.

According to the present specification, the terms "genetic susceptibility to hair shape", "hair shape determining marker" and "marker for the type of hair shape" respectively refer to the genetic predisposition related to the specific hair shape possessed by an individual, and a marker for determining the predisposition.

The term "Affected Sib-Pair Linkage Analysis" as used herein refers to one technique for estimating the location of a target gene (e.g., disease susceptibility gene or the like) using linkage, and is a representative analysis technique for non-parametric linkage analysis which does not assume any mode of inheritance (e.g., autosomal dominant inheritance, recessive heredity, sex-linked gene, or the like) or the penetrance. In the affected sib-pair linkage analysis, family lines including sibs (e.g., brothers and sisters) that are affected (or have a particular trait) are collected, calculation of the likelihood is carried out on the basis of the data obtained by observation of these family lines, and the genetic locus regions of the marker linked to the disease (or the particular trait) are narrowed down. In the case of a group of general (i.e., not affected, or not having a particular trait) sibs, in one genetic locus, a child receives one of the two alleles of one parent (even if the one parent is a homozygote, the alleles are considered to be different from each other). Therefore, in this case, there exist a case in which the sibs receive the same allele, and a case in which the sibs receive different alleles. Since each of the two alleles of a child originates one allele from each of the parents, when the question of how many identical alleles sibs will receive from their parents is considered, there are three cases such as 0, 1 and 2. These three cases are said to have an IBD (Identity By Descent) of 0, 1 and 2, respectively. When a number of sib-pairs are considered, the numbers of the pairs having an IBD=0, the pairs having an IBD=1, and the pairs having an IBD=2 should be counted, and the proportion of the numbers constitutes a certain proportion (1:2:1) according to the probability laws. On the contrary, when sibs that are affected (or have a particular trait) are collected, and the same investigation is carried out with this group, if an observed marker gene is linked to the disease (or the particular trait), this ratio (1:2:1) is deviated (i.e., the number of the pairs having an IBD=2 increases, and the number of the pairs having an IBD=0 decreases). In addition, for a marker gene which is not linked to a gene that is related to the disease (or the particular trait), it can be considered that the ratio has the same distribution (1:2:1) as any arbitrary sibs. In the affected sib-pair linkage analysis, the likelihood of observation data is calculated by utilizing this hypothesis, by taking the difference of the ratio of shared alleles in affected sib-pairs as an index. The likelihood is represented by the following formula:

$$L(Z) = \prod_{j=1}^{N} \sum_{i=0}^{2} Z_i W_{ij}$$

wherein $W_{ij}$ represents the probability that the affected sib-pair of the $j^{th}$ family line has an IBD=i. The variable is Z=(Z0, Z1, Z2), and the degree of freedom is 2 (Z2=1−Z1−Z0, there are only two independent variables of Z0 and Z1). The ratio with the likelihood in the case where a marker gene and a gene associated with a disease (or a particular trait) are not linked (that is, Z0=0.25, Z1=0.5, Z2=0.25) is taken, and the value of Z which gives the maximum likelihood is determined by the likelihood maximization method (maximum likelihood estimation).

The term "gene frequency" as used herein refers to the proportion occupied by the allele at a genetic locus among the total number of genes present in a group.

The term "haplotype" as used herein means a combination of genetic variations existing in one allele (haploid).

The term "linkage disequilibrium analysis" or "haplotype analysis" as used herein means an analysis of the degree of the intensity of linkage disequilibrium in a genomic region.

The term "linkage disequilibrium" as used herein refers to a phenomenon in the population genetics, in which a non-random correlation is observed in a group between alleles or genetic markers (polymorphisms) at plural genetic loci, that is, the frequency of such a particular combination (haplotype) is significantly increased. They are generally on the same chromosome and constitute genetic linkage, but there are occasions in which even if the alleles are linked, linkage disequilibrium is not observed. Further, in some exceptional cases, linkage disequilibrium may be seen over different chromosomes. For example, when a genetic locus X has alleles a and b (these exist at the same frequency), and a neighboring genetic locus Y has alleles c and d (these exist at the same frequency), the haplotype ac, which is a combination of the respective genetic polymorphisms, is expected to exist at a frequency of 0.25 in the group. When the frequency of the haplotype ac is higher than such an expected value, that is, when a specific genotype denoted as ac appears frequently, it is said that the allele ac is in linkage disequilibrium. Linkage disequilibrium is occurred as a result that the time of natural selection or introduction into a group of a particular combination of alleles is evolutionarily recent, and may be occurred as a result that linked alleles have not reached equilibrium. Therefore, the mode of linkage disequilibrium varies with different groups, such as nations or races, and even in the case where the allele ac in a certain group is in linkage disequilibrium, there are occasions in which the allele ad is in a relation of linkage disequilibrium in other groups. The detection of genetic polymorphism in the linkage disequilibrium is effective in detecting the susceptibility to a disease, regardless of whether the polymorphism itself directly causes the disease. For example, in regard to an allele a of a certain genetic locus X, although the allele is not a causative genetic factor of a disease, the allele may exhibit susceptibility to a disease through the linkage disequilibrium with an allele c of a genetic locus Y.

The "haplotype block" as used herein is defined as a region that is categorized as a genome region for which most of the historical recombination has not been acknowledged, and includes strong linkage disequilibrium. Identification of a haplotype block can be appropriately achieved by those having ordinary skill in the art based on the strength of the linkage disequilibrium, but for example, the identification can be carried out according to the report of Gabriel, et al. (Gabriel, S. B., et al., Science, 296 (5576), p. 2225-2229, 2002). The term "strong linkage disequilibrium" as used herein means the state in which the upper limit of the 95% confidence interval of the linkage disequilibrium coefficient D', which is calculated in a linkage disequilibrium analysis, exceeds 0.98, and the lower limit is higher than 0.7. The phrase "there is an evidence of strong historical recombination" means a state in which the upper limit of the 95% confidence interval of the linkage disequilibrium coefficient D' is lower than 0.9.

The term "minor allele" as used herein means an allele having a low gene frequency when two alleles exist in one genetic locus.

According to the present specification, the terms "gene frequency" and "allele frequency" are used for the same meaning, and are terms meaning the proportion occupied by a particular allele in an arbitrary group of genes.

The phrase "statistically significantly different" as used herein means a state in which when a test is carried out according to any statistical technique, the risk (p value) is less than 0.1%, preferably less than 0.07%, even more preferably less than 0.05%, and still more preferably less than 0.01%.

2. IDENTIFICATION OF HAIR SHAPE SUSCEPTIBILITY GENE AND HAIR SHAPE SUSCEPTIBILITY SNP MARKER

Search and identification of a causative gene that determines the natural shape of human hair, which is a multifactorial general trait (hair shape susceptibility gene), can be carried out by a genetic statistical analysis using a technique for trait mapping. That is, SNP(s) that are in the linkage disequilibrium state with the hair shape susceptibility gene can be effectively selected through the identification of curly hair trait loci by an affected sib-pair linkage analysis and case-control association analysis on the curly hair trait loci, and a gene present in a haplotype block containing the SNP(s) can be identified as a hair shape susceptibility gene.

The identification of the hair shape susceptibility gene and the hair shape susceptibility SNP marker of the present invention can be carried out, as will be described specifically in Examples below, by performing an identification method having the following steps:

(i) a step of defining hair shapes, and collecting curly hair family lines, people having a curly hair trait (case), and people having a straight hair trait (control);

(ii) a step of performing an affected sib-pair linkage analysis directed to the entire genome using samples derived from the curly hair family lines, and identifying a curly hair trait locus;

(iii) a step of selecting plural SNP markers which are not unevenly distributed over the entire region in the curly hair trait locus identified in step (ii);

(iv) a step of performing typing of the SNP markers selected in step (iii) using case-derived and control-derived samples, comparing the results of the typing through a statistical processing, and identifying a SNP marker that is recognized to have a significant difference, as a hair shape susceptibility SNP marker;

(v) a step of determining, with regard to the hair shape susceptibility SNP marker, a region where linkage disequilibrium is recognized within an object candidate region and a hair shape susceptibility SNP marker is contained (haplotype block), using the HapMap PHASE data of the International HapMap Project Database, and thereby identifying a hair shape susceptibility gene; and (vi) a step of determining, for the haplotype extracted from the haplotype block specified in step (v), a SNP locus that is linked with the hair shape susceptibility SNP marker locus determined in step (iv) using the HapMap PHASE data of the International HapMap Project Database, and additionally identifying the SNP thus-determined as an additional hair shape susceptibility SNP marker.

The step (i) is a step of defining hair shapes (curly hair or straight hair) and collecting analysis objects for trait mapping. In regard to the trait mapping, it is necessary to handle the subject trait quantitatively to a certain extent, and thus, the operation of defining hair shape, by which the objects are defined to have a curly hair trait or a straight hair trait, constitutes an important step when the trait mapping is carried out. There are a variety of human hair shapes, and the method for measurement thereof and the method for classification or defining are also various. For instance, examples of the method of defining hair shapes include a method of binarizing the hair shape, in such a manner that curly hair=1 and straight hair=0; a method of measuring the degree of curly hair by any method and quantifying the degree; and a method that is well known to those having ordinary skill in the art (for example, see Japanese Patent Application Laid-Open (JP-A) No. 2005-350801, JP-A No. 2008-268229, Japanese Patent No. 4159515, and the like), but the method is not limited to these. As a more specific example of the method of defining hair shapes, there may be mentioned a method of classifying hair shapes into several grades (for example, 2 to 10 grades, preferably 3 to 8 grades, and more preferably 5 to 7 grades) based on the features such as the overall shape, the degree of curl of the hair (radius of curl), the frequency of the appearance of curl, and/or the synchrony of curl with the groups of hair in the surroundings; and defining, in regard to such classifications, a hair shape having a tendency of a small radius of curl, such as kinky hair and curled hair or strongly wavy hair, as a curly hair trait, and defining a hair shape having a tendency of a large radius of curl, such as wavy hair, almost straight hair or slightly wavy hair, or straight hair, as a straight hair trait.

The step (ii) is a step of carrying out an affected sib-pair linkage analysis on the entire genome using samples derived from a curly hair family line. The constituent members of the curly hair family line for carrying out the affected sib-pair linkage analysis are sibs (a pair among brothers and sisters, two people) determined to have the curly hair trait by the step (i). More preferably, the constituent members consist of a family of 4 people (or 3 people) including the parents of the sibs, and other brothers and sisters (irrespective of the hair shape) or grandparents may also be further added. Furthermore, the number of the curly hair family lines needed to carry out the affected sib-pair linkage analysis can be determined by estimating and/or observing the frequency in the population of the curly hair trait, the frequency of the causative gene (allele frequency), the sib relative risk, or the like, and calculating the number by through simulation. However, the number of the curly hair family line needed is generally 50 family lines to several hundred family lines.

The genetic marker used in the affected sib-pair linkage analysis is not particularly limited as long as it is a genetic polymorphism, but a microsatellite that exists uniformly in the genome and has a large number of alleles is used with preference. A kit for amplifying and detecting a microsatellite (linkage mapping set) is commercially available from Applied Biosystems Corp. (ABI). Meanwhile, in the present invention, ABI PRISM Linkage Mapping Set-MD 10 v2.5 (manufactured by ABI) which covers human chromosome at an average interval of 9.2 cM, and ABI PRISM Linkage Mapping Set-HD 5 v2.5 (manufactured by ABI) which covers human chromosome at an average interval of 5 cM were used.

Furthermore, the microsatellite that serves as a genetic marker can be arbitrarily selected, and can be retrieved from the Comprehensive Human Genetic Maps of the Mammalian Genotyping Service (http://research.marshfieldclinic.org/genetics/GeneticResearch/compMaps.asp), NCBI (http://www.ncbi.nlm.nih.gov/) and the like. In this case, it is preferable to select a microsatellite which exists in the genome at an interval of 0.1 to several cM, and has many alleles and high heterozygosity. Furthermore, microsatellite markers can be added to a chromosome in which linkage has been recognized, and the linkage region can be narrowed (detailed mapping). Meanwhile, for the PCR primer for amplifying and detecting the microsatellites that have been arbitrarily selected and added, the base sequence can be retrieved from the NCBI (http://www.ncbi.nlm.nih.gov/), and the primer can be produced based on the retrieved sequence according to an ordinary method using, for example, a commercially available nucleotide synthesizer. At this time, it is preferable to label the probe with a radioactive substance, a fluorescent substance, a chemiluminescent substance, an enzyme or the like so that the detection of the amplification product can be achieved rapidly and easily.

In the affected sib-pair linkage analysis, PCR is carried out using a genomic DNA derived from a curly hair family line as a template, and using a linkage mapping set (ABI) or an amplification primer of a microsatellite marker arbitrarily selected, and thus an amplification product (fragment) is detected. The operations of PCR and the detection of the amplification product can be carried out according to ordinary methods. At this time, when various amplification primers are labeled with different fluorescent dyes (for example, any dyes emitting different fluorescent light, such as 6-FAM (blue), VIC (green), or NED (yellow)), even if amplification products having an identical size are obtained, plural amplification primers can be rapidly detected by separately discriminating the various fluorescent colors.

A statistical test of the linkage can be carried out using commercially available or publicly disclosed genetic statistic software programs which are capable of non-parametric analysis (for example, Genehunter, Linkage Package, Mapmaker/sibs, and the like).

The determination of the region where linkage is recognized was based on the criteria for obtaining a false positive linkage, according to the guidelines provided by Lander and Kruglyak (Nat. Genet., 11 (3), 241-247, 1995) shown below. The guidelines by Lander and Kruglyak (linkage analysis over the entire genome with a multifactorial disease) has come to be actively carried out, but in the linkage analysis of individual genes, the determination of whether the gene function can be causative is also added. However, since the gene function is not taken into consideration in that stage in the analysis of the entire genome, determination criteria (threshold) of significance purely in terms of mathematical genetics are required. Thus, they provided criteria for significance of linkage as shown in the following Table 2 according to simulations.

TABLE 2

| | |
|---|---|
| Suggestive Linkage (Criteria for obtaining a result of one false positive linkage from the entire genome) | $P < 7.4 \times 10^{-4}$ LOD > 2.2 |
| Significant Linkage (Criteria for obtaining a result of 0.05 false positive linkages from the entire genome) | $P < 2.2 \times 10^{-5}$ LOD > 3.6 |
| High Significant Linkage (Criteria for obtaining a result of 0.01 false positive linkages from the entire genome) | $P < 3.0 \times 10^{-7}$ LOD > 5.4 |

Through this process, the whole chromosome can be screened, and a region on the chromosome where linkage with the curly hair trait is recognized can be detected. Through further detailed mapping, a specific region on the chromosome can be identified as a curly hair trait locus. The region identified as such is a region where the presence of a hair shape susceptibility gene is strongly suggested.

The step (iii) is a step of selecting, in the curly hair trait locus region identified in the step (ii), plural SNP markers which are not unevenly distributed over the entire region. The SNP markers can be selected by using various databases related to SNP, such as the dbSNP database (http://www.ncbi.nim.nih.gov/SNP/) and the JSNP database (http://snp.ims.u-tokyo.ac.jp/index_ja.html).

Upon the selection of the SNP marker, a SNP which is useful for the identification of a hair shape susceptibility gene is selected. Specifically, in a Japanese group, a SNP having a gene frequency of minor allele of 10% or greater, and more preferably 15% or greater, is selected. When a SNP having such a gene frequency is used, a SNP marker having high reliability can be selected.

In addition, when a SNP marker is selected by using the gene frequency as an index, there are occasions in which the SNP marker is unevenly distributed in a specific narrow region. In this case, if all of the selected SNP markers are used in the identification of a hair shape susceptibility gene, the experiment becomes complicated, and it is also not very effective that SNPs which are neighboring with each other are in the state of linkage disequilibrium. Therefore, it is preferable to select and use SNP markers which are present at a certain interval from one another. As such, when uneven distribution of markers is eliminated by providing a certain interval between them, a comprehensive association analysis can be carried out over the entire object candidate region, and the identification of the hair shape susceptibility gene can be easily carried out. The distance between adjacent SNP markers that are selected as such is preferably 5 kb or greater, and more preferably 5 kb to 10 kb. If this distance is too long, there is a possibility that a region may occur where the extent of the strength of mutual linkage disequilibrium between SNP markers cannot be checked. Furthermore, if this distance is too short, there are so many SNPs for which strong mutual linkage disequilibrium is recognized, and therefore, it is not efficient.

In the comprehensive selection of SNP markers over the entire object candidate region, apart from this distance between SNP markers, the state of scattering of markers in the object candidate region, that is, the number of markers per unit distance of genome, can be expressed as "marker density." The marker density is 0.5 SNPs or more, preferably 1 SNP or more, and more preferably 1 SNP to 2 SNPs, per 10 kb of genome. If the marker density is too low, the distance between markers is too long, and there is a possibility that a region may occur where the degree of the strength of linkage disequilibrium between SNP markers cannot be checked, as described above. On the other hand, if the marker density is too high, the distance between markers is too short, and as described above, markers are selected overcrowdedly, so that in the case of identifying a hair shape susceptibility gene, a large amount of experiment is needed, which is not so efficient.

The step (iv) is a step of carrying out a case-control association analysis for the SNP markers selected in step (iii). The case-control association analysis is a method of comparing the allele frequencies for a certain hereditary marker between a case (affected people: people having the curly hair trait) group and a control (control people: people having the straight hair trait), and detecting a marker which can exhibit a significant difference in the allele frequency between the two groups. For example, samples derived from people having the curly hair trait (case) and people having the straight hair trait (control) are used, and typing is carried out. The results are compared by statistical processing, and a SNP marker with which a significant difference is recognized is identified as a hair shape susceptibility SNP marker. The sample required for trait mapping is not particularly limited as long as the sample contains genomic DNA, but examples include blood such as peripheral blood, body fluids such as saliva and sweat, somatic cells, and tissues or organs including somatic cells. The number of case and control required to perform a case-control association analysis can be estimated based on the frequency in a population having the curly hair trait, the gene frequency (allele frequency) causative of the trait, the genotype relative risk, and the like, but the number is generally 50 to several thousand people. Furthermore, it is possible to obtain a relatively high power of test by a stepwise refinement method under the conditions of limited sample size, limited number of typing operations or the like. Furthermore, the case and the control are preferably constituted of the same human race as the race for which the hair shape susceptibility gene is specified, and for example, in order to identify a hair shape susceptibility gene of Japanese people, it is preferable that the object of analysis be constituted of Japanese people.

As the method for SNP typing, methods that are well known to those having ordinary skill in the art, such as PCR-SSCP, PCR-RLFP, PCR-SSO, PCR-ASP, a direct sequencing method, SNaPshot, dHPLC, a Sniper method, and a MALDI-TOF/MS method, can be used (see, for example, Nojima, Hiroshi, Ed., "Forefront of Genomic Drug Discovery", p. 44-p. 54, Yodosha Co., Ltd., 2001). For example, it is effective to utilize TaqMan SNP Genotyping Assays (registered trademark) (manufactured by ABI), and to employ a SNP typing method which utilizes a TaqMan system.

The association analysis is typically achieved by comparing the gene frequency of each of the SNP markers between the case group and the control group, and carrying out a $\chi^2$ test on whether the difference in the frequency is statistically meaningful or not (see, University of Tokyo, College of Arts and Sciences, Department of Social Sciences, Statistics Section, Edited, "Tokeigaku Nyumon—Kisotokeigaku I (Introduction to Statistics—Fundamental Statistics I)", University of Tokyo Press, 1991). However, the association analysis may also be carried out based on the genotype frequency for each SNP marker, the genotype frequency in the case of employing a dominant (or recessive) model, the frequency of allele in terms of positive ratio, and the like. Furthermore, in addition to the $\chi^2$ test, the association analysis can be carried out by any other well-known statistical processing, as long as it is possible to compare the case group and the control group, that is, to test the relations between a phenotype that can be divided into plural groups, such as a trait, a disease, and a genetic polymorphism.

Meanwhile, in order to evaluate the typing error of a genotype, and the validity of sampling, a Hardy-Weinberg equilibrium test is carried out. Hardy-Weinberg equilibrium is well known in the field of genome statistics, and in which two alleles (for example, C and T) exists as in an SNP or the like, and the respective frequencies in a group are represented by p and q (p+q=1), the genotype frequencies of C/C homo, C/T hetero and T/T homo may be represented by $p^2$, $2pq$ and $q^2$, respectively ($p^2+2pq+q^2=1$). When an association analysis is carried out, it is desirable that the Hardy-Weinberg equilibrium is established for the control group. However, the selected SNP marker can be evaluated as valid, as long as the number of alleles, whose genotype frequency is statistically significantly different from Hardy-Weinberg equilibrium, is in a predictable range of the significance level (typically, p=0.01 to 0.05).

According to an embodiment, typing is carried out for the respective samples obtained from a case group and a control group, and a significant difference test is carried out by a $\chi^2$ test by four methods involving the genotype, allele type, dominance model and recessive model. That is, if a certain genetic variation is causative of hair shape change, the difference in the allele frequency or the like between the case and the control can be predicted. In regard to the test, when the association analysis is carried out on a relatively small number of objects, or when the power of test of the significant difference between the objects is increased, the level of significance is set loose. When the number of objects is relatively large, or when the significant difference is strictly determined, the level of significance can be set strict. A SNP which exhibits a significant difference in the gene frequency by a test is identified as a hair shape susceptibility SNP marker.

The step (v) that is subsequently carried out is a step of determining a hair shape susceptibility gene by specifying, in connection with the hair shape susceptibility SNP marker determined as described above, a region where linkage disequilibrium is recognized in an object candidate region and the hair shape susceptibility SNP marker is included (haplotype block), using the HapMap PHASE data of the International HapMap Project Database.

The analysis of haplotype (linkage disequilibrium analysis) is a method well known to those having ordinary skill in the art, and can be carried out by various linkage disequilibrium analyses that are conventionally carried out (for example, Kamatani, Naoyuki, Edited., "Post-Genome Jidai no Iden Tokeigaku (Genetic Statistics in Post-Genomic Era)", p. 183-201, Yodosha Co., Ltd., 2002). The haplotype analysis can be carried out using various genetic statistics software programs that are commercially available or made public (for example, Haploview, Arlequin, SNP disease-associated analysis software, SNPalyze (registered trademark) (manufactured by Dynacom Co., Ltd.), and the like). More specifically, the linkage disequilibrium coefficient D' (pair-wise LD coefficient) is calculated and an analysis is carried out, through a linkage disequilibrium analysis based on the EM algorithm (Laird, N.: "The EM Algorithm", Chap. 14, pp. 509-520, Handbook of Statistics, Vol. 9, Computational Statistics, C. R. Rao (ed.), Elsevier Science Publishers B.V., 1993). More specifically, in the haplotype analysis, it is analyzed whether linkage disequilibrium exists between the hair shape susceptibility SNP marker specified above and another SNP marker, and the region where linkage disequilibrium exists is identified as the haplotype block. The other SNP marker used in the linkage disequilibrium analysis can be freely selected among the SNPs existing in the upstream and the downstream of the genome sequence with respect to the hair shape susceptibility SNP marker. For example, the linkage disequilibrium analysis may be sequentially carried out for the SNPs present from proximal positions to distal positions of the hair shape susceptibility SNP marker, or the linkage disequilibrium analysis may be carried out for arbitrarily selected SNPs at distal positions to determine an approximate haplotype block region, and then be carried out for SNPs at more proximal positions to determine a more specific haplotype block region. The number of the other SNP markers used in the linkage disequilibrium analysis is 4 SNPs or more including the hair shape susceptibility SNP marker, preferably 20 SNPs or more, and even more preferably 32 SNPs or more, and the analysis is carried out for a series of SNP marker groups including these plural SNP markers. Here, the linkage disequilibrium coefficient D' is obtained from the following equation when, in two SNPs, the respective alleles of a first SNP are designated as (A, a), the respective alleles of a second SNP are designated as (B, b), and the respective frequencies of four haplotypes (AB, Ab, aB, ab) are designated as $P_{AB}$, $P_{Ab}$, $P_{aB}$, and $P_{ab}$. Furthermore, Min $[(P_{AB}+P_{aB})(P_{aB}+P_{ab}), (P_{AB}+P_{Ab})(P_{Ab}+P_{ab})]$ in the equation means that the smaller value between the values of $(P_{AB}+P_{aB})$ $(P_{aB}+P_{ab})$ and $(P_{AB}+P_{Ab})(P_{Ab}+P_{ab})$ is taken.

$$D'=(P_{AB}P_{ab}-P_{Ab}P_{aB})/\text{Min}[(P_{AB}+P_{aB})(P_{aB}+P_{ab}), (P_{AB}+P_{Ab})(P_{Ab}+P_{ab})]$$

The number of markers in the SNP marker group may appropriately vary with the size of the region forming the haplotype block related to the hair shape susceptibility gene to be identified (linkage disequilibrium block). Furthermore, when a discontinuity of block can be predicted in advance, it is also possible to carry out the analysis on about 6 SNPs located over the blocks. Furthermore, it is also acceptable to carry out a linkage disequilibrium analysis for a hair shape susceptibility SNP marker and 5 SNPs each existing on both sides of the hair shape susceptibility SNP marker 11 SNPs in total. If necessary, the number of markers to be analyzed may be increased.

As the linkage disequilibrium analysis is carried out, a region where SNPs are linked within an object candidate region (a haplotype block including the group of SNP markers among which strong linkage disequilibrium is recognized) is determined. For example, the linkage disequilibrium coefficient D' is calculated for all combinations between 2 SNPs for the selected SNP markers, combinations showing the relation: D'>0.9 are selected, and a series of regions including a region sandwiched between the remotest SNPs among them are detected. Subsequently, D' is calculated between three consecutive SNPs that are adjacent to the region in the outside of the detected region, and the SNPs in the region. Even among any combinations thus calculated, when it is verified that D' is 0.9 or less, the region is specified as a "haplotype block."

When a haplotype block is determined in this manner, for example, in connection with that region, genes present in the haplotype block under attention can be determined using a database associated with the genome, or the like. Furthermore, even in the case of not using a database, the base sequence in the vicinity of SNP markers present in the haplotype block region are determined by ordinary methods, and genes can also be determined from the base sequence.

The step (vi) is a step of determining, for the haplotype extracted from the haplotype block specified in the step (v), a SNP locus that is linked to the locus of the hair shape susceptibility SNP marker identified in the step (iv) using the HapMap PHASE data of the International HapMap Project Database, and additionally identifying the SNP thus-determined as an additional hair shape susceptibility SNP marker.

In the step (v), it is possible to extract all haplotypes consisting of the respective nucleotides of the SNP marker group used in the haplotype analysis, while simultaneously determining the haplotype block, and to thereby determine the frequency of the haplotype or the like.

When the combinations of the respective nucleotides of the extracted haplotype, that is, the SNP marker group, are compared, a SNP locus that is linked to the locus of the hair shape susceptibility SNP marker identified in the step (iv) can be identified, and the SNP locus thus identified can be designated as an additional hair shape susceptibility SNP marker.

Through the steps (i) to (vi), a chromosome region where linkage with curly hair is recognized is determined, and then a hair shape susceptibility SNP marker is selected from the chromosome region. Furthermore, through a haplotype analysis of the selected SNP marker, a haplotype block and gene in the chromosome region that are related to hair shape are identified. Thereafter, a SNP locus that is linked to the locus of the hair shape susceptibility SNP marker is further determined, and thereby, a hair shape susceptibility SNP marker that is present in the haplotype block or gene can be identified.

Examples of the chromosome region where linkage to curly hair is recognized, which is determined in the steps described above, include chromosome 1 and chromosome 11, more specifically the 1q32.1 to 1q32.2 region of chromosome 1 (a region sandwiched between microsatellites D1S249 and D1S2891) (maximum LOD score=2.14). These regions are determined as curly hair trait loci, and it is strongly suggested that hair shape susceptibility genes exist in these regions.

Examples of the haplotype block specified by the steps described above include, among the genomic regions of human chromosome 1, a 3,926-bp region represented by the base sequence set forth in SEQ ID NO:1, a 76,945-bp region represented by the base sequence set forth in SEQ ID NO:2, and a 68,637-bp region represented by the base sequence set forth in SEQ ID NO:3.

A gene which overlaps with such a haplotype block, and contains a portion or the entirety of the base sequence of the haplotype block, is identified as a hair shape susceptibility gene. Here, the "gene which overlaps with the haplotype block" means both a gene which has the same base sequence as that of a partial region of the haplotype block, and a gene which has the same base sequence as the base sequence of the entire region of the haplotype block. Further, a single nucleotide polymorphism (SNP) which exists in such a haplotype block, and whose allele frequency is statistically significantly different between a group having a curly hair trait and a group having a non-curly hair trait, and an SNP that is linked to the SNP, are identified as hair shape susceptibility SNP markers.

An example of the gene which overlaps with the 3,926-bp haplotype block represented by the base sequence set forth in SEQ ID NO:1, may be CSRP1 gene on human chromosome 1. CSRP1 is a gene represented by GeneID:1465 in the Entrez Gene Database (http://www.ncbi.nlm.nih.gov/gene), and as illustrated in Example 5 and FIG. 5, a portion of the base sequence overlaps with the haplotype block described above.

Examples of the hair shape susceptibility SNP marker present in the base sequence set forth in SEQ ID NO:1 include nucleotides represented by Nucleotide Numbers 1 (dbSNP Database ID:rs576697, T or C), 1635 (rs645390, G or A), 2527 (rs3767542, G or A), and 3766 (rs675508, C or A). A preferred example is a nucleotide represented by Nucleotide Number 1 (rs576697, T or C).

Examples of the gene which overlaps with the 76,945-bp haplotype block represented by the base sequence set forth in SEQ ID NO:2 include NAV1 gene, IPO9 gene, and TMEM58 gene on human chromosome 1. NAV1 gene is a gene represented by GeneID:89796 in the Entrez Gene Database, and as illustrated in Example 5 and FIG. 6, a portion of the base sequence overlaps with the haplotype block described above. Further, IPO9 gene is a gene represented by GeneID:55705 in the Entrez Gene Database, and as illustrated in Example 5 and FIG. 6, the entire length of the base sequence overlaps with the haplotype block described above. TMEM58 gene is a gene represented by GeneID:149345 in the Entrez Gene Database, and as illustrated in Example 5 and FIG. 6, a portion of the base sequence overlaps with the haplotype block described above.

Examples of the hair shape susceptibility SNP marker present in the base sequence set forth in SEQ ID NO:2 include nucleotides represented b Nucleotide Numbers 7519 (rs2271763, G or A), 16901 (rs10920260, T or G), 30270 (rs16849387, A or G), 31333 (rs12127375, C or G), 50038 (rs1495840, T or A), and 63008 (rs10920269, G or T). A preferred example may be a nucleotide represented by Nucleotide Number 50038 (rs1495840, T or A).

Examples of the gene which overlaps with the 68,637-bp haplotype block represented by the base sequence set forth in SEQ ID NO:3 include NUCKS1 gene on human chromosome 1. NUCKS1 gene is a gene represented by GeneID: 64710 in the Entrez Gene Database, and as illustrated in Example 5 and FIG. 7, the entire length of the base sequence overlaps with the haplotype block described above.

Examples of the hair shape susceptibility SNP marker present in the base sequence set forth in SEQ ID NO:3 include nucleotides represented by Nucleotide Numbers 24524 (rs3805, T or G), and 60701 (rs823114, G or A). Preferred examples include a nucleotide represented by Nucleotide Number 60701 (rs823114, G or A).

3. HAIR SHAPE DETERMINING MARKER

The present invention also provides a hair shape determining marker in the 1q32.1 to 1q32.2 region (D1S249 to D1S2891) of human chromosome 1, which is an oligo- or polynucleotide, or a complementary strand thereof, wherein the oligo- or polynucleotide contains a partial base sequence of the base sequence of a haplotype block that is determined by a linkage disequilibrium analysis for a SNP marker whose allele frequency is statistically significantly different between a group having a curly hair trait and a group having a non-curly hair trait and consists of a base sequence set forth in any one of SEQ ID NO:1 to NO:3, and wherein the partial base sequence consists of a contiguous base sequence containing one or more single nucleotide polymorphisms (SNPs) wherein the SNPs include an SNP whose allele frequency is statistically significantly different between a group having a curly hair trait and a group having a non-curly hair trait, and an SNP linked to the SNP.

The oligo- or polynucleotides, or complementary strands thereof, defined by these base sequences contain one or more a hair shape susceptibility SNP marker that is a single nucleotide polymorphism (SNP) which is present in a haplotype block, represented by a base sequence set forth in any one of SEQ ID NO:1 to NO:3, and whose allele frequency is statistically significantly different between a group having a curly hair trait and a group having a non-curly hair trait, or an SNP linked to the SNP. When these oligo- or polynucleotides, or complementary strands thereof, are detected, the genetic predisposition of hair shape in a test subject can be examined and/or determined. Therefore, these oligo- or polynucleotides, or complementary strand thereof can be defined and used as markers for determining the genetic predisposition of hair shape possessed by an individual.

The length (nucleotide length) of these oligo- or polynucleotides, or complementary strands, is desirably a length which is specifically recognized in human genome, and there are no particular limitations on the limit. The length is usually equal to or more than 10-mers and equal to or fewer than 1000-mers, preferably equal to or more than 20-mers and equal to or fewer than 500-mers, and more preferably equal to or more than 20-mers and equal to or fewer than 100-mers. Therefore, if necessary, the length can be set to, for example, 11 nucleotides containing a hair shape susceptibility SNP marker present in a haplotype block represented by a base sequence set forth in SEQ ID NO:1 to NO:3 (preferably including 5 nucleotides each on the 5' side and the 3' side of the hair shape susceptibility SNP marker), 21 nucleotides (preferably including 10 nucleotides each on the 5' side and the 3' side of the hair shape susceptibility SNP marker), 101 nucleotides (preferably including 50 nucleotides each on the 5' side and the 3' side of the hair shape susceptibility SNP marker), 601 nucleotides (preferably including 300 nucleotides each on the 5' side and the 3' side of the hair shape susceptibility SNP marker), or the like.

Examples of the hair shape susceptibility SNP marker used in the present invention, which should be included in the hair shape determining marker of the present invention, include the following:

(1) nucleotides represented by Nucleotide Numbers 1 (dbSNP Database ID:rs576697, T or C), 1635 (rs645390, G or A), 2527 (rs3767542, G or A), and 3766 (rs675508, C or A) in the base sequence set forth in SEQ ID NO:1;

(2) nucleotides represented by Nucleotide Numbers 7519 (rs2271763, G or A), 16901 (rs10920260, T or G), 30270 (rs16849387, A or G), 31333 (rs12127375, C or G), 50038 (rs1495840, T or A), and 63008 (rs10920269, G or T) in the base sequence set forth in SEQ ID NO:2; and (3) nucleotides represented by Nucleotide Numbers 24524 (rs3805, T or G), and 60701 (rs823114, G or A) in the base sequence set forth in SEQ ID NO:3.

Among the nucleotides described above, the nucleotide represented by Nucleotide Number 1 (rs576697, T or C) in the base sequence set forth in SEQ ID NO:1, the nucleotide represented by Nucleotide Number 50038 (rs1495840, T or A) in the base sequence set forth in SEQ ID NO:2, and the nucleotide represented by Nucleotide Number 60701 (rs823114, G or A) in the base sequence set forth in SEQ ID NO:3 are preferred.

It is desirable that the hair shape susceptibility SNP marker be located at the center or near the center of the hair shape determining marker of the present invention (for example, within 100 nucleotides, preferably 50 nucleotides, more preferably 30 nucleotides, even more preferably 10 nucleotides, and still more preferably 5 nucleotides, from the center), but it is not necessarily required. Furthermore, when two or more hair shape susceptibility SNP markers are included in the hair shape determining marker of the present invention, all of the hair shape susceptibility SNP markers may be located at the center or near the center of the hair shape determining marker of the present invention; one of the hair shape susceptibility SNP markers is located at the center or near the center, while the others may be located at any positions; or all of the hair shape susceptibility SNP markers may not be located at the center or near the center.

Specific examples of the hair shape determining marker of the invention in which the hair shape susceptibility SNP marker is located at the center include, for example, in the case where a SNP is contained in the nucleotide represented by Nucleotide Number 1 (dbSNP Database ID:rs576697, T or C) in the base sequence set forth in SEQ ID NO:1, a 11-mer polynucleotide consisting of from 5 nucleotides upstream of SEQ ID NO:1 to Nucleotide Number 6, a 21-mer polynucleotide consisting of from 10 nucleotides upstream of SEQ ID NO:1 to Nucleotide Number 11, a 101-mer polynucleotide consisting of from 50 nucleotides upstream of SEQ ID NO: 1 to Nucleotide Number 51, and a 601-mer polynucleotide having a base sequence consisting of from 300 nucleotides upstream of SEQ ID NO:1 to Nucleotide Number 11. Furthermore, complementary strands of these can also be used. In the same manner, the base sequences of markers containing other SNPs are also determined.

4. METHOD FOR DETERMINING GENETIC SUSCEPTIBILITY TO HAIR SHAPE

The present invention also provides a method for determining the genetic susceptibility (genetic predisposition) of a test subject to hair shape. The method for determining the genetic susceptibility to hair shape of the present invention includes the following steps (a) and (b), and there are no particular limitations on the limit:

(a) a step of preparing a genomic DNA derived from a test subject; and (b) a step of detecting, from the genomic DNA, a single nucleotide polymorphism (SNP) whose allele frequency is statistically significantly different between a group having a curly hair trait and a group having a non-curly hair trait, and being present in a haplotype block in the 1q32.1 to 1q32.2 region (D1S249 to D1S2891) of human chromosome 1 that is determined by a linkage disequilibrium analysis on a single nucleotide polymorphism (SNP) marker whose allele frequency is statistically significantly different between a group having a curly hair trait and a group having a non-curly hair trait, and that consists of a base sequence set forth in any one of SEQ ID NO:1 to NO:3, and a single nucleotide polymorphism (SNP) linked to the SNP.

The step (a) (extraction of a genomic DNA) and the step (b) (detection of SNPs) can be carried out using a known method (for example, Birren Bruce et al., Genome Analysis, Vol. 4/A Laboratory Manual Mapping Genomes, Cold Spring Harbor Laboratory, NY, 1999).

In the step (a), the genomic DNA derived from a test subject can be obtained from a material such as all cells (including cultured cells; however, reproductive cells are excluded), tissues (including cultured tissues), organs, or body fluids (for example, blood, saliva, lymph fluid, respiratory tract mucosa, semen, sweat, urine, and the like), which have been isolated from the test subject, clinical specimens therefrom, and the like. The material is preferably leukocytes or monocytes separated from peripheral blood, and is more suitably leukocytes. These materials can be isolated according to those methods usually used in clinical tests.

For example, in the case of using leukocytes as the material, first, leukocytes are separated from the peripheral blood isolated from a test subject, according to an ordinary method. Subsequently, Proteinase K and sodium dodecyl sulfate (SDS) are added to the leukocytes thus obtained to degrade and denature proteins, and then phenol/chloroform extraction is carried out to thereby obtain genomic DNA (including RNA). The RNA can be eliminated with an RNase as necessary. Meanwhile, the extraction of genomic DNA is not limited to the method described above, and can be carried out using a method well-known in the art (for example, Joseph Sambrook et al., Molecular Cloning: A Laboratory Manual (3 Vol. set), Cold Spring Harbor Laboratory, NY, 2001) or using a commercially available DNA extraction kit or the like. Furthermore, if necessary, the DNA containing the 1q32.1 to 1q32.2 region of human chromosome 1, or a DNA containing a haplotype block represented by a base sequence set forth in any one of SEQ ID NO:1 to NO:3 in the genomic region of human chromosome 1, may be isolated. The isolation of the DNA can be carried out by PCR using a primer which hybridizes with the 1q32.1 to 1q.32.2 region or with the corresponding haplotype block and using the genomic DNA as a template, or the like.

In the step (b), detected from the genomic DNA obtained in the step (a) is an SNP which is a polymorphism present in a haplotype block in the 1q32.1 to 1q32.2 region (D1S249 to D1S2891) of human chromosome 1 that is determined by a linkage disequilibrium analysis on a single nucleotide polymorphism (SNP) marker whose allele frequency is statistically different between a group having a curly hair trait and a group having a non-curly hair trait, and the allele frequency of which SNP is higher in any curly hair people group than in any non-curly hair people group, or a SNP that is linked to the SNP. The base sequences set forth in SEQ ID NO:1 to NO:3 include the 3,926-bp base sequence set forth in SEQ ID NO:1, the 76,945-bp base sequence set forth in SEQ ID NO:2, and the 68,637-bp base sequence set forth in SEQ ID NO: 3, in the genomic region of human chromosome 1.

The method for determination of the present invention preferably further includes the following step (c):

(c) a step of determining, if the allele frequency of the detected SNP is statistically significantly higher in the curly hair people group than in the non-curly hair people group, that the test subject has a genetic predisposition to curly hair, and if the allele frequency of the detected SNP is statistically significantly higher in any non-curly hair people group than in the curly hair people group, that the test subject does not have a genetic predisposition to curly hair.

An example of the step (c) may be a step of identifying, for any one or more nucleotides of the nucleotide numbers as indicated in the following table that are present in the base sequences set forth in SEQ ID NO:1 to NO:3 in the genomic DNA derived from a test subject, whether the nucleotide is nucleotide (i) or nucleotide (ii); and determining, when the nucleotide is nucleotide (i), that the test subject has a predisposition to curly hair, and when the nucleotide is nucleotide (ii), that the test subject does not have a predisposition to curly hair.

TABLE 3

| SEQ ID NO. | Nucleotide Number | Nucleotide (i) (having predisposition) | Nucleotide (ii) (No predisposition) |
|---|---|---|---|
| 1 | 1 | C | T |
|   | 1635 | A | G |
|   | 2527 | A | G |
|   | 3766 | A | C |
| 2 | 7519 | A | G |
|   | 16901 | G | T |
|   | 30270 | G | A |
|   | 31333 | G | C |
|   | 50038 | A | T |
|   | 63008 | T | G |
| 3 | 24524 | G | T |
|   | 60701 | A | G |

More specifically, the method of the present invention for determining genetic susceptibility of a test subject to hair shape includes any one step of the following (1) to (12).

(1) In the base sequence set forth in SEQ ID NO:1, it is identified whether the nucleotide represented by Nucleotide Number 1 is T or C, and it is determined, when the nucleotide is C, that the test subject has a predisposition to curly hair, or when the nucleotide is T, the test subject does not have a predisposition to curly hair;

(2) in the base sequence set forth in SEQ ID NO:1, it is identified whether the nucleotide represented by Nucleotide Number 1635 is G or A, and it is determined, when the nucleotide is A, that the test subject has a predisposition to curly hair, or when the nucleotide is G, the test subject does not have a predisposition to curly hair;

(3) in the base sequence set forth in SEQ ID NO:1, it is identified whether the nucleotide represented by Nucleotide Number 2527 is G or A, and it is determined, when the nucleotide is A, that the test subject has a predisposition to curly hair, or when the nucleotide is G, the test subject does not have a predisposition to curly hair;

(4) in the base sequence set forth in SEQ ID NO:1, it is identified whether the nucleotide represented by Nucleotide Number 3766 is C or A, and it is determined, when the nucleotide is A, that the test subject has a predisposition to curly hair, or when the nucleotide is C, the test subject does not have a predisposition to curly hair;

(5) in the base sequence set forth in SEQ ID NO:2, it is identified whether the nucleotide represented by Nucleotide Number 7519 is G or A, and it is determined, when the nucleotide is A, that the test subject has a predisposition to curly hair, or when the nucleotide is G, the test subject does not have a predisposition to curly hair;

(6) in the base sequence set forth in SEQ ID NO:2, it is identified whether the nucleotide represented by Nucleotide Number 16901 is T or G, and it is determined, when the nucleotide is G, that the test subject has a predisposition to curly hair, or when the nucleotide is T, the test subject does not have a predisposition to curly hair;

(7) in the base sequence set forth in SEQ ID NO:2, it is identified whether the nucleotide represented by Nucleotide Number 30270 is A or G, and it is determined, when the nucleotide is G, that the test subject has a predisposition to curly hair, or when the nucleotide is A, the test subject does not have a predisposition to curly hair;

(8) in the base sequence set forth in SEQ ID NO:2, it is identified whether the nucleotide represented by Nucleotide Number 31333 is C or G, and it is determined, when the nucleotide is G, that the test subject has a predisposition to curly hair, or when the nucleotide is C, the test subject does not have a predisposition to curly hair;

(9) in the base sequence set forth in SEQ ID NO:2, it is identified whether the nucleotide represented by Nucleotide Number 50038 is T or A, and it is determined, when the nucleotide is A, that the test subject has a predisposition to curly hair, or when the nucleotide is T, the test subject does not have a predisposition to curly hair;

(10) in the base sequence set forth in SEQ ID NO:2, it is identified whether the nucleotide represented by Nucleotide Number 63008 is G or T, and it is determined, when the nucleotide is T, that the test subject has a predisposition to curly hair, or when the nucleotide is G, the test subject does not have a predisposition to curly hair;

(11) in the base sequence set forth in SEQ ID NO:3, it is identified whether the nucleotide represented by Nucleotide Number 24524 is T or G, and it is determined, when the nucleotide is G, that the test subject has a predisposition to curly hair, or when the nucleotide is T, the test subject does not have a predisposition to curly hair;

(12) in the base sequence set forth in SEQ ID NO:3, it is identified whether the nucleotide represented by Nucleotide Number 60701 is G or A, and it is determined, when the nucleotide is A, that the test subject has a predisposition to curly hair, or when the nucleotide is G, the test subject does not have a predisposition to curly hair.

In addition, the SNP detected in the method of the present invention for determining the genetic susceptibility (genetic predisposition) to hair shape may be any one of the SNPs described above, or may be two or more thereof. Preferably, two or more SNPs are detected, and thereby, the type or the presence or absence of the genetic predisposition of the test subject to the hair shape, which is a general polygenic trait, can be made clear, while a gene which serves as a main factor determining the hair shape of the test subject can be retrieved with higher accuracy.

The detection of the SNPs can be carried out by directly determining the base sequence of the 1q32.1 to 1q32.2 region of human chromosome 1 further isolated from a sample containing the genomic DNA, or the base sequence of the haplotype block represented by the base sequences set forth in SEQ ID NO:1 to NO:3 in the genomic regions of human chromosome 1. Alternatively, as a method for detecting a polymorphism, in addition to the method of directly determining the gene sequence of the region as described above, there are available a method of determining, when the polymorphism sequence is a restriction enzyme recognition site, the genotype by using the difference in the restriction enzyme cleavage pattern (hereinafter, called RFLP); and methods based on hybridization using a polymorphism-specific probe (for example, a method of determining the type of polymorphism by attaching particular probes on a chip, a glass slide or a nylon film and detecting the difference in the intensity of hybridization with respect to those probes, or a method of determining the genotype by detecting the efficiency of hybridization of a specific probe as the amount of the probe decomposed by a polymerase during amplification of the two strands of a template; a method of detecting the temperature difference in the fusion of two strands by tracing the temperature change of fluorescence emitted by a certain type of two-stranded specific fluorescent dye, and thereby determining the polymorphism; a method of attaching complementary sequences to the two ends of a polymorphic site-specific oligo-probe, and determining the genotype by utilizing the difference between the case where the probe makes a secondary structure within the molecules of the probe itself due to temperature, and the case where the probe hybridizes with the target region; and the like). Further examples include methods of carrying out a nucleotide extension reaction by a polymerase from a template-specific primer, and determining a nucleotide that is accepted to the polymorphic site at that time (a method of using dideoxynucleotides, including fluorescently labeling each of them and detecting the fluorescence of each, and a method of detecting the accepted dideoxynucleotides by mass spectrometry); a method of recognizing the presence or absence of a complementary base pair or a non-complementary base pair at a mutation site by means of an enzyme, subsequent to a template-specific primer, and the like.

Now, conventionally well-known, representative methods for detecting genetic polymorphisms will be listed below, but the present invention is not at all intended to be limited to these: (a) a RFLP (restriction enzyme-cleaved fragment length polymorphism) method; (b) a PCR-SSCP method (analysis of single-stranded DNA higher structure polymorphism, Biotechniques, 16, p. 296-297, 1994, and Biotechniques, 21, p. 510 to 514, 1996); (c) an ASO hybridization method (Clin. Chim. Acta., 189, p. 153-157, 1990); (d) a direct sequencing method (Biotechniques, 11, p. 246-249, 1991); (e) an ARMS method (Nuc. Acids Res., 19, p. 3561-3567, 1991, and Nuc. Acids Res., 20, p. 4831-4837, 1992); (f) a denaturant concentration gradient gel electrophoresis (DGGE) method (Biotechniques, 27, p. 1016-1018, 1999); (g) an RNaseA cleavage method (DNA Cell Biol., 14, p. 87-94, 1995); (h) a chemical cleavage method (Biotechniques, 21, p. 216-218, 1996); (i) a DOL method (Genome Res., 8, p. 549-556, 1998); (j) a TaqMan-PCR method (Genet. Anal., 14, p. 143-149, 1999, and J. Clin. Microbiol., 34, p. 2933-2936, 1996); (k) an invader method (Science, 5109, p. 778-783, 1993, J. Bio. Chem., 30, p. 21387-21394, 1999, and Nat. Biotechnol., 17, p. 292-296, 1999); (l) a MALDI-TOF/MS method (Genome Res., 7, p. 378-388, 1997, and Eur. J. Clin. Chem. Clin. Biochem., 35, p. 545-548, 1997); (m) a TDI method (Proc. Natl. Acad. Sci. USA, 94, p. 10756-10761, 1997); (n) a molecular beacon method (Nat. Biotechnol., 16, p. 49-53, 1998); (O) a dynamic allele specific hybridization (DASH) method (Nat. Biotechnol., 17, p. 87-88, 1999); (p) a padlock probe method (Nat. Genet., 3, p. 225-232, 1998); (q) a DNA chip or DNA microarray (Nakamura, Yusuke, et al., "SNP Idenshi Takei no Senryaku (Strategy for SNP Gene Polymorphism)", Nakayama Shoten Co., Ltd., p. 128-135, 2000); and (r) an ECA method (Anal. Chem., 72, p. 1334-1341, 2000).

Those described above are representative methods for gene polymorphism detection; however, the method of the present invention for determining the genetic susceptibility (genetic predisposition) to hair shape is not limited to these, and any other gene polymorphism detection methods that are already known or will be developed in the future can be broadly used. Furthermore, in regard to the gene polymorphism detection of the present invention, these methods for gene polymorphism detection may be used singly, or two or more methods can also be used in combination. Hereinafter, as representative methods, the TaqMan-PCR method and the invader method that are used in the Examples described below will be explained in more detail.

(1) TaqMan-PCR Method

The TaqMan-PCR method is a method of using a fluorescent-labeled, allele-specific oligonucleotide (TaqMan probe), and PCR by a Taq DNA polymerase. As the TaqMan probe, an oligonucleotide containing a contiguous base sequence of about 15 to about 30 nucleotides, which is a partial base sequence of a haplotype block represented by any one of SEQ ID NO:1 to NO:3 in the genomic region of human chromosome 1, and contains several polymorphic sites described above (for example, a nucleic acid probe contained in the reagent for hair shape determination of the present invention that will be described below), is used. The probe is labeled with a fluorescent dye such as FAM or VIC at the 5'-terminal, and with a quencher (quenching substance) such as TAMRA at the 3'-terminal, respectively, and in the state as received, since the quencher absorbs the fluorescent energy, fluorescence is not detected. It is preferable to produce probes for both alleles, and to label the probes with fluorescent dyes having different fluorescence wavelengths for batch detection (for example, FAM for one allele and VIC for the other). Furthermore, the 3'-terminal is phosphorylated so that a PCR extension reaction from the TaqMan probe does not occur. When a PCR is carried out using a primer which is designed to amplify a partial sequence of the genomic DNA containing a region that hybridizes with the TaqMan probe, as well as a TaqDNA polymerase, the TaqMan probe hybridizes with the template DNA, and at the same time, an extension reaction from the PCR primer occurs. However, when the extension reaction proceeds, the hybridized TaqMan probe is cleaved due to the 5' nuclease activation of the Taq DNA polymerase, and the fluorescent dye is released and is no longer affected by the quencher, so that fluorescence is detected. With the amplification of the template, the fluorescence intensity increases exponentially. For example, in the detection of a polymorphism in the nucleotide represented by Nucleotide Number 1 (rs576697, T or C) in the base sequence set forth in SEQ ID NO:1, when an allele-specific oligonucleotide containing the nucleotide (having a length of about 15 to about 30-mers; the C allele is labeled with FAM, and the T allele is labeled with VIC, respectively, at the 5'-terminals, and the 3'-terminals are both labeled with TAMRA) is used as the TaqMan probe, if the genotype of the test subject is CC or TT, high fluorescence intensity of FAM or VIC is recognized in the respective cases, while the other fluorescence is almost unrecognizable. On the other hand, if the genotype of the test subject is CT, fluorescence of both FAM and VIC is detected.

(2) Invader Method

In the invader method, unlike the TaqMan-PCR method, the allele-specific oligonucleotide (allele probe) itself is not labeled, and the oligonucleotide has a sequence having no complementarity to the template DNA on the 5' side of the nucleotides at the polymorphic site (flap) and has a complementary sequence specific to the template on the 3' side. In the invader method, use is made of an oligonucleotide having a complementary sequence specific to the 3' side of the polymorphic site of the template (invader probe; the nucleotides corresponding to the polymorphic site, which is the 5'-terminal of the probe, are arbitrary), and a FRET (Fluorescence Resonance Energy Transfer) probe characterized in that the 5' side has a sequence capable of adopting a hairpin structure, and the sequence contiguous from the nucleotides forming pairs with the nucleotides of the 5'-terminal to the 3' side when a hairpin structure is formed, is a sequence complementary to the flap of the allele probe. The 5'-terminal of the FRET probe is fluorescent labeled (for example, FAM, VIC, or the like), and a quencher (for example, TAMRA, or the like) is bonded in the vicinity thereof, so that in the state as received (hairpin structure), fluorescence is not detected. When the template genomic DNA is allowed to react with the allele probe and the invader probe, upon the complementary binding of the three entities, the 3'-terminal of the invader probe penetrates into the polymorphic site. When the single-stranded portion of the allele probe (that is, the flap portion on the 5' side from the nucleotides of the polymorphic site) is cut using an enzyme which recognizes the structure of this polymorphic site (Cleavase), the flap complementarily binds with the FRET probe, and the polymorphic site of the flap penetrates into the hairpin structure of the FRET probe. When Cleavase recognizes and cleaves this structure, the fluorescent dye used to label the terminal of the FRET probe is released and is no longer affected by the quencher, and thus fluorescence is detected. An allele probe whose nucleotides of the polymorphic site do not match with the template is not cleaved by Cleavase, since an allele probe which is not cleaved can also hybridize with the FRET probe, fluorescence is similarly detected. However, because the reaction efficiency is different, in the allele probe whose nucleotides of the polymorphic site match the template, the fluorescence intensity is markedly stronger than that of the allele probe which does not match. Usually, it is preferable to have the template DNA amplified by PCR using a primer capable of amplifying the region containing the portions where the allele probe and the invader probe hybridize, before the template DNA is allowed to react with the three kinds of probes and Cleavase.

The hair shape of a person can be freely changed by a permanent treatment, a styling agent treatment, brushing or the like, and also can change in an acquired manner, through changes in aging, metabolism, and the like. For this reason, it is difficult to correctly determine or classify the intrinsic natural hair shape of a person based only on the phenotype. Furthermore, since the hair shape can be considered as a general trait of complicated polygenicity, it can be speculated that for individual persons, the gene which serves as a main causative factor for determining the hair shape among the hair shape susceptibility genes of the present invention described above, may vary in different individuals. Therefore, when the genetic predisposition to hair shape is examined and/or determined, a method for regulating the hair shape appropriate for the individuals can be provided.

Furthermore, according to the method, the susceptibility to an acquired change in the hair shape of a test subject, that is, the risk of hair shape change, can be determined. The risk of hair shape change can be mechanically determined using the polymorphisms described above as the reference (index), without requiring the judgment of a person having expertise such as a doctor. Accordingly, the method of the present invention can also be used as a method for detecting the risk of hair shape change.

Through the method of the present invention for determining the genetic susceptibility (genetic predisposition) of a test subject to hair shape, the type or the presence or absence of the genetic predisposition of the test subject to hair shape, which is a general polygenic trait, can be made clear, and a gene which serves as the main causative factor that determines the hair shape of the test subject can be searched among the hair shape susceptibility genes of the present invention. Furthermore, appropriate measures for promoting the regulation of hair shape in the test subject can be devised based on the results of the search. Therefore, the present invention is extremely useful as a method for the examination and/or determination for the fundamental regulation of hair shape.

5. REAGENT FOR DETERMINATION OF GENETIC SUSCEPTIBILITY (GENETIC PREDISPOSITION) TO HAIR SHAPE AND KIT INCLUDING THE REAGENT

The present invention also provides a reagent to be used in the determination method of the present invention, and a kit including the reagent. That is, the reagent for determination of the invention and the kit including the reagent include a nucleic acid probe and/or a primer capable of detecting one or more SNPs selected from the group consisting of an SNP in the 1q32.1 to 1q32.2 region (D1S249 to D1S2891) of human chromosome 1, which is determined by a linkage disequilibrium analysis on a single polynucleotide polymorphism (SNP) marker whose allele frequency is statistically significantly different between a group having a curly hair trait and a group having a non-curly hair trait, and is present in a haplotype block having a 3,926-bp base sequence set forth in SEQ ID NO: 1, a 76,945-bp base sequence set forth in SEQ ID NO:2, or a 68,637-bp base sequence set forth in SEQ ID NO:3, and which has a higher allele frequency in an arbitrary curly hair people group than in an arbitrary non-curly hair people group, and an SNP linked to the SNP.

According to an embodiment, the nucleic acid probe used in the reagent for determination of the present invention and the kit including the reagent, is a nucleic acid which specifically hybridizes with the region of a genomic DNA containing the nucleotides of the SNP site to be detected in the method for examination and/or determination of the present invention, and is, for example, a probe which specifically hybridizes with the hair shape determining marker sequence of the present invention. The nucleic acid probe is not particularly limited in the length (length of nucleotides in the portion that hybridizes with the genomic DNA), as long as the nucleic acid probe is specific to a target site to be hybridized and can easily detect polymorphisms. For example, the length is about 10 nucleotides or more, preferably about 15 nucleotides or more, more preferably about 15 to about 600 nucleotides, even more preferably about 15 to about 200 nucleotides, and still more preferably about 15 to about 50 nucleotides. Meanwhile, the phrase "specifically hybridizes with a target site (sequence)" means that cross-hybridization with another DNA does not occur significantly under standard hybridization conditions, preferably under stringent hybridization conditions (for example, conditions described in Joseph Sambrook et al., Molecular Cloning: A Laboratory Manual (3 Vol. set), Cold Spring Harbor Laboratory, NY, 2001). Suitably, the nucleic acid probe preferably has a base sequence complementary to the base sequence of a region containing nucleotides of the polymorphic site to be detected; however, if such specific hybridization is possible, the nucleic acid probe does not need to be completely complementary.

The nucleic acid probe may contain an additional sequence appropriate for the detection of polymorphism (a sequence which is not complementary to the genomic DNA). For example, the allele probe used in the invader method has an additional sequence called flap, at the 5'-terminal of the nucleotides of the polymorphic site. Furthermore, the probe may also be labeled with an appropriate labeling agent, for example, a radioisotope (for example, $^{125}I$, $^{131}I$, $^{3}H$, and $^{14}C$), an enzyme (for example, β-galactosidase, β-glucosidase, alkali phosphatase, peroxidase, malate dehydrogenase, or the like), a fluorescent substance (for example, fluorescamine, fluorescein isothiocyanate, or the like), or a luminescent substance (for example, luminol, a luminol derivative, luciferin, lucigenin, or the like). Alternatively, the probe may also be further bonded, in the vicinity of a fluorescent substance (for example, FAM, VIC, or the like), with a quencher (quenching substance) which absorbs the fluorescent energy emitted by the fluorescent substance. In such an embodiment, the fluorescent substance and the quencher are separated at the time of the detection reaction, and fluorescence is detected.

The nucleic acid probe can also be used after being immobilized on an arbitrary solid phase. For this reason, the reagent of the present invention and the kit including the reagent can be provided as an immobilized probe in which the probe is immobilized on an arbitrary solid support (for example, a gene chip, a cDNA microarray, an oligo-DNA array, a membrane filter, or the like, on which a probe is immobilized). Suitably, the immobilized probe is provided as a DNA chip for hair shape susceptibility gene detection.

The solid support used in immobilization is not particularly limited as long as nucleic acid can be immobilized thereon, and examples include a glass plate, a nylon membrane, microbeads, a silicon chip, a capillary, other supports, or the like. The immobilization of a nucleic acid on a solid support may be carried out by a method of mounting a previously synthesized nucleic acid on a solid phase, or by a method of synthesizing a target nucleic acid on a solid phase. The immobilization method is, for example, in the case of a DNA microarray, well known in the art according to the type of the immobilization probe, e.g., a commercially available spotter (manufactured by Amersham Biosciences Corp.), or the like (for example, in situ synthesis of oligonucleotides by photolithographic technology (Affymetrix, Inc.) or inkjet technology (Rosetta Inpharmatics, Inc.), and the like).

The nucleic acid primer used in the reagent for determination of the present invention and the kit including the reagent, may be any nucleic acid primer as long as it is designed to be capable of specifically hybridizing with the region of a genomic DNA containing the nucleotides of the SNP site to be detected in the method for examination and/or determination of the present invention, and specifically amplifying the nucleic acid sequence. For example, the primer is a primer which specifically hybridizes with the nucleic acid sequence of the hair shape determining marker of the present invention and amplifies the hair shape determining marker. Here, the phrase "specifically hybridizes with a target site (sequence)" means that cross-hybridization with another DNA does not occur significantly under the standard hybridization conditions, preferably under stringent hybridization conditions (for example, the conditions described in Joseph Sambrook et al., Molecular Cloning: A Laboratory Manual (3 Vol. set), Cold Spring Harbor Laboratory, NY, 2001).

The method for amplifying the nucleic acid sequence using a primer is not particularly limited as long as it is a method ordinarily used in the art. For example, generally, a PCR method is broadly used, but examples include RCA (Rolling Circle Amplification; Proc. Natl. Acad. Sci., Vol. 92, 4641-4645 (1995)), ICAN (Isothermal and Chimeric primer-initiated Amplification of Nucleic acids), LAMP (Loop-Mediated Isothermal Amplification of DNA; Bio Industry, vol. 18, No. 2 (2001)), NASBA (Nucleic acid Sequence-based Amplification method; Nature, 350, 91-(19.91)), TMA (Transcription Mediated Amplification method; J. Clin. Microbiol. Vol. 31, 3270-(1993), and the like). The number and type of the nucleic acid primer required for amplification can vary depending on the amplification method. For example, in the case of using a PCR method, the required primer may be a pair of nucleic acid primers, which is a combination of a nucleic acid containing a base sequence having about 10 to about 50 nucleotides, preferably about 15 to about 50 nucleotides, and more preferably about 15 to about 30 nucleotides, that is a partial base sequence of a haplotype block represented by a base sequence set forth in any one of SEQ ID NO:1 to NO:3 in the genomic region of human chromosome 1, and specifically hybridizes with a portion of the complementary strand sequence on the 5' side relative to the nucleotides of the polymorphic site to be detected, and a nucleic acid containing a base sequence having about 10 to about 50 nucleotides, preferably about 15 to about 50 nucleotides, and more preferably about 15 to about 30 nucleotides, that is the partial base sequence and specifically hybridizes with a portion of the complementary strand sequence on the 3' side relative to the nucleotides of the polymorphic site, the fragment of the nucleic acid to be amplified by the combination of nucleic acids having a length of about 50 to about 1000 nucleotides, preferably about 50 to about 500 nucleotides, and more preferably about 50 to about 200 nucleotides.

The primer may also contain an additional sequence appropriate for the detection of polymorphism (a sequence that is not complementary to the genomic DNA), for example, a linker sequence. Furthermore, the primer may also be labeled with an appropriate labeling agent, for example, a radioisotope (for example, $^{125}$I, $^{131}$I, $^{3}$H, or $^{14}$C), an enzyme (for example, β-galactosidase, β-glucosidase, alkali phosphatase, peroxidase, or malate dehydrogenase), a fluorescent substance (for example, fluorescamine, or fluorescein isothiocyanate), or a luminescent substance (for example, luminol, a luminol derivative, luciferin, or lucigenin).

Preferably, the nucleic acid probe and/or primer used in the reagent for determination of the present invention and the kit including the reagent include the hair shape susceptibility SNP marker of the present invention, that is, the nucleotides shown below:

(1) in the base sequence set forth in SEQ ID NO:1, nucleotides represented by Nucleotide Numbers 1 (dbSNP Database ID:rs576697, T or C), 1635 (rs645390, G or A), 2527 (rs3767542, G or A), and 3766 (rs675508, C or A);

(2) in the base sequence set forth in SEQ ID NO:2, nucleotides represented by Nucleotide Numbers 7519 (rs2271763, G or A), 16901 (rs10920260, T or G), 30270 (rs16849387, A or G), 31333 (rs12127375, C or G), 50038 (rs1495840, T or A), and 63008 (rs10920269, G or T); and (3) in the base sequence set forth in SEQ ID NO:3, nucleotides represented by Nucleotide Numbers 24524 (rs3805, T or G), and 60701 (rs823114, G or A).

More preferably, the nucleic acid probe and/or primer used in the reagent for determination of the invention and the kit including the reagent, contains a nucleotide represented by Nucleotide Number 1 (rs576697, T or C) in the base sequence set forth in SEQ ID NO:1; a nucleotide represented by Nucleotide Number 50038 (rs1495840, T or A) in the base sequence set forth in SEQ ID NO:2; and a nucleotide represented by Nucleotide Number 60701 (rs823114, G or A) in the base sequence set forth in SEQ ID NO:3.

As the nucleic acid probe having the nucleotides of the polymorphic sites described above, a nucleic acid having the nucleotides of any one of the alleles for various polymorphic sites can be used, or two nucleic acids having the nucleotides each respectively corresponding to each of the alleles can also be used, depending on the method for detecting polymorphism used. Meanwhile, in regard to the invader probe used in the invader method, the nucleotides of the polymorphic site (that is, the nucleotides at the 3'-terminal) may be any arbitrary nucleotides.

The nucleic acid probe and/or primer used in the reagent for determination of the present invention and the kit including the reagent may be a DNA or an RNA, and may be single-stranded or double-stranded. In the case of being double-stranded, the nucleic acid probe and/or primer may be any one of a double-stranded DNA, a double-stranded RNA, and a DNA/RNA hybrid. The nucleic acid probe and/or primer can be produced, based on the information of the base sequence, according to an ordinary method using, for example, a commercially available nucleotide synthesizer.

The nucleic acid probe and/or primer described above can be respectively separately (or if possible, in a mixed state) dissolved in water or an appropriate buffer solution (for example, TE buffer, or the like) to an appropriate concentration (for example, 1 to 50 μM, or the like at 2 to 20× concentration), and can be stored at about −20° C. The reagent for determination of the present invention and the kit including the reagent may further include, as constituents, other components necessary for carrying out the method, for example, a buffer for hybridization reaction, an enzyme for nucleic acid amplification reaction, a buffer and other necessary reagents, a reagent for labeling, a reagent for label detection, and apparatuses needed for those reactions or procedure, depending on the method for detecting polymorphism used. For example, when the reagent and the kit including the reagent are for polymorphism detection according to a TaqMan-PCR method, the reagent and the kit including the reagent can further include a 10×PCR reaction buffer solution, a 10× aqueous solution of $MgCl_2$, a 10× aqueous solution of dNTPs, a Taq DNA polymerase (5 U/μL) and the like.

The reagent for determination of the present invention and the kit including the reagent can be used for the examination and/or determination of the genetic susceptibility (genetic predisposition) to hair shape.

6. USE OF HAIR SHAPE SUSCEPTIBILITY GENE OR PROTEIN ENCODING THE GENE

In regard to the hair shape susceptibility gene identified by the procedure described above or an expression product thereof, the expression or activity changes in association with the hair shape. Therefore, the hair shape susceptibility gene and an expression product thereof can be used as a marker for the type of hair shape for detecting and/or determining the type of hair shape of a test subject. Alternatively, when the amount of expression of the hair shape susceptibility gene or an expression product thereof is measured and evaluated, the evaluation or selection of a regulating agent for the hair shape of a person can be carried out. Furthermore, alternatively, when the amount of expression of the hair shape susceptibility gene or an expression product thereof is controlled, the hair shape of a person can be regulated.

According to the present invention, the person who can serve as an object in need of the detection and/or determination of the type of hair shape or the regulation of hair shape, is not particularly limited to a specific human race or group, but Asian race is preferred, while Japanese people are more preferred.

The hair shape susceptibility gene and an expression product thereof that are used as the hair shape determining marker may be a gene which overlaps with the haplotype block having a base sequence set forth in any one of SEQ ID NO:1 to NO:3 or an expression product thereof. However, preferred examples include CSRP1 gene, NAV1 gene, IPO9 gene, TMEM58 gene and NUCKS1 gene, and expression products thereof, and among these, CSRP1 gene, IPO9 gene and NUCKS1 gene, and expression products thereof, are more preferred.

CSRP1 gene is a gene containing a polynucleotide set forth in SEQ ID NO:42, and CSRP1 protein encoded by the gene has an amino acid sequence set forth in SEQ ID NO:43. CSRP1 gene is reported as a gene which has a LIM domain that is believed to function in various scenes including the transcription or generation of genes, through protein-protein recognition or cytoskeleton interaction, and for which a possibility of participation in the regulation processes important for the generation and cellular differentiation is suggested (Wang X. et al., J. Biol. Chem., 267(13), p. 9176-84, 1992). The gene can be accessed at the NCBI gene database under GeneID: 1465. The gene can be acquired by a known technique for gene manipulation. CSRP1 protein can be obtained by expressing a gene containing a polynucleotide set forth in SEQ ID NO:42, or can also be produced by a general chemical synthesis method, according to the amino acid sequence information set forth in SEQ ID NO:43.

As shown in the Examples that will be described below, gene expression in the hair root areas of Japanese curly hair people and Japanese non-curly hair people was analyzed, and it was found that as compared with the non-curly hair group, the amount of expression of CSRP1 gene is significantly higher in the curly hair group. Further, when a substance having a hair straightening action, such as *Amomum cardmomum*, is administered, curly hair is alleviated, and the amount of expression of CSRP1 gene is decreased.

IPO9 gene is a gene containing a polynucleotide set forth in SEQ ID NO:44, and IPO9 protein encoded by the gene has an amino acid sequence set forth in SEQ ID NO:45. IPO9 gene is reported to have a function that is responsible for material transfer from the cytoplasm to the inside of the nucleus (Okada N. et al., J. Cell. Mol. Med. 12(53), p. 1863-71, 2008). The gene can be accessed at the NCBI gene database under GeneID: 55705. The gene can be acquired by a known technique for gene manipulation. IPO9 protein can be obtained by expressing a gene containing a polynucleotide set forth in SEQ ID NO:44, or can also be produced by a general chemical synthesis method according to the amino acid sequence set forth in SEQ ID NO:45.

As shown in the Examples that will be described below, gene expression in the hair root area of Japanese curly hair people and Japanese non-curly hair people was analyzed, and it was found that as compared with the non-curly hair group, the amount of expression of IPO9 gene is significantly lower in the curly hair group. Further, when a substance having a hair straightening action, such as *Centipeda minima*, is administered, curly hair is alleviated, and the amount of expression of IPO9 gene is increased.

NUCKS1 gene is a gene containing a polynucleotide set forth in SEQ ID NO:46, and NUCKS1 protein encoded by the gene has an amino acid sequence set forth in SEQ ID NO:47. NUCKS1 gene is reported as a gene that encodes a highly phosphorylated DNA-binding protein present in the nucleus (Ostvold A C et al., Eur. J. Biochem. 268 (8), p. 2430-40, 2001). The gene can be accessed at the NCBI gene database under GeneID: 64710. The gene can be acquired by a known technique for gene manipulation. NUCKS1 protein can be obtained by expressing a gene containing a polynucleotide set forth in SEQ ID NO:46, or can also be produced by a general chemical synthesis method according to the amino acid sequence set forth in SEQ ID NO:47.

As shown in the Examples that will be described below, gene expression in the hair root area of Japanese curly hair people and Japanese non-curly hair people was analyzed, and it was found that as compared with the non-curly, hair group, the amount of expression of NUCKS1 gene is significantly lower in the curly hair group. Further, when a substance having a hair straightening action, such as *Amomum cardamorzium*, is administered, curly hair is alleviated, and the amount of expression of NUCKS1 gene is increased.

(1) Polynucleotide Marker for Detecting and/or Determining Type of Hair Shape

According to the present invention, the marker for detecting and/or determining the type of hair shape (marker for the type of hair shape) may be a polynucleotide having the base sequence of the hair shape susceptibility gene of the present invention, or a partial polynucleotide thereof. For example, examples of the marker for the type of hair shape of the invention include a polynucleotide consisting of the base sequences of CSRP1 gene, NAV1 gene, IPO9 gene, TMEM58 gene or NUCKS1 gene; preferably a polynucleotide consisting of the base sequences of CSRP1 gene, IPO9 gene or NUCKS1 gene; and more preferably a polynucleotide consisting of the base sequences set forth in SEQ ID NO:42, SEQ ID NO:44 or SEQ ID NO:46, polynucleotides consisting of base sequences complementary to these, and partial polynucleotides thereof.

Furthermore, the marker for the type of hair shape of the present invention can contain a strain consisting of a base sequence which is in a further complementary relation with respect to the base sequence of the polynucleotide consisting of complementary base sequence or a partial polynucleotide thereof described above.

The polynucleotides described above and complementary strands thereof may be respectively used as the marker of the present invention in a single-stranded form, or may also be used as the marker of the present invention in a double-stranded form.

Examples of the partial polynucleotide include a partial polynucleotide of the polynucleotide consisting of the base sequence of the hair shape susceptibility gene of the present invention or a base sequence complementary to this, in which the partial polynucleotide has, for example, a length of contiguous 15 nucleotides or more. The length of the partial polynucleotide can be appropriately set in accordance with the use.

(2) Primer for Amplifying Marker for Type of Hair Shape, and Probe for Detecting the Marker A partial polynucleotide of the polynucleotide consisting of the base sequence of the hair shape susceptibility gene of the present invention or a base sequence complementary to this, can serve as a primer for amplifying the marker for the type of hair shape. Preferably, the primer amplifies a polynucleotide consisting of a base sequence set forth in SEQ ID NO:42, SEQ ID NO:44, or SEQ ID NO:46, or a base sequence complementary to this, or a partial polynucleotide of such a polynucleotide.

Furthermore, a polynucleotide consisting of the base sequence of the hair shape susceptibility gene of the present invention or a base sequence complementary to this, or a partial polynucleotide thereof, can serve as a probe for detecting the marker for the type of hair shape. Preferably, the probe detects a polynucleotide consisting of a base sequence set forth in SEQ ID NO: 42, SEQ ID NO:44, or SEQ ID NO:46, or a base sequence complementary to this, or a partial polynucleotide of such a polynucleotide.

That is, a primer for specifically recognizing and amplifying an RNA produced as a result of the expression of CSRP1 gene, IPO9 gene or NUCKS1 gene, or a polynucleotide derived therefrom, or a probe for specifically detecting the RNA or the polynucleotide derived therefrom, is included the primer or probe described above.

Specifically, the polynucleotide or partial polynucleotide can be used as a primer or a probe according to a standard method, in the methods known to specifically detect a particular gene, such as a Northern Blotting method, an RT-PCR method, and an in situ hybridization method.

In the case of using the polynucleotide or partial polynucleotide as a primer, the nucleotide length thereof is usually 15 to 100 nucleotides, preferably 15 to 50 nucleotides, and more preferably 15 to 35 nucleotides.

Furthermore, in the case of using the polynucleotide or partial polynucleotide as a detection probe, one having a nucleotide length of usually 15 nucleotides or more, preferably 15 to 1000 nucleotides, and more preferably 100 to 1000 nucleotides, may be used.

Here, the term "specifically recognizes" means that, as in the case where, for example, in a Northern Blotting method, a polynucleotide consisting of a base sequence set forth in SEQ ID NO:42, SEQ ID NO:44 or SEQ ID NO:46, or a base sequence complementary to this, or a partial polynucleotide thereof can be specifically detected, and as in the case where, for example, in an RT-PCR method, the polynucleotide is specifically produced, the detected substance or the product can be considered as a polynucleotide consisting of a base sequence set forth in SEQ ID NO:42, SEQ ID NO:44 or SEQ ID NO:46, or a base sequence complementary to this, or a partial polynucleotide thereof.

The partial polynucleotide of a polynucleotide consisting of a base sequence set forth in SEQ ID NO:42, SEQ ID NO:44 or SEQ ID NO:46, or a base sequence complementary to this, can be designed based on the base sequence of CSRP1 gene, IPO9 gene or NUCKS1 gene as set forth in the sequence numbers described above, for example, through the software program of Primer 3 or Vector NTI. The candidate sequence of the primer or probe thus obtainable, or a sequence containing the sequence in a portion, can be designed as a primer or a probe.

(3) Polypeptide Marker for Detecting and/or Determining Type of Hair Shape

Like the hair shape susceptibility genes listed above, expression products of these genes (proteins encoded by the hair shape susceptibility genes, or polypeptides derived therefrom, or partial polypeptides thereof) can also serve as the marker (polypeptide) for the type of hair shape.

Examples of the expression products include CSRP1 protein, NAV1 protein, IPO9 protein, TMEM58 protein, and NUCKS1 protein (or also referred to as CSRP1, NAV1, IPO9, TMEM58 and NUCKS1), which are proteins encoded by CSRP1 gene, NAV1 gene, IPO9 gene, TMEM58 gene or NUCKS1 gene, respectively; polypeptides derived from these proteins; and partial polypeptides thereof. Preferred examples include CSRP1, IPO9 and NUCKS1, polypeptides derived from these, and partial polypeptides thereof.

More preferably, the expression products are proteins encoded by polynucleotides consisting of base sequences set forth in SEQ ID NO:42, SEQ ID NO:44 and SEQ ID NO:46, and even more preferably, proteins consisting of amino acid sequences set forth in SEQ ID NO:43, SEQ ID NO:45 and SEQ ID NO:47.

Furthermore, the expression products also include proteins which have amino acid sequences resulting from deletions, substitutions or additions of one or several amino acids in the amino acid sequences set forth in SEQ ID NO:43, SEQ ID NO:45 or SEQ ID NO:47, and having biological functions equivalent to and/or having equivalent immunological activity to those of proteins consisting of the amino acid sequences set forth in SEQ ID NO:43, SEQ ID NO:45 and SEQ ID NO:47 (so-called homologues of CSRP1, IPO9 or NUCKS1).

Here, examples of proteins which have equivalent biological functions include proteins that are equivalent to CSRP1, IPO9 or NUCKS1 in terms of the biochemical or pharmacological functions. Further, examples of proteins having equivalent immunological activity include proteins that have an ability to induce a specific immune reaction in an appropriate animal or cells thereof, and to bind specifically to the antibodies to CSRP1, IPO9 or NUCKS1.

Meanwhile, an indicator that determines the substitution, insertion or deletion of amino acid residues can be found by using a computer program well known to those having ordinary skill in the art, for example, DNA Star software program. For example, the number of variations is typically 10% or less of the total number of amino acids, preferably 5% or less of the total number of amino acids, and more preferably 1% or less of the total number of amino acids. Furthermore, from the viewpoint of maintaining the structure of protein, the amino acid to be substituted is preferably an amino acid having properties that are similar to those of amino acids before substitution in terms of the polarity, charge, solubility, hydrophobicity, hydrophilicity, amphiphilicity and the like of the amino acid.

The partial polypeptide may be a polypeptide consisting of at least 5 contiguous amino acids, and preferably 10 to 100 amino acids, in an amino acid sequence encoded by the hair shape susceptibility gene of the invention (for example, an amino acid sequence set forth in SEQ ID NO:43, SEQ ID NO: 45 or SEQ ID NO:47), and having a biological function and/or immunological activity equivalent to those of an expression product of the hair shape susceptibility gene of the invention (for example, CSRP1, IPO9 or NUCKS1).

The polypeptide encoded by the hair shape susceptibility gene of the present invention can be obtained by operations of DNA cloning, establishment of various plasmids, transfection of the plasmid to a host, culture of the transformant, and collection of protein from the culture, based on the base sequence information of the hair shape susceptibility gene. These operations can be carried out according to known methods, for example, the methods described in Molecular Cloning, T. Maniatis et al., CSH Laboratory (1983); DNA Cloning, D M. Glover, IRL PRESS (1985); and the like.

Specifically, the polypeptide can be obtained by producing a recombinant DNA (e.g., expression vector) that can be expressed by a gene encoding CSRP1, IPO9 or NUCKS1 in a desired host cell is produced, introducing this into a host cell to thereby transform the recombinant DNA, culturing the transformant, and collecting.

Furthermore, the polypeptide encoded by the hair shape susceptibility gene of the present invention can also be produced by a general chemical synthesis method in accordance with an amino acid sequence encoded by the hair shape susceptibility gene.

(4) Antibody Specifically Recognizing Marker (Polypeptide) for Type of Hair Shape An antibody which specifically recognizes a polypeptide consisting of an amino acid sequence encoded by the hair shape susceptibility gene of the present invention or a partial polypeptide thereof, may be an antibody for detecting the marker (polypeptide) for the type of hair shape described above.

As will be described below, when such an antibody is used, the presence or absence of the expression of the marker (polypeptide) for the type of hair shape (for example, CSRP1, IPO9, NUCKS1, or a polypeptide derived therefrom, or a partial polypeptide thereof) in a tissue of a test subject, and the level of the expression of the marker can be detected. Specifically, when a portion of the hair root area of a test subject or the like is collected by a biopsy method or the like, a protein is produced therefrom according to an ordinary method, and the antibody of the present invention is used according to an ordinary method in, for example, a known detection method such as a Western Blotting method or an ELISA method, the marker (polypeptide) for the type of hair shape present in the tissue can be detected.

The antibody for the detection of the type of hair shape may be a polyclonal antibody or a monoclonal antibody, which are both directed to the marker (polypeptide) for the type of hair shape as an immunizing antigen.

These antibodies can be produced according to known methods (Current protocols in Molecular Biology, edited by Ausubel et al., (1987) published by John Wiley and Sons, Section 11.12-11.13). Specifically, a polyclonal antibody can be obtained by immunizing a non-human animal such as rabbit with using a polypeptide consisting of an amino acid sequence encoded by the hair shape susceptibility gene of the invention (for example, CSRP1, IPO9 or NUCKS1), which has been expressed in *Escherichia coli* or the like and purified by ordinary methods, or with synthesizing a partial polypeptide of the polypeptide above synthesized according to an ordinary method, and collecting the polyclonal antibody from the blood serum of the immunized animal according to an ordinary method.

On the other hand, a monoclonal antibody can be obtained from a hybridoma cell prepared by immunizing a non-human animal such as a mouse with the polypeptide expressed in *Escherichia coli* or the like and purified according to ordinary methods as described above, or a partial polypeptide thereof, and subjecting spleen cells obtained from the animal and myeloma cells to cell fusion (Current protocols in Molecular Biology, edited by Ausubel et al., (1987), published by John Wiley and Sons, Section 11.4-11.11).

The partial polypeptide used herein is an oligopeptide having a partial amino acid sequence of a polypeptide consisting of an amino acid sequence encoded by the hair shape susceptibility gene of the invention (for example, CSRP1, IPO9 or NUCKS1). It is not necessary for the partial polypeptide to have a functional biological activity, but it is preferable that the partial polypeptide have the same immunogenic characteristics as those of proteins consisting of the amino acid sequences described above. For example, there may be mentioned an oligopeptide consisting of at least 8 contiguous amino acids, preferably 15 amino acids, and more preferably 20 amino acids, in the amino acid sequences described above, which oligopeptide has immunogenic characteristics equivalent to those of proteins consisting of the amino acid sequences described above, and preferably CSRP1, IPO9 or NUCKS1.

The production of an antibody to such a partial polypeptide can be carried out by increasing the immunological response using various adjuvants depending on the host. Although there are no limitations, examples of such adjuvants include Freund's adjuvant; mineral gels such as aluminum hydroxide; surface-active substances such as lysolecithin, pluronic polyol, polyanions, peptides, oil emulsifying agents, keyhole limpet hemocyanin, and dinitrophenol; and human adjuvants such as *bacillus* Calmette-Guerin (BCG) and *corynebacterium parvum*.

(5) Detection and/or Determination of Type of Hair Shape

Detection/determination of the type of hair shape involves collecting a portion of hair root tissue or the like of a test subject by a biopsy method or the like, and detecting and/or determining the type of hair shape by using the marker for the type of hair shape of the present invention contained in the tissue as an indicator. For example, in the method described above, the type of hair shape is detected and/or determined by measuring the expression level (amount of expression) of the hair shape susceptibility gene of the invention (for example, CSRP1 gene, IPO9 gene or NUCKS1 gene), a complementary strand thereof, or a partial polynucleotide thereof, or the amount of expression of a protein derived from the gene (for example, CSRP1, IPO9 or NUCKS1), a homologue thereof, or a partial polypeptide thereof.

Furthermore, the method for detection/determination of the present invention is also used, for example, in the case where a pharmaceutical product, a cosmetic product or the like for alleviating curly hair is administered to a curly hair person, so as to determine the presence or absence or the degree of an alleviation of the curly hair.

1) Biological Sample

Examples of the biological sample used herein include epithelial tissue or epithelial cells of a test subject, for example, a tissue containing cells that are capable of expressing the hair shape susceptibility gene of the invention (for example CSRP1 gene, IPO9 gene or NUCKS1 gene), such as the hair root area or skin; an RNA produced from this tissue; a polynucleotide further produced from the RNA. These RNA, polynucleotide and protein can be prepared, for example, by collecting a portion of the hair root area of a test subject by a biopsy method or the like, and then according to ordinary methods.

2) Detection and/or Measurement of Marker

The detection and measurement of a marker may vary depending on the type of the biological sample used as the object of measurement, and specifically, the detection and measurement are carried out as follows.

(i) Case of Using RNA as Biological Sample of Measurement

In the case of using an RNA as a biological sample, the detection and measurement is carried out by detecting and measuring the expression level of a marker (polynucleotide) for the type of hair shape of the invention in the RNA, for example, CSRP1 gene, IPO9 gene, NUCKS1 gene, or a partial polynucleotide.

Here, specifically, the measurement of the amount of expression of the market can be carried out by carrying out a known method such as a Northern Blotting method, an RT-PCR method, a DNA chip analysis method, or an in situ hybridization analysis method, using a primer for amplifying a polynucleotide that can serve as the marker of the present invention described above, or a probe for detecting the polynucleotide.

In the case of using a Northern Blotting method, when the probe of the invention is used, the presence or absence of the expression of the marker (for example, CSRP1 gene, IPO9 gene, NUCKS1 gene, or a partial polynucleotide thereof) in the RNA, and the level of the expression can be detected and measured.

Specifically, there may be mentioned a method in which, first, the probe DNA is labeled with a radioisotope ($^{32}$P, $^{33}$P, or the like; RI), a fluorescent substance or the like; subsequently, the labeled disease marker thus obtainable is hybridized with an RNA derived from a biological tissue of a test subject that has been transferred onto a nylon membrane or the like according to an ordinary method; and then the double strand of the labeled disease marker (DNA) and the RNA thus formed is detected and measured by measuring the signal originating from the labeled material (RI, a fluorescent substance or the like) of the labeled disease marker with a radiation detector (BAS-1800 II, manufactured by Fujifilm Holdings Corp.), a fluorescence detector or the like.

Furthermore, a method using an AlkPhos Direct™ Labelling and Detection System (manufactured by Amersham Pharamcia Biotech, Inc.) can also be available, in which the method includes labeling a probe DNA according to the protocol of AlkPhos Direct™, hybridizing the probe DNA with an RNA derived from a biological tissue of a test subject, and then detecting and measuring the signal originating from the labeled material of the probe DNA with a multibioimager STORM860 (manufactured by Amersham Pharmacia Biotech, Inc.).

In the case of using an RT-PCR method, the presence or absence of the expression of the marker in the RNA, and the level of the expression can be detected and measured using the primer of the present invention. Specifically, first, a cDNA is prepared from an RNA derived from a biological tissue of a test subject according to an ordinary method, and by using this cDNA as a template, a pair of primers (a forward strand which binds to the cDNA (minus strand) and a reverse strand which binds to the plus strand) prepared from the marker polynucleotide of the present invention is hybridized with the cDNA, so that the region of the target marker can be amplified. Thereafter, a PCR method is carried out according to an ordinary method, and thus the amplified double-stranded DNA thus obtained is detected.

For the detection of the amplified double-stranded DNA, a method of detecting a labeled double-stranded DNA produced by carrying out the PCR using primers which have been labeled in advance with RI, a fluorescent substance or the like; a method of transferring the produced double-stranded DNA onto a nylon membrane or the like according to an ordinary method, hybridizing this double-stranded DNA by using a labeled disease marker as a probe, and detecting the hybridization product; and the like can be used. The labeled double-stranded DNA product thus produced can be measured with an Agilent 2100 Bioanalyzer (manufactured by Yokogawa Analytical Systems, Inc.) or the like. Furthermore, an RT-PCR reaction solution is prepared using SYBR (registered trademark) Green RT-PCR Reagents (manufactured by Applied Biosystems, Inc.) according to the protocol, the reaction liquid is allowed to react with ABI PRIME (registered trademark) 7700 Sequence Detection System (manufactured by Applied Biosystems), and the reaction product may be detected. The detection and measurement of the level of expression of the marker (polynucleotide) for the type of hair shape of the present invention in the RNA of a test subject using such an RT-PCR method, will be described in Examples.

In the case of using a DNA chip analysis, a DNA chip bonded with the DNA probe (single-stranded or double-stranded) of the present invention is provided, and this is hybridized with a cRNA prepared from an RNA derived from a biological tissue of a test subject according to a conventional method, the two strands of the DNA and cRNA thus formed are bound with a labeled probe prepared from the marker polynucleotide of the present invention, and thereby, the presence or absence of the expression of the marker of the present invention and the level of the expression can be detected and measured.

Furthermore, a DNA chip capable of detecting and measuring the level of expression of the marker of the present invention can also be used as the DNA chip. As the DNA chip, for example, GeneChip (registered trademark) Human Genome U133 plus 2 manufactured by Affymetrix, Inc. may be used.

(ii) Case of Using Protein as Biological Sample of Object of Measurement

When a protein is used as an object of measurement, the measurement is carried out by contacting the antibody of the invention with a biological sample, detecting the marker (polypeptide) for the type of hair shape of the invention in the biological sample, which has been bound to the antibody, for example, CSRP1, IPO9, NUCKS1, or a partial polypeptide thereof, and measuring the amount (level) of the marker.

Here, the measurement of the amount of protein binding can be carried out by using a known method such as a Western Blotting method.

The Western Blotting method can be carried out by using the antibody of the present invention as a primary antibody, subsequently; labeling the primary antibody using, as a secondary antibody, an antibody which binds to the primary antibody labeled with a radioisotope such as $^{125}$I, a fluorescent substance, an enzyme such as horse radish peroxidase (HRP), or the like; and determining the signals originating from these labeled substances with a radiation meter, a fluorescence detector or the like. Furthermore, after using the antibody of the present invention as the primary antibody, the primary antibody is detected using an ECL Plus Western Blotting Detection System (manufactured by Amersham Pharmacia Biotech, Inc.) according to the protocol, and measurement can be made using a multibioimager STORM 860 (manufactured by Amersham Pharmacia Biotech, Inc.).

3) Determination of Type of Hair Shape

The determination of the type of hair shape can be carried out by comparing the level of the marker of the invention (for example, the level of gene expression of CSRP1 gene, IPO9 gene, or NUCKS1 gene, or the amount of CSRP1, IPO9, or NUCKS1) in a biological sample of a test subject, which has been measured as described above, with the corresponding level of a non-curly hair person, and determining the difference between the two levels.

The comparison of the level of expression of the marker polynucleotide or polypeptide between the biological sample of a test subject and the biological sample of a non-curly hair person can be carried out by carrying out the measurements directed to the biological sample of a test subject and the biological sample of a non-curly hair person in parallel. Furthermore, even if the measurements are not carried out in parallel, the average level or a statistical median value of the level of gene expression of the marker polynucleotide (CSRP1 gene, IPO9 gene, NUCKS1 gene, a partial polynucleotide thereof, or the like) or the level of expression of the marker polypeptide (CSRP1, IPO9, NUCKS1, a partial polypeptide thereof, or the like), which has been determined in advance in the tissues of plural (at least 2, preferably 3 or more, and more preferably 5 or more) non-curly hair persons under the same measurement conditions, can be used for the comparison with the test subjects, as the measured value for the test subject with the level of expression of the marker polynucleotide or polypeptide of a non-curly hair person.

The determination of the type of hair shape of a test subject can be carried out by using, as an index, the extent of increase or decrease (for example, higher or lower by two times or more, and preferably three times or more) in the case of comparing the gene expression level of the marker polynucleotide (CSRP1 gene, IPO9 gene, NUCKS1 gene, a partial polynucleotide thereof, or the like) or the expression level of the marker polypeptide (CSRP1, IPO9, NUCKS1, a partial polypeptide thereof, or the like) in the tissue of the test subject, with the levels of a non-curly hair person.

For example, if the expression level of CSRP1 gene or CSRP1 protein of the test subject is higher than such a level of a non-curly hair person, the test subject can be determined as a curly hair person, or is suspected to have the onset of curly hair in the future.

Furthermore, for example, if the expression level of IPO9 gene or IPO9 protein of the test subject is lower than such a level of a non-curly hair person, the test subject can be determined as a curly hair person, or is suspected to have the onset of curly hair in the future.

Further, for example, if the expression level of NUCKS1 gene or NUCKS1 protein of the test subject is lower than such a level of a non-curly hair person, the test subject can be determined as a curly hair person, or is suspected to have the onset of curly hair in the future.

7. METHOD FOR REGULATING HAIR SHAPE

When the nucleotides located at the hair shape susceptibility SNP marker of the present invention are modified, the hair shape of individuals can be fundamentally regulated.

That is, the present invention also provides a method for regulating the hair shape of an individual. According to an embodiment, the method may be a non-therapeutic method for regulating hair shape for cosmetic purposes, and can be carried out by a beautician or a barber. Meanwhile, according to the present specification, the term "non-therapeutic" is a concept which does not encompass medical acts, that is, acts of remedy to human body through treatment.

The method can be achieved by changing the nucleotides located at the hair shape susceptibility SNP markers of the present invention listed above. The specific technique is not particularly limited as long as it is a method capable of achieving the purpose described above, and conventionally known methods and techniques that will be developed in the future can all be used; however, for example, a method of utilizing genetic recombination may be used.

Alternatively, the method for regulating hair shape of the present invention is carried out by controlling the expression of the hair shape susceptibility gene of the present invention in the hair root area of a person in need of regulation of hair shape (for example, suppression of curly hair or kinky hair, or waving of scalp hair).

For example, in a person who is worried about curly hair or kinky hair, curly hair or kinky hair can be suppressed by inducing or promoting the expression of a hair shape susceptibility gene whose expression contributes to the phenotype of straight hair, for example, IPO9 gene or NUCKS1 gene. Alternatively, curly hair or kinky hair can be suppressed by inhibiting the expression of a hair shape susceptibility gene whose expression contributes to the phenotype of curly hair or kinky hair, for example, CSRP1 gene. On the other hand, in a person who wishes for waving of the scalp hair, waving can be expressed or promoted by inducing or promoting the expression of a hair shape susceptibility gene whose expression contributes to the phenotype of curly hair or kinky hair, for example, CSRP1 gene. Alternatively, waving can be expressed or promoted by inhibiting the expression of a hair shape susceptibility gene whose expression contributes the phenotype of straight hair, for example, IPO9 gene or NUCKS1 gene.

For example, in the case of suppressing curly hair or kinky hair, the expression level of IPO9 gene or NUCKS1 gene in the human hair root area may be brought to a value equal to or higher than the mRNA expression level of the relevant gene in a non-curly hair person, and for example, it is desirable to increase the expression level to a value of about 3 to 10 times higher or more. On the other hand, in the case of intending to promote waving, the expression level of IPO9 gene or NUCKS1 gene may be brought to a value lower than the mRNA expression level of the gene in a non-curly hair person, and for example, it is desirable to decrease the expression level to a value of about 3 to 10 times lower or less.

Furthermore, for example, in the case of suppressing curly hair or kinky hair, the expression level of CSRP1 gene in the human hair root area may be brought to a value equal to or lower than the mRNA expression level of the gene in a non-curly hair person, and for example, it is desirable to decrease the expression level to a value of about 3 to 10 times lower or less. On the other hand, in the case of intending to promote waving, the expression level of CSRP1 gene may be brought to a value higher than the mRNA expression level of the gene in a non-curly hair person, and for example, it is desirable to increase the expression level to a value of about 3 to 10 times higher or more.

The suppression, induction or promotion of the expression of a hair shape susceptibility gene in the human hair root area can be carried out according to an ordinary method. For example, in the suppression of gene, a method based on an antisense nucleotide, for example, a technique based on a method of inhibiting the translation from mRNA, or the like, may be used, and in the induction or promotion, a technique of expressing a hair shape susceptibility gene through gene transduction by means of a viral vector or the like may be used, or the like. Furthermore, in the suppression of the expression of a protein encoded by a hair shape susceptibility gene can be basically realized by a technique of suppressing the expression of the gene, and in the induction or promotion of the expression of the protein, a technique of expressing the gene at a high level, as well as a technique of direct intracutaneous injection of a human recombinant protein of the protein or the like may be used.

The gene transduction utilizing an antisense nucleotide can be carried out in the same manner as in the methods ordinarily used in gene therapy. For example, gene transduction can be carried out by a method of directly administering an antisense oligonucleotide or a chemical modification product thereof into the body of a test subject and thereby suppressing the expression of the hair shape susceptibility gene of the present invention, or a method of introducing an antisense RNA to a target cell of a patient and thereby suppressing the expression of the hair shape susceptibility gene of the present invention in the cell.

Here, the term "antisense nucleotide" encompasses an antisense oligonucleotide, an antisense RNA, an antisense DNA and the like, which all correspond to a portion of at least 8 nucleotides or more in a hair shape susceptibility gene of the present invention. Examples of the chemical modification products thereof include derivatives which are capable of increasing the transferability into cells or stability in the cells, such as phosphorothioates, phosphorodithioates, alkyl phosphotriesters, alkylphosphonates, and alkyl phosphoamidates ("Antisense RNA and DNA", published by WILEY-LISS, 1992., pp. 1-50; J. Med. Chem. 36, 1923-1937 (1993)).

The antisense nucleotide or a chemical modification product thereof can suppress the expression of a hair shape susceptibility gene, that is, the expression of a protein encoded by a hair shape susceptibility gene, by binding to a sense strand mRNA in a cell, and can thereby control the function (activity) of the protein.

In the method of directly administering an antisense oligonucleotide or a chemical modification product thereof into a living body, an antisense oligonucleotide or a chemical modification product thereof used therein may have a length of preferably 5 to 200 nucleotides, more preferably 8 to 25 nucleotides, and most preferably 12 to 25 nucleotides. Upon the administration, the antisense oligonucleotide or a chemical modification product thereof can be formulated into a preparation using a stabilizer, a buffer solution, a solvent and the like that are ordinarily used.

In the method of introducing an antisense RNA into a target cell of a test subject, the antisense RNA used therein may have a length of preferably 100 nucleotides or more, more preferably 300 nucleotides or more, and even more preferably 500 nucleotides or more. Furthermore, this method encompasses an in vivo method of introducing an antisense gene into the cells of a living body, and an ex vivo method of first introducing an antisense gene into the cells that have been extracted out of body, and returning the cells into the body (see Nikkei Science, April 1994, pp. 20-45; Gekkan Yakuji (Pharmaceuticals Monthly) 36 (1), 23-48 (1994); Jikken Igaku (Experimental Medicine) Special Issue, 12 (15), whole page (1994); and the like). Among these, an in vivo method is preferred, and examples thereof include a viral transduction method (a method of using a recombinant virus) and a non-viral transduction method (see the various documents described above).

As the method of using a recombinant virus, for example, methods of inserting an antisense nucleotide of MLTK gene into the genome of a virus such as retrovirus, adenovirus, adeno-associated virus, herpes virus, vaccinia virus, polio virus, or Sindbis virus, and introducing the product into the living body, may be used. Among these methods, methods of using retrovirus, adenovirus, adeno-associated virus and the like are particularly preferred. As the non-viral transduction method, a liposome method, a lipofectin method and the like may be used, and particularly, a liposome method is preferred. As other non-viral transduction methods, for example, a microinjection method, a calcium phosphate method, an electroporation method and the like may also be used.

A preparation composition for gene transduction contains, as active ingredients, the antisense nucleotide described above or a chemical modification product thereof, recombinant viruses containing these, infected cells to which these viruses have been introduced, and the like.

The administration of the composition to a test subject can be carried by, for example, intravenous, intraarterial, subcutaneous, or intramuscular administration in an appropriate dosage form such as an injection, and can be introduced by directly administering the composition through the skin of a patient. In the case of employing an in vivo method, the composition for gene transduction can be formulated into a dosage form such as an injection containing an antisense nucleotide of a hair shape susceptibility gene, as well as a form in which, for example, a viral vector containing an antisense nucleotide of a hair shape susceptibility gene that is embedded in a liposome or a membrane-fused liposome (Sendai virus (HVJ)-liposome, or the like). These liposome dosage forms include a suspending agent, a freezing agent, a centrifuge concentration freezing agent, and the like. Furthermore, the composition for gene transduction can also be formulated into a form of a culture fluid of cells infected with a virus to which a vector containing the antisense nucleotide of a hair shape susceptibility gene has been introduced. The amount of administration of the active ingredient in these various preparation forms can be appropriately adjusted on the basis of the severity of the disease intended to treat, the age and body weight of the patient, and the like. Usually, in the case of an antisense nucleotide for a hair shape susceptibility gene, the amount of administration may be an amount by which about 0.0001 to 100 mg, and preferably about 0.001 to 10 mg, is administered once in several days to several months to an adult as a test subject.

In the case of a retrovirus vector containing an antisense nucleotide, the amount can be selected in the range of an amount which gives a retrovirus titer of about $1 \times 10^3$ pfu to $1 \times 10^{15}$ pfu per day per kg of the patient's body weight. In the case of a cell having an antisense nucleotide introduced therein, an amount of about $1 \times 10^4$ cells/body to $1 \times 10^{15}$ cells/body may be administered.

8. METHOD FOR EVALUATION OR SELECTION OF HAIR SHAPE REGULATING AGENT

The present invention also provides a method for evaluating or selecting a hair shape regulating agent (screening method).

The screening method may be carried out by, for example, steps such as described below:

(a) a step of administering a test substance into a cell containing the hair shape susceptibility gene of the present invention; and (b) a step of selecting, among the administered test substances, a substance which converts a nucleotide polymorphism of the hair shape susceptibility SNP marker of the present invention present on the hair shape susceptibility gene or the vicinity thereof, for example, on the haplotype block containing the gene, to another polymorphism, as a hair shape regulating agent.

The cell used in the step (a) (step of administering a test substance) may be any cell which can be introduced a haplotype block in the genomic region of human chromosome 1, which is represented by a base sequence set forth in any one of SEQ ID NO:1 to NO:3, or a gene which at least overlaps with the haplotype block, that is, the hair shape susceptibility gene of the present invention, and can retain the gene stably, and there are no particular limitations on the origin of the cell (for example, the cell is not limited to a prokaryotic cell or a eukaryotic cell, or to an insect cell or an animal cell, or the like). Meanwhile, gene transduction, cell culture and the like can be carried out by arbitrarily using any methods conventionally known in the art (for example, Joseph Sambrook et al., Molecular Cloning: A Laboratory Manual (3 Vol. Set), Cold Spring Harbor Laboratory, NY, 2001; The Japanese Tissue Culture Association, Ed., "Technology of Tissue Culture, $3^{rd}$ Edition, Fundamentals and Applications", Asakura Shoten, 1996; and the like). The cell can be effectively utilized as a screening tool in the method for evaluating or selecting a substance effective for regulating the hair shape (screening method).

There are no particular limitations on the test substance that is administered. Examples include single compounds such as a natural compound, an organic compound, an inorganic compound, a protein and a peptide; and arbitrary compounds or compositions such as a compound library, expression products of a gene library, a cell extract, a cell culture supernatant, products of a fermentation microorganism, a marine extract, and a vegetable extract.

In regard to the step (b) (step of selecting a hair shape regulating agent), the presence or absence of the conversion of a nucleotide polymorphism and the type of the nucleotide after conversion are detected. The method for detecting the presence or absence of the conversion of a nucleotide polymorphism and the type of the converted nucleotide may be a method of directly measuring the type of nucleotides, or a method capable of indirectly evaluating the change of nucleotides. Examples of the method of directly measuring nucleotides include methods that are well known to those having ordinary skill in the art, such as PCR-SSCP, PCR-RLFP, PCR-SSO, PCR-ASP, a direct sequencing method, SNaPshot, dHPLC, a Sniper method, and a MALDI-TOF/MS method. Examples of the method of indirectly evaluating nucleotides, include methods of measuring a function, activity, the amount of a specific mRNA, or the amount of a protein, which may be produced/increased, or lost/decreased as a result of the conversion of the target nucleotides.

The substance selected by the method can be used as a hair shape regulating agent effective for the regulation of hair shape, and can also be used for the preparation of a pharmaceutical product, a quasi-drug, a cosmetic material, a health food, or the like, which all contain the agent. When the selected substance is further subjected to other pharmacological tests, clinical tests and toxicology tests as necessary, a hair shape regulating agent that is more effective and safe to human beings can be obtained.

Alternatively, the screening method described above can be carried out by using, for example, the expression of a hair shape susceptibility gene of the present invention or a protein encoded by the gene in a tissue or cell capable of expressing the gene or protein, as an indicator.

Specifically, the screening method can be carried out by the following steps (a) to (d):

(a) a step for contacting a test substance with a tissue or cell capable of expressing the hair shape susceptibility gene of the present invention or a protein encoded by the gene;

(b) a step of measuring the amount of expression of the gene or the protein in the tissue or cell;

(c) a step of comparing the amount of expression measured in step (b) with the amount of expression of the gene or the protein in a control tissue or cell which has not been contacted with the test substance; and (d) a step of selecting, based on the results of step (c), a test substance which decreases or increases the amount of expression of the gene or the protein, as a hair shape regulating agent.

Here, as the tissue or cell capable of expressing the hair shape susceptibility gene of the present or a protein encoded by the gene, the type of the tissue or cell does not matter as long as the tissue or cell which expresses the gene or the protein. However, examples include a tissue or a cell of a mammal, for example, the skin tissue, hair root area tissue (hair follicle tissue), epidermal keratinocytes, hair root area-derived cells, an established epithelial cell line, and the like, all collected from a human being. The cell also includes a transformant which has been transformed with the hair shape susceptibility gene of the present invention (an expression vector having the gene).

The contact between the tissue or cell and a test substance can be carried out by, for example, adding the test substance in advance to a culture fluid to a predetermined concentration, and then placing the tissue or cell in the culture fluid, or by adding the test substance to a culture fluid in which the tissue or cell is placed, to a predetermined concentration.

Examples of the culture fluid include DMEM medium, MCDB medium, Willams' E medium, RPMI1640 medium, DMEM/HamF12 (1:1) medium, various commercially available media for epithelial cells, and the like, and appropriately agar or gelatin may also be added. Furthermore, if necessary, an antibiotic substance, an amino acid, blood serum, a growth factor, a biological extract, and the like may also be added.

Tissue culture can be carried out by, for example, inserting a collected hair root area tissue (hair follicle tissue) into a 24-well plate to which a culture fluid has been added, and culturing the tissue usually for 10 to 30 days, and preferably 1 to 21 days, in a gas phase of air containing $CO_2$ at a temperature of 37° C.

Furthermore, cell culture can be carried out by, for example, inserting cells into a 24-well plate to which a culture fluid has been added, and culturing the cells usually for 1 to 7 days, and preferably 1 to 3 days, in a gas phase of air containing $CO_2$ at a temperature of 37° C.

The measurement (quantification) of the expression of the gene can be carried out according to the method described in connection with the detection/measurement of a marker for the type of hair shape described above ((5)-2)-(i)). That is, the measurement can be carried out by performing a known method such as a Northern Blotting method, an RT-PCR method, a DNA chip analysis method, or an in situ hybridization analysis method, using a primer for amplifying a polynucleotide that can serve as the marker of the present invention, or a probe for detecting the polynucleotide.

Furthermore, the measurement (quantification) of the expression of the protein can be carried out according to the method described in connection with the detection/measurement of a marker for the type of hair shape described above ((5)-2)-(ii)). That is, the measurement can be achieved according to a known method such as a Western Blotting method, using an antibody which recognizes the marker (polypeptide) for the type of hair shape of the present invention.

2) The measurement of the expression level of the hair shape susceptibility gene of the present invention can also be carried out by introducing into a cell line a fusion gene in which a reporter gene such as, for example, luciferase gene, is linked to a gene region controlling the expression of the gene (regulatory region), and measuring the amount or activity of a protein derived from the reporter gene.

That is, the method for evaluating or selecting a hair shape regulating agent according to the present invention can be carried out by the following steps of (a) to (c):

(a) a step of introducing a fusion gene of the regulatory region of a hair shape susceptibility gene of the present invention and a reporter gene, into a cell capable of expressing the hair shape susceptibility gene of the present invention, and culturing the cell in the presence and in the absence of a test substance;

(b) a step of measuring the amount of expression of an expression product of the reporter gene in the cell culture cultured in the presence of the test substance, and comparing the amount with the amount of expression of an expression product of the reporter gene in the cell culture cultured in the absence of the test substance; and (c) a step of selecting, based on the comparison results obtained in step (b), a test substance which increases or decreases the amount of expression of the reporter gene expression product, as a hair shape regulating agent.

As the reporter gene, a structural gene of an enzyme which catalyzes a light emission reaction or a color reaction is preferred. Specifically, examples include the luciferase gene described above, secreted alkali phosphatase gene, chloramphenichol acetyltransferase gene, β-glucuronidase gene, β-galactosidase gene, aequorin gene, and the like.

Furthermore, as the regulatory region of the hair shape susceptibility gene, for example, about 1 kb to about 10 kb, and preferably about 2 kb, upstream of the transcription initiation site of the gene can be used, and for example, the regions having base sequences set forth in SEQ ID NO:48 to NO:50 in CSRP1 gene, IPO9 gene, or NUCKS1 gene, respectively, may be used. The preparation of a fusion gene and the measurement of the activity originating from a reporter gene can be carried out by known methods.

A substance which decreases the amount of expression of the hair shape susceptibility gene may be a substance which suppresses the expression of or promotes the degradation of a mRNA complementary to the polynucleotide constituting the gene, and a substance which decreases the amount of expression of a protein encoded by the hair shape susceptibility gene may be a substance which suppresses the expression of the hair shape susceptibility gene or a protein thereof, or promotes the degradation of the gene or a protein thereof, and consequently decreases the amount of expression of the protein.

A substance which increases the amount of expression of the hair shape susceptibility gene of the present invention may be a substance which promotes the expression of or suppresses the degradation of a mRNA complementary to the polynucleotide constituting the gene, and a substance which increases the amount of expression of a protein encoded by the hair shape susceptibility gene may be a substance which promotes the expression of the hair shape susceptibility gene or a protein thereof, or suppresses the degradation of the gene or a protein thereof, and consequently increases the amount of expression of the protein.

A substance which increases the amount of expression of the hair shape susceptibility gene or a protein encoded by the gene serves as a reducing or promoting agent for curly hair or kinky hair. For example, a substance which increases the amount of expression of CSRP1 gene, IPO9 gene or NUCKS1 gene, or a protein encoded thereby, can serve as a reducing or improving agent for curly hair or kinky hair, while a substance which decreases the expression of such a gene or protein can serve as a promoting agent for curly hair or kinky hair, or a waving promoting agent. Furthermore, for example, a substance which increases the amount of expression of IVL gene or a protein encoded thereby, can serve as a promoting agent for curly hair or kinky hair, or a waving promoting agent, while a substance which decreases the expression of the gene or protein can serve as a reducing or improving agent for curly hair or kinky hair. Such a hair shape regulating agent can function as a pharmaceutical product, a cosmetic product or the like for an amelioration of curly hair or kinky hair, or for the promotion of waving of scalp hair, when administered to a human being.

3) Furthermore, the method for evaluating or selecting the hair shape regulating agent of the present invention can be carried out by using the function (activity) of a protein encoded by the hair shape susceptibility gene of the present invention as an indicator.

Examples of the function or activity of the protein include the acetylcholine receptor activity (Nguyen V T et al., J. Biol. Chem., 275(38), p. 29466-76, 2000), and phosphatidylserine binding ability (Goebeler V et al., FEBS Lett. 546(2-3), p. 359-64, 2003). The amount of the protein and the function or activity therefore have a certain correlation. Therefore, when the measurement of the function or activity of the protein described above is measured instead of the measurement of the amount of the protein, an evaluation or selection of a hair shape regulating agent can be carried out.

Specifically, the evaluation or selection is carried out by the following steps (a), (b) and (c):

(a) a step for contacting a test substance with an aqueous solution, tissue cells, or a cell fraction prepared from the tissue cells containing a protein encoded by the hair shape susceptibility gene of the present invention;

(b) a step of measuring the function or activity of the protein in the aqueous solution, tissue cells or cell fraction that has been contacted with the test substance, and comparing the function or activity with the function or activity of the protein in a control aqueous solution, control cells or control cell fraction which has not been contacted with the test substance; and (c) a step of selecting, based on the comparison results of the step (b), a test substance which increases or decreases the function or activity of the protein.

As the aqueous solution containing a protein encoded by the hair shape susceptibility gene, examples include aqueous solutions of CSRP1, IPO9, or NUCKS1, as well as a tissue cell lysate, a nucleus extract, and cell culture supernatant, which contain such a protein, and the like. The cell used herein may be a cell which expresses the hair shape susceptibility gene of the invention (for example, CSRP1 gene, IPO9 gene, or NUCKS1 gene), and has a protein encoded by such a gene as an expression product. Specifically, a tissue or cell of a mammal, for example, the skin tissue, hair root area tissue (hair follicle tissue), epidermal keratinocytes, hair root area-derived cells, an established epithelial cell line, and the like, all collected from a human being, can be used. The cell also includes a transformant which has been transformed with the hair shape susceptibility gene of the present invention (or an expression vector having the gene). Examples of host cells used, in the transformation include well known cells such as Hela cell, COS cell, HEK293 cell, MDCK cell, CHO cell, and HL60 cell. Furthermore, a cell fraction means one of various fractions derived from the cells described above, and includes, for example, a cell membrane fraction, a cell cytoplasm fraction, a cell nucleus fraction, and the like.

The activity of a protein encoded by the hair susceptibility gene of the present invention can be measured, for example, in the case of measuring the acetylcholine receptor activity or the phosphatidylserine binding ability, by known methods such as a binding assay, a co-immunoprecipitation method, a pulldown assay, a two-hybrid method (Y2H), a fluorescence polarization method, and a time-resolved fluorescence resonance energy transfer (TR-FRET) method (for example, Hiromitsu Nakauchi, Ed., "Immunological Protocol", Yodosha Co., Ltd., 2004; Tadaomi Takenawa, Ed., "Optimal Methods Clarifying Protein Interaction", Biotechnology Journal, Vol. 5, No. 6, Yodosha Co., Ltd., 2005). That is, the activity can be measured by immobilizing a protein encoded by a hair shape susceptibility gene on a membrane or a plate using an aqueous solution containing the protein, and detecting the amount of radioisotope-labeled acetylcholine or phosphatidylserine binding to the protein. A substance which suppresses (decreases) the function (activity) of the protein may be a substance which decreases the acetylcholine receptor activity or the phosphatidylserine binding ability, while a substance which enhances (increases) the function (activity) of the protein may be a substance which increases the acetylcholine receptor activity or the phosphatidylserine binding ability. For example, a substance which enhances the function (activity) of IPO9 or NUCKS1 can serve as an ameliorating agent for curly hair or kinky hair, and a substance which suppresses the function (activity) of such a protein can serve as a waving promoting agent. For example, a substance which enhances the function (activity) of IPO9 or NUCKS1 can serve as an improving agent for curly hair or kinky hair, and a substance which suppresses the function (activity) of such a protein can serve as a waving promoting agent. Furthermore, for example, a substance which enhances the function (activity) of CSRP1 can serve as a waving promoting agent, while a substance which suppresses the function (activity) of such a protein can serve as an ameliorating agent for curly hair or kinky hair.

EXAMPLES

Hereinafter, the present invention will be described by way of Examples.

Example 1

Definition of Hair Shape and Collection of Curly Hair Family Lines

In the present Example, an affected sib-pair linkage analysis and a case-control association analysis were carried out on a Japanese group, in order to identify the hair shape susceptibility gene.

In general, hair shape varies with the human race, and the people of the Asian race relatively more frequently have straight hair, while the people of the African race mainly have kinky hair (or curled hair). A large proportion of the people of the Indo-European race have a trait of wavy hair (wave hair) which is intermediate of the two. Since a Japanese group is a straight hair-dominant group, people having a curly hair trait as the hair shape were defined as the affected (case), while the straight hair trait was defined as the control (control). In a genetic analysis such as a linkage analysis, it is necessary to handle the object traits quantitatively to a certain extent, and thus, for example, a method of binarizing the traits in such a manner that curly hair=1 and straight hair=0, or a method of measuring the degree of curly hair by a certain method, and quantifying the degree were considered. However, in the current situation, various and diverse hair shapes of human being are available, and the method for measurement or classification has not been sufficiently established. Thus, first, an accurate classification of the phenotypes of hair shape was carried out. The hair shape is defined by the overall feature of the hair and the degree of curl (curl radius). Furthermore, factors defining the hair shape include not only the curl characteristics of a single hair, but also the synchrony of curl with the groups of hair in the surroundings. Thus, the phenotypes of hair shape were classified as indicated in Table 4, based on the actual states of hair shape in various human races. This classification is applicable to various racial groups, including Japanese groups. Furthermore, FIG. 1 presents images of the phenotypes of hair shape.

TABLE 4

Classification of phenotypes of hair shape

| | Feature | Curl radius | Type of hair shape |
|---|---|---|---|
| Type 1 | Hair which exhibits one curl in overall even if the length of the hair changes, or has one curl only at the hair tips | 9.5 cm or larger over the entire hair, or 3 cm or larger only at the hair tip | Straight hair |
| | | Smaller than 9.5 cm over the entire hair, or smaller than 3 cm only at the hair tip | Almost straight hair, or slightly wavy hair |
| Type 2 | Hair which has several repeated curls along the length of the hair with an inherent curl radius, and has a curl period synchronizing with the hair in the surroundings | 9.5 cm or larger over the entire hair | Almost straight hair, or slightly wavy hair |
| | | Equal to or larger of 3 cm and smaller than 9.5 cm over the entire hair | Wavy hair |
| | | A curl of smaller than 3 cm in the entire hair | Curly hair, or strongly wavy hair |
| Type 3 | Hair in which individual hairs have finely repeated curls, and the curl period does not synchronize with the hair in the surroundings | | Kinky hair |

On the other hand, the phenotype is the hair shape is a quantitative trait which can be continuously changed in a group, and it has been established to which extent should be determined as the curly hair trait or as the straight hair trait. In the present invention, among the classifications based on the actual states of hair shape, kinky hair, and curly hair or strongly wavy hair are defined as the curly hair traits, and wavy hair, almost straight hair or slightly wavy hair, and straight hair are defined as the straight hair (non-curly hair) traits.

As such, the phenotypes of hair shape could be accurately classified, but in regard to the collection of the objects of genetic analysis, the following problem to be solved emerged. That is, problems arise when the hair at the time point of collection is markedly short and it is impossible to evaluate the shape, and when the original hair shape has changed by permanent treatment, hair dyeing, and chemical treatments by various styling agents. For this reason, all candidates who could become the objects of a genetic analysis were each requested to submit a photograph of the candidate himself/ herself that was taken at a time when the phenotype of the hair shape could be discriminated (for example, childhood). That is, it is a photograph of a hair state which is not a markedly short hair and has not been subjected to a chemical treatment of hair. At the same time, all of the candidates were requested to submit several hair strands. The submitted hair strands were subjected to a detailed shape evaluation of torsion or kink of the hair, crimp, curl characteristics, and the like under water immersion conditions by which the effect of chemical treatment is lost. The objects of a genetic analysis were determined based on the evaluation of hair shape from the submitted photographs of the candidates themselves, and the evaluation of the shape of the submitted hair, and finally based on an investigation of hair shape through interviews.

As such, it took about two years to collect curly hair family lines of 68 families with 283 members among 3000 or more candidates applied from all over Japan. The specific details include 41 groups of two siblings, 22 groups of three siblings, 4 groups of four siblings, and one group of five siblings, and 100 pairs were defined as the final affected sib-pairs (brothers or sisters having the curly hair trait). Since it was predicted that this number of sib-pairs was sufficient to characterize the genetic locus in consideration of the strength of the genetic factor and the risk in the siblings, it was decided to carry out an affected sib-pair linkage analysis.

In regard to the collection of specimens from the objects of the genetic analysis, specimens were collected only when an approval was granted in advance by the ethics committee, subsequently the person in charge of the implementation of informed consent explained the contents of the study to the objects using a written explanation, and written consent was obtained.

A doctor or a nurse collected about 20 mL of blood from each of the objects of the genetic analysis. The genomic DNA was extracted from the blood specimen using PUREGENE Genomic DNA Purification Kit (manufactured by Gentra Systems, Inc.) according to the manual. The genomic DNA was dissolved in 2 mL of a DNA Hydration Solution, the concentration was measured, and the solution was stored at 4° C. The average yield of the genomic DNA was 576.2 g/20 ml of blood.

Example 2

Affected Sib-Pair Linkage Analysis on Entire Genome

In the present Example, an affected sib-pair linkage analysis covering the entire genome was carried out for the first time on the Japanese curly hair family lines. To briefly describe the principle of this method, since siblings that are affected have inherited from their parents an allele causative of a disease, the siblings necessarily share the allele. On the other hand, the number of alleles shared by brothers is 1 (a value based on the null hypothesis). When many cases of allele sharing could be observed from the number of alleles based on the null hypothesis by examining the number of alleles shared by many affected sib-pairs, it was determined that linkage was recognized.

The affected sib-pair linkage analysis was carried out using a linkage mapping set (ABI PRISM Linkage Mapping Set-MD 10 v2.5) manufactured by Applied Biosystems, Inc. (ABI). This is a set of 400 fluorescent primers for typing in total, intended to amplify microsatellites, which are short repeating sequences rich in polymorphisms that are evenly scattered in the genome, and the kit covers human chromosome at an average interval of 9.2 cm.

The genomic DNA prepared in Example 1 was used as a template, and PCR (GeneAmp PCR System 9700G, manufactured by ABI) was carried out using a linkage mapping set. Detection of the amplification product (fragment) was carried out using an ABI PRISM 3100 Genetic Analyzer (manufactured by ABI). The fluorescent primer set for typing includes primers labeled with three types of fluorescent dyes such as 6-FAM (blue), VIC (green) and NED (yellow), and therefore, even with fragments of the same size, three types of colors can be separately discriminated. Accordingly, large amounts of samples could be rapidly processed.

The typing of the fragments was carried out by means of Genotyper Software v3.7 (manufactured by ABI) and GeneScan Software (manufactured by ABI):

A statistical test of the linkage was carried out using Genehunter v2.1_r5 Software (Kruglyak, L. et al., Am. J. Hum. Genet., 58(6), 1347-1363, 1996), which is a non-parametric analysis. Determination of the region where linkage is recognized was carried out according to the guidelines of Lander and Kruglyak (Nat. Genet., 11(3), 241-247, 1995) as described below, based on the criteria for obtaining false positive linkage.

A linkage analysis came to be actively carried out over the entire genome through the guidelines of Lander and Kruglyak (polygenic diseases), but in a linkage analysis of individual genes, the determination of whether the gene function can be a cause of a disease, is also needed. However, in an analysis over the entire genome, since the gene function is not taken into consideration at that stage, determination criteria (threshold values) that are purely meaningful in terms of mathematical genetics are required. Thus, they have provided significant linkage criteria as shown in the following Table 5, according to simulation results.

TABLE 5

| | |
|---|---|
| Suggestive Linkage (Criteria for obtaining one false positive linkage result over the entire genome) | $P < 7.4 \times 10^{-4}$ LOD > 2.2 |
| Significant Linkage (Criteria for obtaining 0.05 false positive linkage results over the entire genome) | $P < 2.2 \times 10^{-5}$ LOD > 3.6 |
| High Significant Linkage (Criteria for obtaining 0.01 false positive linkage results over the entire genome) | $P < 3.0 \times 10^{-7}$ LOD > 5.4 |

Figure 2:
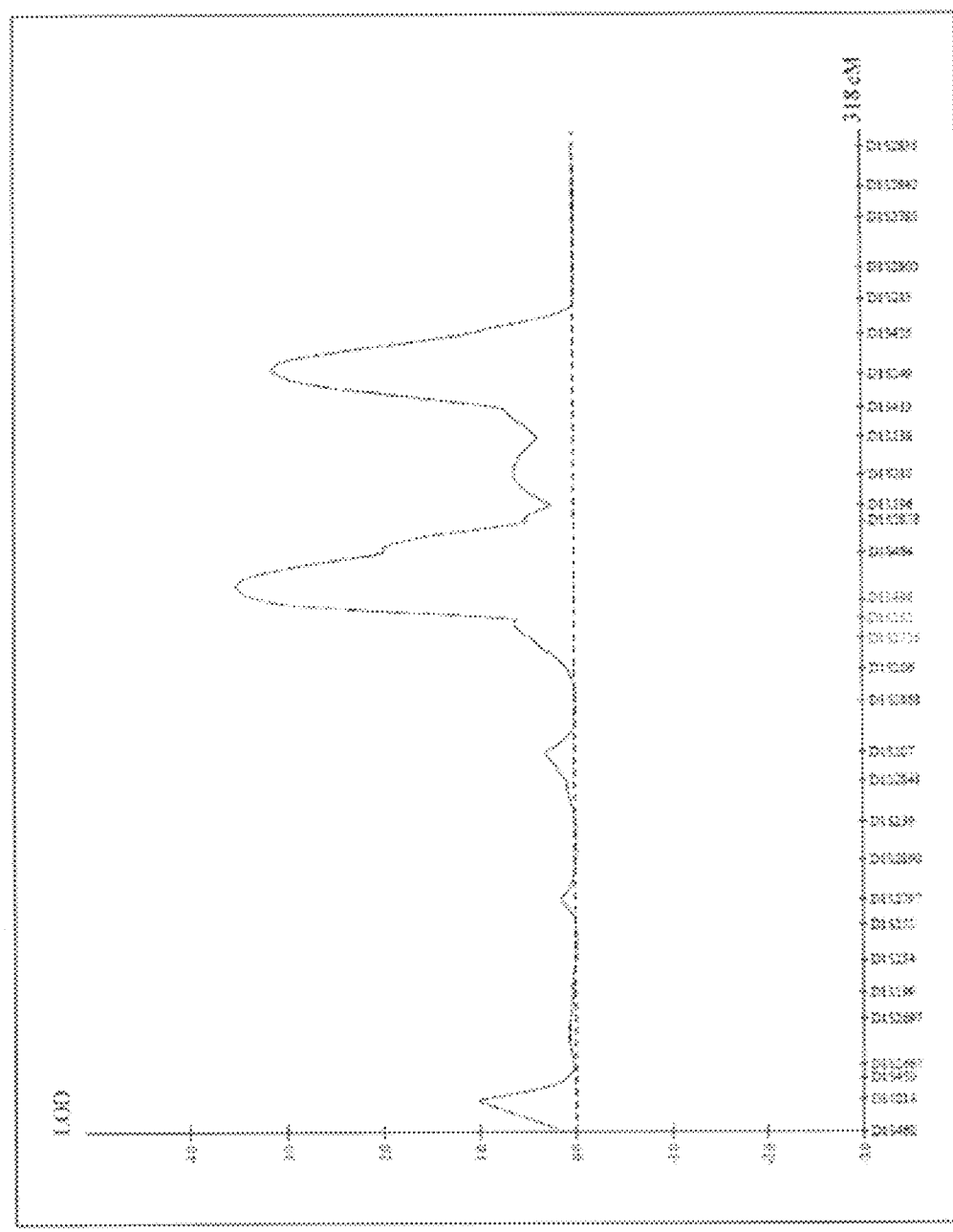
FIG. 2 is a diagram showing microsatellite markers and the maximum LODs obtained by an affected sib-pair linkage analysis on chromosome 1.
Figure 3:
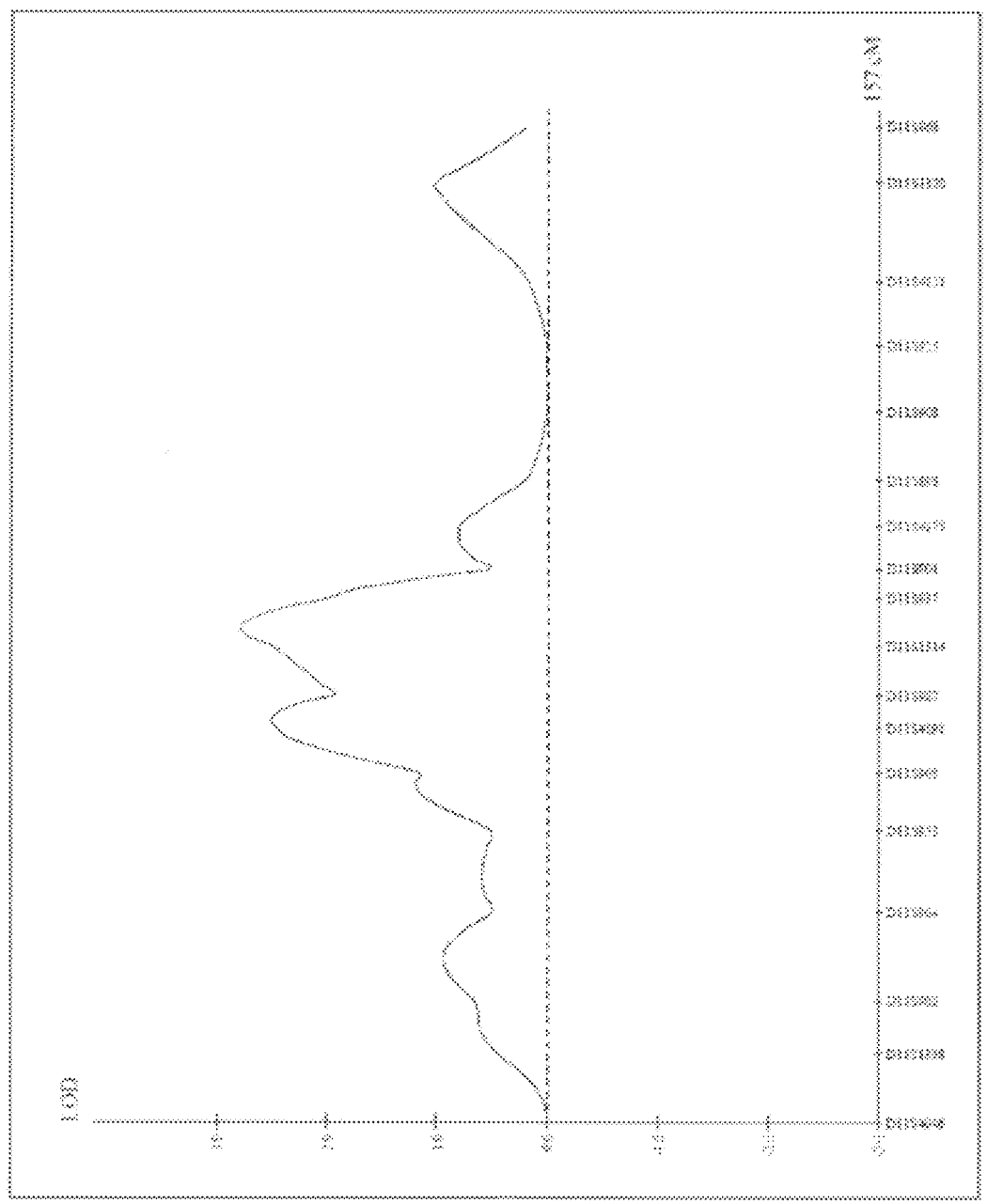
FIG. 3 is a diagram showing microsatellite markers and the maximum LODs obtained by an affected sib-pair linkage analysis on chromosome 11.

As a result of the screening of whole chromosome, linkages were recognized on chromosome 1 and chromosome 11. The results are respectively presented in FIG. 2 and FIG. 3. As shown in FIG. 2, in chromosome 1, a maximum LOD score of 3.49 was obtained in the 1q21 to 1q23.1 region (near D1S498), and a maximum LOD score of 3.13 was obtained in the 1q32 to 1q41 region (D1S249-D1S213). As shown in FIG. 3, in chromosome 11, a maximum LOD score of 2.78 was obtained in the 11q12 to 11q13.5 region (D11S905 to D11S937). The values thus obtained satisfied the criteria of Suggestive Linkage defined by Lander and Kruglyak. Therefore, the curly hair trait locus could be specified on chromosome 1 and chromosome 11, and it was strongly suggested that hair shape susceptibility genes exist in these regions.

Example 3

Detailed Mapping in Candidate Regions

Subsequently, chromosome 1 where linkages was recognized in Example 2 was subjected to an affected sib-pair linkage analysis (detailed mapping), by further using microsatellite markers, for the purpose of narrowing the linkage regions.

The microsatellites used as a marker for the detailed mapping, were searched using Comprehensive human genetic maps of the Mammalian Genotyping Service (http://research-.marshfieldclinic.org/genetics/GeneticResearch/compMaps.asp). Microsatellites which were present in the genome at an interval of 1 to 2 cM and had high heterozygosity were selected. Furthermore, the fluorescent primers for typing, which were intended to amplify the microsatellites, were designed based on the Genome Database Project (GDB) (http://www.gdb.org/). Here, although the GDB has terminated the operation, currently retrieval and design can be carried out through the NCBI (http://www.ncbi.nlm.nih-.gov/). Fluorescent primers for typing manufactured by ABI were used, and for some of the fluorescent primers for typing, those included in a linkage mapping set (ABI PRISM Linkage Mapping Set-HD 5 v2.5, manufactured by ABI) were used. The microsatellites used as the markers for detailed mapping, and the fluorescent primers for typing are presented in Table 6-1 and Table 6-2 (see SEQ ID NO:4 to NO:41).

TABLE 6-1

Microsatellites used as markers for detailed mapping, and fluorescent primers for typing

| ABI | Microsatellite | Location (cM) | GenBank Accession | Heterozygosity | Amplification product (fragment) size | Label | Forward primer | Reverse primer |
|---|---|---|---|---|---|---|---|---|
| MD10 | AFM249zg9 D1S252 | 150.27 | Z17138 | 0.82 | 99-119 | | | |
| | GATA12A07 D1S534 | 151.88 | G07791 | 0.83 | 196-212 | VIC | AGCACATAGCAGGCACTAGC (SEQ ID NO: 4) | CGATTGTGCCACTACACAGT (SEQ ID NO: 5) |
| | AFMa297xg9 D1S2696 | 153.59 | Z52819 | 0.88 | 159-185 | 6-FAM | AAAAAATGAGTCCAGTAGAAGCCT (SEQ ID NO: 6) | AGCCAGATTTACATCCCAG (SEQ ID NO: 7) |

TABLE 6-1-continued

Microsatellites used as markers for detailed mapping, and fluorescent primers for typing

| ABI | Microsatellite | Location (cM) | GenBank Accession | Heterozygosity | Amplification product (fragment) size | Label | Forward primer | Reverse primer |
|---|---|---|---|---|---|---|---|---|
| MD10 | AFM336xb1 D1S498 | 155.89 | Z24441 | 0.82 | 183-205 | | | |
| | AFM207yh6 D1S2346 | 158.75 | Z51162 | 0.83 | 89-115 | VIC | TATCTTGCCCTGCACC (SEQ ID NO: 8) | AAGTGGGTCTCCCCAG (SEQ ID NO: 9) |
| | AFMb009zb9D1S2721 | 161.05 | Z53073 | 0.74 | 233-247 | VIC | TTGCTCGGCCAGAGTCT (SEQ ID NO: 10) | ACGCATCACACCTGGCTAGT (SEQ ID NO: 11) |
| | AFMa127wh9D1S506 | 163.34 | Z24627 | 0.58 | 123-141 | VIC | GGGCCTATGGCTGGAA (SEQ ID NO: 12) | GGCTATGCTGGGGCAA (SEQ ID NO: 13) |
| HD5 | AFMa133ye5D1S2635 | 165.62 | Z52215 | 0.86 | 142-159 | | | |
| | AFMb334xb1D1S2771 | 168.52 | Z53685 | 0.72 | 243-259 | 6-FAM | CAGTTCCATAGGCTGACG (SEQ ID NO: 14) | CATTGCTGATGCTGGAGG (SEQ ID NO: 15) |
| MD10 | AFM297wb9 D1S484 | 169.68 | Z24182 | 0.64 | 136-142 | | | |
| MD10 | AFMa057ze5D1S2878 | 177.86 | Z51743 | 0.84 | 169-195 | | | |
| | AFMb316zb9D1S2762 | 179.10 | Z53529 | 0.81 | 232-250 | NED | CCTTAATTGTGGTGTTGGT (SEQ ID NO: 16) | AAAAATCTGGAAGGCATAAA (SEQ ID NO: 17) |
| MD10 | AFM063xg9 D1S196 | 181.49 | Z16503 | 0.73 | 267-279 | | | |
| | AFMb359xf5D1S2799 | 183.19 | Z53881 | 0.87 | 191-209 | 6-FAM | AGCAAGACCCTGTCTCAAAA (SEQ ID NO: 18) | TGGATAGCTTTCCACCACT (SEQ ID NO: 19) |
| HD5 | AFM248wg5 D1S452 | 188.85 | Z23809 | 0.76 | 119-131 | | | |
| MD10 | AFM157xe7 D1S218 | 191.52 | Z16701 | 0.83 | 266-286 | | | |
| | AFM123yc5 D1S460 | 194.32 | Z23379 | 0.84 | 145-159 | 6-FAM | ACAAGGTGACCGGAAAGACC (SEQ ID NO: 20) | AGCTCTGGCAAGTTGAAGGA (SEQ ID NO: 21) |
| HD5 | AFMc025xh9D1S2818 | 198.30 | Z54047 | 0.70 | 258-268 | | | |
| | AFM348tg1 D1S2848 | 200.96 | Z51502 | 0.82 | 105-123 | VIC | ATCTGGGTTCACTATTAAACAGAGTTGGGCAAGGTAGAATATGTG (SEQ ID NO: 22) | (SEQ ID NO: 23) |
| MD10 | AFM205xg1 D1S238 | 202.73 | Z16920 | 0.86 | 272-302 | | | |
| HD5 | AFMa057vb5D1S2877 | 205.40 | Z51735 | 0.72 | 143-157 | | | |
| HD5 | AFM031xd12D1S412 | 209.15 | Z23298 | 0.71 | 129-147 | | | |
| MD10 | AFM165xc9 D1S413 | 212.44 | Z23420 | 0.77 | 246-262 | | | |
| | UT492 D1S373 | 214.08 | L16266 | 0.90 | 283-330 | VIC | GGGTGACAGAGCAAGACTC (SEQ ID NO: 24) | CCCTGACCTCCCTTACAGA (SEQ ID NO: 25) |
| | AFM136xa7 D1S1723 | 215.17 | Z51003 | 0.83 | 167-181 | NED | AACTGTGTCCAGCAGCAACT (SEQ ID NO: 26) | TATGTGCCTGTTGTGTGCAT (SEQ ID NO: 27) |
| | AFMa190xd5D1S2655 | 216.82 | Z52412 | 0.90 | 224-260 | VIC | AGGGTCCCCAAAGAGCCTTC (SEQ ID NO: 28) | ATGGCAGCACATCCTGCTTC (SEQ ID NO: 29) |
| | AFMa224xc1D1S2668 | 218.46 | Z52594 | 0.77 | 233-247 | VIC | AATCACTTGAACCTGGGAG (SEQ ID NO: 30) | ACTGACTGGCTGTTTCTGAG (SEQ ID NO: 31) |

TABLE 6-2

| ABI | Microsatellite | Location (cM) | GenBank Accession | Heterozygosity | Amplification product (fragment) size | Label | Forward primer | Reverse primer |
|---|---|---|---|---|---|---|---|---|
| MD10 | AFM234wf6 D1S249 | 220.65 | Z17051 | 0.87 | 155-185 | | | |
| HD5 | AFMa290xd1D1S2692 | 222.84 | Z52805 | 0.87 | 276-316 | | | |
| | AFMa082wf9D1S2891 | 224.50 | Z51920 | 0.75 | 211-273 | 6-FAM | ACTGCTTATTCGGAGTTGGA (SEQ ID NO: 32) | CCAAGAGTTTTCTTAG-CAAATC-AC (SEQ ID NO: 33) |
| HD5 | AFM224xc1 D1S245 | 227.81 | Z17011 | 0.83 | 239-257 | | | |
| | AFM108ya3 D1S205 | 229.13 | Z16585 | 0.80 | 94-112 | 6-FAM | CTGAGCACAGCAGTGGTCTC (SEQ ID NO: 34) | AAGGCTTATCAAGAGCGAGG (SEQ ID NO: 35) |

TABLE 6-2-continued

| ABI | Microsatellite | | Location (cM) | GenBank Accession | Heterozygosity | Amplification product (fragment) size | Label | Forward primer | Reverse primer |
|---|---|---|---|---|---|---|---|---|---|
| MD10 | AFM203zb6 | D1S425 | 231.11 | Z23538 | 0.81 | 92-108 | | | |
| | GATA87F04 | D1S2141 | 233.38 | G07856 | 0.82 | 236-263 | 6-FAM | AGACTTACAGCACTGGCTGC (SEQ ID NO: 36) | TGCTCCTAGGAAAGGAAACA (SEQ ID NO: 37) |
| | AFM297xc1 | D1S2827 | 234.52 | Z51306 | 0.78 | 142-152 | 6-FAM | GCTTCTGGCCTCTGTCA (SEQ ID NO: 38) | AATTTTGCGTGTGTGTGC (SEQ ID NO: 39) |
| HD5 | AFM184yf6 | D1S227 | 238.52 | Z16806 | 0.71 | 61-75 | | | |
| | AFMa052zd1 | D1S2871 | 241.26 | Z51685 | 0.84 | 215-241 | NED | TGAAGTGTGCATTCTNTACATCA (SEQ ID NO: 40) | CGAGACATTTGCATCATCA (SEQ ID NO: 41) |
| MD10 | AFM147xf8 | D1S213 | 242.34 | Z16668 | 0.86 | 104-124 | | | |

Figure 4:
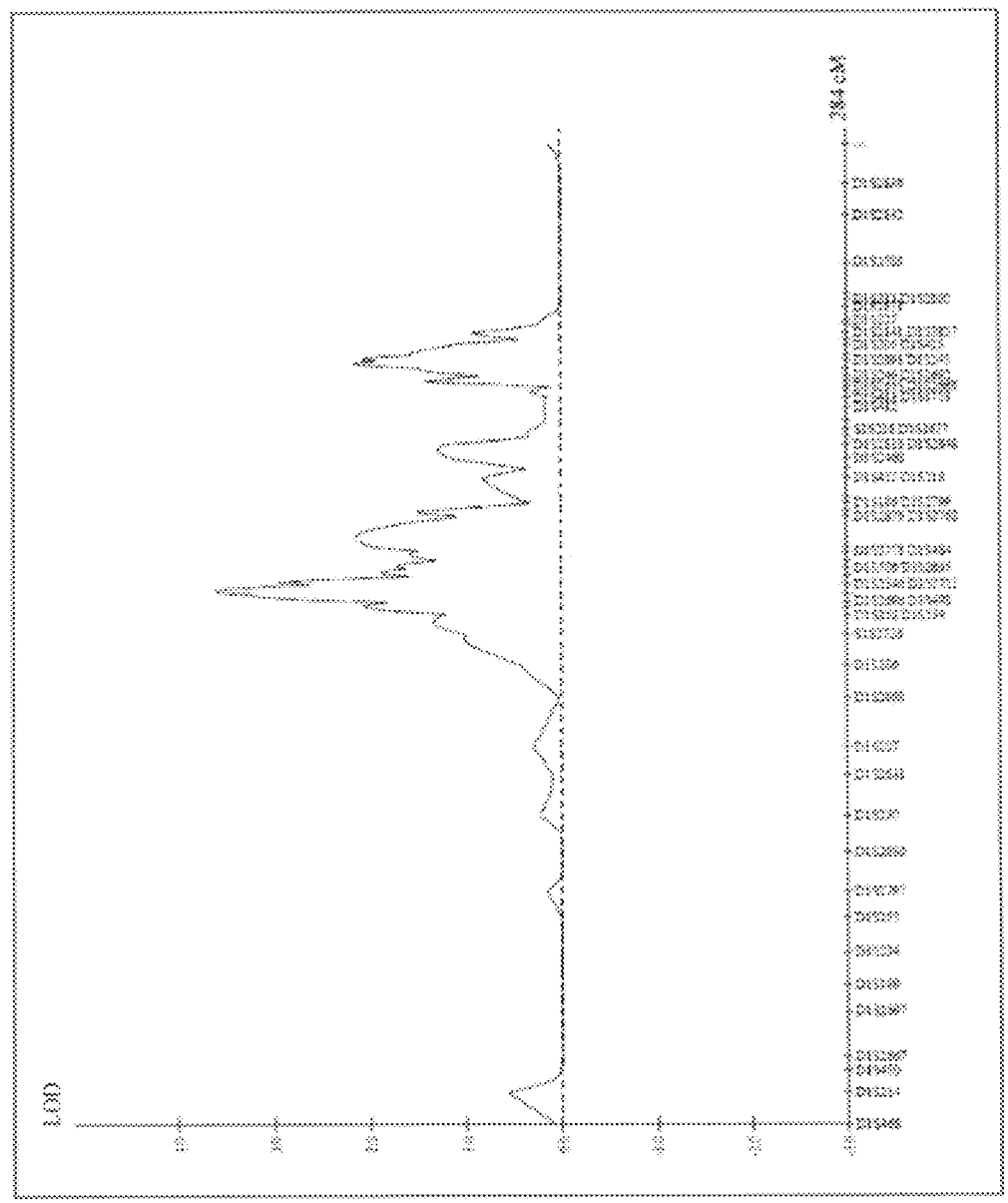
FIG. 4 is a diagram showing microsatellite markers and the maximum LODs obtained by an affected sib-pair linkage analysis on chromosome 1.

The results obtained by carrying out an affected sib-pair linkage analysis (detailed mapping) on chromosome 1 in the same manner as in Example 2, are presented in FIG. 4. As shown in FIG. 4, a maximum LOD score of 3.60 was obtained in the 1q21.3 region (D1S2696-D1S2346), and a maximum LOD score of 2.14 was obtained in the 1q32.1 to 1q32.2 region (D1S249 to D1S2891). The values thus obtained were considered to satisfy the criteria of Significant Linkage and Suggestive Linkage, respectively, defined by Lander and Kruglyak as described in Example 2. Therefore, the curly hair trait loci on chromosome 1 could be narrowed, and it was strongly suggested that hair shape susceptibility genes exist in these regions.

Example 4

Case-Control Association Analysis

In order to identify a hair shape susceptibility gene from the 1q32.1 to 1q32.2 region (D1S249 to D1S2891) on chromosome 1, where strong linkage was recognized in Example 3 above, a comparison of the allele frequency for the single nucleotide polymorphism (SNP) markers present in the region was made by a case-control association analysis.

Since it is necessary that the cases (affected: those having the curly hair trait) and the controls (control: those having the straight hair trait) consist of people of the same race as the race for whom the hair shape susceptibility gene is identified, in the present invention, non-family related Japanese people having the curly hair trait and non-family related Japanese people having the straight hair trait were employed as objects. Objects were collected in the same manner according to the criteria described in Example 1, and genomic DNA was obtained from each of 43 non-family related Japanese people having the curly hair trait and 51 non-family related Japanese people having the straight hair trait.

With reference was made to the dbSNP database (http://www.ncbi.nlm.nih.gov/SNP/) and the JSNP database (http://snp.ims.u-tokyo.ac.jp/index_ja.html), SNPs which represented certain regions in the region to be analyzed, and had a gene frequency of the minor allele of 10% or higher in a panel of Japanese people, were selected as SNPs to be typed. Thus, 57 SNPs were selected from the region to be analyzed.

The typing of SNPs was carried out according to a TaqMan PCR method, using TaqMan SNP Genotyping Assays (manufactured by ABI, formerly known as Assays-on-Demand or Assays-by-Design). Furthermore, the apparatuses of Applied Biosystems 7900HT Fast Real-time PCR System (manufactured by ABI) and Applied Biosystems 7500 Real-time PCR System (manufactured by ABI) were used. The method was carried out according to the respective manuals attached to the apparatuses.

The typing data thus obtained were totalized for each of the cases and the controls, and a significant difference test was carried out through $\chi^2$ test by four methods involving the genotype, allele type, dominant model and recessive model. That is, if any genetic variation is causative of changes in the hair shape, differences in the allele frequency and the like are expected between the cases and the controls. Furthermore, in the present Example, since the association analysis was carried out on a relatively small number of objects, the significance level was set at $p<0.05$. Further, in some part, the significance level was set to be loose ($p<0.1$) in order to increase the power of the test.

As a result, it was found that there is a statistically significant ($p<0.05$) difference between the cases and the controls.

In SNP: rs1495840 (single nucleotide polymorphism represented by Nucleotide Number 50038 in the base sequence set forth in SEQ ID NO:2), the proportion of homozygous T-allele carriers was significantly higher in the people having the straight hair trait as compared with the people having the curly hair trait (Table 7-1), and even by the allele type, a significant difference was observed between the people having the straight hair trait and the people having the curly hair trait (Table 7-1).

Furthermore, it was found that even the two SNPs shown below exhibit a difference between the cases and the controls.

In SNP:rs576697 (single nucleotide polymorphism represented by Nucleotide Number 1 in the base sequence set forth in SEQ ID NO:1), the proportion of homozygous C-allele carriers was higher in the people having the curly hair trait as compared with the people having the straight hair trait (p=0.096) (Table 7-2).

In SNP:rs823114 (single nucleotide polymorphism represented by Nucleotide Number 60701 in the base sequence set forth in SEQ ID NO:3), the proportion of homozygous A-allele carriers was higher in the people having the curly hair trait as compared with the people having the straight hair trait (p=0.065) (Table 7-3).

These three SNPs all satisfied the Hardy-Weinberg equilibrium. Therefore, these three SNPs were determined to be hair shape susceptibility SNPs, and their relations with hair shape were confirmed.

TABLE 7-1

Association analysis on SNP: rs1495840

| | SNP: rs1495840 | | | | |
|---|---|---|---|---|---|
| | Allele type | | Genotype | | |
| | A | T | AA | AT | TT |
| Curly hair trait | 21.4% | 78.6% | 2.4% | 38.1% | 59.5% |
| Straight hair trait (control) | 10.8% | 89.2% | 0.0% | 26.1% | 78.4% |

| p value ($\chi^2$ test) | Allele type | 0.046 |
|---|---|---|
| | Genotype | 0.102 |
| | AA vs AT, TT | 0.048 |

TABLE 7-2

Association analysis on SNP: rs576697

| | SNP: rs576697 | | | | |
|---|---|---|---|---|---|
| | Allele type | | Genotype | | |
| | T | C | TT | TC | CC |
| Curly hair trait | 14.0% | 86.0% | 2.3% | 23.3% | 74.4% |
| Straight hair trait (control) | 23.5% | 76.5% | 5.9% | 35.3% | 58.8% |

| p value ($\chi^2$ test) | Allele type | 0.096 |
|---|---|---|
| | Genotype | 0.261 |
| | TT, TC vs CC | 0.112 |

TABLE 7-3

Association analysis on SNP: rs823114

| | SNP: rs823114 | | | | |
|---|---|---|---|---|---|
| | Allele type | | Genotype | | |
| | G | A | GG | GA | AA |
| Curly hair trait | 40.7% | 59.3% | 18.6% | 44.2% | 37.2% |
| Straight hair trait (control) | 52.0% | 48.0% | 24.0% | 56.0% | 20.0% |

| p value ($\chi^2$ test) | Allele type | 0.123 |
|---|---|---|
| | Genotype | 0.183 |
| | GG vs GT, TT | 0.065 |

Example 5

Haplotype Analysis

As a result of the analyses in Example 4, three hair shape susceptibility SNPs were found. Further, a haplotype analysis was carried out in order to found a correlation between hair shape and polymorphiosms that are present in the surrounding regions of the SNPs, particularly those that have not been typed, and to identify hair shape susceptibility genes.

In the analysis, the linkage disequilibrium coefficient D' (pair-wise LD coefficient) based on the EM algorithm was calculated using Haploview 4.1 Software (Barrett, J C, et al., Bioinformatics, 21 (2), 263-265, 2005), and the analysis was carried out. A linkage disequilibrium analysis was carried out on the SNPs found above and the SNPs present in the surrounding regions, using the HapMap PHASE data of the International HapMap Project Database (HapMap Data ReI 21/PhaseII July 6, on NCBI Build 35 assembly, dbSNP b125). Meanwhile, the analysis panel consisted of JPT+CHB (Japanese people in Tokyo, Japan, and Chinese people of Han race in Beijing, China).

The method for inferring the haplotype block used the confidence interval (Gabriel, S B, et al., Science, 296 (5576), p. 2225-2229, 2002). That is, it can be considered that the haplotype blocks to be determined are mostly in the genome range where historical recombination has not been recognized, and strong linkage disequilibrium exists within the regions. Usually, when the upper limit of the 95% confidence interval of the linkage disequilibrium coefficient D' is lower than 0.9, the region is considered as a region having an evidence of historical recombination. On the other hand, when the upper limit of the 95% confidence interval of D' is higher than 0.98 and the lower limit is higher than 0.7, the region can be considered as a region where strong linkage disequilibrium exists.

As a result, haplotype blocks of the following items (1) to (3) containing the three hair shape susceptibility SNPs shown below were found.

Figure 5:
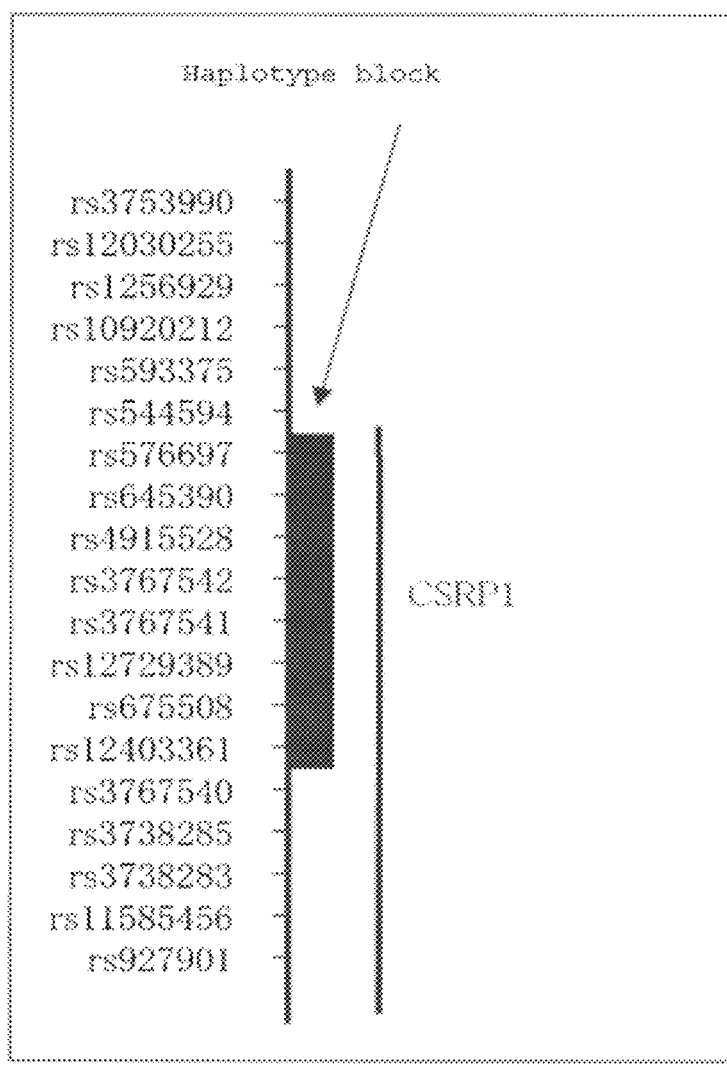
FIG. 5 is a conceptual diagram of a 3,926-bp haplotype block represented by a base sequence set forth in SEQ ID NO:1, which contains SNP: rs576697 and extends from SNP: rs576697 to SNP: rs12403361.

(1) A 3,926-bp haplotype block ranging from SNP: rs576697 to SNP:rs12403361 containing SNP:rs576697 and represented by the base sequence set forth in SEQ ID NO:1 (FIG. 5). This haplotype block was a region containing CSRP1 gene. From this result, CSRP1 gene was identified as a hair shape susceptibility gene.

Figure 6:
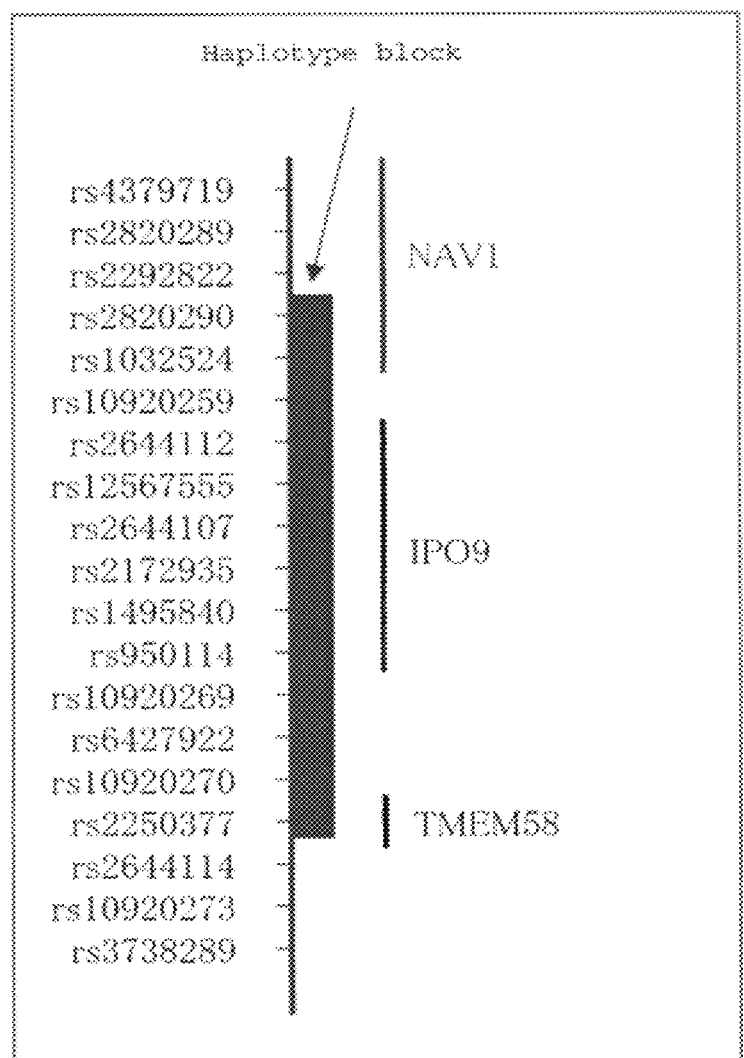
FIG. 6 is a conceptual diagram of a 76,945-bp haplotype block represented by a base sequence set forth in SEQ ID NO:2, which contains SNP: rs1495840 and extends from SNP: rs2820290 to SNP: rs2250377.

(2) A 76,945-bp haplotype block ranging from SNP: rs2820290 to SNP:rs2250377 containing SNP:rs1495840 and represented by the base sequence set forth in SEQ ID NO: 2 (FIG. 6). This haplotype block was a region containing NAV1 gene, IPO9 gene, and TMEM58 gene. From this result, NAV1 gene, IPO9 gene, and TMEM58 gene were identified as hair shape susceptibility gene.

Figure 7:
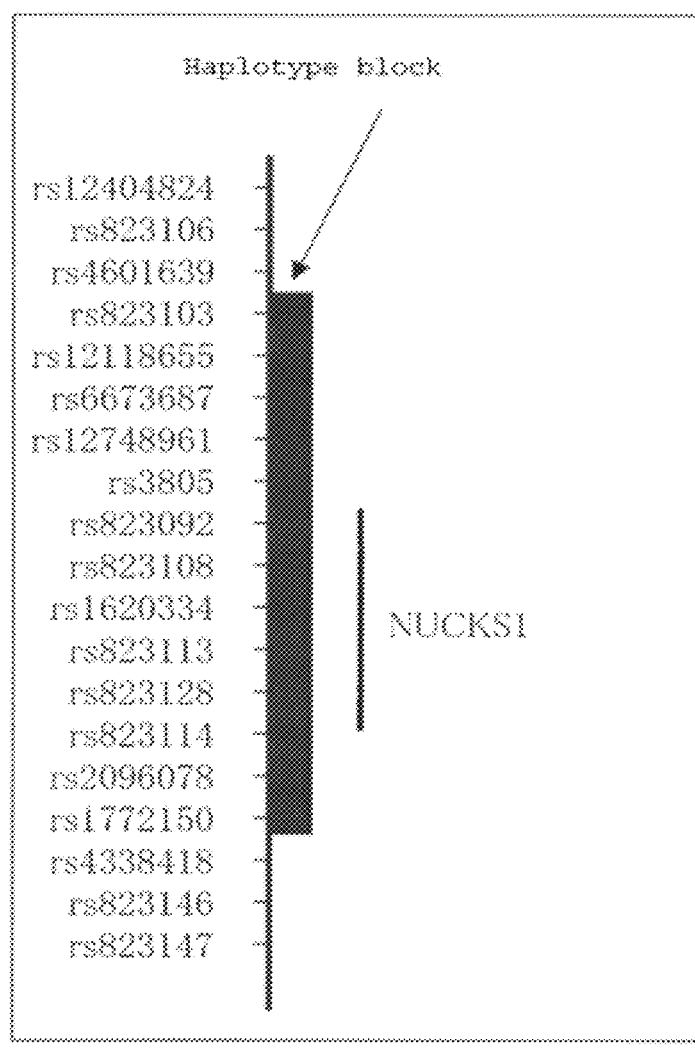
FIG. 7 is a conceptual diagram of a 68,637-bp haplotype block represented by a base sequence set forth in SEQ ID NO:3, which contains SNP: rs823114 and extends from SNP: rs823103 to SNP: rs1772150.

(3) A 68,637-bp haplotype block ranging from SNP: rs823103 to SNP:rs1772150 containing SNP:rs823114 and represented by the base sequence set forth in SEQ ID NO:3 (FIG. 7). This haplotype block was a region containing NUCKS1 gene. From this result, NUCKS1 gene was identified as a hair shape susceptibility gene.

Example 6

Identification of Hair Shape Susceptibility SNP Marker

While haplotype blocks were found in the haplotype analysis in Example 5, a haplotype was extracted from each of the haplotype blocks using the same Haploview 4.1 Software (Barrett, J C et al., Bioinformatics, 21(2), 263-265, 2005). By comparing the respective nucleotide combinations of the extracted haplotypes, that is, the SNP marker groups, SNP loci that were linked to the hair shape susceptibility SNP marker loci were identified. The SNP loci thus identified can be identified as additional hair shape susceptibility SNP markers.

As a result, additional hair shape susceptibility SNP markers shown below were respectively found in the haplotype blocks of (1) to (3) shown in Example 4.

(1) 3,926-bp haplotype block represented by the base sequence set forth in SEQ ID NO:1: There were seven principal haplotypes in this haplotype block (Table 8). As the SNP loci that are linked to a hair shape susceptibility SNP marker, SNP:rs576697, additional three hair shape susceptibility SNP markers shown below were identified.

SNP:rs645390 (single nucleotide polymorphism represented by Nucleotide Number 1635 in the base sequence set forth in SEQ ID NO:1), SNP:rs3767542 (single nucleotide polymorphism represented by Nucleotide Number 2527), and SNP:rs675508 (single nucleotide polymorphism represented by Nucleotide Number 3766).

rs1495840, additional 5 hair shape susceptibility SNP markers shown below were identified.

SNP:rs2271763 (single nucleotide polymorphism represented by Nucleotide Number 7519 in the base sequence set forth in SEQ ID NO:2), SNP:rs10920260 (single nucleotide polymorphism represented by Nucleotide Number 16901), SNP:rs16849387 (single nucleotide polymorphism represented by Nucleotide Number 30270), SNP:rs12127375 (single nucleotide polymorphism represented by Nucleotide Number 31333), and SNP:rs10920269 (single nucleotide polymorphism represented by Nucleotide Number 63008).

TABLE 8

| SNP marker | Nucleotide number in base sequence set forth in SEQ ID NO: 1 | Haplotype 1 | 2 | 3 | 4 | 5 | 6 | 7 | Hair shape susceptibility SNP |
|---|---|---|---|---|---|---|---|---|---|
| rs576697 | 1 | T | T | C | T | T | T | T | ○ (Example 4) |
| rs645390 | 1635 | G | G | A | G | G | G | G | ○ |
| rs4915528 | 2491 | C | C | C | C | C | A | C | |
| rs3767542 | 2527 | G | A | A | A | A | G | A | ○ |
| rs3767541 | 2622 | C | C | C | T | C | C | C | |
| rs12729389 | 3511 | G | G | G | T | G | G | G | |
| rs675508 | 3766 | C | C | A | C | C | C | A | ○ |
| rs12403361 | 3926 | T | A | T | A | T | T | T | |

(2) 76,945-bp haplotype block represented by the base sequence set forth in SEQ ID NO:2: There were ten principal haplotypes in this haplotype block (Table 9). As SNP loci that are linked to a hair shape susceptibility SNP marker, SNP:

TABLE 9

| SNP marker | Nucleotide number in base sequence set forth in SEQ ID NO: 2 | Haplotype 1 | 2 | 3 | 4 | 5 | 6 | 7 | 8 | 9 | 10 | Hair shape susceptibility SNP |
|---|---|---|---|---|---|---|---|---|---|---|---|---|
| rs2820290 | 1 | A | A | G | A | A | G | A | G | A | A | |
| rs2820292 | 606 | A | A | C | A | A | C | A | C | A | A | |
| rs1022361 | 6589 | G | A | A | G | A | A | A | A | A | A | |
| rs1032524 | 7145 | T | T | C | T | T | C | T | C | T | T | |
| rs2271763 | 7519 | G | G | G | G | G | A | G | A | G | G | ○ |
| rs2644128 | 9759 | C | C | G | C | C | G | C | G | C | C | |
| rs10920259 | 14015 | C | T | T | C | T | C | T | C | T | T | |
| rs4950794 | 16645 | T | A | T | T | A | T | T | T | A | A | |
| rs10920260 | 16901 | T | T | T | T | T | G | T | G | T | T | ○ |
| rs2820295 | 17187 | G | G | A | G | G | G | G | G | G | G | |
| rs2644112 | 22425 | T | T | C | T | T | T | T | T | T | T | |
| rs2644119 | 24095 | C | C | T | C | C | C | C | C | C | C | |
| rs2644122 | 26726 | A | A | G | A | A | A | A | A | A | A | |
| rs12567555 | 28279 | G | G | G | G | A | G | G | G | A | G | |
| rs16849387 | 30270 | A | A | A | A | G | A | G | A | A | A | ○ |
| rs6701026 | 30323 | C | C | T | C | C | T | T | T | C | C | |
| rs12562614 | 31313 | A | G | A | G | A | A | A | G | G | | |
| rs12127375 | 31333 | C | C | C | C | C | G | C | G | C | C | ○ |
| rs12042456 | 32891 | A | G | G | G | G | G | G | G | G | | |
| rs12722743 | 33262 | C | C | C | C | C | T | C | C | C | C | |
| rs2644107 | 34948 | T | T | C | T | T | T | T | T | T | T | |
| rs1400875 | 37762 | T | T | C | T | T | T | T | T | T | T | |
| rs2172935 | 42659 | C | C | T | C | C | C | C | C | C | C | |
| rs1495840 | 50038 | T | T | T | T | T | A | T | A | T | T | ○ (Example 4) |
| rs950114 | 56529 | C | T | T | T | T | T | T | T | T | T | |
| rs2820311 | 57795 | A | A | G | A | A | A | A | A | A | A | |
| rs2271764 | 60376 | T | T | T | T | T | T | T | T | C | T | |
| rs1043823 | 61751 | C | C | C | C | C | C | T | C | C | C | |
| rs8024 | 61894 | C | C | A | C | C | C | C | C | C | C | |
| rs10920269 | 63008 | G | G | G | G | G | T | G | T | G | G | ○ |
| rs12032537 | 64678 | | | | | | | | | | | |
| rs6427922 | 71731 | G | G | G | G | A | G | A | G | A | | |
| rs10920270 | 72840 | C | C | C | G | C | C | C | C | C | C | |
| rs2250377 | 76945 | G | A | G | G | G | G | G | G | G | | |

(3) 68,637-bp haplotype block represented by the base sequence set forth in SEQ ID NO:3: There were seven principal haplotypes in this haplotype block (Table 10). As SNP loci that are linked to a hair shape susceptibility SNP markers, SNP:rs823114, additional one hair shape susceptibility SNP markers shown below were identified.

SNP:rs3805 (single nucleotide polymorphism represented by Nucleotide Number 24524 in the base sequence set forth in SEQ ID NO:3).

and using forceps and a needle teeth, the outer hair root sheath and the inner hair root sheath were removed from the hair root part as much as possible, and the hair root of the hair shaft only (hair shaft keratinized region) was separated and prepared. The hair shaft keratinized region was introduced in a 1.5-mL tube containing 0.5 mL of an RNA extraction solution, ISOGEN (manufactured by Nippon Gene Co., Ltd.), and the tissue was sufficiently crushed with a mini codeless grinder and a homogenization pestle. 0.5 mL of ISOGEN and

TABLE 10

| SNP marker | Nucleotide number in base sequence set forth in SEQ ID NO: 3 | Haplotype 1 | 2 | 3 | 4 | 5 | 6 | 7 | Hair shape susceptibility SNP |
|---|---|---|---|---|---|---|---|---|---|
| rs823103 | 1 | G | A | G | A | A | A | G | |
| rs1172199 | 108 | C | T | C | T | T | T | C | |
| rs12132270 | 2109 | T | C | C | C | C | C | C | |
| rs1891091 | 2587 | T | C | C | C | C | C | C | |
| rs12752037 | 2783 | C | A | C | A | A | A | C | |
| rs10751444 | 3313 | C | T | T | T | T | T | T | |
| rs1172198 | 3887 | | | | | | | | |
| rs6676110 | 4146 | A | G | G | G | G | G | G | |
| rs12118655 | 4647 | G | A | A | A | A | A | A | |
| rs6673687 | 11538 | A | T | A | T | T | A | A | |
| rs12748961 | 17432 | C | T | T | T | T | C | T | |
| rs12030754 | 19212 | G | C | G | C | G | G | C | |
| rs16856186 | 19295 | | | | | | | | |
| rs3805 | 24524 | G | T | T | T | G | G | T | ○ |
| rs10900522 | 25236 | T | C | T | C | T | T | C | |
| rs951366 | 26521 | T | C | T | C | T | T | C | |
| rs823092 | 29042 | T | T | A | T | T | T | T | |
| rs823093 | 30396 | A | A | G | A | A | A | A | |
| rs11240557 | 33183 | | | | | | | | |
| rs823108 | 34770 | C | C | T | C | C | C | C | |
| rs3761919 | 35889 | G | A | G | A | G | G | A | |
| rs1772146 | 37690 | T | T | G | T | T | T | T | |
| rs1772147 | 37840 | A | A | G | A | A | A | A | |
| rs1620334 | 39014 | T | T | C | T | T | T | T | |
| rs7513645 | 39195 | G | A | G | A | G | G | A | |
| rs823113 | 52406 | G | G | C | G | G | G | G | |
| rs823128 | 54547 | A | A | G | A | A | A | A | |
| rs2298143 | 57838 | | | | | | | | |
| rs823114 | 60701 | A | G | G | G | A | A | G | ○ (Example 4) |
| rs823117 | 64682 | A | A | T | A | A | A | A | |
| rs2096078 | 64947 | G | G | G | A | G | G | A | |
| rs823122 | 66197 | T | T | C | T | T | T | T | |
| rs823123 | 66515 | T | T | C | T | T | T | T | |
| rs1626710 | 68635 | A | A | C | A | A | A | A | |
| rs1772150 | 68637 | A | A | G | A | A | A | A | |

Example 7

Analysis of Gene Expression in Scalp Hair Roots in Curly Hair People and Straight Hair People Ten curly hair people and ten straight hair people were collected according to the classifications of Example 1, and an analysis was carried out on the expression of the hair shape susceptibility gene in the scalp hair roots of each test subject. In regard to the collection of specimens from the test subjects, an approval was granted in advance by the ethics committee, subsequently the person in charge of the implementation of informed consent explained the contents of the study to the objects using a written explanation, and written consent was obtained.

About 60 scalp hair strands per person were pulled out from all over the whole head of each test subject, and only those scalp hair root parts that were determined to be in the growth period from the shape of the hair root part, were collected in a petri dish filled with ice-cooled PBS (manufactured by Invitrogen, Inc.). Under a stereoscopic microscope 200 μL of chloroform were added thereto, and the mixture was sufficiently stirred in a vortex mixer and then was centrifuged (15000 rpm, for 15 minutes) using a small-sized microcentrifuge. Thus, about 500 μL of an aqueous phase containing RNA was collected. 50 μL of 3 M sodium acetate and 1 μL of Ethachinmate (manufactured by Nippon Gene Co., Ltd.) were added to the collected solution, and the mixture was sufficiently stirred. Furthermore, 1 mL of isopropanol was added and stirred, and the mixture was centrifuged (15000 rpm, for 20 minutes) with a small-sized microcentrifuge to precipitate total RNA. The supernatant was discarded, and then 75% ethanol was added to the precipitate. The mixture was centrifuged again (15000 rpm, for 10 minutes) with a small-sized microcentrifuge. The supernatant was discarded, and the precipitate was dried in air and was dissolved in 20 μL of Nuclease-free Water (manufactured by Invitrogen, Inc.). A portion of this was used to measure the RNA concentration using an absorption spectrometer (GeneQuant: manufactured by Pharmacia AB, or NonoDrop: manufactured by Nanodrop Technologies, Inc.), or RiboGreen RNA Reagent and Kit (manufactured by Invitrogen, Inc.). cDNA was synthesized from 1 μg of the total RNA thus obtained using QuantiTect Reverse Transcription Kit (manufactured by Qiagen N.V.) according to the attached protocol, and the cDNA was used in the quantification of the amount of gene expression by PCR.

The quantification of the amount of gene expression was carried out using TaqMan (registered trademark) Gene Expression Assays manufactured by Applied Biosystems, Inc. (ABI). According to the attached protocol, the synthesized cDNA, a primer & probe set specific to the gene to be detected and quantified, a real-time PCR reagent and the like (manufactured by ABI) were mixed, and fragments of the gene to be detected and quantified were amplified with Applied Biosystems 7500 Real-Time PCR System (manufactured by ABI). At this time, real-time PCR was carried out in the same manner using a known cDNA derived from an standard hair shaft keratinized region sample, and a calibration curve was produced. Thus, standardization of the amount of gene expression was carried out. Furthermore, standardization of the amount of expression of the gene to be detected and quantified was carried out using GAPDH gene as an internal standard, and also employing KRT31 gene and KRT85 gene, which is recognized to be uniformly expressed in the sample hair shaft keratinized region, as internal standards.

In order to detect and quantify the amount of expression of CSRP1 gene, Assay Number Hs00187916_m1 of TaqMan Gene Expression Assays (manufactured by ABI) was used as a specific primer & probe set.

In order to detect and quantify the amount of expression of IPO9 gene, Assay Number Hs00949771_m1 of TaqMan Gene Expression Assays (manufactured by ABI) was used as a specific primer & probe set.

In order to detect and quantify the amount of expression of NUCKS1 gene, Assay Number Hs00224144_m1 of TaqMan Gene Expression Assays (manufactured by ABI) was used as a specific primer & probe set.

Figures 1, 8:
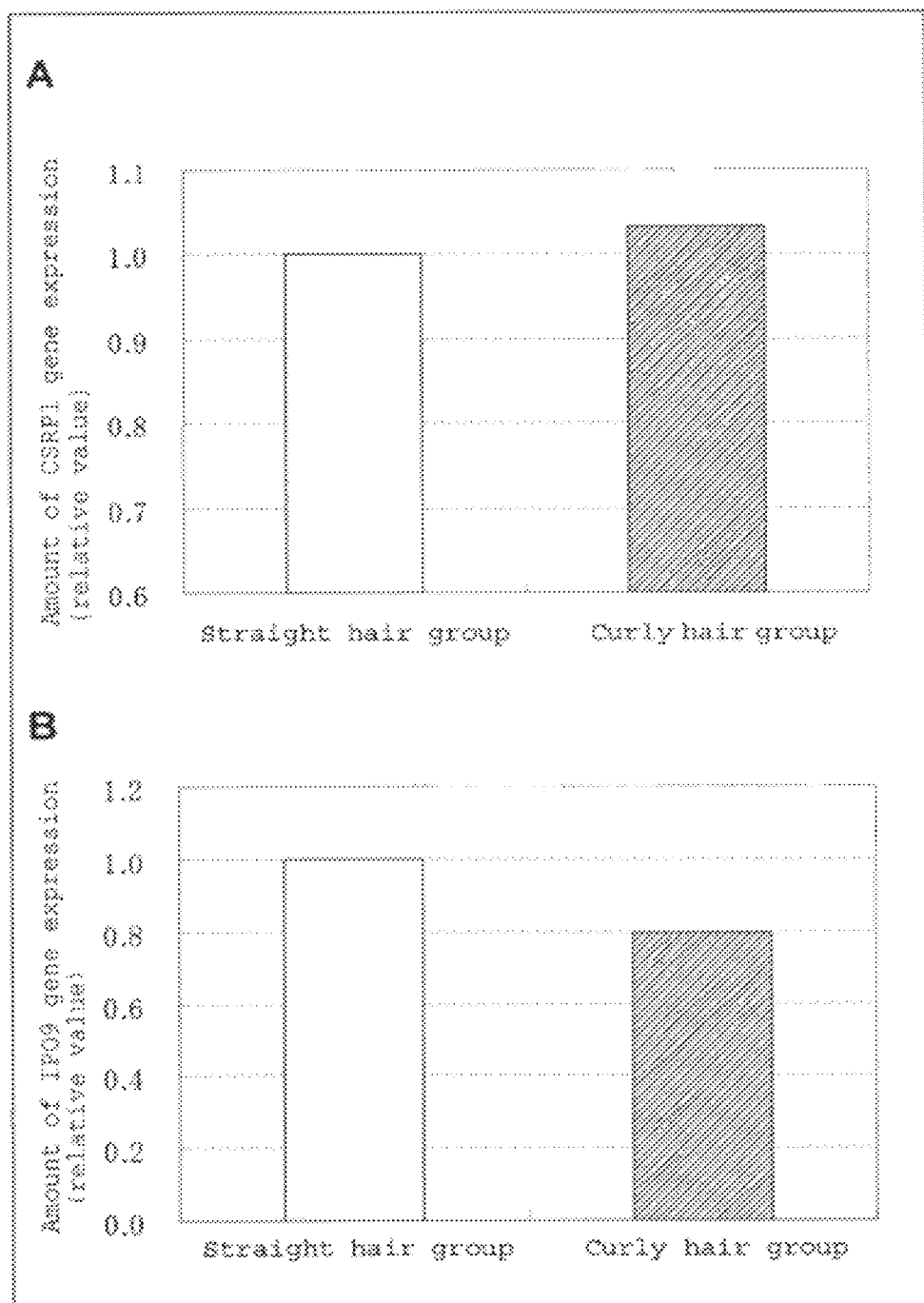

The amounts of expression of the hair shape susceptibility genes in the scalp hair roots of the curly hair group and the straight hair group are presented in FIG. 8A to FIG. 8C. From the results shown in FIG. 8, decreases in the amount of expression of IPO9 gene and NUCKS1 gene were observed and an increase in the amount of expression of CSRP1 gene was observed in the curly hair group, as compared with the straight hair group. Therefore, it was made clear that CSRP1 gene, IPO9 gene and NUCKS1 are hair shape susceptibility genes serving as indicators for the evaluation of hair shape, and the measurement of the amounts of expression of these genes in the hair root area is valuable.

Example 8

Screening of Substance Regulating Amount of Expression of Hair Shape Susceptibility Gene Normal human neonatal foreskin epidermal keratinocytes (KK-4009, manufactured by Kurabo Industries, Ltd.) were used in the screening. Normal human neonatal foreskin epidermal keratinocytes in a frozen state were melted, and then the cells were seeded in a 75-cm$^2$ flask or a 25-cm$^2$ flask at a density of 2500 cells/cm$^2$. The cells were cultured in a serum-free medium for human keratinocyte culture (Defined Keratinocyte-SFM, manufactured by Invitrogen, Inc.) containing added supplements, under the conditions of 37° C. and a $CO_2$ concentration of 5%. The cells were subcultured at the time point at which the cells reached a sub-confluent state, and the cells were seeded in a 6-well plate at a cell density of 2500 cells/cm$^2$. At the time point at which the cells had reached a sub-confluent state (Day 0), the medium was exchanged to a serum-free medium for human keratinocyte culture containing no supplements, and the cells on Day 1 were used as the cells for screening.

To the medium (serum-free medium for human keratinocyte culture containing no supplements) for the cells for screening prepared as described above, a plant extract was added to a final concentration of 0.1% or 1%, and the cells were cultured for 24 hours under the conditions of 37° C. and a $CO_2$ concentration of 5%. Furthermore, as control, 50% ethanol (control) was similarly added to a final concentration of 0.1% or 1%, and the cells were cultured.

After completion of the culture (Day 2), the medium was removed by suction, the cells were washed two times with PBS (manufactured by Invitrogen, Inc.), and then 1 mL per well of ISOGEN (manufactured by Nippon Gene Co., Ltd.) was added to the cells. The cells were sufficiently lysed and mixed through pipetting, and the solution was collected in a 1.5-mL tube. Total RNA was extracted by the same method as the method described in Example 7, and cDNA for use in the quantification of the amount of gene expression by PCR was obtained. The quantification of the amount of expression of the hair shape susceptibility gene was also carried out by the method described in Example 7.

In regard to the determination criteria for a substance that regulates the amount of expression of a gene, for example, if the amount of gene expression is higher by 10%, preferably 30%, and more preferably 50% or more, as compared with the control, the amount of expression is then said to be significantly high, and the test substance can be selected as an expression promoting agent for the hair shape susceptibility gene. Furthermore, for example, if the amount of gene expression is lower by 10%, preferably 30%, and more preferably 50% or more, as compared with the control, the amount of expression is then said to be significantly low, and the test substance can be selected as an expression suppressing agent for the hair shape susceptibility gene.

Approximately 700 kinds of plant extracts were evaluated by the screening system described above, and a search was made for substances that regulate the amount of expression of the hair shape susceptibility gene. As a result, expression promoting agents and expression suppressing agent for the genes were respectively found as indicated in Table 11.

TABLE 11

Substances that regulate the amounts of expression of the hair shape susceptibility genes

| | Name of plant extract | Amount of CSRP1 gene expression (relative to control as 1) |
|---|---|---|
| Expression promoting agent | Verbena officinalis (whole plant extract) | 3.26 |
| | Solanum lyratum (whole plant extract) | 2.61 |
| | Eucommia ulmoides (bark extract) | 2.34 |
| Expression suppressing agent | Amomum cardamomum (seed extract) | 0.67 |
| | Eupatorium perfoliatum (leaf and spike extract) | 0.44 |
| | Morun alba (leaf extract | 0.32 |

TABLE 11-continued

Substances that regulate the amounts of expression of the hair shape susceptibility genes

| | Name of plant extract | Amount of IPO9 gene expression (relative to control as 1) |
|---|---|---|
| Expression promoting agent | Fraxinus americana (bark extract) | 2.54 |
| | Aesculus hippocastanum (bark extract) | 2.17 |
| | Centipeda minima (whole plant extract) | 1.83 |
| Expression suppressing agent | Corylus heterophylla (seed kernel extract) | 0.58 |
| | Zingiber officinale (root extract) | 0.48 |
| | Euonymus atropurpureus (bark extract) | 0.32 |
| | | Amount of NUCKS1 gene (relative to control as 1) |
| Expression promoting agent | Hippophae rhamnoides (fruit extract) | 2.08 |
| | Centipeda minima (whole plant extract) | 1.96 |
| | Beta vulgaris vulgaris L. (whole plant extract) | 1.66 |
| Expression suppressing agent | Swertia japonica (whole plant extract) | 0.49 |
| | Lappula squarrosa (fruit extract) | 0.34 |
| | Eriobotrya japonica (leaf extract) | 0.20 |

Reference Example

Relations Between Hair Shape and Form of Hair Follicle

In general, the hair shape varies with the human races, and the people of the Asian race relatively more frequently have straight hair, while the people of the African race mainly have kinky hair (or curled hair). A large proportion of the people of the Indo-European race have a trait of wavy hair (wave hair) which is intermediate of the two. As a feature related to such variation of hair shape, the form of the hair follicle at the hair root part may be mentioned. That is, if the form of the hair follicle is curved, the hair is curved, and if the form of the hair follicle is straight, the hair is straight (Thibaut, S. et al., Br. J. Dermatol., 152(4), p. 632-638, 2005).

In order to investigate the relations between the hair shape and the form of the hair follicle in more detail, tissue specimens of hair follicle were produced from the human scalp tissues of various races, and the form of the hair follicle was observed. Meanwhile, in regard to the collection of specimens from the test subjects, an approval was granted in advance by the ethics committee, subsequently the person in charge of the implementation of informed consent explained the contents of the study to the objects using a written explanation, and written consent was obtained. The collected hair follicles were frozen after being embedded in Tissue-Tek OCT Compound (manufactured by Miles Laboratories, Inc.), which is an embedding medium for frozen tissue section preparation, and frozen section specimens were produced according to a standard method. Subsequently, the specimens were subjected to HE staining, and were observed with a microscope.

Figure 9:
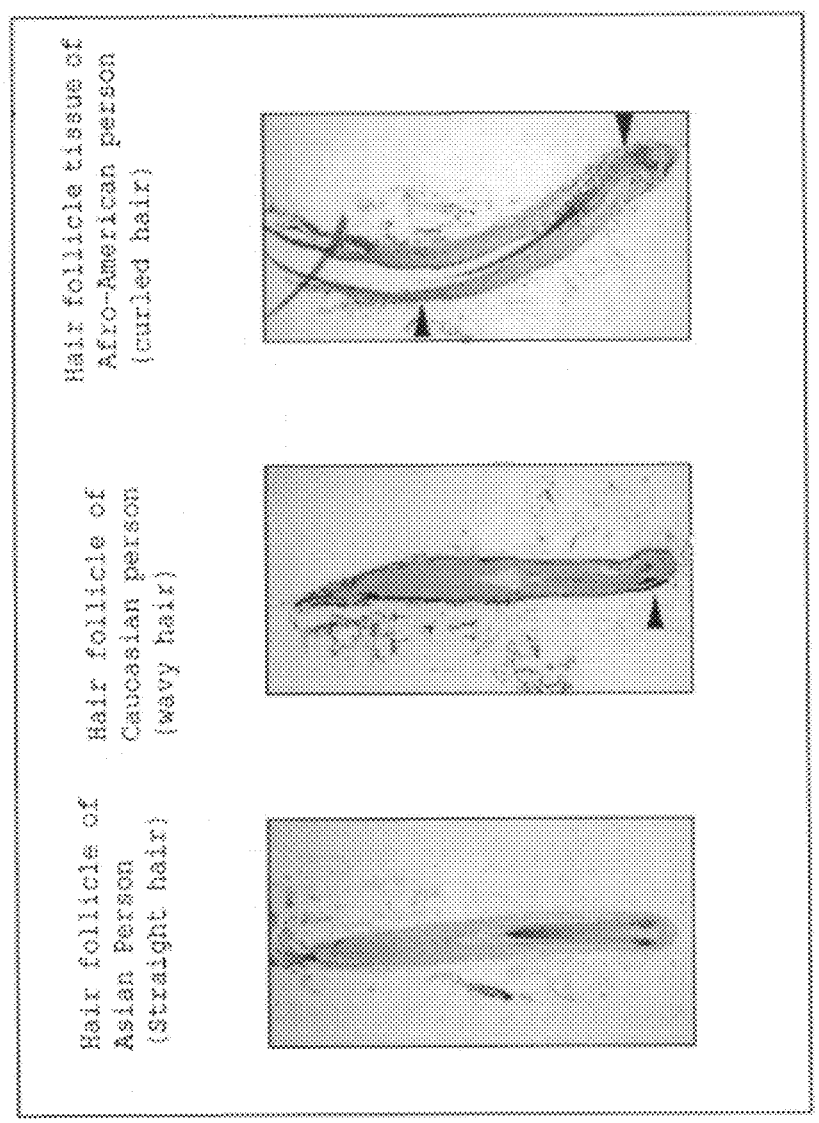
FIG. 9 is a set of photographs showing the images of hair follicle tissue of various human races, while the arrows indicate curved regions.

FIG. 9 presents images of the hair follicle tissue of various human races. As can be seen from the results shown in FIG. 9, the hair follicle of an Asian person having straight hair was straight, while the hair follicle of a Caucasian person having wavy hair was bent only at the lowermost part of the hair root. Furthermore, in the case of an Afro-American having curled hair, it was found that the entire hair follicle tissue was curved. Therefore, it could be confirmed that the hair shape and the form of the hair follicle were closely related to each other.

Example 9

Evaluation of Form of Hair Follicle Through Culture of Human Hair Follicle Organ As a method for evaluating the hair shape and the form of the hair follicle, an investigation was conducted on an evaluation method based on the culture of the human hair follicle organ. The scalp tissues of the temporal region or the occipital region of men and women in the age of 30's to 80's, which had been excised by cosmetic plastic surgery and became unnecessary, were obtained and used in the experiment. Meanwhile, in regard to the collection of specimens, an approval was granted in advance by the ethics committee, subsequently the surgeon explained the contents of the study to the objects using a written explanation, and written consent was obtained.

The human scalp tissue thus obtained was recovered in a petri dish filled with Williams' E medium (manufactured by Sigma-Aldrich Company) containing 1% of antibiotic/antifungal agents (manufactured by Invitrogen, Inc.). The hair follicles were aseptically isolated one by one under a stereoscopic microscope and using forceps and a scalpel or a needle teeth. The isolated hair follicles were separated from the epidermal tissue at the position of the lower part of the sebaceous gland, and any extra connective tissue, adipocytes and the like attached to the lower part of the hair follicle, were removed as much as possible. The isolated hair follicles thus prepared were transferred, one hair follicle per well, onto a 24-well plate to which Williams' E medium (manufactured by Sigma-Aldrich Company) containing 400 µL of 10 µg/mL insulin (manufactured by Invitrogen, Inc.), 40 ng/mL of hydrocortisone (manufactured by Sigma-Aldrich Company), 2 mM L-glutamine (manufactured by Invitrogen, Inc.), and 1% antibiotic/antifungal agents (manufactured by Invitrogen, Inc.) had been added, and culture was initiated. The culture was carried out in the manner of suspension culture, under the conditions of 37° C. and a $CO_2$ concentration of 5%. Thereafter, the medium was exchanged at an interval of 2 to 3 days, and at the same time, photographs of the hair follicles were taken.

Figure 10:
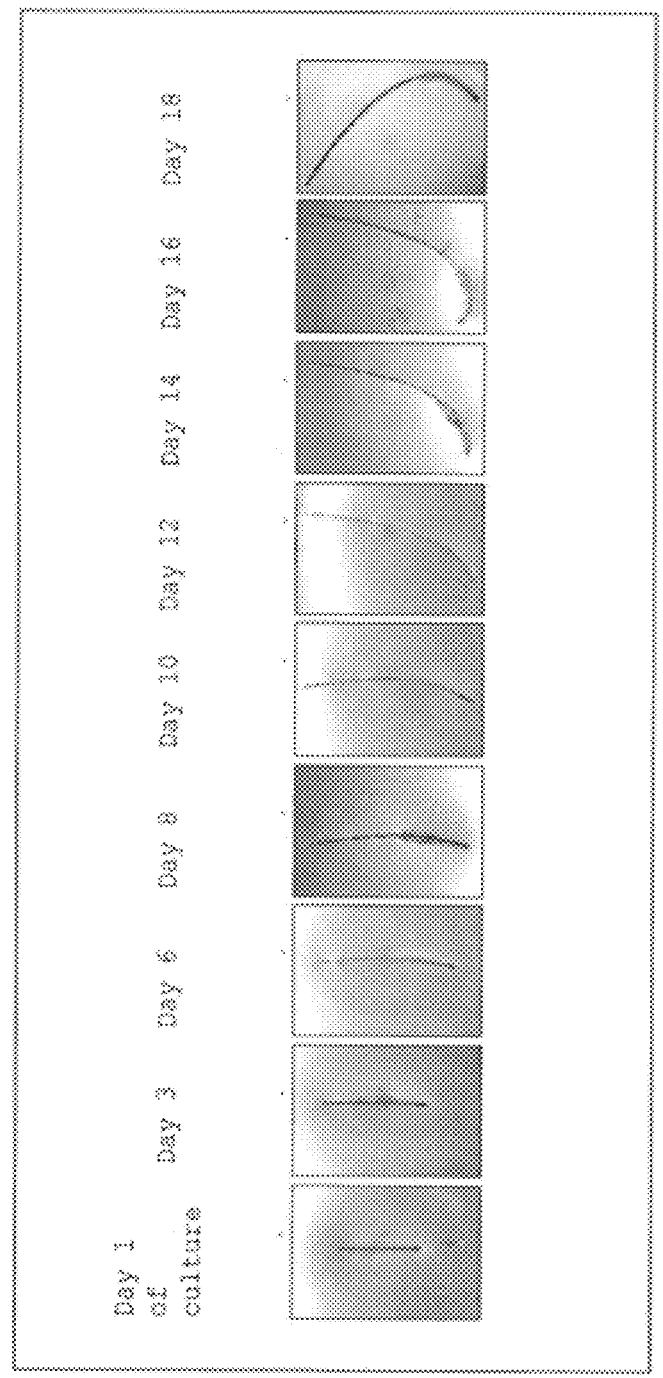
FIG. 10 is a set of photographs showing the changes in the shape of a hair follicle during culturing in a human hair follicle organ culture system.

The photographs of the change in the form of the hair follicle during culturing days are presented in FIG. 10. The hair shaft in the hair follicle grew with the progress of the culture, and thereby elongated. Furthermore, along with the progress of the culture, it was observed that the hair follicle was straight (straight hair) after one day from the initiation of culture (Day 1), but the hair follicle (hair shaft) was gradually curved with the culturing days.

In order to quantify the degree of curvature of the hair follicle (hair shaft), the ratio of end-to-end distance was calculated. The ratio of end-to-end distance is one of the indices representing the degree of curl, and can be determined by the following calculation (Hrdy, D., Am. J. Phys. Anthropol., 39(1), p. 7-17, 1973).

Straight Length Between the Ends of the Object (Hair, Hair Follicle)/Curve Length Along the Axis of the Object (Hair or Hair Follicle)

That is, according to the formula shown above, the ratio of end-to-end distance represents a value between 0 and 1, so that a straight object gives a value close to 1, and an object with a large degree of curvature gives a value close to zero (0).

The photographs of the hair follicles shown in FIG. 10 were analyzed using an image analyzing software (Nexus NewQube Ver. 4.23, manufactured by IMAX Systems, Inc.), and the length of the hair follicle (hair shaft) and the ratio of end-to-end distance were determined (Table 12).

As a result, it could be confirmed that the hair follicle (hair shaft) elongated with the culturing days, and at the same time, the hair follicle was gradually being curved. Therefore, it was found that when this evaluation system is used, search for an agent for curling of hair, or a curly hair ameliorating agent (hair straightening agent) can be conducted. That is, a test substance is added to the evaluation system of human hair follicle organ culture, the hair follicle organ is cultured, and the ratio of end-to-end distance of the hair follicle (hair shaft) which has elongated to a certain length is measured. When the hair follicle is cultured in the presence of a test substance, if the ratio of end-to-end distance becomes smaller as compared with a control cultured without adding the test substance, the test substance can be selected as a hair curling agent. When the hair follicle is cultured in the presence of a test substance, if the ratio of end-to-end distance becomes larger as compared with a control cultured without adding the test substance, the test substance can be selected as a curly hair ameliorating agent (hair straightening agent).

TABLE 12

Changes in the length of hair follicle (hair shaft) and the ratio of end-to-end distance in the hair follicle during culturing

| Culturing days (day) | Length of hair follicle (mm) | Ratio of end-to-end distance |
|---|---|---|
| 1 | 3.465 | 1.005 |
| 3 | 4.419 | 1.002 |
| 6 | 5.732 | 0.997 |
| 8 | 6.748 | 0.988 |
| 10 | 7.571 | 0.973 |
| 12 | 8.131 | 0.958 |
| 14 | 8.758 | 0.901 |
| 16 | 9.433 | 0.825 |
| 18 | 9.720 | 0.818 |

Example 10

Evaluation of an Agent of Regulating the Expression of in Human Hair Follicle Organ Culture For the purpose of verifying the effect of an agent of regulating the expression of hair shape susceptibility gene on the form of the hair follicle, an evaluation was conducted using the evaluation system for human hair follicle organ culture.

The human hair follicle was prepared according to Example 9. The isolated hair follicles were divided into two groups, with 12 hair strands in each group, so that there was no fluctuation in the size. One of the groups was suspension cultured for 15 days in a medium for organ culture (400 μL) to which a *Centipede minima* extract, which is an expression promoting agent for IPO9 gene and NUCKS1 gene as described in Table 11, was added at a final concentration of 0.2%. The other group was suspension cultured for 15 days in a medium for organ culture (400 μL) to which 50% EtOH (a final concentration of 0.83%) was added, as a control. According to the same procedure, a group added with an *Amomum cardamomum* extract (final concentration 0.2%), which is a CSRP1 gene expression suppressant as described in Table 11, and a control group (50% EtOH, final concentration 0.83%) were prepared (n=12 for each group).

After the initiation of culture, the medium was exchanged at an interval of 2 to 3 days, and at the same time, photographs of the hair follicles were taken. From the images of hair follicles thus taken, the degree of elongation and the degree of curvature (ratio of end-to-end distance) of the hair follicles were respectively measured.

Figure 11:
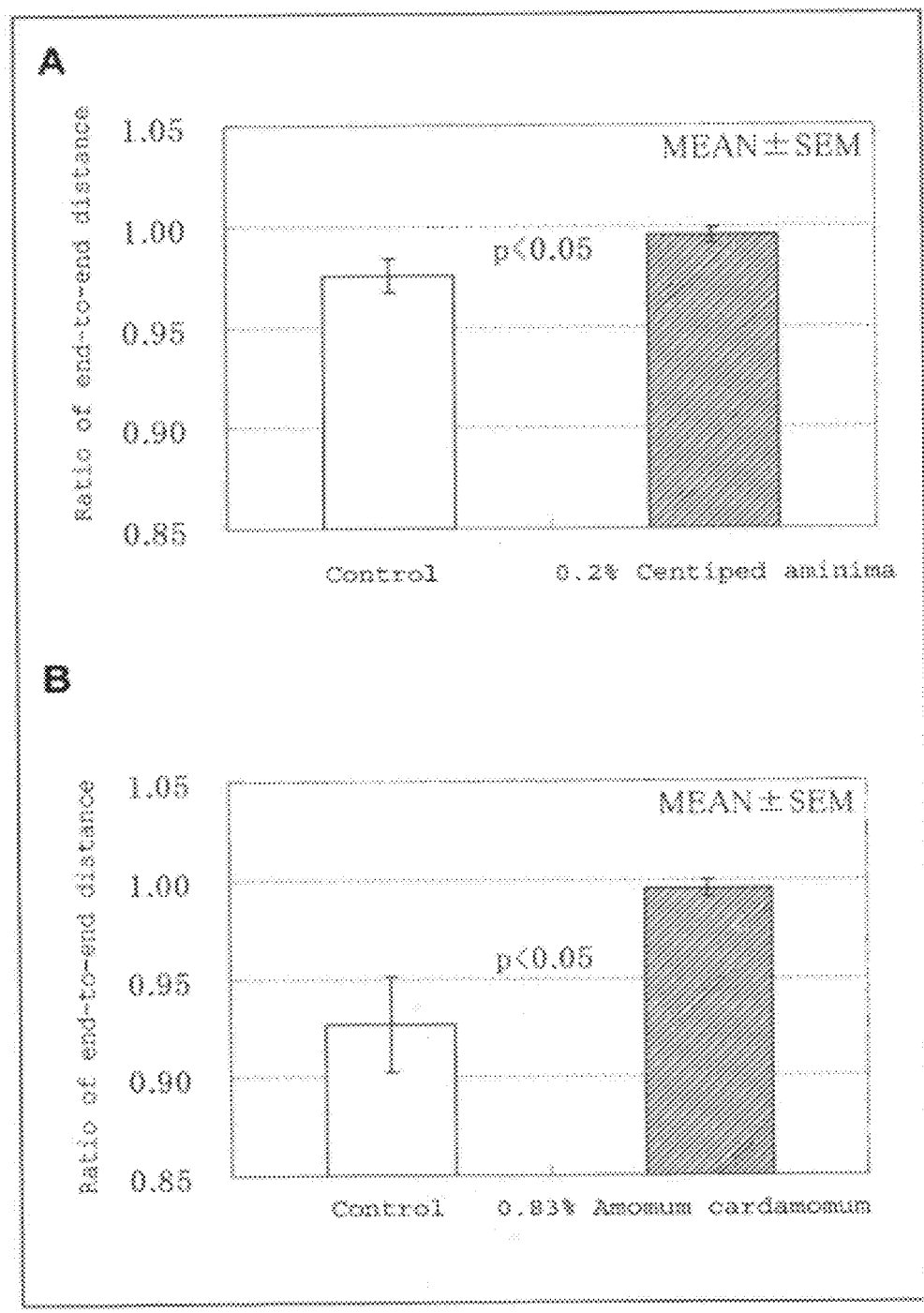
FIG. 11 is a graph showing the effect of a hair shape susceptibility gene expression regulating agent on the hair follicle shape, A: *centipeda minima*, B: round cardamon.

At the time point at which the length of the hair follicle (hair shaft) elongated by 1.5 mm or more as compared with the length at the initiation of culture, the ratio of end-to-end distance of the hair follicle (hair shaft) was measured. As a result, it was found that the *Centipeda minima* extract and the *Amomum cardamomum* extract significantly increase the ratio of end-to-end distance, which indicates the degree of curvature of the hair follicle (hair shaft), as compared with the 50% EtOH-added control (FIG. 11). From these results, it could be seen that an agent of regulating the expression of hair shape susceptibility gene can be selected as a curly hair ameliorating agent (hair straightening agent) for the hair.

What is claimed is:

1. A method for evaluating or selecting a hair shape regulating agent, comprising the following steps (a) to (f):
   (a) culturing cells in the presence of a test substance, wherein the cells are capable of expressing a human CSRP1 gene, or a protein encoded by the gene, and wherein the cells are selected from the group consisting of epidermal keratinocytes, human hair follicle tissue cells and hair root area-derived cells;
   (b) measuring the amount of expression of the CSRP1 gene or the protein in the cells that were cultured in the presence of the test substance;
   (c) selecting, based on the results of step (b), a test substance that decreases or increases the amount of expression of the gene or the protein, as compared to that in control cells cultured in the absence of the test substance;
   (d) culturing a human hair follicle in organ culture in the presence of the test substance that is selected in step (c);
   (e) determining the degree of curl of the hair follicle's hair shaft that occurs as a result of the culturing as compared to that of the hair shaft of a control hair follicle that is cultured in the absence of the test substance; and
   (f) selecting a test substance from step (e) that both (i) increases or decreases the amount of expression of the gene or the protein in step (c) and (ii) alters the degree of curl of the hair follicle's hair shaft in step (e), as a hair shape regulating agent; wherein a test substance that increases the amount of expression and curl is selected as a hair curling agent and a substance that decreases the amount of expression and curl is selected as a hair straightening agent.

2. The method of claim 1, wherein the test substance increases the amount of expression of the gene or the protein.

3. The method of claim 1, wherein the test substance decreases the amount of expression of the gene or the protein.

4. The method of claim 1, wherein the CSRP1 gene encodes a CSRP1 protein having the amino acid sequence of SEQ ID NO: 43.

5. The method of claim 4, wherein the sequence of the CSRP1 gene is that of SEQ ID NO: 42.

6. The method of claim 1, wherein the cells in step (a) are epidermal keratinocytes.

7. The method of claim 1, wherein the cells in step (a) are human hair follicle tissue cells.

8. The method of claim 1, wherein the cells in step (a) are hair root area-derived cells.

9. The method according to claim 1, wherein step (f) is selecting a test substance that increases the amount of expression and curl as a hair curling agent.

10. The method according to claim 1, wherein step (f) is selecting a test substance that decreases the amount of expression and curl as a hair straightening agent.

11. A method for evaluating or selecting a hair shape regulating agent, comprising the following steps (a) to (g):
   (a) introducing a fusion gene to cells, wherein, in the fusion gene, a human CSRP1 gene's regulatory region is linked to and controls expression of a reporter gene, and wherein the cells are capable of expressing an expression product of the reporter gene and are selected from the group consisting of epidermal keratinocytes, human hair follicle tissue cells and hair root area-derived cells;
   (b) culturing the cells that contain the fusion gene of step (a) in the presence of a test substance;
   (c) measuring the amount of expression of the expression product of the reporter gene in the cells cultured in the presence of the test substance;
   (d) selecting, based on the results of step (c), a test substance that increases or decreases the amount of the expression product of the reporter gene, as compared to that in control cells cultured in the absence of the test substance;
   (e) culturing a human hair follicle in organ culture in the presence of the test substance that is selected in step (d);
   (f) determining the degree of curl of the hair follicle's hair shaft that occurs as a result of the culturing as compared to that of the hair shaft of a control hair follicle that is cultured in the absence of the test substance; and
   (g) selecting a test substance from step (f) that both (i) increases or decreases the amount of expression of the protein encoded by the reporter gene in step (d) and (ii) alters the degree of curl of the hair follicle's hair shaft in step (f) as a hair shape regulating agent,
   wherein a test substance that increases the amount of expression and curl is selected as a hair curling agent and a substance that decreases the amount of expression and curl of is selected as a hair straightening agent.

12. The method of claim 11, wherein the test substance increases the amount of expression of the reporter gene.

13. The method of claim 11, wherein the test substance decreases the amount of expression of the reporter gene.

14. The method of claim 11, wherein the sequence of the regulatory region of the CSRP1 gene is that of SEQ ID NO: 48.

15. The method of claim 11, wherein the cells in step (a) are epidermal keratinocytes.

16. The method of claim 11, wherein the cells in step (a) are human hair follicle tissue cells.

17. The method of claim 11, wherein the cells in step (a) are hair root area-derived cells.

18. The method according to claim 11, wherein step (g) is selecting a test substance that increases the amount of the expression product of the reporter gene and curl, as a hair curling agent.

19. The method according to claim 11, wherein step (g) is selecting a test substance that decreases the amount of the expression product of the reporter gene and curl, as a hair straightening agent.

* * * * *